(12) United States Patent
Challita-Eid et al.

(10) Patent No.: US 7,067,130 B2
(45) Date of Patent: Jun. 27, 2006

(54) NUCLEIC ACID AND CORRESPONDING PROTEIN ENTITLED 161P2F10B USEFUL IN TREATMENT AND DETECTION OF CANCER

(75) Inventors: Pia M. Challita-Eid, Encino, CA (US); Arthur B. Raitano, Los Angeles, CA (US); Mary Faris, Los Angeles, CA (US); Rene S. Hubert, Los Angeles, CA (US); Karen Jane Meyrick Morrison, Santa Monica, CA (US); Aya Jakobovits, Beverly Hills, CA (US)

(73) Assignee: Agensys, Inc., Santa Monica, CA (US)

( * ) Notice: Subject to any disclaimer, the term of this patent is extended or adjusted under 35 U.S.C. 154(b) by 445 days.

(21) Appl. No.: 10/062,109

(22) Filed: Jan. 31, 2002

(65) Prior Publication Data

US 2003/0165505 A1 Sep. 4, 2003

Related U.S. Application Data

(62) Division of application No. 10/005,480, filed on Nov. 7, 2001, now abandoned.

(51) Int. Cl.
*A61K 39/395* (2006.01)
*C12N 15/00* (2006.01)
*C12N 15/63* (2006.01)

(52) U.S. Cl. ................. 424/139.1; 424/133.1; 424/141.1; 424/146.1; 424/155.1; 424/178.1; 432/69.1; 432/69.6; 432/320.1

(58) Field of Classification Search ............ 424/130.1, 424/133.1, 135.1, 139.1, 141.1, 143.1, 155.1, 424/181.1, 183.1; 435/69.1, 69.6
See application file for complete search history.

(56) References Cited

U.S. PATENT DOCUMENTS

| 6,323,321 B1 * | 11/2001 | Buhring |
| 6,342,219 B1 * | 1/2002 | Thorpe et al. |
| 2002/0137139 A1 | 9/2002 | Byatt et al. |

FOREIGN PATENT DOCUMENTS

| WO | WO9960164 | 11/1999 |
| WO | WO200021990 A1 | 4/2000 |
| WO | WO200157272 A2 | 8/2001 |
| WO | WO200157273 | 8/2001 |
| WO | WO200157275 A2 | 8/2001 |
| WO | WO200157276 A2 | 8/2001 |
| WO | WO200157277 A2 | 8/2001 |
| WO | WO200157278 A2 | 8/2001 |
| WO | WO200160860 | 8/2001 |
| WO | WO2001157274 A2 | 8/2001 |
| WO | WO200175067 A2 | 10/2001 |
| WO | WO200186003 A2 | 11/2001 |
| WO | WO200279411 | 10/2002 |
| WO | WO2003004514 | 1/2003 |
| WO | WO2003016475 | 2/2003 |
| WO | WO2003040340 | 5/2003 |

OTHER PUBLICATIONS

Reiger et al. Glossary of Genetics and Cytogenetics, Classical and Molecular, 4th Ed., Springer–Verlay, Berlin, 1976.*
Burgess et al. Journal of Cell Biology, 111:2129–2138, Nov. 1990.*
Lazar et al. Molecular and Cellular Biology, vol. 8 No. 3 1247–1252, Mar. 1988.*
Schwartz et al. Proc Natl Acad Sci USA vol. 84:6408–6411, 1987.*
Lederman et al. Molecular Immunology 28:1171–1181, 1991.*
Li et al. Proc. Natl. Acad. Sci. USA 77:3211–3214, 1980.*
Coleman P. M. Research in Immunology, 145:33–36, 1994.*
Buhring et al. Blood 94(7):2343–2356, Oct. 1, 1999.*
Buhring et al. Blood 97(10):3303–3305, May 15, 2001.*
Hua et al. Genomics 45(2):412–415, 1997.*
Paul (Ed.), Fundamental Immunology, 3rd ed., p. 242, 1993.
Deissler et al., Journal of Biological Chemistry (1995) 270(17):9849–9855.
International Search Report for PCT/US02/36002, mailed on Jan. 5, 2005, 5 pages.

* cited by examiner

Primary Examiner—Larry R. Helms
Assistant Examiner—David J. Blanchard
(74) Attorney, Agent, or Firm—Morrison & Foerster LLP

(57) ABSTRACT

A gene (designated 161P2F10B) and its encoded protein are described wherein 161P2F10B exhibits tissue specific expression in normal adult tissue, it is aberrantly expressed in the cancers listed in Table I. Consequently, 161P2F10B provides a diagnostic, prognostic, prophylactic and/or therapeutic target for cancer. The 161P2F10B gene or fragment thereof, or its encoded protein or a fragment thereof, can be used to elicit a humoral or cellular immune response.

12 Claims, 31 Drawing Sheets

Figure 1: 161P2F10B SSH sequence of 182 nucleotides (SEQ. ID. No. 742)

```
  1 GATCACACAT TAGGTTATNG ACTTCAATAT TTTCAAATGG TTCAACTTCA GTCTTCTCTT
 61 TAAAACTGGG TCCATGTGCC AAGAAAGATA GCCTCCATGC TCCTAAACTC ATTGTTATAA
121 CCATGGTTGC CTCCTCCACA ATTTGTATTT GATTTACTCC TAACAGCCAG CCACTGTTGA
181 TC
```

Figure 2.

Figure 2A. The cDNA (SEQ ID. NO. : 744) and amino acid sequence (SEQ ID. NO. : 743) of 161P2F10B.

```
                                                    M   E   S   T   L   T
  1 ctactttattctgataaaacaggtctatgcagctaccaggacaATGGAATCTACGTTGAC
      7   L   A   T   E   Q   P   V   K   K   N   T   L   K   K   Y   K   I   A   C   I
 61 TTTAGCAACGGAACAACCTGTTAAGAAGAACACTCTTAAGAAATATAAAATAGCTTGCAT
     27   V   L   L   A   L   L   V   I   M   S   L   G   L   G   L   G   L   G   L   R
121 TGTTCTTCTTGCTTTGCTGGTGATCATGTCACTTGGATTAGGCCTGGGGCTTGGACTCAG
     47   K   L   E   K   Q   G   S   C   R   K   K   C   F   D   A   S   F   R   G   L
181 GAAACTGGAAAAGCAAGGCAGCTGCAGGAAGAAGTGCTTTGATGCATCATTTAGAGGACT
     67   E   N   C   R   D   V   A   C   K   D   R   G   D   C   W   D   F   E
241 GGAGAACTGCCGGTGTGATGTGGCATGTAAAGACCGAGGTGATTGCTGCTGGGATTTTGA
     87   D   T   C   V   E   S   T   R   I   W   M   C   N   K   F   R   C   G   E   T
301 AGACACCTGTGTGGAATCAACTCGAATATGGATGTGCAATAAATTTCGTTGTGGAGAGAC
    107   R   L   E   A   S   L   C   S   C   S   D   D   C   L   Q   K   K   D   C   C
361 CAGATTAGAGGCCAGCCTTTGCTCTTGTTCAGATGACTGTTTGCAGAAGAAAGATTGCTG
    127   A   D   Y   K   S   V   C   Q   G   E   T   S   W   L   E   E   N   C   D   T
421 TGCTGACTATAAGAGTGTTTGCCAAGGAGAAACCTCATGGCTGGAAGAAAACTGTGACAC
    147   A   Q   Q   S   Q   C   P   E   G   F   D   L   P   P   V   I   L   F   S   M
481 AGCCCAGCAGTCTCAGTGCCCAGAAGGGTTTGACCTGCCACCAGTTATCTTGTTTTCTAT
    167   D   G   F   R   A   E   Y   L   Y   T   W   D   T   L   M   P   N   I   N   K
541 GGATGGATTTAGAGCTGAATATTTATACACATGGGATACTTTAATGCCAAATATCAATAA
    187   L   K   T   C   G   I   H   S   K   Y   M   R   A   M   Y   P   T   K   T   F
601 ACTGAAAACATGTGGAATTCATTCAAAATACATGAGAGCTATGTATCCTACCAAAACCTT
    207   P   N   H   Y   T   I   V   T   G   L   Y   P   E   S   H   G   I   I   D   N
661 CCCAAATCATTACACCATTGTCACGGGCTTGTATCCAGAGTCACATGGCATCATTGACAA
    227   N   M   Y   D   V   N   L   N   K   N   F   S   L   S   S   K   E   Q   N   N
721 TAATATGTATGATGTAAATCTCAACAAGAATTTTTCACTTTCTTCAAAGGAACAAAATAA
    247   P   A   W   H   G   Q   P   M   W   L   T   A   M   Y   Q   G   L   K   A
781 TCCAGCCTGGTGGCATGGGCAACCAATGTGGCTGACAGCAATGTATCAAGGTTTAAAAGC
    267   A   T   Y   F   W   P   G   S   E   V   A   I   N   G   S   F   P   S   I   Y
841 CGCTACCTACTTTTGGCCCGGATCAGAAGTGGCTATAAATGGCTCCTTTCCTTCCATATA
    287   M   P   Y   N   G   S   V   P   F   E   E   R   I   S   T   L   L   K   W   L
901 CATGCCTTACAACGGAAGTGTCCCATTTGAAGAGAGGATTTCTACACTGTTAAAATGGCT
    307   D   L   P   K   A   E   R   P   R   F   Y   T   M   Y   F   E   E   P   D   S
961 GGACCTGCCCAAAGCTGAAAGACCCAGGTTTTATACCATGTATTTTGAAGAACCTGATTC
    327   S   G   H   A   G   G   P   V   S   A   R   V   I   K   A   L   Q   V   V   D
```

Figure 2A-1

```
1021 CTCTGGACATGCAGGTGGACCAGTCAGTGCCAGAGTAATTAAAGCCTTACAGGTAGTAGA
 347  H   A   F   G   M   L   M   E   G   L   K   Q   R   N   L   H   N   C   V   N
1081 TCATGCTTTTGGGATGTTGATGGAAGGCCTGAAGCAGCGGAATTTGCACAACTGTGTCAA
 367  I   I   L   L   A   D   H   G   M   D   Q   T   Y   C   N   K   M   E   Y   M
1141 TATCATCCTTCTGGCTGACCATGGAATGGACCAGACTTATTGTAACAAGATGGAATACAT
 387  T   D   Y   F   P   R   I   N   F   F   Y   M   Y   E   G   P   A   P   R   I
1201 GACTGATTATTTTCCCAGAATAAACTTCTTCTACATGTACGAAGGGCCTGCCCCCCGCAT
 407  R   A   H   N   I   P   H   D   F   F   S   F   N   S   E   E   I   V   R   N
1261 CCGAGCTCATAATATACCTCATGACTTTTTTAGTTTTAATTCTGAGGAAATTGTTAGAAA
 427  L   S   C   R   K   P   D   Q   H   F   K   P   Y   L   T   P   D   L   P   K
1321 CCTCAGTTGCCGAAAACCTGATCAGCATTTCAAGCCCTATTTGACTCCTGATTTGCCAAA
 447  R   L   H   Y   A   K   N   V   R   I   D   K   V   H   L   F   V   D   Q   Q
1381 GCGACTGCACTATGCCAAGAACGTCAGAATCGACAAAGTTCATCTCTTTGTGGATCAACA
 467  W   L   A   V   R   S   K   S   N   T   N   C   G   G   G   N   H   G   Y   N
1441 GTGGCTGGCTGTTAGGAGTAAATCAAATACAAATTGTGGAGGAGGCAACCATGGTTATAA
 487  N   E   F   R   S   M   E   A   I   F   L   A   H   G   P   S   F   K   E   K
1501 CAATGAGTTTAGGAGCATGGAGGCTATCTTTCTGGCACATGGACCCAGTTTTAAAGAGAA
 507  T   E   V   E   P   F   E   N   I   E   V   Y   N   L   M   C   D   L   L   R
1561 GACTGAAGTTGAACCATTTGAAAATATTGAAGTCTATAACCTAATGTGTGATCTTCTACG
 527  I   Q   P   A   P   N   N   G   T   H   G   S   L   N   H   L   L   K   V   P
1621 CATTCAACCAGCACCAAACAATGGAACCCATGGTAGTTTAAACCATCTTCTGAAGGTGCC
 547  F   Y   E   P   S   H   A   E   E   V   S   K   F   S   V   C   G   F   A   N
1681 TTTTTATGAGCCATCCCATGCAGAGGAGGTGTCAAAGTTTTCTGTTTGTGGCTTTGCTAA
 567  P   L   P   T   E   S   L   D   C   F   C   P   H   L   Q   N   S   T   Q   L
1741 TCCATTGCCCACAGAGTCTCTTGACTGTTTCTGCCCTCACCTACAAAATAGTACTCAGCT
 587  E   Q   V   N   Q   M   L   N   L   T   Q   E   E   I   T   A   T   V   K   V
1801 GGAACAAGTGAATCAGATGCTAAATCTCACCCAAGAAGAAATAACAGCAACAGTGAAAGT
 607  N   L   P   F   G   R   P   R   V   L   Q   K   N   V   D   H   C   L   L   Y
1861 AAATTTGCCATTTGGGAGGCCTAGGGTACTGCAGAAGAACGTGGACCACTGTCTCCTTTA
 627  H   R   E   Y   V   S   G   F   G   K   A   M   R   M   P   M   W   S   S   Y
1921 CCACAGGGAATATGTCAGTGGATTTGGAAAAGCTATGAGGATGCCCATGTGGAGTTCATA
 647  T   V   P   Q   L   G   D   T   S   P   L   P   P   T   V   P   D   C   L   R
1981 CACAGTCCCCCAGTTGGGAGACACATCGCCTCTGCCTCCCACTGTCCCAGACTGTCTGCG
 667  A   D   V   R   V   P   P   S   E   S   Q   K   C   S   F   Y   L   A   D   K
2041 GGCTGATGTCAGGGTTCCTCCTTCTGAGAGCCAAAAATGTTCCTTCTATTTAGCAGACAA
 687  N   I   T   H   G   F   L   Y   P   P   A   S   N   R   T   S   D   S   Q   Y
2101 GAATATCACCCACGGCTTCCTCTATCCTCCTGCCAGCAATAGAACATCAGATAGCCAATA
 707  D   A   L   I   T   S   N   L   V   P   M   Y   E   E   F   R   K   M   W   D
2161 TGATGCTTTAATTACTAGCAATTTGGTACCTATGTATGAAGAATTCAGAAAAATGTGGGA
 727  Y   F   H   S   V   L   L   I   K   H   A   T   E   R   N   G   V   N   V   V
```

Figure 2A-2

```
2221 CTACTTCCACAGTGTTCTTCTTATAAACATGCCACAGAAAGAAATGGAGTAAATGTGGT
 747   S   G   P   I   F   D   Y   N   Y   D   G   H   F   D   A   P   D   E   I   T
2281 TAGTGGACCAATATTTGATTATAATTATGATGGCCATTTTGATGCTCCAGATGAAATTAC
 767   K   H   L   A   N   T   D   V   P   I   P   T   H   Y   F   V   V   L   T   S
2341 CAAACATTTAGCCAACACTGATGTTCCATCCCAACACACTACTTTGTGGTGCTGACCAG
 787   C   K   N   K   S   H   T   P   E   N   C   P   G   W   L   D   V   L   P   F
2401 TTGTAAAAACAAGAGCCACACACCGGAAAACTGCCCTGGGTGGCTGGATGTCCTACCCTT
 807   I   I   P   H   R   P   T   N   V   E   S   C   P   E   G   K   P   E   A   L
2461 TATCATCCCTCACCGACCTACCAACGTGGAGAGCTGTCCTGAAGGTAAACCAGAAGCTCT
 827   W   V   E   E   R   F   T   A   H   I   A   R   V   R   D   V   E   L   L   T
2521 TTGGGTTGAAGAAAGATTTACAGCTCACATTGCCCGGGTCCGTGATGTAGAACTTCTCAC
 847   G   L   D   F   Y   Q   D   K   V   Q   P   V   S   E   I   L   Q   L   K   T
2581 TGGGCTTGACTTCTATCAGGATAAAGTGCAGCCTGTCTCTGAAATTTTGCAACTAAAGAC
 867   Y   L   P   T   F   E   T   T   I   *
2641 ATATTTACCAACATTTGAAACCACTATTTAActtaataatgtctacttaatatataattt
2701 actgtataaagtaattttggcaaaatataagtgattttttctggagaattgtaaaataaa
2761 gttttctattttccttaaaaaaaaaccggaattccgggcttgggaggctgaggcagga
2821 gactcgcttgaacccgggaggcagaggttgcagtgagccaagattgcgccattgcactcc
2881 agagcctgggtgacagagcaagactacatctcaaaaaataaataaataaaataaaagtaa
2941 caataaaaataaaaagaacagcagagagaatgagcaaggagaaatgtcacaaactattgc
3001 aaaatactgttacactggggttggctctccaagaagatactggaatctcttcagccatttg
3061 cttttcagaagtagaaaccagcaaaccacctctaagcggagaacatacgattctttatta
3121 agtagctctggggaaggaaagaataaaagttgatagctccctgattgggaaaaatgcac
3181 aattaataaagaatgaagatgaaagaaagcatgcttatgttgtaacacaaaaaaaattca
3241 caaacgttggtggaaggaaaacagtatagaaaacattactttaactaaaagctggaaaaa
3301 ttttcagttgggatgcgactgacaaaaagaacgggatttccaggcataaagttggcgtga
3361 gctacagagggcaccatgtggctcagtggaagacccttcaagattcaaagttccatttga
3421 cagagcaaaggcacttcgcaaggagaagggtttaaattatgggtccaaaagccaagtggt
3481 aaagcgagcaatttgcagcataactgcttctcctagacagggctgagtgggcaaaatacg
3541 acagtacacacagtgactattagccactgccagaaacaggctgaacagccctgggagaca
3601 agggaaggcaggtggtgggagttgttcatggagagaaggagagttttagaaccagcaca
3661 tccactggagatgctgggccaccagacccctcccagtcaataaagtctggtgcctcattt
3721 gatctcagcctcatcatgaccctggagagaccctgataccatctgccagtccccgacagc
3781 ttaggcactccttgccatcaacctgaccccccgagtggttctccaggctccctgccccac
3841 ccattcaggccggaattc
```

Figure 2A-3

Figure 2B: The cDNA (SEQ ID. NO. : 746) and amino acid sequence (SEQ ID. NO. : 745) of 161P2F10B variant 1.

```
   1                                           M   E   S   T   L   T
   1 ctactttattctgataaaacaggtctatgcagctaccaggacaATGGAATCTACGTTGAC
   7  L   A   T   E   Q   P   V   K   K   N   T   L   K   K   Y   K   I   A   C   I
  61 TTTAGCAACGGAACAACCTGTTAAGAAGAACACTCTTAAGAAATATAAAATAGCTTGCAT
  27  V   L   L   A   L   L   V   I   M   S   L   G   L   G   L   G   L   R
 121 TGTTCTTCTTGCTTTGCTGGTGATCATGTCACTTGGATTAGGCCTGGGGCTTGGACTCAG
  47  K   L   E   K   Q   G   S   C   R   K   K   C   F   D   A   S   F   R   G   L
 181 GAAACTGGAAAAGCAAGGCAGCTGCAGGAAGAAGTGCTTTGATGCATCATTTAGAGGACT
  67  E   N   C   R   C   D   V   A   C   K   D   R   G   D   C   C   W   D   F   E
 241 GGAGAACTGCCGGTGTGATGTGGCATGTAAAGACCGAGGTGATTGCTGCTGGGATTTTGA
  87  D   T   C   V   E   S   T   R   I   W   M   C   N   K   F   R   C   G   E   T
 301 AGACACCTGTGTGGAATCAACTCGAATATGGATGTGCAATAAATTTCGTTGTGGAGAGAC
 107  R   L   E   A   S   L   C   S   C   S   D   D   C   L   Q   R   K   D   C   C
 361 CAGATTAGAGGCCAGCCTTTGCTCTTGTTCAGATGACTGTTTGCAGAGGAAAGATTGCTG
 127  A   D   Y   K   S   V   C   Q   G   E   T   S   W   L   E   E   N   C   D   T
 421 TGCTGACTATAAGAGTGTTTGCCAAGGAGAAACCTCATGGCTGGAAGAAAACTGTGACAC
 147  A   Q   Q   S   Q   C   P   E   G   F   D   L   P   P   V   I   L   F   S   M
 481 AGCCCAGCAGTCTCAGTGCCCAGAAGGGTTTGACCTGCCACCAGTTATCTTGTTTTCTAT
 167  D   G   F   R   A   E   Y   L   Y   T   W   D   T   L   M   P   N   I   N   K
 541 GGATGGATTTAGAGCTGAATATTTATACACATGGGATACTTTAATGCCAAATATCAATAA
 187  L   K   T   C   G   I   H   S   K   Y   M   R   A   M   Y   P   T   K   T   F
 601 ACTGAAAACATGTGGAATTCATTCAAAATACATGAGAGCTATGTATCCTACCAAAACCTT
 207  P   N   H   Y   T   I   V   T   G   L   Y   P   E   S   H   G   I   I   D   N
 661 CCCAAATCATTACACCATTGTCACGGGCTTGTATCCAGAGTCACATGGCATCATTGACAA
 227  N   M   Y   D   V   N   L   N   K   N   F   S   L   S   S   K   E   Q   N   N
 721 TAATATGTATGATGTAAATCTCAACAAGAATTTTTCACTTTCTTCAAAGGAACAAAATAA
 247  P   A   W   W   H   G   Q   P   M   W   L   T   A   M   Y   Q   G   L   K   A
 781 TCCAGCCTGGTGGCATGGGCAACCAATGTGGCTGACAGCAATGTATCAAGGTTTAAAAGC
 267  A   T   Y   F   W   P   G   S   E   V   A   I   N   G   S   F   P   S   I   Y
 841 CGCTACCTACTTTTGGCCCGGATCAGAAGTGGCTATAAATGGCTCCTTTCCTTCCATATA
 287  M   P   Y   N   G   S   V   P   F   E   E   R   I   S   T   L   L   K   W   L
 901 CATGCCTTACAACGGAAGTGTCCCATTTGAAGAGAGGATTCTACACTGTTAAAATGGCT
 307  D   L   P   K   A   E   R   P   R   F   Y   T   M   Y   F   E   E   P   D   S
 961 GGACCTGCCCAAAGCTGAAAGACCCAGGTTTTATACCATGTATTTTGAAGAACCTGATTC
 327  S   G   H   A   G   G   P   V   S   A   R   V   I   K   A   L   Q   V   V   D
1021 CTCTGGACATGCAGGTGGACCAGTCAGTGCCAGAGTAATTAAAGCCTTACAGGTAGTAGA
 347  H   A   F   G   M   L   M   E   G   L   K   Q   R   N   L   H   N   C   V   N
1081 TCATGCTTTTGGGATGTTGATGGAAGGCCTGAAGCAGCGGAATTTGCACAACTGTGTCAA
 367  I   I   L   L   A   D   H   G   M   D   Q   T   Y   C   N   K   M   E   Y   M
1141 TATCATCCTTCTGGCTGACCATGGAATGGACCAGACTTATTGTAACAAGATGGAATACAT
```

Figure 2B-1

```
387  T  D  Y  F  P  R  I  N  F  F  Y  M  Y  E  G  P  A  P  R  I
1201 GACTGATTATTTTCCCAGAATAAACTTCTTCTACATGTACGAAGGGCCTGCCCCCCGCAT
407  R  A  H  N  I  P  H  D  F  F  S  F  N  S  E  E  I  V  R  N
1261 CCGAGCTCATAATATACCTCATGACTTTTTTAGTTTTAATTCTGAGGAAATTGTTAGAAA
427  L  S  C  R  K  P  D  Q  H  F  K  P  Y  L  T  P  D  L  P  K
1321 CCTCAGTTGCCGAAAACCTGATCAGCATTTCAAGCCCTATTTGACTCCTGATTTGCCAAA
447  R  L  H  Y  A  K  N  V  R  I  D  K  V  H  L  F  V  D  Q  Q
1381 GCGACTGCACTATGCCAAGAACGTCAGAATCGACAAAGTTCATCTCTTTGTGGATCAACA
467  W  L  A  V  R  S  K  S  N  T  N  C  G  G  G  N  H  G  Y  N
1441 GTGGCTGGCTGTTAGGAGTAAATCAAATACAAATTGTGGAGGAGGCAACCATGGTTATAA
487  N  E  F  R  S  M  E  A  I  F  L  A  H  G  P  S  F  K  E  K
1501 CAATGAGTTTAGGAGCATGGAGGCTATCTTTCTGGCACATGGACCCAGTTTTAAAGAGAA
507  T  E  V  E  P  F  E  N  I  E  V  Y  N  L  M  C  D  L  L  R
1561 GACTGAAGTTGAACCATTTGAAAATATTGAAGTCTATAACCTAATGTGTGATCTTCTACG
527  I  Q  P  A  P  N  N  G  T  H  G  S  L  N  H  L  L  K  V  P
1621 CATTCAACCAGCACCAAACAATGGAACCCATGGTAGTTTAAACCATCTTCTGAAGGTGCC
547  F  Y  E  P  S  H  A  E  E  V  S  K  F  S  V  C  G  F  A  N
1681 TTTTTATGAGCCATCCCATGCAGAGGAGGTGTCAAAGTTTTCTGTTTGTGGCTTTGCTAA
567  P  L  P  T  E  S  L  D  C  F  C  P  H  L  Q  N  S  T  Q  L
1741 TCCATTGCCCACAGAGTCTCTTGACTGTTTCTGCCCTCACCTACAAAATAGTACTCAGCT
587  E  Q  V  N  Q  M  L  N  L  T  Q  E  E  I  T  A  T  V  K  V
1801 GGAACAAGTGAATCAGATGCTAAATCTCACCCAAGAAGAAATAACAGCAACAGTGAAAGT
607  N  L  P  F  G  R  P  R  V  L  Q  K  N  V  D  H  C  L  L  Y
1861 AAATTTGCCATTTGGGAGGCCTAGGGTACTGCAGAAGAACGTGGACCACTGTCTCCTTTA
627  H  R  E  Y  V  S  G  F  G  K  A  M  R  M  P  M  W  S  S  Y
1921 CCACAGGGAATATGTCAGTGGATTTGGAAAAGCTATGAGGATGCCCATGTGGAGTTCATA
647  T  V  P  Q  L  G  D  T  S  P  L  P  P  T  V  P  D  C  L  R
1981 CACAGTCCCCCAGTTGGGAGACACATCGCCTCTGCCTCCCACTGTCCCAGACTGTCTGCG
667  A  D  V  R  V  P  P  S  E  S  Q  K  C  S  F  Y  L  A  D  K
2041 GGCTGATGTCAGGGTTCCTCCTTCTGAGAGCCAAAAATGTTCCTTCTATTTAGCAGACAA
687  N  I  T  H  G  F  L  Y  P  P  A  S  N  R  T  S  D  S  Q  Y
2101 GAATATCACCCACGGCTTCCTCTATCCTCCTGCCAGCAATAGAACATCAGATAGCCAATA
707  D  A  L  I  T  S  N  L  V  P  M  Y  E  E  F  R  K  M  W  D
2161 TGATGCTTTAATTACTAGCAATTTGGTACCTATGTATGAAGAATTCAGAAAAATGTGGGA
727  Y  F  H  S  V  L  L  I  K  H  A  T  E  R  N  G  V  N  V  V
2221 CTACTTCCACAGTGTTCTTCTTATAAAACATGCCACAGAAAGAAATGGAGTAAATGTGGT
747  S  G  P  I  F  D  Y  N  Y  D  G  H  F  D  A  P  D  E  I  T
2281 TAGTGGACCAATATTTGATTATAATTATGATGGCCATTTTGATGCTCCAGATGAAATTAC
767  K  H  L  A  N  T  D  V  P  I  P  T  H  Y  F  V  V  L  T  S
2341 CAAACATTTAGCCAACACTGATGTTCCCATCCCAACACACTACTTTGTGGTGCTGACCAG
787  C  K  N  K  S  H  T  P  E  N  C  P  G  W  L  D  V  L  P  F
2401 TTGTAAAAACAAGAGCCACACACCGGAAAACTGCCCTGGGTGGCTGGATGTCCTACCCTT
807  I  I  P  H  R  P  T  N  V  E  S  C  P  E  G  K  P  E  A  L
2461 TATCATCCCTCACCGACCTACCAACGTGGAGAGCTGTCCTGAAGGTAAACCAGAAGCTCT
827  W  V  E  E  R  F  T  A  H  I  A  R  V  R  D  V  E  L  L  T
```

Figure 2B-2

```
2521 TTGGGTTGAAGAAGATTTACAGCTCACATTGCCCGGGTCCGTGATGTAGAACTTCTCAC
 847  G   L   D   F   Y   Q   D   K   V   Q   P   V   S   E   I   L   Q   L   K   T
2581 TGGGCTTGACTTCTATCAGGATAAAGTGCAGCCTGTCTCTGAAATTTTGCAACTAAAGAC
 867  Y   L   P   T   F   E   T   T   I   *
2641 ATATTTACCAACATTTGAAACCACTATTTAActtaataatgtctacttaatatataattt
2701 actgtataaagtaattttggcaaaatataagtgattttttctggagaattgtaaaataaa
2761 gttttctattttttccttaaaaaaaaaaccggaattccgggcttgggaggctgaggcagga
2821 gactcgcttgaacccgggaggcagaggttgcagtgagccaagattgcgccattgcactcc
2881 agagcctgggtgacagagcaagactacatctcaaaaaataaataaataaaataaaagtaa
2941 caataaaaataaaaagaacagcagagagaatgagcaaggagaaatgtcacaaactattgc
3001 aaaatactgttacactggggttggctctccaagaagatactggaatctcttcagccatttg
3061 cttttcagaagtagaaaccagcaaaccacctctaagcggagaacatacgattctttatta
3121 agtagctctggggaaggaaagaataaaagttgatagctccctgattgggaaaaaatgcac
3181 aattaataaagaatgaagatgaaagaaagcatgcttatgttgtaacacaaaaaaaattca
3241 caaacgttggtggaaggaaaacagtatagaaaacattactttaactaaaagctggaaaaa
3301 ttttcagttgggatgcgactgacaaaaagaacgggatttccaggcataaagttggcgtga
3361 gctacagagggcaccatgtggctcagtggaagaccttcaagattcaaagttccatttga
3421 cagagcaaaggcacttcgcaaggagaagggtttaaattatgggtccaaaagccaagtggt
3481 aaagcgagcaatttgcagcataactgcttctcctagacagggctgagtgggcaaaatacg
3541 acagtacacacagtgactattagccactgccagaaacaggctgaacagccctgggagaca
3601 agggaaggcaggtggtgggagttgttcatggagagaaggagagttttagaaccagcaca
3661 tccactggagatgctgggccaccagacccctcccagtcaataaagtctggtgcctcattt
3721 gatctcagcctcatcatgaccctggagagaccctgataccatctgccagtccccgacagc
3781 ttaggcactccttgccatcaacctgacccccgagtggttctccaggctccctgccccac
3841 ccattcaggccggaattc
```

Figure 2B-3

Figure 3A. Amino acid sequence of 161P2F10B (SEQ ID. NO. : 747). The 161P2F10B protein has 875 amino acids.

```
  1 MESTLTLATE QPVKKNTLKK YKIACIVLLA LLVIMSLGLG LGLGLRKLEK QGSCRKKCFD
 61 ASFRGLENCR CDVACKDRGD CCWDFEDTCV ESTRIWMCNK FRCGETRLEA SLCSCSDDCL
121 QKKDCCADYK SVCQGETSWL EENCDTAQQS QCPEGFDLPP VILFSMDGFR AEYLYTWDTL
181 MPNINKLKTC GIHSKYMRAM YPTKTFPNHY TIVTGLYPES HGIIDNNMYD VNLNKNFSLS
241 SKEQNNPAWW HGQPMWLTAM YQGLKAATYF WPGSEVAING SFPSIYMPYN GSVPFEERIS
301 TLLKWLDLPK AERPRFYTMY FEEPDSSGHA GGPVSARVIK ALQVVDHAFG MLMEGLKQRN
361 LHNCVNIILL ADHGMDQTYC NKMEYMTDYF PRINFFYMYE GPAPRIRAHN IPHDFFSFNS
421 EEIVRNLSCR KPDQHFKPYL TPDLPKRLHY AKNVRIDKVH LFVDQQWLAV RSKSNTNCGG
481 GNHGYNNEFR SMEAIFLAHG PSFKEKTEVE PFENIEVYNL MCDLLRIQPA PNNGTHGSLN
541 HLLKVPFYEP SHAEEVSKFS VCGFANPLPT ESLDCFCPHL QNSTQLEQVN QMLNLTQEEI
601 TATVKVNLPF GRPRVLQKNV DHCLLYHREY VSGFGKAMRM PMWSSYTVPQ LGDTSPLPPT
661 VPDCLRADVR VPPSESQKCS FYLADKNITH GFLYPPASNR TSDSQYDALI TSNLVPMYEE
721 FRKMWDYFHS VLLIKHATER NGVNVVSGPI FDYNYDGHFD APDEITKHLA NTDVPIPTHY
781 FVVLTSCKNK SHTPENCPGW LDVLPFIIPH RPTNVESCPE GKPEALWVEE RFTAHIARVR
841 DVELLTGLDF YQDKVQPVSE ILQLKTYLPT FETTI
```

Figure 3B. Amino acid sequence of 161P2F10B variant 1 (SEQ ID. NO. : 748). The 161P2F10B variant 1 protein has 875 amino acids.

```
  1 MESTLTLATE QPVKKNTLKK YKIACIVLLA LLVIMSLGLG LGLGLRKLEK QGSCRKKCFD
 61 ASFRGLENCR CDVACKDRGD CCWDFEDTCV ESTRIWMCNK FRCGETRLEA SLCSCSDDCL
121 QRKDCCADYK SVCQGETSWL EENCDTAQQS QCPEGFDLPP VILFSMDGFR AEYLYTWDTL
181 MPNINKLKTC GIHSKYMRAM YPTKTFPNHY TIVTGLYPES HGIIDNNMYD VNLNKNFSLS
241 SKEQNNPAWW HGQPMWLTAM YQGLKAATYF WPGSEVAING SFPSIYMPYN GSVPFEERIS
301 TLLKWLDLPK AERPRFYTMY FEEPDSSGHA GGPVSARVIK ALQVVDHAFG MLMEGLKQRN
361 LHNCVNIILL ADHGMDQTYC NKMEYMTDYF PRINFFYMYE GPAPRIRAHN IPHDFFSFNS
421 EEIVRNLSCR KPDQHFKPYL TPDLPKRLHY AKNVRIDKVH LFVDQQWLAV RSKSNTNCGG
481 GNHGYNNEFR SMEAIFLAHG PSFKEKTEVE PFENIEVYNL MCDLLRIQPA PNNGTHGSLN
541 HLLKVPFYEP SHAEEVSKFS VCGFANPLPT ESLDCFCPHL QNSTQLEQVN QMLNLTQEEI
601 TATVKVNLPF GRPRVLQKNV DHCLLYHREY VSGFGKAMRM PMWSSYTVPQ LGDTSPLPPT
661 VPDCLRADVR VPPSESQKCS FYLADKNITH GFLYPPASNR TSDSQYDALI TSNLVPMYEE
721 FRKMWDYFHS VLLIKHATER NGVNVVSGPI FDYNYDGHFD APDEITKHLA NTDVPIPTHY
781 FVVLTSCKNK SHTPENCPGW LDVLPFIIPH RPTNVESCPE GKPEALWVEE RFTAHIARVR
841 DVELLTGLDF YQDKVQPVSE ILQLKTYLPT FETTI
```

Figure 4A Amino acid alignment of 161P2F10B (SEQ. ID. No. 747) with ENPP3 (SEQ. ID. No. 765).

```
161P2F10B   mestltlateqpvkkntlkkykiacivllallvimslglg    40
ENPP3       mestltlateqpvkkntlkkykiacivllallvimslglg    40

161P2F10B   lglglrkleqgscrkkcfdaasfrglencrcdvackdrgd    80
ENPP3       lglglrklekqgscrkkcfdaasfrglencrcdvackdrgd   80

161P2F10B   ccwdfedtcvestriwmcnkfrcgetrleaslccsdddcl   120
ENPP3       ccwdfedtcvestriwmcnkfrcgetrleaslccsdddcl   120

161P2F10B   qkkdccadyksvcqgetswleencdtaggsqcpegfdlpp   160
ENPP3       qkkdccadyksvcqgetswleencdtaggsqcpegfdlpp   160

161P2F10B   vilfsmdgffraeylytwdtlmpninklktcgihskymram   200
ENPP3       vilfsmdgffraeylytwdtlmpninklktcgihskymram   200

161P2F10B   yptktfpnhytivtglypeshgiiidnnmydvnlnknfsls   240
ENPP3       yptktfpnhytivtglypeshgiiidnnmydvnlnknfsls   240

161P2F10B   skeqnnpawwhgqpmwltamyqglkaatyfwpgsevaing   280
ENPP3       skeqnnpawwhgqpmwltamyqglkaatyfwpgsevaing   280

161P2F10B   sfpsiympyngsvpfeeristilkwldlpkaerprfytmy   320
ENPP3       sfpsiympyngsvpfeeristilkwldlpkaerprfytmy   320

161P2F10B   feepdssghaggpvsarvikalqvvdhafgmlmeglkqrn   360
ENPP3       feepdssghaggpvsarvikalqvvdhafgmlmeglkqrn   360

161P2F10B   lhncvniiilladhgmdgtycnkmeymtdyfprinffymye   400
ENPP3       lhnrvniiilladhgmdgtycnkmeymtdyfprinffymye   400

161P2F10B   gpaprirahnhiphdffstnseeivrinlscrkpdqhffkpyl   440
ENPP3       gpaprirahnhiphdffstnseeivrinlscrkpdqhffkpyl   440

161P2F10B   tpdlpkkrlhyaknvridkvhlfvdqqwlavrsksntncgg   480
ENPP3       tpdlpkkrlhyaknvridkvhlfvdqqwlavrsksntncgg   480

161P2F10B   gnhgynneffrsmeaiflahgpsfkekteveffenievynl   520
ENPP3       gnhgynneffrsmeaiflahgpsfkekteveffenievynl   520

161P2F10B   mcdllriqpapnngthgslnhllkvpfyepshaeevskfs   560
```

Figure 4A-1

```
ENPP3      mcdllriqpapnngthgslnhllkvpfyepshaeevskfs              560

161P2F10B  vcgfanplptesldchrplhlqnsdcphlqnstqleqvngmhlegi          600
ENPP3      vcgfanplptesldchrplhlqnsdcphlqnstqleqvngmhleei          600

161P2F10B  tatvkvnrlpfgrpgrlpflgknvdhcllyhreyyvshrgmkamrm          640
ENPP3      tatvkvnrlpfgrpgrlpflgknvdhcllyhreyyvshrgmkamrm          640

161P2F10B  pmwssytvpqgdtspippptvpdclradvrvppseskqsgwsqkcs          680
ENPP3      pmwssytvpqgdtspippptvpdclradvrvppseskqsgwsqkcs          680

161P2F10B  fyladkniithgflyppasnrtsdsqydalltsnlvpmyevpmyee          720
ENPP3      fyladkniithgflyppasnrtsdsqydalltsnlvpmyevpmyee          720

161P2F10B  frkmwdyfhsvllikhaterngvvsgpifddynydghhfdvdghffd         760
ENPP3      frkmwdyfhsvllikhaterngvvsgpifddynydghhfdvdghffd         760

161P2F10B  apdeitkhlantdvpipthyfvvlshtpenccpgwgpgw                 800
ENPP3      apdeitkhlantdvpipthyfvvlshtpenccpgwgpgw                 800

161P2F10B  ldvlpfiiphrptnvescpegkpealwveerffttahiaarvr             840
ENPP3      ldvlpfiiphrptnvescpegkpealwveerffttahiaarvr             840

161P2F10B  dvellltgldfyqddkvqppvseeilqlqlktyylpteffettii           875
ENPP3      dvellltgldfyqddkvqppvseeilqlqlktyylpteffettii           875
```

Figure 4A-2

Figure 4B  Amino acid alignment of 161P2F10B (SEQ. ID. No. 747) with 161P2F10B variant 1 (SEQ. ID. No. 748).

Figure 4B-1

```
161P2F10B variant 1   mcdllriqpapnngthgslnhllkvpfyepshaeevskfs    560

161P2F10B           vcgffanplptesldcfcphlgnstgleqvngmlnltqeei    600
161P2F10B variant 1   vcgffanplptesldcfcphlgnstgleqvngmlnltqeei    600

161P2F10B           tatvkvnlpfgrprvlqknvdhcllyhreyvsgfgkamrm    640
161P2F10B variant 1   tatvkvnlpfgrprvlqknvdhcllyhreyvsgfgkamrm    640

161P2F10B           pmwssytvpqlgdtsplpptvpdclrradvrvppsesqkcs    680
161P2F10B variant 1   pmwssytvpqlgdtsplpptvpdclrradvrvppsesqkcs    680

161P2F10B           fyladknithgflyppasnrtsdsqydalitsnlvpmyee    720
161P2F10B variant 1   fyladknithgflyppasnrtsdsqydalitsnlvpmyee    720

161P2F10B           frkmwdyfhsvllikhaterngvnvvsgpifdynydghfd    760
161P2F10B variant 1   frkmwdyfhsvllikhaterngvnvvsgpifdynydghfd    760

161P2F10B           apdeitkhlantdvpiptchyfvvltscknkshtpencpgw    800
161P2F10B variant 1   apdeitkhlantdvpiptchyfvvltscknkshtpencpgw    800

161P2F10B           ldvlpffiiphrptnvescpegkpealwveerfftahiarvr    840
161P2F10B variant 1   ldvlpffiiphrptnvescpegkpealwveerfftahiarvr    840

161P2F10B           dvellltgldfyqddkvqpvseilqlktylptfetti    875
161P2F10B variant 1   dvellltgldfyqddkvqpvseilqlktylptfetti    875
```

Figure 4B-2

Figure 4C Alignment of 161P2F10B (SEQ. ID. No. 749) and SNP variant 2 (SEQ. ID. No. 750) carrying a T to P mutation at position 874.

```
Query: 492
MEAIFLAHGPSFKEKTEVEPFENIEVYNLMCDLLRIQPAPNNGTHGSLNHLLKVPFYEPS 551

MEAIFLAHGPSFKEKTEVEPFENIEVYNLMCDLLRIQPAPNNGTHGSLNHLLKVPFYEPS
Sbjct: 1
MEAIFLAHGPSFKEKTEVEPFENIEVYNLMCDLLRIQPAPNNGTHGSLNHLLKVPFYEPS 60
Query: 552
HAEEVSKFSVCGFANPLPTESLDCFCPHLQNSTQLEQVNQMLNLTQEEITATVKVNLPFG 611

HAEEVSKFSVCGFANPLPTESLDCFCPHLQNSTQLEQVNQMLNLTQEEITATVKVNLPFG
Sbjct: 61
HAEEVSKFSVCGFANPLPTESLDCFCPHLQNSTQLEQVNQMLNLTQEEITATVKVNLPFG 120
Query: 612
RPRVLQKNVDHCLLYHREYVSGFGKAMRMPMWSSYTVPQLGDTSPLPPTVPDCLRADVRV
671

RPRVLQKNVDHCLLYHREYVSGFGKAMRMPMWSSYTVPQLGDTSPLPPTVPDCLRADVRV
Sbjct: 121
RPRVLQKNVDHCLLYHREYVSGFGKAMRMPMWSSYTVPQLGDTSPLPPTVPDCLRADVRV 180
Query: 672
PPSESQKCSFYLADKNITHGFLYPPASNRTSDSQYDALITSNLVPMYEEFRKMWDYFHSV 731

PPSESQKCSFYLADKNITHGFLYPPASNRTSDSQYDALITSNLVPMYEEFRKMWDYFHSV
Sbjct: 181
PPSESQKCSFYLADKNITHGFLYPPASNRTSDSQYDALITSNLVPMYEEFRKMWDYFHSV 240
Query: 732
LLIKHATERNGVNVVSGPIFDYNYDGHFDAPDEITKHLANTDVPIPTHYFVVLTSCKNKS 791

LLIKHATERNGVNVVSGPIFDYNYDGHFDAPDEITKHLANTDVPIPTHYFVVLTSCKNKS
Sbjct: 241
LLIKHATERNGVNVVSGPIFDYNYDGHFDAPDEITKHLANTDVPIPTHYFVVLTSCKNKS 300
Query: 792
HTPENCPGWLDVLPFIIPHRPTNVESCPEGKPEALWVEERFTAHIARVRDVELLTGLDFY 851

HTPENCPGWLDVLPFIIPHRPTNVESCPEGKPEALWVEERFTAHIARVRDVELLTGLDFY
Sbjct: 301
HTPENCPGWLDVLPFIIPHRPTNVESCPEGKPEALWVEERFTAHIARVRDVELLTGLDFY 360
Query: 852  QDKVQPVSEILQLKTYLPTFETTI 875
             QDKVQPVSEILQLKTYLPTFET I
Sbjct: 361  QDKVQPVSEILQLKTYLPTFETPI 384
```

Figure 5: 161P2F10B Hydrophilicity profile
(Hopp T.P., Woods K.R., 1981. Proc. Natl. Acad. Sci. U.S.A. 78:3824-3828)
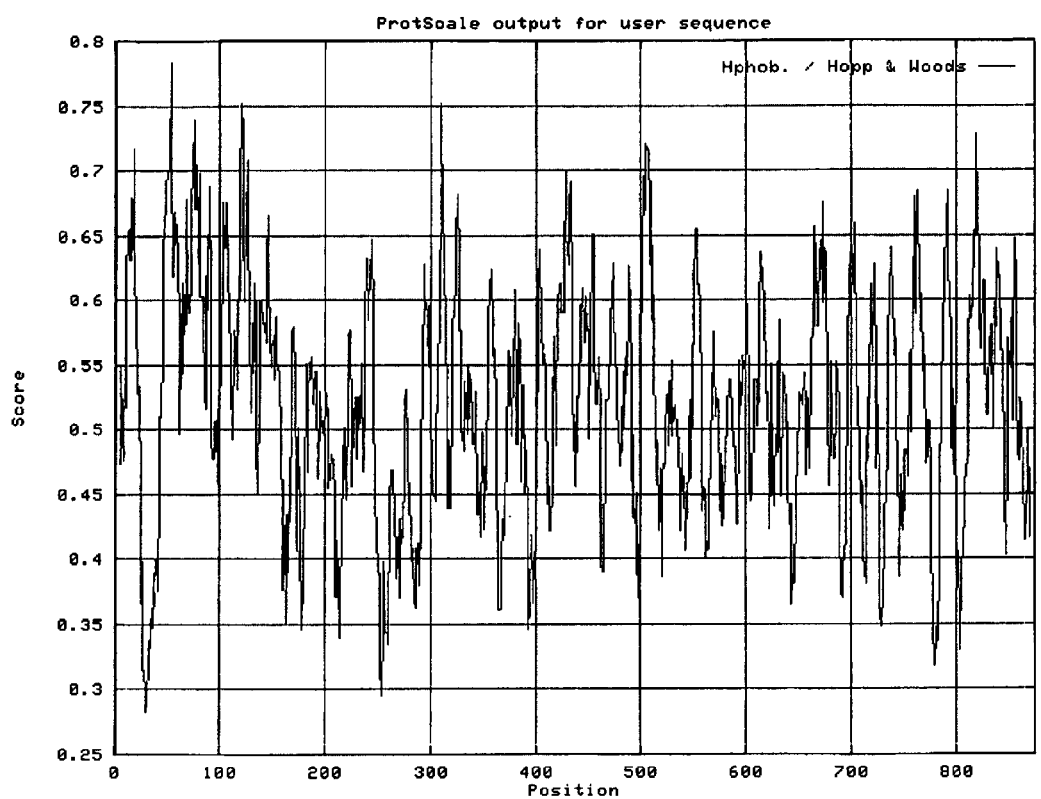

Figure 6: 161P2F10B Hydropathicity Profile
(Kyte J., Doolittle R.F., 1982. J. Mol. Biol. 157:105-132)
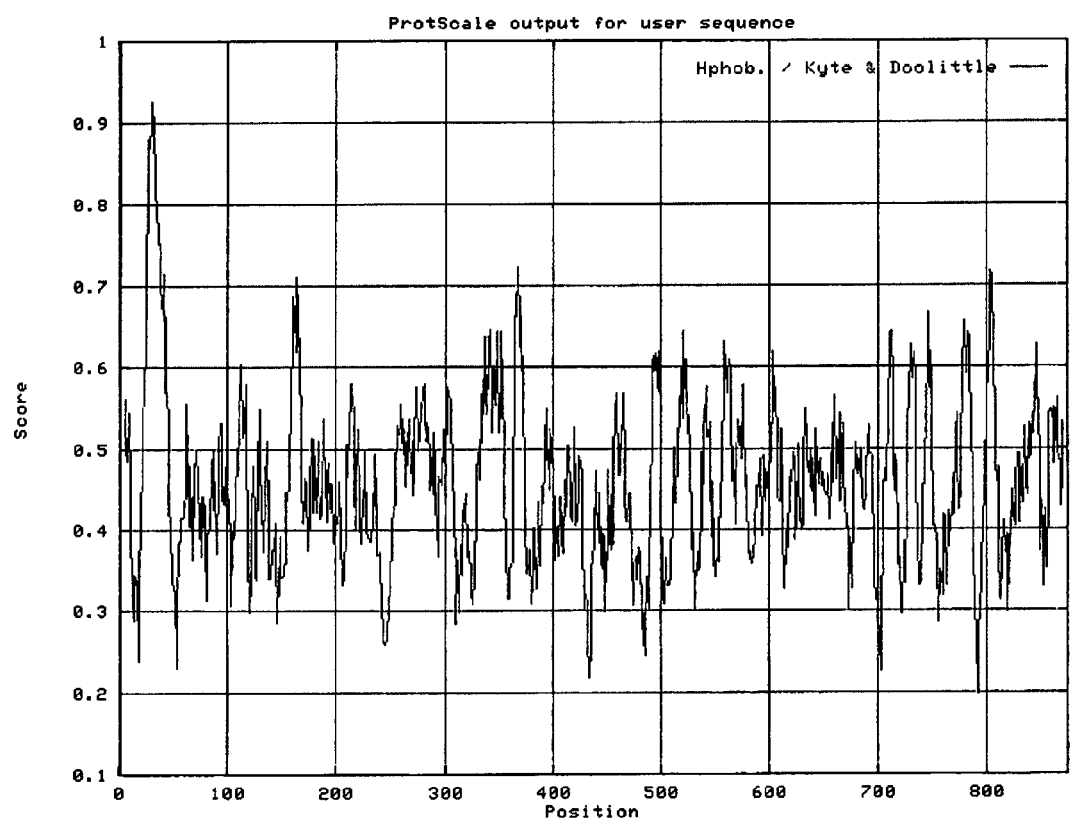

Figure 7: 161P2F10B % Accessible Residues Profile
(Janin J., 1979. Nature 277:491-492)
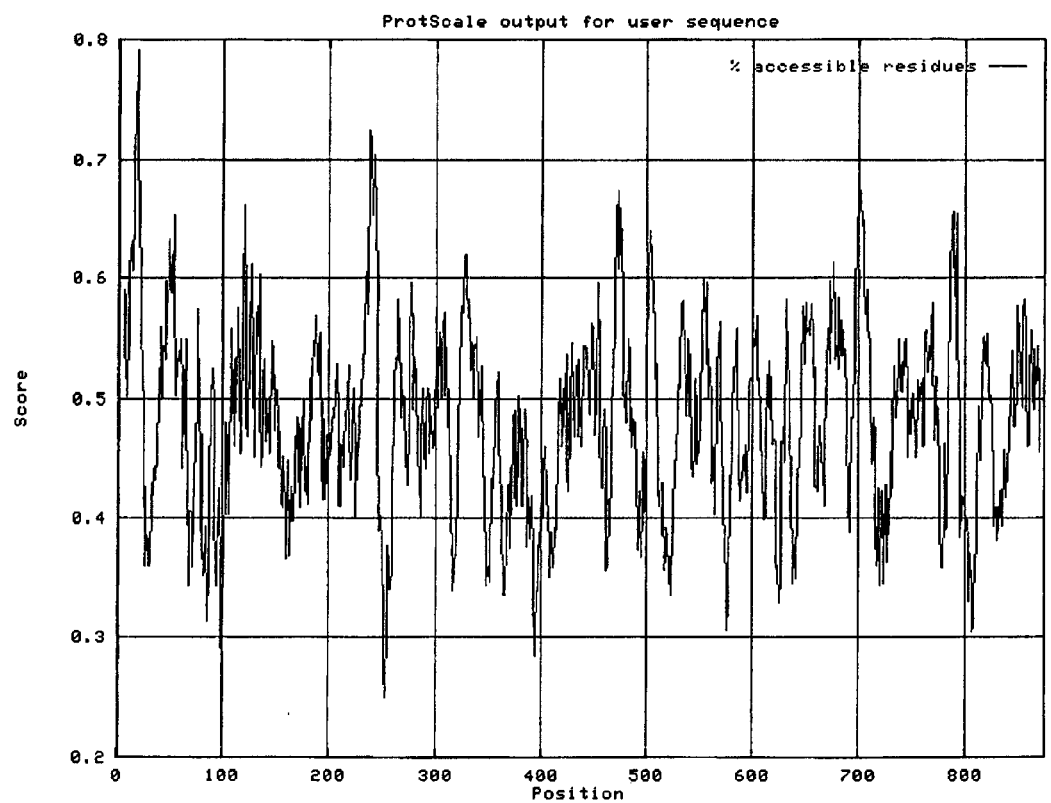

Figure 8: 161P2F10B Average Flexibility Profile
(Bhaskaran R., Ponnuswamy P.K., 1988.
Int. J. Pept. Protein Res. 32:242-255)
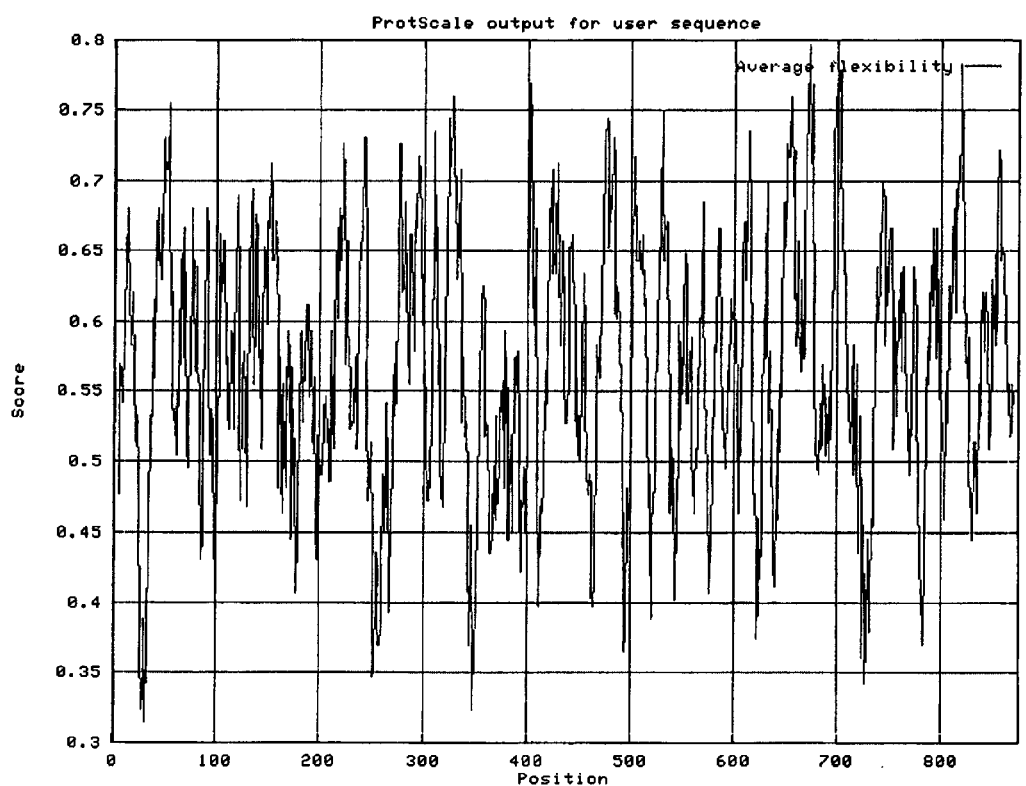

Figure 9: 161P2F10B Beta-turn Profile
(Deleage, G., Roux B. 1987. Protein Engineering 1:289-294)
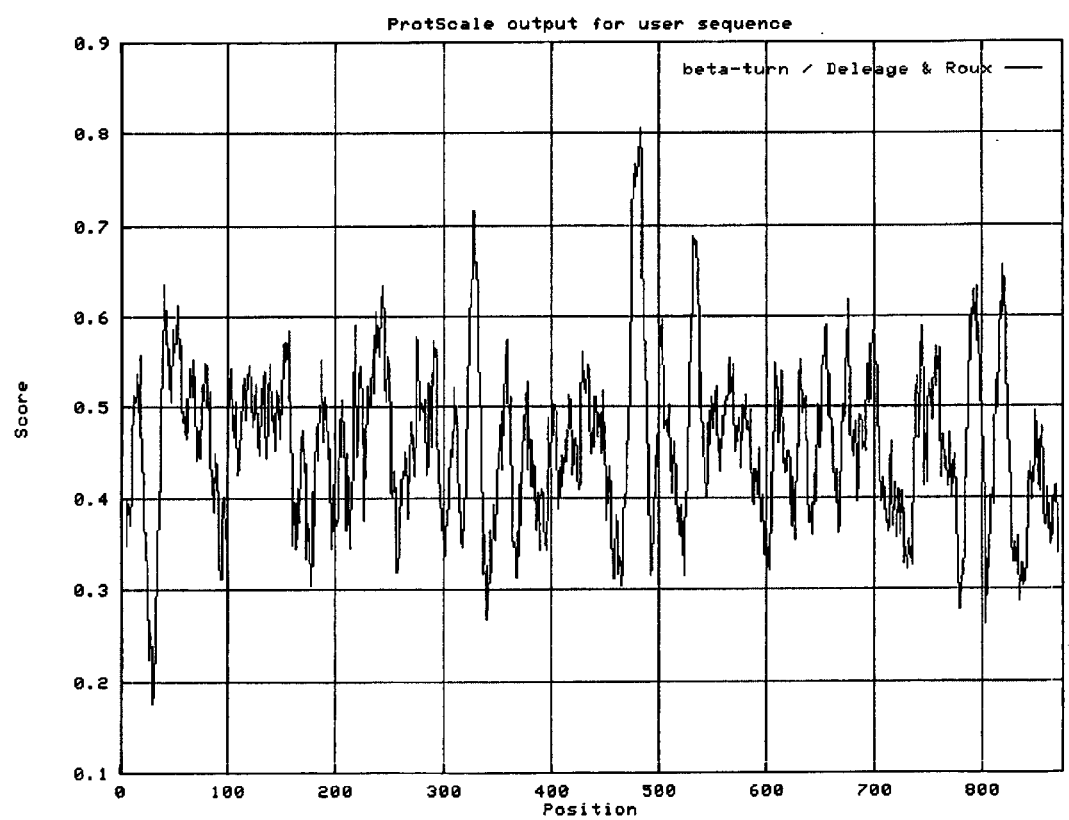

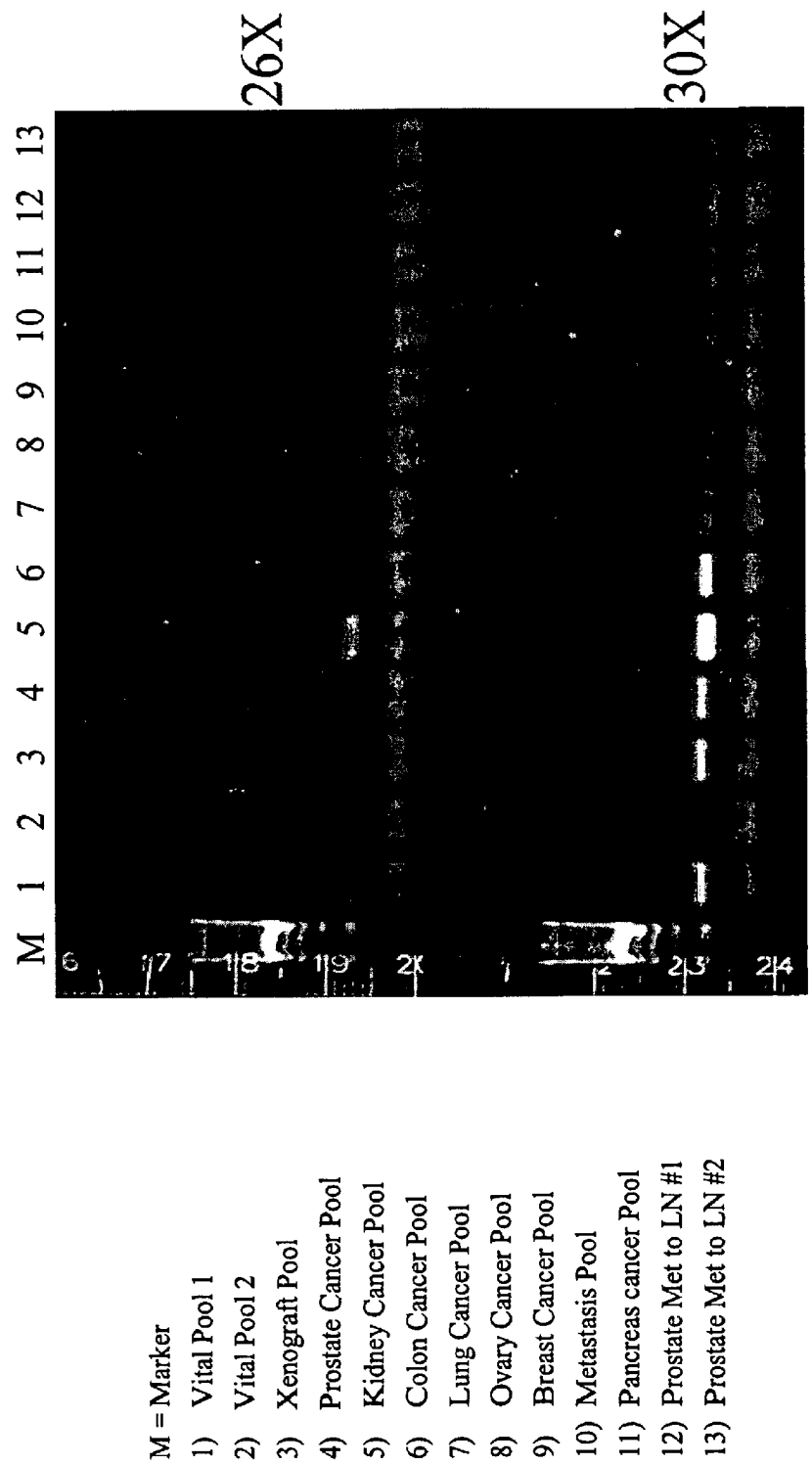
Figure 10: Expression of 161P2F10B by RT-PCR

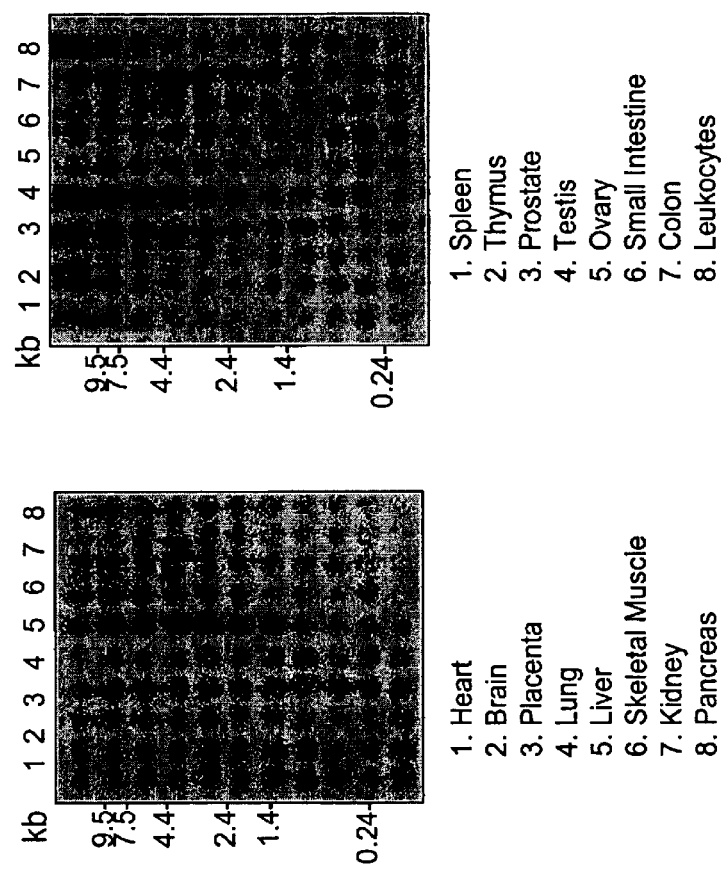
Figure 11: Expression of 161P2F10B in Normal Tissues

Figure 12: Expression of 161P2F10B in Patient Kidney Cancer Specimens and in Normal Tissues
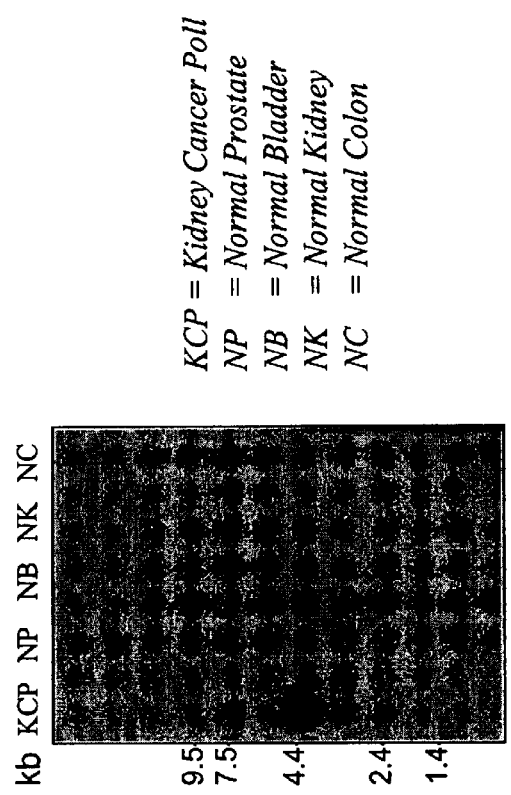

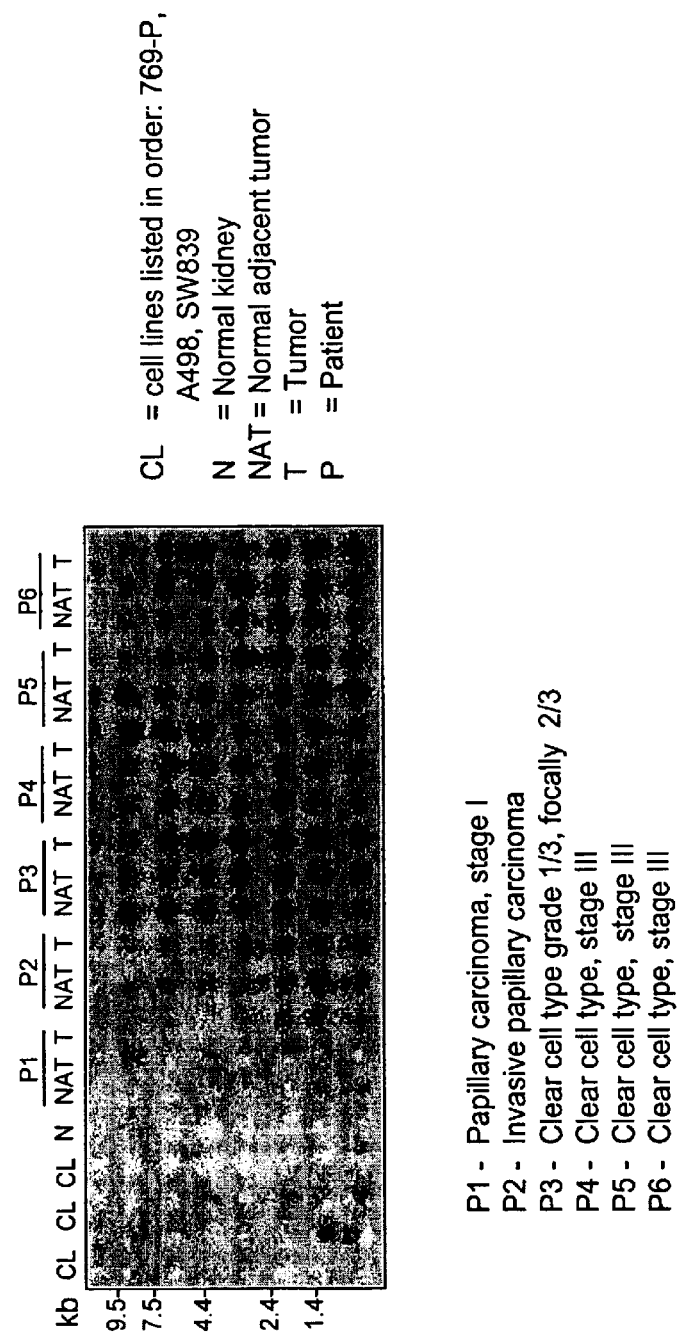
Figure 13: Expression of 161P2F10B in Kidney Cancer Patient Specimens

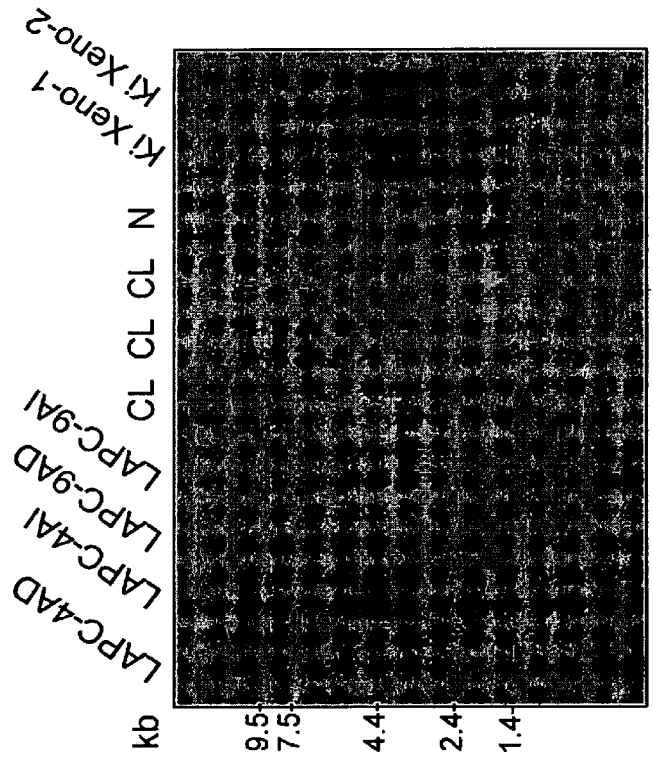
Figure 14: Expression of 161P2F10B in Kidney Cancer Xenografts

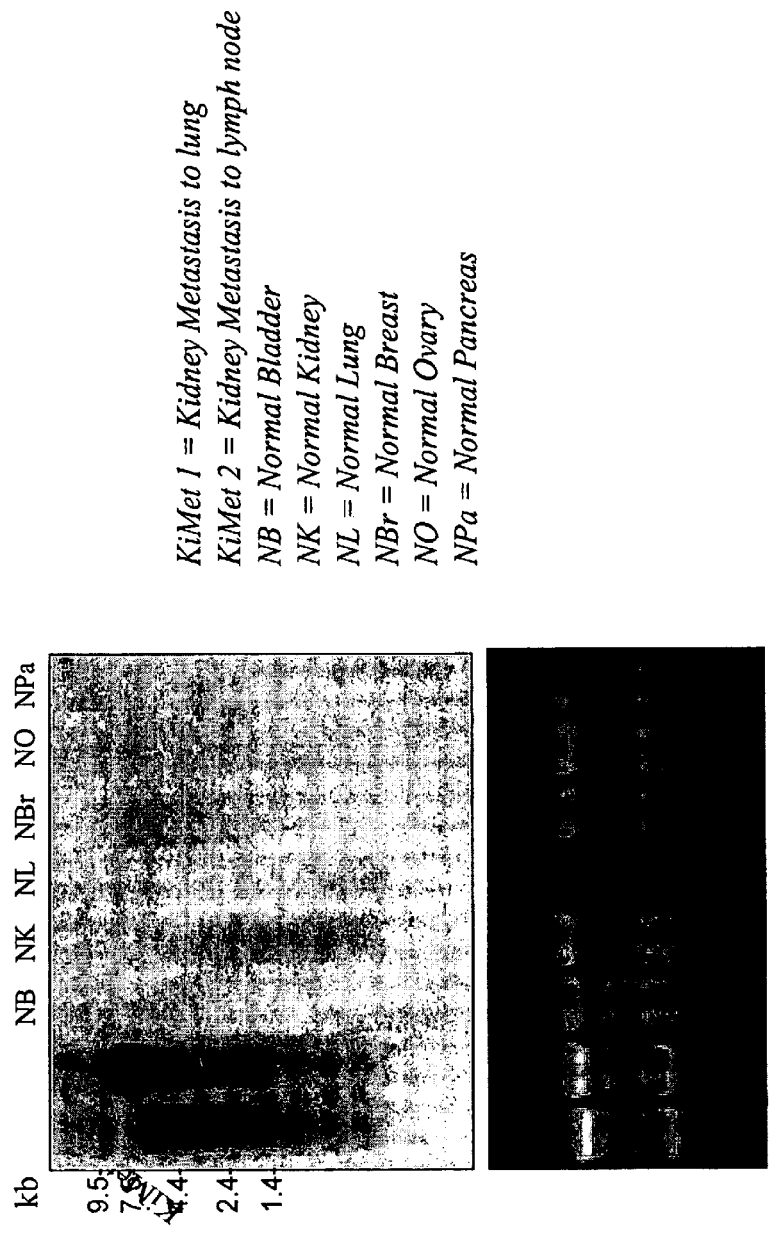
Figure 15: Expression of 161P2F10B in Kidney Cancer Metastasis Specimens and in Normal Tissues
KiMet 1 = Kidney Metastasis to lung
KiMet 2 = Kidney Metastasis to lymph node
NB = Normal Bladder
NK = Normal Kidney
NL = Normal Lung
NBr = Normal Breast
NO = Normal Ovary
NPa = Normal Pancreas

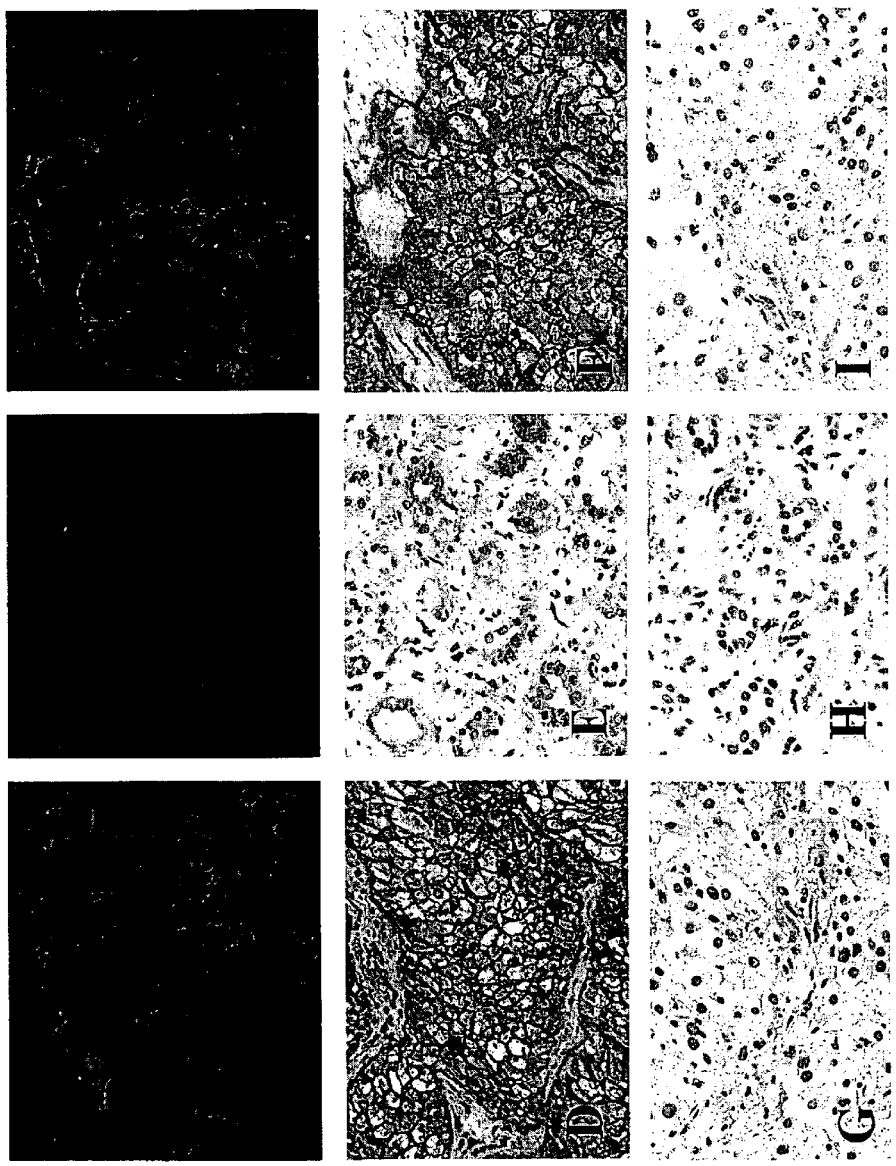
Figure 16: Expression of 161P2F10B Protein by Immunohistochemistry in Kidney Cancer Patient Specimens

Figure 17: Expression of 161P2F10B Protein on the Cell Surface of Renal Cell Carcinoma Xenografts
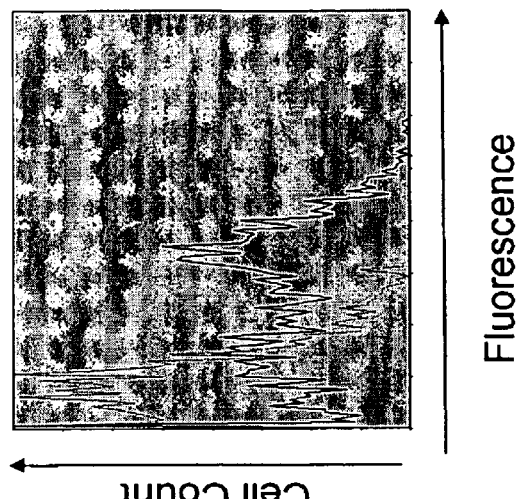
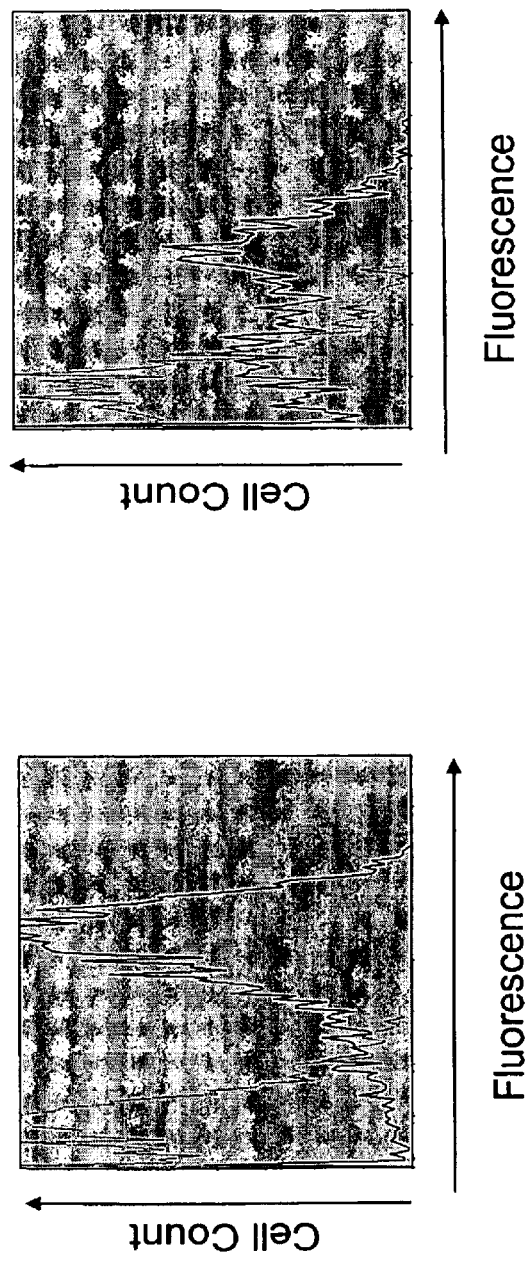
A. Clear Cell Carcinoma
B. Renal Cancer Metastasis to LN

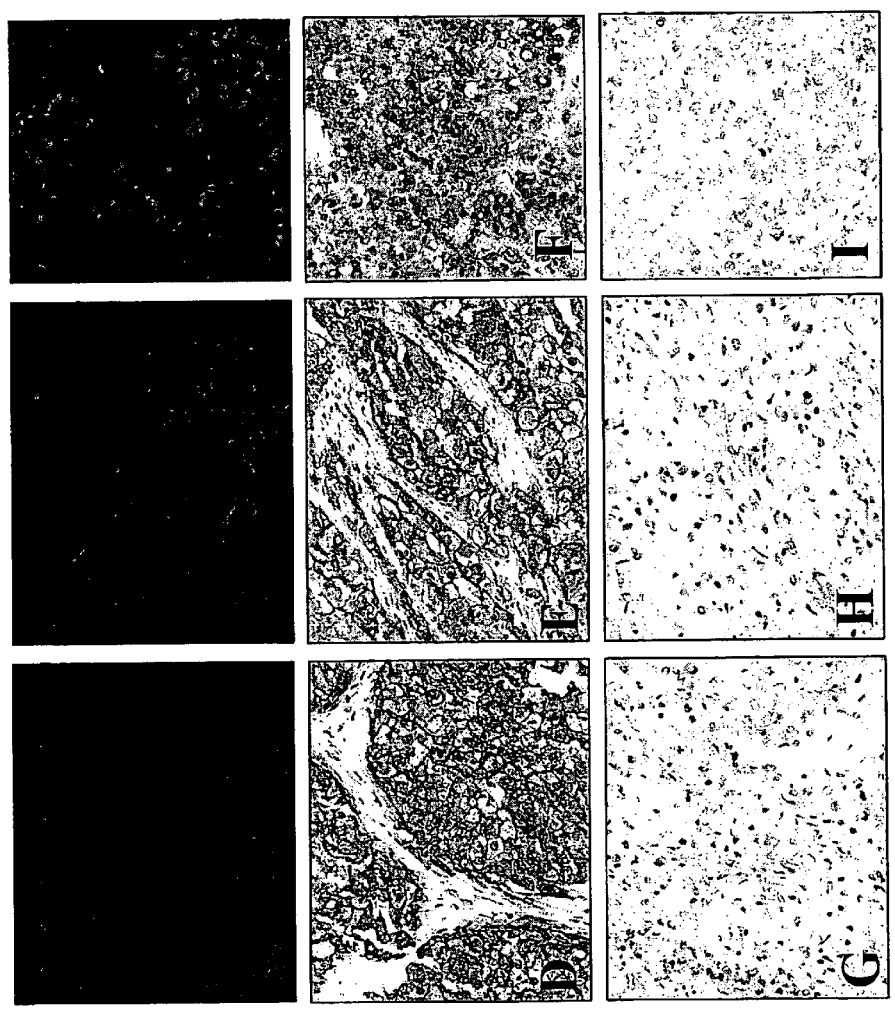
Figure 18: Expression of 161P2F10B Protein by Immunohistochemistry in Human Cancer Xenograft Tissues

Figure 19A (Seq. ID. No. 751)

```
            10         20         30         40         50         60         70
            |          |          |          |          |          |          |
MESTLTLATEQPVKKNTLKKYKIACIVLLALLVIMSLGLGLGLGLRKLEKQGSCRKKCFDASFRGLENCR
cccceeeeecccccccchhhhhhhhhhhhhhhhhhhhhchhhhhhhhhhhccccccccccccccchhcccc
CDVACKDRGDCCWDFEDTCVESTRIWMCNKFRCGETRLEASLCSCSDDCLQKKDCCADYKSVCQGETSWL
cccccccccccccccccchhhhhehhhhhccccccceeechccccccccccccccccccccccccccch
EENCDTAQQSQCPEGFDLPPVILFSMDGFRAEYLYTWDTLMPNINKLKTCGIHSKYMRAMYPTKTFPNHY
ccccccccccccccccccceeeeeccccchhhhhhhhhhhchhhhccccchhhhheeccccccccccce
TIVTGLYPESHGIIDNNMYDVNLNKNFSLSSKEQNNPAWWHGQPMWLTAMYQGLKAATYFWPGSEVAING
eeeeeccccccchhccccccccccceeeccccccccccccchhhhhhhhhcccceeeeccccceeeecc
SFPSIYMPYNGSVPFEERISTLLKWLDLPKAERPRFYTMYFEEPDSSGHAGGPVSARVIKALQVVDHAFG
cccceeeccccccchhhhhhhhhhhhcccccccceeeeeccccccccccchhhhhhhhhhhhhhhhhh
MLMEGLKQRNLHNCVNIILLADHGMDQTYCNKMEYMTDYFPRINFFYMYEGPAPRIRAHNIPHDFFSFNS
hhhhhhhhhhccccceeeeeeccccccccccchhhhhhhcceeeeeecccccccccccccccchhhcch
EEIVRNLSCRKPDQHFKPYLTPDLPKRLHYAKNVRIDKVHLFVDQQWLAVRSKSNTNCGGGNHGYNNEFR
hhhhhhhccccccccccccccccchhhhhccccchhhhhhhhheeeecccccccccccccccchhhh
SMEAIFLAHGPSFKEKTEVEPFENIEVYNLMCDLLRIQPAPNNGTHGSLNHLLKVPFYEPSHAEEVSKFS
hhhhhhhhcccccccccccchhhhhhhhhhhcccccccccccchheecccccccccchccee
VCGFANPLPTESLDCFCPHLQNSTQLEQVNQMLNLTQEEITATVKVNLPFGRPRVLQKNVDHCLLYHREY
eecccccccccchhccccccchhhhhhhhhhchhhhheeeecccccccehcccccceeeehhhh
VSGFGKAMRMPMWSSYTVPQLGDTSPLPPTVPDCLRADVRVPPSESQKCSFYLADKNITHGFLYPPASNR
hhcccccceeeccccccccccccccccccccccccccceeeecccccccccccccccc
TSDSQYDALITSNLVPMYEEFRKMWDYFHSVLLIKHATERNGVNVVSGPIFDYNYDGHFDAPDEITKHLA
ccchhhhhhhhccccchhhhhhhhhhhhhhhhhehhcccccceeeccccccccccchhhhhhhhcc
NTDVPIPTHYFVVLTSCKNKSHTPENCPGWLDVLPFIIPHRPTNVESCPEGKPEALWVEERFTAHIARVR
cccccccceeeeeeeccccccccccccccccceeeeccccccccccccchhhhhhhhhhhhhhhh
DVELLTGLDFYQDKVQPVSEILQLKTYLPTFETTI
hheehcccccchcchhchhhhehhhhcccccccc
``` c: random coil (31.31%)
e: extended strand (11.31%)
h: alpha helix (57.37%)

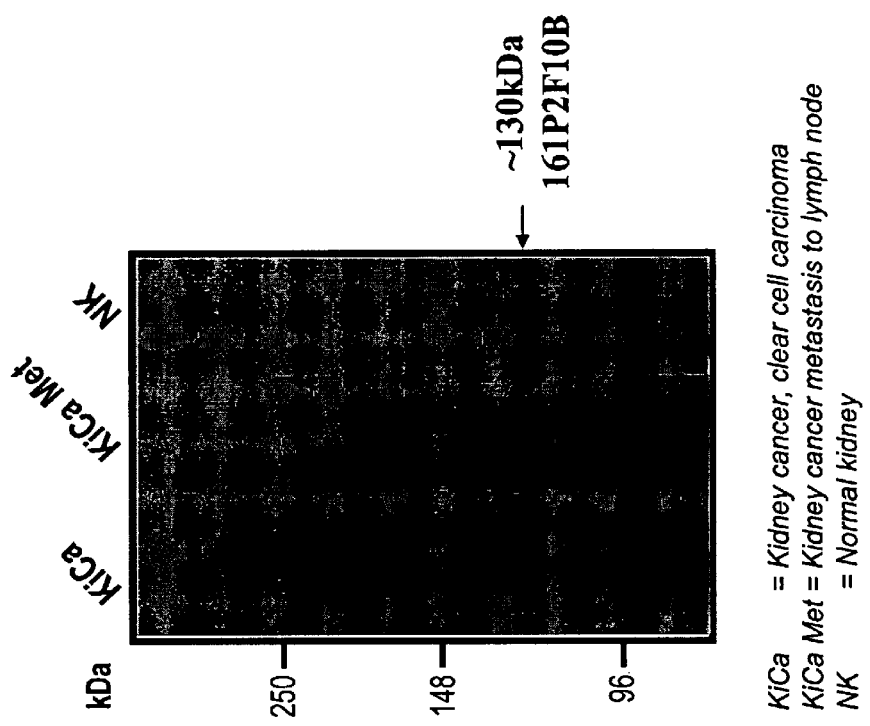
Figure 20 Expression of 161P2F10B in Human Patient Cancers by Western Blot

Figure 21 Expression of 161P2F10B in Human Xenograft Tissues by Western Blot
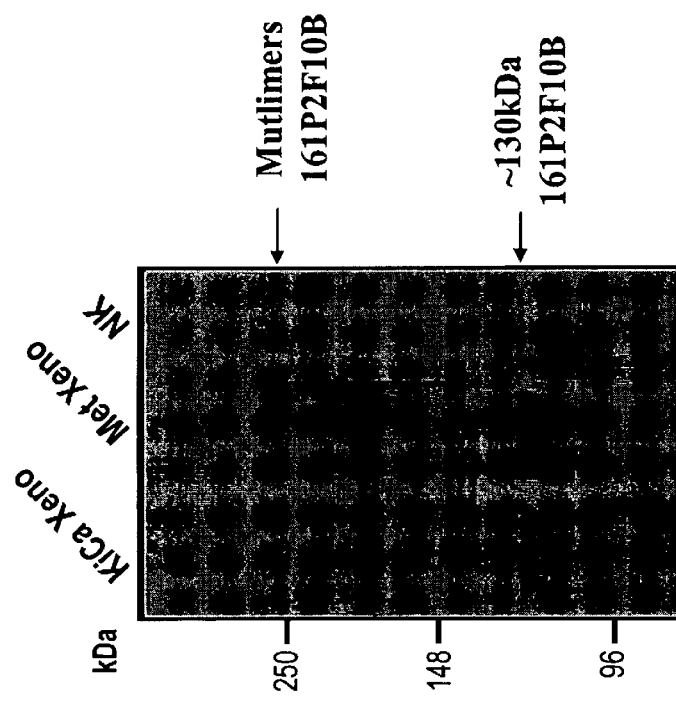
KiCa Xeno = Xenograft of kidney cancer, clear cell carcinoma
Met Xeno = Xenograft from Kidney cancer metastasis to lymph node
NK = Normal kidney ered pages.

NUCLEIC ACID AND CORRESPONDING PROTEIN ENTITLED 161P2F10B USEFUL IN TREATMENT AND DETECTION OF CANCER

This application is a divisional of U.S. Ser. No. 10/005,480 filed 7 Nov. 2001, now abandoned. The contents of this application are incorporated herein by reference.

FIELD OF THE INVENTION

The invention described herein relates to a gene and its encoded protein, termed 161P2F10B, expressed in certain cancers, and to diagnostic and therapeutic methods and compositions useful in the management of cancers that express 161P2F10B.

SUBMISSION ON COMPACT DISC

The contents of the following submission on compact discs are incorporated herein by reference in its entirety. A compact disc copy of the Sequence Listing (COPY 1) (file name: 5115820062.txt, date recorded: May 16, 2002, size: 166 KB); a duplicate compact disc copy of Sequence Listing (COPY 2) (file name: 5115820062.txt, date recorded: May 16, 2002, size: 166 KB); a computer readable form copy of the Sequence Listing (C.R.F. COPY) (file name: 5115820062.txt, date recorded: May 16, 2002, size: 166 KB).

BACKGROUND OF THE INVENTION

Cancer is the second leading cause of human death next to coronary disease. Worldwide, millions of people die from cancer every year. In the United States alone, as reported by the American Cancer Society, cancer causes the death of well over a half-million people annually, with over 1.2 million new cases diagnosed per year. While deaths from heart disease have been declining significantly, those resulting from cancer generally are on the rise. In the early part of the next century, cancer is predicted to become the leading cause of death.

Worldwide, several cancers stand out as the leading killers. In particular, carcinomas of the lung, prostate, breast, colon, pancreas, and ovary represent the primary causes of cancer death. These and virtually all other cancinomas share a common lethal feature. With very few exceptions, metastatic disease from a carcinoma is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients experience physical debilitations following treatment. Furthermore, many cancer patients experience a recurrence.

Worldwide, prostate cancer is the fourth most prevalent cancer in men. In North America and Northern Europe, it is by far the most common cancer in males and is the second leading cause of cancer death in men. In the United States alone, well over 30,000 men die annually of this disease—second only to lung cancer. Despite the magnitude of these figures, there is still no effective treatment for metastatic prostate cancer. Surgical prostatectomy, radiation therapy, hormone ablation therapy, surgical castration and chemotherapy continue to be the main treatment modalities. Unfortunately, these treatments are ineffective for many and are often associated with undesirable consequences.

On the diagnostic front, the lack of a prostate tumor marker that can accurately detect early-stage, localized tumors remains a significant limitation in the diagnostic and management of this disease. Although the serum prostate specific antigen (PSA) assay has been a very useful tool, however its specificity and general utility is widely regarded as lacking in several important respects.

Progress in identifying additional specific markers for prostate cancer has been improved by the generation of prostate cancer xenografts that can recapitulate different stages of the disease in mice. The LAPC (Los Angeles Prostate Cancer) xenografts are prostate cancer xenografts that have survived passage in severe combined immune deficient (SCID) mice and have exhibited the capacity to mimic the transition from androgen dependence to androgen independence (Klein et al., 1997, Nat. Med. 3:402). More recently identified prostate cancer markers include PCTA-1 (Su et al., 1996, Proc. Natl. Acad. Sci. USA 93: 7252), prostate-specific membrane (PSM) antigen (Pinto et al., Clin Cancer Res 1996 Sep. 2 (9): 1445–51), STEAP (Hubert, et al., Proc Natl Acad Sci U S A, 1999 Dec. 7; 96(25): 14523–8) and prostate stem cell antigen (PSCA) (Reiter et al., 1998, Proc. Natl. Acad. Sci. USA 95: 1735).

While previously identified markers such as PSA, PSM, PCTA and PSCA have facilitated efforts to diagnose and treat prostate cancer, there is need for the identification of additional markers and therapeutic targets for prostate and related cancers in order to further improve diagnosis and therapy.

Renal cell carcinoma (RCC) accounts for approximately 3 percent of adult malignancies. Once adenomas reach a diameter of 2 to 3 cm, malignant potential exists. In the adult, the two principal malignant renal tumors are renal cell adenocarcinoma and transitional cell carcinoma of the renal pelvis or ureter. The incidence of renal cell adenocarcinoma is estimated at more than 29,000 cases in the United States, and more than 11,600 patients died of this disease in 1998. Transitional cell carcinoma is less frequent, with an incidence of approximately 500 cases per year in the United States.

Surgery has been the primary therapy for renal cell adenocarcinoma for many decades. Until recently, metastatic disease has been refractory to any systemic therapy. With recent developments in systematic therapies, particularly immunotherapies, metastatic renal cell carcinoma may be approached aggressively in appropriate patients with a possibility of durable responses. Nevertheless, there is a remaining need for effective therapies for these patients.

Of all new cases of cancer in the United States, bladder cancer represents approximately 5 percent in men (fifth most common neoplasm) and 3 percent in women (eighth most common neoplasm). The incidence is increasingly slowly, concurrent with an increasing older population. In 1998, there was an estimated 54,500 cases, including 39,500 in men and 15,000 in women. The age-adjusted incidence in the United States is 32 per 100,000 for men and 8 per 100,000 in women. The historic male/female ratio of 3:1 may be decreasing related to smoking patterns in women. There were an estimated 11,000 deaths from bladder cancer in 1998 (7,800 in men and 3,900 in women). Bladder cancer incidence and mortality strongly increases with age and will be an increasing problem as the population becomes more elderly.

Most bladder cancers recur in the bladder. Bladder cancer is managed with a combination of transurethral resection of the bladder (TUR) and intravesical chemotherapy or immunotherapy. The multifocal and recurrent nature of bladder cancer points out the limitations of TUR. Most muscle-invasive cancers are not cured by TUR alone. Radical cystectomy and urinary diversion is the most effective means to eliminate the cancer but carry an undeniable impact on urinary and sexual function. There continues to be a significant need for treatment modalities that are beneficial for bladder cancer patients.

An estimated 130,200 cases of colorectal cancer occurred in 2000 in the United States, including 93,800 cases of colon cancer and 36,400 of rectal cancer. Colorectal cancers are the third most common cancers in men and women. Incidence rates declined significantly during 1992–1996 (−2.1% per year). Research suggests that these declines have been due to increased screening and polyp removal, preventing progression of polyps to invasive cancers. There were an estimated 56,300 deaths (47,700 from colon cancer, 8,600 from rectal cancer) in 2000, accounting for about 11% of all U.S. cancer deaths.

At present, surgery is the most common form of therapy for colorectal cancer, and for cancers that have not spread, it is frequently curative. Chemotherapy, or chmeotherapy plus radiation, is given before or after surgery to most patients whose cancer has deeply perforated the bowel wall or has spread to the lymph nodes. A permanent colostomy (creation of an abdominal opening for elimination of body wastes) is occasionally needed for colon cancer and is infrequently required for rectal cancer. These continues to be a need for effective diagnostic and treatment modalities for colorectal cancer.

There were an estimated 164,100 new cases of lung and bronchial cancer in 2000, according for 14% of all U.S. cancer diagnoses. The incidence rate of lung and bronchial cancer is declining significantly in men, from a high of 86.5 per 100,000 in 1984 to 70.0 in 1996. In the 1990s, the rate of increase among women began to slow. In 1996, the incidence rate in women was 42.3 per 100,000.

Lung and bronchial cancer caused an estimated 156,900 deaths in 2000, accounting for 28% of all cancer deaths. During 1992–1996, mortality from lung cancer declined significantly among men (−1.7% per year) while rates for women were still significantly increasing (0.9% per year). Since 1987, more women have died each year of lung cancer than breast cancer, which, for over 40 years, was the major cause of cancer death in women. Decreasing lung cancer incidence and mortality rates most likely resulted from decreased smoking rates over the previous 30 years; however, decreasing smoking patterns among women lag behind those of men. Of concern, although the declines in adult tobacco use have slowed, tobacco use in youth is increasing again.

Treatment options for lung and bronchial cancer are determined by the type and stage of the cancer and include surgery, radiation therapy, and chemotherapy. For many localized cancers, surgery is usually the treatment of choice. Because the disease has usually spread by the time it is discovered, radiation therapy and chemotherapy are often needed in combination with surgery. Chemotherapy alone or combined with radiation is the treatment of choice for small cell lung cancer; on this regimen, a large percentage of patients experience remission, which in some cases is long lasting. There is however, an ongoing need for effective treatment and diagnostic approaches for lung and bronchial cancers.

An estimated 182,800 new invasive cases of breast cancer were expected to occur among women in the United States during 2000. Additionally, about 1,400 new cases of breast cancer were expected to be diagnosed in men in 2000. After increasing about 4% per year in the 1980s, breast cancer incidence rates in women have leveled off in the 1990s to about 110.6 cases per 100,000.

In the U.S. alone, there were an estimated 41,200 deaths (40,800 women, 400 men) in 2000 due to breast cancer. Breast cancer ranks second among cancer deaths in women. According to the most recent data, mortality rates declined significantly during 1992–1996 with the largest decreases in younger women, both white and black. These decreases were probably the result of earlier detection and improved treatment.

Taking into account the medical circumstances and the patient's preferences, treatment of breast cancer may involve lumpectomy (local removal of the tumor) and removal of the lymph nodes under the arm; mastectomy (surgical removal of the breast) and removal of the lymph nodes under the arm; radiation therapy; chemotherapy; or hormone therapy. Often, two or more methods are used in combination. Numerous studies have shown that, for early stage disease, long-term survival rates after lumpectomy plus radiotherapy are similar to survival rates after modified radical mastectomy. Significant advances in reconstruction techniques provide several options for breast reconstruction after mastectomy. Recently, such reconstruction has been done at the same time as the mastectomy.

Local excision of ductal carcinoma in situ (DCIS) with adequate amounts of surrounding normal breast tissue may prevent the local recurrence of the DCIS. Radiation to the breast and/or tamoxifen may reduce the chance of DCIS occurring in the remaining breast tissue. This is important because DCIS, if left untreated, may develop into invasive breast cancer. Nevertheless, there are serious side effects or sequelae to these treatments. There is, therefore, a need for efficacious breast cancer treatments.

There were an estimated 23,100 new cases of ovarian cancer in the United States in 2000. It accounts for 4% of all cancers among women and ranks second among gynecologic cancers. During 1992–1996, ovarian cancer incidence rates were significantly declining. Consequent to ovarian cancer, there were an estimated 14,000 deaths in 2000. Ovarian cancer causes more deaths than any other cancer of the female reproductive system.

Surgery, radiation therapy, and chemotherapy are treatment options for ovarian cancer. Surgery usually includes the removal of one or both ovaries, the fallopian tubes (salpingo-oophorectomy), and the uterus (hysterectomy). In some very early tumors, only the involved ovary will be removed, especially in young women who wish to have children. In advanced disease, an attempt is made to removal all intra-abdominal disease to enhance the effect of chemotherapy. There continues to be an important need for effective treatment options for ovarian cancer.

There were an estimated 28,300 new cases of pancreatic cancer in the United States in 2000. Over the past 20 years, rates of pancreatic cancer have declined in men. Rates among women have remained approximately constant but may be beginning to decline. Pancreatic cancer caused an estimated 28,200 deaths in 2000 in the United States. Over the past 20 years, there has been a slight but significant decrease in mortality rates among men (about −0.9% per year) while rates have increased slightly among women.

Surgery, radiation therapy, and chemotherapy are treatment options for pancreatic cancer. These treatment options can extend survival and/or relieve symptoms in many patients but are not likely to produce a cure for most. There is a significant need for additional therapeutic and diagnostic options for pancreatic cancer.

As will be discussed in detail below, the gene and corresponding protein referred to as 161P2F10B is identical to ENPP3 phosphodiesterase (also called CD203c or PD-1 beta). ENPP3 is an ecto-enzyme belonging to a family of ectonucleotide phosphodiesterases and pyrophosphatases. ENPP3 is a phosphodiesterase I ecto-enzyme. It is expressed in normal prostate and uterus, as well as on basophils and mast cells. Expression on the hematopoietic cells is upregulated in presence of allergen or by cross-linking with IgE (Buring et al., 1999, Blood 94: 2343). Members of the ENPP family possess ATPase and ATP pyrophosphatase activities. They hydrolyze extracellular nucleotides, nucleoside phosphates, and NAD. They are involved in extracellular nucleotide metabolism, nucleotide signaling, and recycling of extracellular nucleotides. They are also involved in cell-cell and cell-matrix interactions. ENPP enzymes differ in their substrate specificity and tissue distribution. ENPP enzymes also play a role in recycling extracellular nucleotides. It has been demonstrated that ENPP1 allows activated T-cells to use NAD+ from dying cells as a source of adenosine. ENPP3 expressed in the intestine may also be involved in the hydrolysis of nucleotides derived from food (Byrd et al 1985, Scott et al. 1997).

SUMMARY OF THE INVENTION

The present invention relates to a gene, designated 161P2F10B, that has now been found to be over-expressed in the cancer(s) listed in Table I. Northern blot expression analysis of 161P2F10B gene expression in normal tissues shows a restricted expression pattern in adult tissues. The nucleotide (FIG. 2) and amino acid (FIG. 2, and FIG. 3) sequences of 161P2F10B are provided. The tissue-related profile of 161P2F10B in normal adult tissues, combined with the over-expression observed in the tumors listed in Table I, shows that 161P2F10B is aberrantly over-expressed in at least some cancers, and thus serves as a useful diagnostic, prophylactic, prognostic, and/or therapeutic target for cancers of the tissue(s) such as those listed in Table I.

The invention provides polynucleotides corresponding or complementary to all or part of the 161P2F10B genes, mRNAs, and/or coding sequences, preferably in isolated form, including polynucleotides encoding 161P2F10B-related proteins and fragments of 4, 5, 6, 7, 8, 9, 10, 11, 12, 13, 14, 15, 16, 17, 18, 19, 20, 21, 22, 23, 24, 25, or more than 25 contiguous amino acids; at least 30, 35, 40, 45, 50, 55, 60, 65, 70, 80, 85, 90, 95, 100 or more than 100 contiguous amino acids of a 161P2F10B-related protein, as well as the peptides/proteins themselves; DNA, RNA, DNA/RNA hybrids, and related molecules, polynucleotides or oligonucleotides complementary or having at least a 90% homology to the 161P2F10B genes or mRNA sequences or parts thereof, and polynucleotides or oligonucleotides that hybridize to the 161P2F10B genes, mRNAs, or to 161P2F10B-encoding polynucleotides. Also provided are means for isolating cDNAs and the genes encoding 161P2F10B. Recombinant DNA molecules containing 161P2F10B polynucleotides, cells transformed or transduced with such molecules, and host-vector systems for the expression of 161P2F10B gene products are also provided. The invention further provides antibodies that binds to 161P2F10B proteins and polypeptide fragments thereof, including polyclonal and monoclonal antibodies, murine and other mammalian antibodies, chimeric antibodies, humanized and fully human antibodies, and antibodies labeled with a detectable marker or therapeutic agent. In certain embodiments there is a proviso that the entire nucleic acid sequence of FIG. 2 is not encoded and/or the entire amino acid sequence of FIG. 2 is not prepared. In certain embodiments, the entire nucleic acid sequence of FIG. 2 is encoded and/or the entire amino acid sequence of FIG. 2 is prepared, either of which are in respective human unit dose forms.

The invention further provides methods for detecting the presence and status of 161P2F10B polynucleotides and proteins in various biological samples, as well as methods for identifying cells that express 161P2F10B. A typical embodiment of this invention provides methods for monitoring 161P2F10B gene products in a tissue or hematology sample having or suspected of having some form of growth dysregulation such as cancer.

The invention further provides various immunogenic or therapeutic compositions and strategies for treating cancers that express 161P2F10B such as cancers of tissues listed in Table I, including therapies aimed at inhibiting the transcription translation, processing or function of 161P2F10B as well as cancer vaccines. In one aspect, the invention provides compositions, and methods comprising them, for treating a cancer that expresses 161P2F10B in a human subject wherein the composition comprises a carrier suitable for human use and a human unit dose of one or more than one agent that inhibits the production or function of 161P2F10B. Preferably, the carrier is a uniquely human carrier. In another aspect of the invention, the agent is a moiety that is immunoreactive with 161P2F10B protein. Non-limiting examples of such moieties include, but are not limited to, antibodies (such as single chain, monoclonal, polyclonal, humanized, chimeric, or human antibodies), functional equivalents thereof (whether naturally occurring or synthetic), and combinations thereof. The antibodies can be conjugated to a diagnostic or therapeutic moiety. In another aspect, the agent is a small molecule as defined herein.

In another aspect, the agent comprises one or more than one peptide which comprises a cytotoxic T lumphocyte (CTL) epitope that binds an HLA class I molecule in a human to elicit a CTL response to 161P2F10B and/or one or more than one peptide which comprises a helper T lymphocyte (HTL) epitope which binds an HLA class II molecule in a human to elicit an HTL response. The peptides of the invention may be on the same or on one or more separate polypeptide molecules. In a further aspect of the invention, the agent comprises one or more than one nucleic acid molecule that expresses one or more than one of the CTL or HTL response stimulating peptides as described above. In yet another aspect of the invention, the one or more than one nucleic acid molecule may express a moiety that is immunologically reactive with 161P2F10B as described above. The one or more than one nucleic acid molecule may also be, or encodes, a molecule that inhibits production of 161P2F10B. Non-limiting examples of such molecules include, but are not limited to, those complementary to a nucleotide sequence essential for production of 161P2F10B (e.g. antisense sequences or molecules that form a triple helix with a nucleotide double helix essential for 161P2F10B production) or a ribozyme effective to lyse 161P2F10B mRNA.

BRIEF DESCRIPTION OF THE FIGURES

FIG. 1. The 161P2F10B SSH sequence.

FIG. 2. The cDNA and amino acid sequence of 161P2F10B (FIG. 2A), and the nucleic acid and amino acid sequence of 161P2F10B variant 1 (FIG. 2B). The codon for the start methionine is underlined. The open reading frame for each extends from nucleic acid 44 to 2671 including the stop codon FIG. 3. Amino acid sequence of 161P2F10B (FIG. 3A) and the amino acid sequence of 161P2F10B variant 1 (FIG. 3B). Each protein has 857 amino acids.

FIG. 4. FIG. 4A provides the amino acid alignment of 161P2F10B with ENPP3; FIG. 4B provides an amino acid alignment of 161P2F10B with 161P2F10B variant 1; FIG. 4C provides the Alignment of 161P2F10B and SNP variant 2 carrying a T to P mutation at position 874.

FIG. 5. Hydrophilicity amino acid profile of 161P2F10B determined by computer algorithm sequence analysis using the method of Hopp and Woods (Hopp T. P., Woods, K. R., 1981. Proc. Natl. Acad. Sci. U.S.A. 78:3824–3828).

FIG. 6. Hydropathicity amino acid profile of 161P2F10B determined by computer algorithm sequence analysis using the method of Kyte and Doolittle (Kyte, J., Doolittle, R. F., 1982. J. Mol. Biol. 157:105–132) accessed on the ProtScale website through the ExPasy molecular biology server.

FIG. 7. Percent accessible residues amino acid profile of 161P2F10B determined by computer algorithm sequence analysis using the method of Janin (Janin J., 1979 Nature 277:491–492) accessed on the ProtScale website through the ExPasy moelcular biology server.

FIG. 8. Average flexibility amino acid profile of 161P2F10B determined by computer algorithm sequence analysis using the method of Bhaskaran and Ponnuswamy (Bhaskaran, R., and Ponnuswamy, P. K., 1988. Int. J. Pept. Protein Res. 32:242–255) accessed on the ProtScale website through the ExPasy molecular biology server.

FIG. 9. Beta-turn amino acid profile of 161P2F10B determined by computer algorithm sequence analysis using the method of Deleage and Roux (Deleage, G., Roux B. 1987 Protein Engineering 1:289–294) accessed on the ProtScale website through the ExPasy molecular biology server.

FIG. 10. Expression of 161P2F10B by RT-PCR. First strand cDNA was prepared from vital pool 1 (VP1: liver, lung and kidney), vital pool 2 (VP2, pancreas, colon and stomach), prostate xenograft pool (LAPC-4AD, LAPC-4A1, LAPC-9AD, LAPC-9AJ), normal thymus, prostate cancer pool, kidney cancer pool, colon cancer pool, lung cancer pool, ovary cancer pool, breast cancer pool, metastatsis cancer pool, pancreas cancer pool, and prostate cancer metastatsis to lymph node from two different patients. Normalization was performed by PCR using primers to actin and GAPDH. Semi-quantitative PCR, using primers to 161P2F10B, was performed at 26 and 30 cycles of amplification. Strong expression of 161P2F10B was observed in kidney cancer pool. Expression was also detected in VP1, prostate cancer xenograft pool, prostate cancer pool and colon cancer pool. Low expression was observed in VP2, lung cancer pool, ovary cancer pool, breast cancer pool, metastasis pool, pancreatic cancer pool, and in the two different prostate cancer metastatsis to lymph node.

FIG. 11. Expression of 161P2F10B in normal human tissues. Two multiple tissue Northern blots, with 2 mg of mRNA/lane, were probed with the 161P2F10B sequence. Size strands in kilobases (kb) are indicated on the side. The results show expression of two 161P2F10B transcripts comigrating at approximately 4.4 kb, in kidney, prostate and colon, and to lower levels, in thymus.

FIG. 12. Expression of 161P2F10B in kidney cancer xenografts. RNA was extracted from normal kidney (N), prostate cancer xenografts, LAPC-4AD, LAPC-4AI, LAPC-9AD, and LAPC-9AI, and two kidney cancer xenografts (Ki Xeno-1 and Ki Xeno-2). A Northern blot with 10 mg of total RNA/lane was probed with the 161P2F10B sequence. Size standards in kilobases (kb) are indicated on the side. The results showed expression of 161P2F10B in both kidney xenografts, LAPC-4AI, LAPC-9AI, but not in normal kidney or the tested cell line.

FIG. 13. Expression of 161P2F10B in partial kidney cancer specimens and in normal tissues. RNA was extracted from a pool of three kidney cancers, as well as from normal prostate (NP), normal bladder (NB), normal kidney (NK), and normal colon (NC). A Northern blot with 10 mg of total RNA/lane was probed with the 161P2F10B sequence. Size standards in kilobases (kb) are indicated on the side. The results showed expression of 161P2F10B in the kidney cancer pool but not in the normal tissues tested.

FIG. 14. Expression of 161P2F10B in kidney cancer patient specimens. RNA was extracted from kidney cancer cell lines (CL), normal kidney (N), kidney tumors (T), and matched normal adjacent tissue (NAT) isolated from kidney cancer patients. Northern blots with 10 mg of total RNA/lane were probed with the 161P2F10B sequence. Size standards in kilobases (kb) are indicated on the side. The results showed expression of 161P2F10B in all four clear cell carcinoma kidney tumors, but not in partially carcinoma nor in normal kidney tissues.

FIG. 15. Expression of 161P2F10B in kidney cancer metastasis specimens and in normal tissues. RNA was extracted from kidney cancer metastasis to lung, kidney cancer metastatsis to lymph node, normal bladder (NB), normal kidney (NK), and normal lung (NL), normal breast (NBr), normal ovary (NO), and normal pancreas (NPa). Northern blots with 10 mg of total RNA/lane were probed with the 161P2F10B sequence. Size standards in kilobases (kb) are indicated on the side. The results showed expression of 161P2F10B in the two kidney cancer metastatsis tested. Weak expression was detected in normal kidney and normal breast but not in other normal tissues, but not in normal tissues. The ethidium-bromide starting of the gel showed equivalent loading of the RNA samples.

FIG. 16: Detection of 161P2F10B protein by immunohistochemistry in kidney cancer patient specimens. Renal clear cell carcinoma tissue and its matched normal adjacent tissue as well as its metastatic cancer to lymph node were obtained from a kidney cancer patient. Frozen tissues were cut into 4 micron sections and fixed in acetone for 10 minutes. The sections were then incubated with PE-labeled mouse monoclonal anti-ENPP3 antibody (Couler-Imunotech, Marseilles, France) for 3 hours (FIG. 16 panels A–F), or isotype control antibody (FIG. 16 panels G–I). The slides were washed three times in buffer, and either analyzed by fluorescence microscopy (FIG. 16 panels A, B and C), or further incubated with DAKO EnVision+™ peroxidase-conjugated goat anti-mouse secondary antibody (DAKO Corporation, Carpenteria, Calif.) for 1 hour (FIG. 16 panels D, E, and F). The sections were then washed in buffer, developed using the DAB kit (SIGMA Chemicals), counterstrained using hematoxylin, and analyzed by bright field microscopy (FIG. 16 panels D, E and F)., The results showed strong expression of 161P2F10B in the renal carcinoma patient tissue (FIG. 16 panels A and D) and the kidney cancer metastatsis to lymph node tissue (FIG. 16 panels C and F), but weakly in normal kidney (FIG. 16 B and E). The expression was detected mostly around the cell membrane indicating that 161P2F10B is membrane associated in kidney cancer tissues. The weak expression detected in normal kidney was localized to the kidney tubules. The sections stained with the isotype control antibody were negative showing the specificity of the anti-ENPP3 antibody (FIG. 16 panels G–I).

FIG. 17: Expression of 161P2F10B protein on the cell surface of renal cell carcinoma xenografts. Renal cell carcinoma xenograft tissues (FIG. 17 A) and renal cell carcinoma metastatsis to lymph node xenograft tissues (FIG. 17 B) were harvested from animals and dispersed into single cell suspension. The cells were stained using the commercially available antibody 97A6 specific for ENPP3 protein (laso called anti-Cd203c) (Immunotech, Marseilles, France). They were then washed in PBS and analyzed by flow cytometry. The results showed strong expression of 161P2F10B in both renal cell carcinoma xenograft (FIG. 17 A) as well as renal cancer metastasis xenograft (FIG. 17 B). These data demonstrate that 161P2F10B is expressed on the cell surface of the kidney cancer and kidney cancer metastasis xenograft cells.

FIG. 18. Detection of 161P2F10B protein by immunohistochemistry in human cancer xenograft tissues. Renal cell carcinoma (FIG. 18 panels, A, D, G), renal cell carcinoma metastasis to lymph node (FIG. 18 panels B, E, H), and prostate cancer LAPC-4AI (FIG. 18 panels C, F, I) xenografts were grown in SCID mice. Xenograft tissues were harvested, 4 micron thick frozen sections were cut and fixed in acetone for 10 minutes. The section were then incubated with PE-labeled mouse monoclonal anti-ENPP3 antibody (Immunotech, Marseilles, France) for 3 hours (FIG. 18 panels A–F), or isotype control antibody (FIG. 18 panels G–I). The slides were washed three times in buffer, and either analyzed by fluorescence microscopy (FIG. 18 panels A–C), or further incubated with DAKO EnVision+™ peroxidase-conjugated goat anti-mouse secondary antibody (DAKO Corporation, Carpenteria, Calif.) for 1 hour (FIG. 18 panels D–I). The sections were then washed in buffer, developed using the DAB kit (SIGMA Chemical), counterstained using hematoxylin, and analyzed by bright field microscopy (FIG. 18 panels C–F). The results showed strong expression of 161P2F10B in the renal cell carcinoma xenograft tissue (FIG. 18 panels A and D), in the kidney cancer metastasis to lymph node (FIG. 18 panels B and E) as well as in the LAPC-4AI prostate xenograft (C and F) but not in the negative isotype control sections (FIG. 18 panels G, H, I). The expression was detected mostly around the cell membrane indicating that 161P2F10B is membrane-associated.

FIG. 20. Expression of 161P2F10B in Human Patient Cancers by Western Blot. Cell lysates from kidney cancer tissues (KiCa), kidney cancer metastasis to lymph node (KiCa Met), as well as normal kidney (NK) were subjected to Western analysis using an anti-161P2F10B mouse monoclonal antibody. Briefly, tissues (~25 µg total protein) was solubilized in SDS-PAGE sample buffer and separated on a 10–20% SDS-PAGE gel and transferred to nitrocellulose. Blots were blocked in Tris-buffered saline (TBS)+3% non-fat milk and then probed with purified anti-161P2F10B antibody in TBS+0.15% Tween-20+1% milk. Blots were then washed and incubated with a 1:4,000 dilution of anti-mouse IgG-HRP conjugated secondary antibody. Following washing, anti-161P2F10B immunoreactive bands were developed and visualized by enhanced chemiluminescence and exposure to autoradiographic film. The specific anti-161P2F10B immunoreactive bands represent a monomeric form of the 161P2F10B protein, which runs at approximately 130 kDa. These results demonstrate that 161P2F10B may be useful as a diagnostic and therapeutic target for kidney cancers, metastatic cancers and potentially other human cancers.

FIG. 21. Expression of 161P2F10B in Human Xeograft Tissues by Western Blot. Cell lysates from kidney cancer xenograft (KiCa Xenon), kidney cancer metastasis to lymph node xenograft (Met Xeno), as well as normal kidney (NK) were subjected to Western analysis using an anti-161P2F10B mouse monoclonal antibody. Briefly, tissues (~25 µg total protein) were solubilized in SDS-PAGE sample buffer and separated on a 10–20% SDS-PAGE gel and transferred to nitrocellulose. Blots were blocked in Tris-buffered saline (TBS)+3% non-fat milk and then probed with purified anti-161P2F10B antibody in TBS+0.15% Tween-20+1% milk. Blots were then washed and incubated with a 1:4,000 dilution of anti-mouse IgG-HRP conjugated secondary antibody. Following washing, anti-161P2F10B immunoreactive bands were developed and visualized by enhanced chemiluminescence and exposure to autoradiographic film. The specific anti-161P2F10B immunoreactive bands represent a monomeric form of the 161P2F10B protein, which runs at approximately 130 kDa, and a multimer of approximately 260 kDa. These results demonstrate that the human cancer xenograft mouse models can be used to study the diagnostic and therapeutic effects of 161P2F10B.

DETAILED DESCRIPTION OF THE INVENTION

Outline of Sections

Figure 19B:
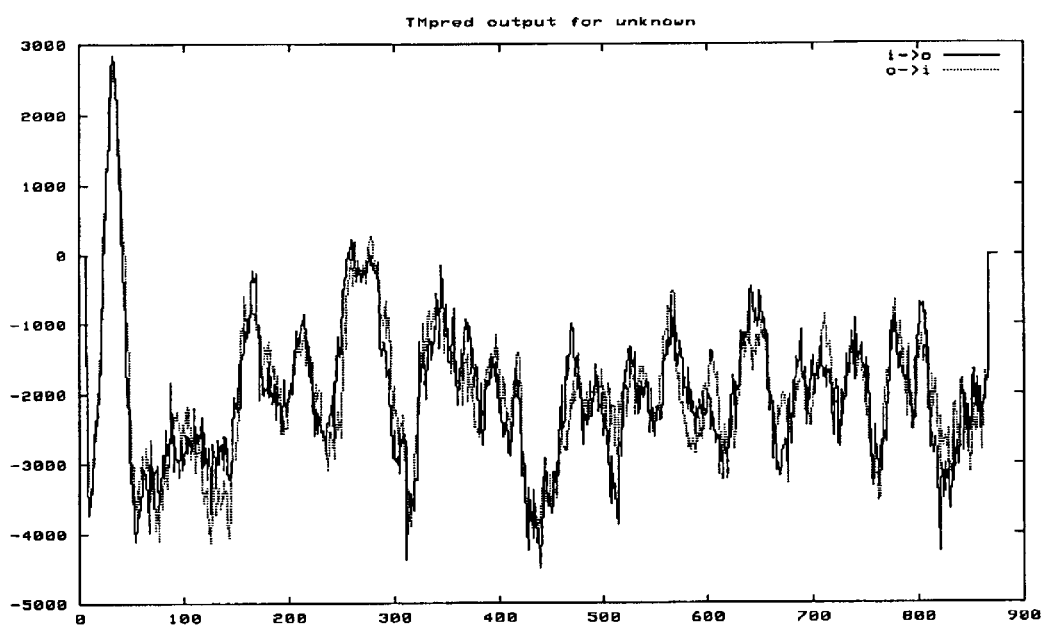
FIG. 19. The secondary structure of 161P2F10B, namely the predicted presence and location of alpha helices, extended strands, and random coils, is predicted from the primary amino acid sequence using the HNN—Hierarchical Neural Network method (Guermeur, 1997, accessed from the ExPasy molecular biology server. The analysis indicates that 161P2F10B is composed 31.31% alpha helix, 11.31% extended strand, and 57.37% random coil (FIG. 19A). Shown graphically in FIG. 19 panels B and C are the results of analysis using the TMpred (FIG. 19B) and TMHMM (FIG. 19C) prediction programs depicting the location of the transmembrane domain.

I.) Definitions
II.) 161P2F10B Polynucleotides
   II.A.) Uses of 161P2F10B Polynucleotides
      II.A.1.) Monitoring of Genetic Abnormalities
      II.A.2.) Antisense Embodiments
      II.A.3.) Primers and Primer Pairs
      II.A.4.) Isolation of 161P2F10B-Encoding Nucleic Acid Molecules
      II.A.5.) Recombinant Nucleic Acid Molecules and Host-Vector Systems
III.) 161P2F10B-related Proteins
   III.A.) Motif-bearing Protein Embodiments
   III.B.) Expression of 161P2F10B-related Proteins
   III.C.) Modifications of 161P2F10B-related Proteins
   III.D.) Uses of 161P2F10B-related Proteins
IV.) 161P2F10B Antibodies
V.) 161P2F10B Cellular Immune Responses
VI.) 161P2F10B Transgenic Animals
VII.) Methods for the Detection of 161P2F10B
VIII.) Methods for Monitoring the Status of 161P2F10B-related Genes and Their Products
IX.) Identification of Molecules That Interact With 161P2F10B
X.) Therapeutic Methods and Compositions
   X.A.) Anti-Cancer Vaccines
   X.B.) 161P2F10B as a Target for Antibody-Based Therapy X.C.) 161P2F10B as a Target for Cellular Immune Responses
  X.C.1. Minigene Vaccines
  X.C.2. Combinations of CTL Peptides with Helper Peptides*
  X.C.3. Combinations of CTL Peptides with T Cell Priming Agents
  X.C.4. Vaccine Compositions Comprising DC Pulsed with CTL and/or HTL Peptides
X.D.) Adoptive Immunotherapy
X.E.) Administration of Vaccines for Therapeutic or Prophylactic Purposes
XI.) Diagnostic and Prognostic Embodiments of 161P2F10B.
XII.) Inhibition of 161P2F10B Protein Function
  XII.A.) Inhibition of 161P2F10B With Intracellular Antibodies
  XII.B.) Inhibition of 161P2F10B with Recombinant Proteins
  XII.C.) Inhibition of 161P2F10B Transcription or Translation
  XII.D.) General Considerations for Therapeutic Strategies
XIII.) KITS
I) Definitions Unless otherwise defined, all terms of art, notations and other scientific terms or terminology used herein are intended to have the meaning commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedure described or referenced herein are well understood and commonly employed using conventional methodology by those skilled in the art, such as, for example, the widely utilized molecular cloning methodologies described in Sambrook et al., Molecular Cloning: A Laboratory Manual 2nd edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

The terms "advanced prostate cancer", "locally advanced prostate cancer", "advanced disease" and "locally advanced disease" mean prostate cancers that have extended through the prostate capsule, and are meant to include stage C disease under the American Urological Association (AUA) system, stage C1–C2 disease under the Whitmore-Jewett system, and stage T3–T4 and N+ disease under the TNM (tumor, node, metastasis) system. In general, surgery is not recommended for patients with locally advanced disease, and these patients have substantially less favorable outcomes compared to patients having clinically localized (organ-confined) prostate cancer. Locally advanced disease is clinically identified by palpable evidence of induration beyond the lateral border of the prostate, or asymmetry or induration above the prostate base. Locally advanced prostate cancer is presently diagnosed pathologically following radical prostatectomy if the tumor invades or penetrates the prostate capsule, extends into the surgical margin, or invades the seminal vesicles.

"Altering the native glycosylation pattern" is intended for purposes herein to mean deleting one or more carbohydrate moieties found in native sequence 161P2F10B (either by removing the underlying glycosylation site or by deleting the glycosylation by chemical and/or enzymatic means), and/or adding one or more glycosylation sites that are not present in the native sequence 161P2F10B. In addition, the phrase includes qualitative change sin the glycosylation of the native proteins, involving a charge in the nature and proportions of the various carbohydrate moieties present.

The term "analog" refers to a molecule which is structurally similar or shares similar or corresponding attributes with another molecule (e.g. a 161P2F10B-related protein). For example an analog of the 161P2F10B protein can be specifically bound by an antibody or T cell that specifically binds to 161P2F10B.

The term "antibody" is used in the broadest sense. Therefore an "antibody" can be naturally occurring or man-made such as monoclonal antibodies produced by conventional hybridoma technology. Anti-161P2F10B antibodies comprise monoclonal and polyclonal antibodies as well as fragments containing the antigen-binding domain and/or one or more complementarity determining regions of these antibodies.

An "antibody fragment" is defined as at least a portion of the variable region of the immunoglobulin molecule that binds to its target, i.e., the antigen-binding region. In one embodiment it specifically covers single anti-161P2F10B antibodies and clones thereof (including agonist, antagonist and neutralizing antibodies) and anti-161P2F10B antibody compositions with polyepitopic specificity.

The term "codon optimized sequences" refers to nucleotide sequences that have been optimized for a particular host species by replacing any codons having a usage frequency of less than about 20%. Nucleotide sequences that have been optimized for expression in a given host species by elimination of spurious polyadenylation sequences, elimination of exon/intron splicing signals, elimination of transposon-like repeats and/or optimization of GC content in addition of codon optimization are referred to herein as an "expression enhanced sequences."

The term "cytotoxic agent" refers to a substance that inhibits or prevents the expression activity of cells, function of cells and/or causes destruction of cells. The term is intended to include radioactive isotopes chemotherapeutic agents, and toxins such as small molecule toxins or enzymatically active toxins of bacterial, fungal, plant or animal origin, including fragments and/or variants thereof. Examples of cytotoxic agents include, but are not limited to maytansinoids, yttrium, bismuth, ricin, ricin A-chain, doxorubicin, daunorubicin, taxol, ethidium bromide, mitomycin, etoposide tenoposide, vincristine, vinblastine, colchicine, dihydroxy anthrazyin dione, antiomycin, diphtheria toxin, *Pseudomonas* exotoxin (PE) A, PE40, abrin, abrin A chain, modeccin A chain, alpha-sarcin, gelonin, mitogellin, retstrictocin, phenomycin, enomycin, curicin, crotin, calicheamicin, sapaonaria officinalis inhibitor, and glucocorticoid and other chemotherapeutic agents, as well as radioisotopes such as $Ar^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu. Antibodies may also be conjugated to an anti-cancer pro-drug activating enzyme capable of converting the pro-drug to its active form.

The term "homolog" refers to a molecule which exhibits homology to another molecule, by for example, having sequences of chemical residues that are the same or similar at corresponding positions.

"Human Leukocyte Antigen" or "HLA" is a human class I or class II Major Histocompatibility Complex (MHC) protein (see, e.g., Sites, et al., IMMUNOLOGY, 8$^{th}$ Ed., Lange Publishing, Los Angeles, Calif. (1994).

The terms "hybridize", "hybridizing", "hybridizes" and the like, used in the context of polynucleotides, are meant to refer to conventional hybridization conditions, preferably such as hybridization in 50% formamide/6×SSC/0.1% SDS/100 μg/ml ssDNA, in which temperature for hybridization are above 37 degrees C. and temperatures for washing in 0.1×SSC/0.1% SDS are above 55 degrees C.

The phrases "isolated" or "biologically pure" refer to material which is substantially or essentially free from components which normally accompany the material as it is found in its native state. Thus, isolated peptides in accordance with the invention preferably do not contain materials normally associated with the peptides in their in situ environments. For example, a polynucleotide is said to be "isolated" when it is substantially separated from contaminant polynucleotides that correspond or are complementary to genes other than the 161P2F10B gene or that encode polypeptides other than 161P2F10B gene product or fragments thereof. A skilled artisan can readily employ nucleic acid isolation procedures to obtain an isolated 161P2F10B polynucleotide. A protein is said to be "isolated," for example, when physical, mechanical or chemical methods are employed to remove the 161P2F10B protein from cellular constituents that are normally associated with the protein. A skilled artisan can readily employ standard purification methods to obtain an isolated 161P2F10B protein. Alternatively, an isolated protein can be prepared by chemical means.

The term "mammal" refers to any organism classified as a mammal, including mice, rats, rabbits, dogs, cats, cows, horses and humans. In one embodiment of the invention, the mammal is a mouse. In another embodiment of the invention, the mammal is a human.

The terms "metastatic prostate cancer" and "metastatic disease" mean prostate cancers that have spread to regional lymph nodes or to distant sites, and are meant to include stage D disease under the AUA system and stage T×N×M+ under the TNM system. As is the case with locally advanced prostate cancer, surgery is generally not indicated for patients with metastatic disease, and hormonal (androgen ablation) therapy is a preferred treatment modality. Patients with metastatic prostate cancer eventually develop an androgen-refractory state within 12 to 18 months of treatment initiation. Approximately half of these androgen-refractory patients die within 6 months after developing that status. The most common site for prostate cancer metastasis is bone. Prostate cancer bone metastases are often olsteoblastic rather than osteolytic (i.e., resulting in net bone formation). Bone metastatsis are found most frequently in the spine, followed by the femur, pelvis, rib cage, skull and humerus. Other common sites for metastatsis include lymph nodes, lung, liver and brain. Metastatic prostate cancer is typically diagnosed by open or laparoscopic pelvic lymphadenectomy, whole body radionuclide scans, skeletal radiography, and/or bone lesion biopsy.

The term "monoclonal antibody" refers to an antibody obtained from a population of substantially homogeneous antibodies, i.e., the antibodies comprising the population are identical except for possible naturally occurring mutations that are present in minor amounts.

A "motif", as in biological motif of an 161P2F10B-related protein, refers to any pattern of amino acids forming part of the primary sequence of a protein, that is associated with a particular function (e.g. protein-protein interaction, protein-DNA interaction, etc) or modification (e.g. that is phosphorylated, glycosylated or amidated), or localization (e.g. secretory sequence, nuclear localization sequence, etc.) or a sequence that is correlated with begin immunogenic, either humorally or cellularly. A motif can be either contiguous or capable of being aligned to certain positions that are generally correlated with a certain function or property. In the context of HLA motifs, "motif" refers to the pattern of residues in a peptide of defined length, usually a peptide of from about 8 to about 13 amino acids for a class I HLA motif and from about 6 to about 25 amino acids for a class II HLA motif, which is recognized by a particular HLA molecule. Peptide motifs for HLA binding are typically different for each protein encoded by each human HLA allele and differ in the pattern of the primary and secondary anchor residues.

A "pharmaceutical excipient" comprises a material such as an adjuvant, a carrier, pH-adjusting and buffering agents, tonicity adjusting agents, wetting agents, preservative, and the like.

"Pharmaceutically acceptable" refers to a non-toxic, inert, and/or composition that is physiologically compatible with humans or other mammals.

The term "polynucleotide" means a polymeric form of nucleotides of at least 10 bases or base pairs in length, either ribonucleotides or deoxynucleotides or a modified form of either type of nucleotide, and is meant to include single and double stranded forms of DNA and/or RNA. In the art, this term if often used interchangeably with "oligonucleotide". A polynucleotide can comprise a nucleotide sequence disclosed herein wherein thymidine (T) (as shown for example in FIG. 2) can also be uracil (U); this definition pertains to the differences between the chemical structures of DNA and RNA, in particular the observation that one of the four major bases in RNA is uracil (U) instead of thymidine (T).

The term "polypeptide" means a polymer of at least about 4, 5, 6, 7, or 8 amino acids. Throughout the specification, standard three letter or single letter designations for amino acids are used. In the art, this term is often used interchangeably with "peptide" or "protein".

An HLA "primary anchor residue" is an amino acid at a specific position along a peptide sequence which is understood to provide a contact point between the immunogenic peptide and the HLA molecule. One to three, usually two, primary anchor residues within a peptide of defined length generally defines a "motif" for an immunogenic peptide. These residues are understood to fit in close contact with peptide binding groove of an HLA molecule, with their side chains buried in specific pockets of the binding groove. In one embodiment, for example, the primary anchor residues for an HLA class I molecule are located at position 2 (from the amino terminal position) and at the carboxyl terminal position of a 8, 9, 10, 11, or 12 residue epitope in accordance with the invention. In another embodiment, for example, the primary anchor residues of a peptide that will bind an HLA class II molecule are spaced relative to each other, rather than to the termini of a peptide, where the peptide is generally of at least 9 amino acids in length. The primary anchor positions for each motif and supermotif are set forth in Table IV. For example, analog peptides can be created by altering the presence or absence of particular residues in the primary and/or secondary anchor positions shown in Table IV. Such analogs are used to modulate the binding affinity and/or population coverage of a peptide comprising a particular HLA motif or supermotif.

A "recombinant" DNA or RNA molecule is a DNA or RNA molecule that has been subjected to molecular manipulation in vitro.

Non-limiting examples of small molecules include compounds that bind or interact with 161P2F10B, ligands including hormones, neuropeptides, chemokines, odorants, phospholipids, and functional equivalents thereof that bind and preferably inhibit 161P2F10B protein function. Such non-limiting small molecules preferably have a molecular weight of less than about 10 kDa, more preferably below about 9, about 8, about 7, about 6, about 5 or about 4 kDa. In certain embodiments, small molecules physically associate with, or bind, 161P2F10B protein; are not found in naturally occurring metabolic pathways; and/or are more soluble in aqueous than non-aqueous solutions.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured nucleic acid sequences to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers (1995).

"Stringent conditions" or "high stringency conditions", are identified by, but not limited to, those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturating agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDs, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. "Moderately stringent conditions" are described by, but not limited to, those in Sambrook et al., Molecular Cloning: A Laboratory Manual, New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 nM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

An HLA "supermotif" is a peptide binding specificity shared by HLA molecules encoded by two or more HLA alleles.

As used herein "to treat" or "therapeutic" and grammatically related terms, refer to any improvement of any consequence of disease, such as prolonged survival, less morbidity, and/or a lessening of side effects which are the byproducts of an alternative therapeutic modality; full eradication of disease is not required.

A "transgenic animal" (e.g., a mouse or rat) is an animal having cells that contain a transgene, which transgene was introduced into the animal or an ancestor of the animal at a prenatal, e.g., an embryonic stage. A "transgene" is a DNA that is integrated into the genome of a cell from which a transgenic animal develops.

As used herein, HLA or cellular immune response "vaccine" is a composition that contains or encodes one or more peptides of the invention. There are numerous embodiments of such vaccines, such as a cocktail of one or more individual peptides; one or more peptides of the invention comprised by a polyepitopic peptide; or nucleic acids that encode such individual peptides or polypeptides, e.g., a minigene that encodes a polyepitopic peptide. The "one or more peptides" can include any whole unit integer from 1–150 or more, e.g., at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, or 150 or more peptides of the invention. The peptides or polypeptides can optionally be modified, such as by lipidation, addition of targeting or other sequences. HLA class I peptides of the invention can be admixed with, or linked to, HLA class II peptides, to facilitate activation of both cytotoxic T lymphocytes and helper T lymphocytes. HLA vaccines can also comprise peptide-pulsed antigen presenting cells, e.g., dendritic cells.

The term "variant" refers to a molecule that exhibits a variation from a described type or norm, such as a protein that has one or more different amino acid residues in the corresponding position(s) of a specifically described protein (e.g. the 161P2F10B protein shown in FIG. 2 or FIG. 3). An analog is an example of a variant protein.

The 161P2F10B-related proteins of the invention include those specifically identified herein, as well as allelic variants, conservative substitutions variants, analogs and homologs that can be isolated/generated and characterized without undue experimentation following the methods outlined herein or readily available in the art. Fusion proteins that combine parts of different 161P2F10B proteins or fragments thereof, as well as fusion proteins of a 161P2F10B protein and a heterologous polypeptide are also included. Such161P2F10B proteins are collectively referred to as the 161P2F10B-related proteins, the proetin of the invention, or 161P2F10B. The term "161P2F10B-related protein" refers to a polypeptide fragment or an 161P2F10B protein sequence of 4, 5, 6, 7, 8, 9, 10, 11, 12, 13, 14, 15, 16, 17, 18, 19, 20, 21, 22, 23, 24, 25, or more than 25 amino acids; or, at least 30, 35, 40, 45, 50, 55, 60, 65, 70, 80, 85, 90, 95, 100, or more than 100 amino acids.

II.) 161P2F10B Polynucleotides

One aspect of the invention provides polynucleotides corresponding or complementary to all or part of an 161P2F10B gene, mRNA, and/or coding sequence, preferably in isolated form, including polynucleotides encoding an 161P2F10B-related protein and fragments thereof, DNA, RNA, DNA/RNA hybrid, and related molecules, polynucleotides or oligonucleotides complementary to an 161P2F10B gene or mRNA sequence or a part thereof, and polynucleotides or oligonucleotides that hybridize to an 161P2F10B gene, mRNA, or to an 161P2F10B encoding polynucleotide (collectively, "161P2F10B polynucleotides"). In all instances when referred in to this session, T can also be U in FIG. 2.

Embodiments of a 161P2F10B polynucleotide include: a 161P2F10B polynucleotide having the sequence shown in FIG. 2, the nucleotide sequence of 161P2F10B as shown in FIG. 2 wherein T is U; at least 10 contiguous nucleotides of a polynucleotide having the sequence as shown in FIG. 2; or, at least 10 contiguous nucleotides of a polynucleotide having the sequence as shown in FIG. 2 where T is U. For example, embodiments of 161P2F10B nucleotides comprise, without limitation:

(a) a polynucleotide comprising or consisting of the sequence as shown in FIG. 2, wherein T can also be U;

(b) a polynucleotide comprising or consisting of the sequence as shown in FIG. 2, from nucleotide residue number 44 through nucleotide residue number 2671, wherein T can also be U;

(c) a polynucleotide that encodes an 161P2F10B-related protein that is at least 90% homologous to the entire amino acid sequence shown in FIG. 2;

(d) a polynucleotide that encodes an 161P2F10B-related protein that is at least 90% identical to the entire amino acid sequence shown in FIG. 2;

(e) A polynucleotide that encodes at least one peptide set forth in Tables V–XVIII;

(f) a polynucleotide that encodes a peptide region of at least 5 amino acids of FIG. 3 in any whole number increment up to 875 that includes an amino acid position having a value greater than 0.5 in the Hydrophilicity profile of FIG. 5;

(g) a polynucleotide that encodes a peptide region of at least 5 amino acids of FIG. 3 in any whole number increment up to 875 that includes an amino acid position having a value less than 0.5 in the Hydropathicity profile of FIG. 6;

(h) a polynucleotide that encodes a peptide region of at least 5 amino acids of FIG. 3 in any whole number increment up to 875 that includes an amino acid position having a value greater than 0.5 in the Percent Accessible Residues profile of FIG. 7;

(i) a polynucleotide that encodes a peptide region of at least 5 amino acids of FIG. 3 in any whole number increment up to 875 that includes an amino acid position having a value greater than 0.5 in the Average Flexibility profile of FIG. 8;

(j) a polynucleotide that encodes a peptide region of at least 5 amino acids of FIG. 3 in any whole number increment up to 875 that includes an amino acid position having a value greater than 0.5 in the Beta-turn profile of FIG. 9;

(k) a polynucleotide that is fully complementary to a polynucleotide of any one of (a)–(j);

(l) a polynucleotide that selectively hybridizes under stringent conditions to a polynucleotide of (a)–(k);

(m) a peptide that is encoded by any of (a)–(j); and, (n) a polynucleotide of any of (a)–(l) or peptide of (m) together with a pharmaceutical excipient and/or in a human unit dose form.

As used herein, a range is understood to specifically disclose all whole unit positions thereof.

Typical embodiments of the invention disclosed herein include 161P2F10B polynucleotides that encode specific portions of the 161P2F10B mRNA sequence (and those which are complementary to such sequences) such as those that encode the protein and fragments thereof, for example of 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 250, 275, 300, 325, 350, 375, 400, 425, 450, 475, 500, 525, 550, 575, 600, 625, 650, 675, 700, 725, 750, 775, 900, 825, 850, or 875 contiguous amino acids.

For example, representative embodiments of the invention disclosed herein include: polynucleotides and their encoded peptides themselves encoding about amino acid 1 to about amino acid 10 of the 161P2F10B protein shown in FIG. 2 or FIG. 3, polynucleotide encoding about amino acid 10 to about amino acid 20 of the 161P2F10B protein shown in FIG. 2, or FIG. 3, polynucleotides encoding about amino acid 20 to about amino acid 30 of the 161P2F10B protein shown in FIG. 2 or FIG. 3, polynucleotides encoding about amino acid 30 to about amino acid 40 of the 161P2F10B protein shown in FIG. 2 or FIG. 3, polynucleotides encoding about amino acid 40 to about amino acid 50 of the 161P2F10B protein shown in FIG. 2 or FIG. 3, polynucleotides encoding about amino acid 50 to about amino acid 60 of the 161P2F10B protein shown in FIG. 2 or FIG. 3, polynucleotide encoding about amino acid 60 to about amino acid 70 of the 161P2F10B protein shown in FIG. 2 or FIG. 3, polynucleotides encoding about amino acid 70 to about amino acid 80 of the 161P2F10B protein shown in FIG. 2 or FIG. 3, polynucleotides encoding about amino acid 80 to about amino acid 90 of the 161P2F10B protein shown in FIG. 2 or FIG. 3, polynucleotides encoding about amino acid 90 to about amino acid 100 of the 161P2F10B protein shown in FIG. 2 or FIG. 3, in increments of about 10 amino acids, ending at the carboxyl terminal amino acid set forth in FIG. 2 or FIG. 3. Accordingly polynucleotides encoding proteins of the amino acid sequence (of about 10 amino acids), of amino acids 100 through the carboxyl terminal amino acid of the 161P2F10B protein are embodiments of the invention. Wherein it is understood that each particular amino acid position discloses that position plus or minus five amino acid residues.

Polynucleotides encoding relatively long portions of the 161P2F10B protein are also within the scope of the invention. For example, polynucleotides encoding from about amino acid 1 (or 20 or 30 or 40 etc.) to about amino acid 20, (or 30, or 40 or 50 etc.) of the 161P2F10B protein shown in FIG. 2 or FIG. 3 can be generated by a variety of techniques well known in the art. These polynucleotide fragments can include any portion of the 161P2F10B sequence as shown in FIG. 2 or FIG. 3.

Additional illustrative embodiments of the invention disclosed herein include 161P2F10B polynucleotide fragments encoding one or more of the biological motifs contained within the 161P2F10B protein sequence, including one or more of the motif-bearing subsequences of the 161P2F10B protein set forth in Tables V–XVIII. In another embodiment, typical polynucleotide fragments of the invention encode one or more of the regions of 161P2F10B that exhibit homology to a known molecule. In another embodiment of the invention, typical polynucleotide fragments can encode one or more of the 161P2F10B N-glycosylation sites, cAMP and rGMP-dependent protein kinase phosphorylation sites, casein kinase II phosphorylation sites or N-myristoylation site and amidation sites.

II.A.) Uses of 161P2F10B Polynucleotides

II.A.1.) Monitoring of Genetic Abnormalities

The polynucleotides of the preceding paragraphs have a number of different specific uses. The human 161P2F10B gene maps to the chromosomal location set forth in Example 3. For example, because the 161P2F10B gene maps to this chromosome, polynucleotides that encode different regions of the 161P2F10B protein are used to characterize cytogenetic abnormalities of this chromosomal locale, such as abnormalities that are identified as being associated with various cancers. In certain genes, a variety of chromosomal abnormalities including rearrangements have been identified as frequency cytogenetic abnormalities in a number of different cancers (see e.g., Krajinovic et al., Mutat. Res. 382(3–4): 81–83 (1998); Johansson et al., Blood 86(10): 3905–3914 (1995) and Finger et al., P.N.A.S. 85(23): 9158–9162 (1988)). Thus, polynucleotides encoding specific regions of the 161P2F10B protein provide new tools that can be used to delineate, with greater precision than previously possible, cytogenetic abnormalities in the chromosomal region that encodes 161P2F10B that may contribute to the malignant phenotype. In this context, these polynucleotides satisfy a need in the art for expanding the sensitivity of chromosomal screening in order to identify more subtle and less common chromosomal abnormalities (see e.g. Evans et al., Am. J. Obstet. Gynecol 171(4): 1055–1057 (1994)).

Furthermore, as 161P2F10B was shown to be highly expressed in prostate and other cancers, 161P2F10B polynucleotides are used in methods assessing the status of 161P2F10B gene products in normal versus cancerous tissues. Typically, polynucleotides that encode specific regions of the 161P2F10B protein are used to assess the presence of perturbations (such as deletions, insertions, point mutations, or alterations resulting in a loss of an antigen etc.) in specific regions of the 161P2F10B gene, such as regions containing one or more motifs. Exemplary assays include both RT-PCR assays as well as single-strand conformation polymorphis (SSCP) analysis (see, e.g., Marrogi et al., J. Cutan. Pathol. 26(8): 369–378 (1999), both of which utilize polynucleotides encoding specific regions of a protein to examine these regions within the protein.

II.A.2.) Antisense Embodiments

Other specifically contemplated nucleic acid related embodiments of the invention disclosed herein are genomic DNA, cDNAs, ribozymes, and antisense molecules, as well as nucleic acid molecules based on an alternative backbone, or including alternative bases, whether derived from natural sources or synthesized, and include molecules capable of inhibiting the RNA or protein expression of 161P2F10B. For example, antisense molecules can be RNAs or other molecules, including peptide nucleic acids (PNAs) or non-nucleic acid molecules such as phosphorothioate derivatives, that specifically bind DNA or RNA in a base pair-dependent manner. A skilled artisan can readily obtain these classes of nucleic acid molecules using the 161P2F10B polynucleotides and polynucleotide sequences disclosed herein.

Antisense technology entails the administration of exogenous oligonucleotides that bind to a target polynucleotide located within the cells. The term "antisense" refers to the fact that such oligonucleotides are complementary to their intracellular targets, e.g., 161P2F10B. See for example, Jack Cohen, Oligodeoxynucleotides, Antisense Inhibitors of Gene Expression, CRC Press, 1989; and Synthesis 1:1–5 (1988). The 161P2F10B antisense oligonucleotides of the present invention include derivatives such as S-oligonucleotides (phosphorothioate derivatives or S-oligos, see, Jack Cohen, supra), which exhibit enhanced cancer cell growth inhibitory action. S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention can be prepared by treatment of the corresponding O-oligos with 3H-1,2-benzodithiol-3-one-1,1-dioxide, which is a sulfur transfer reagent. See Iyer, R. P. et al, J. Org. Chem. 55:4693–4698 (1990); and Iyer, R. P. et al., J. Am. Chem. Soc. 112:1253–1254 (1990). Additional 161P2F10B antisense oligonucleotides of the present invention include morpholino antisense oligonucleotides known in the art (see, e.g., Partridge et al., 1996, Antisense & Nucleic Acid Drug Development 6: 169–175).

The 161P2F10B antisense oligonucleotides of the present invention typically can be RNA or DNA that is complementary to and stably hybridizes with the first 100 5' codons or last 100 3' codons of the 161P2F10B genomic sequence or the corresponding mRNA. Absolute complementarity is not required, although high degrees of complementarity are preferred. Use of an oligonucleotide complementary to this region allows for the selective hybridization to 161P2F10B mRNA and not to mRNA specifying other regulatory subunits of protein kinase. In one embodiment, 161P2F10B antisense oligonucleotides of the present invention are 15 to 30-mer fragments of the antisense DNA molecules that have a sequence that hybridizes to 161P2F10B mRNA.

Optionally, 161P2F10B antisense oligonucleotide is a 30-mer oligonucleotide that is complementary to a region in the first 10 5' codons or last 10 3' codons of 161P2F10B. Alternatively, the antisense molecules are modified to employ ribozymes in the inhibition of 161P2F10B expression, see, e.g., L. A. Couture & D. T. Stinchcomb; *Trends Genet* 12: 510–515 (1996).

II.A.3.) Primers and Primer Pairs

Further specific embodiments of this nucleotides of the invention include primers and primer pairs, which allow the specific amplification of polynucleotides of the invention or any specific parts thereof, and probes that selectively or specifically hybridize to nucleic acid molecules of the invention or to any part thereof. Probes can be labeled with a detectable marker, such as, for example, a radioisotope, fluorescent compound, bioluminescent compound, a chemiluminescent compound, metal chelator or enzyme. Such probes and primers are used to detect the presence of a 161P2F10B polynucleotide in a sample and as a means for detecting a cell expressing a 161P2F10B protein.

Examples of such probes include polypeptides comprising all or part of the human 161P2F10B cDNA sequence shown in FIG. 2. Examples of primer pairs capable of specifically amplifying 161P2F10B mRNAs are also described in the Examples. As will be understood by the skilled artisan, a great many different primers and probes can be prepared based on the sequences provided herein and used effectively to amplify and/or detect a 161P2F10B mRNA.

The 161P2F10B polynucleotides of the invention are useful for a variety of purposes, including but not limited to their use as probes and primers for the amplification and/or detection of the 161P2F10B gene(s), mRNA(s), or fragments thereof, as reagents for the diagnosis and/or prognosis of prostate cancer and other cancers; as coding sequences capable of directing the expression of 161P2F10B polypeptides; as tools for modulating or inhibiting the expression of the 161P2F10B gene(s) and/or translation of the 161P2F10B transcript(s); and as therapeutic agents.

The present invention includes the use of any probe as described herein to identify and isolate a 161P2F10B or 161P2F10B related nucleic acid sequence from a naturally occurring source, such as humans or other mammals, as well as the isolated nucleic acid sequence per se, which would comprise all or most of the sequences found in the probe used.

II.A.4.) Isolation of 161P2F10B-Encoding Acid Molecules

The 161P2F10B cDNA sequences described herein enable the isolation of other polynucleotides encoding 161P2F10B gene product(s), as well as the isolation of polynucleotides encoding 161P2F10B gene product homologs, alternatively, spliced isoforms, allelic variants, and mutant forms of the 161P2F10B gene product as well as polynucleotides that encode analogs of 161P2F10B-related proteins. Various molecular cloning methods that can be employed to isolate full length cDNAs encoding an 161P2F10B gene are well known (see, for example, Sambrook, J. et al., Molecular Cloning: A Laboratory Manual, 2nd edition, Cold Spring Harbor Press, New York, 1989; Current Protocols in Molecular Biology. Ausubel et al., Eds., Wiley and Sons, 1995). For example, lambda phage containing methodologies can be conveniently employed, using commercially available cloning systems (e.g., Lambda ZAP Express, Stratagene). Phage clones containing 161P2F10B gene cDNAs can be identified by probing with a labeled 161P2F10B cDNA or a fragment thereof. For example, in one embodiment, the 161P2F10B cDNA (FIG. 2) or a portion thereof can be synthesized and used as a probe to retrieve overlapping and full-length cDNAs corresponding to a 161P2F10B gene. The 161P2F10B gene itself can be isolated by screening genomic DNA libraries, bacterial artificial chromosome libraries (BACs), yeast artificial chromosome libraries (YACs), and the like, with 161P2F10B DNA probes or primers.

II.A.5.) Recombinant Nucleic Acid Molecules and Host-Vector Systems

The invention also provides recombinant DNA or RNA molecules containing an 161P2F10B polynucleotide, a fragment, analog or homolgue thereof, including but not limited to phages, plasmid, phagemids, cosmids, YACs, BACs as well as various viral and non-viral vectors well known in the art, and cell transformed or transfected with such recombinant DNA or RNA molecules. Methods for generating such molecules are well known (see, for example, Sambrook et al, 1989, supra).

The invention further provides a host-vector system comprising a recombinant DNA molecule containing a 161P2F10B polynucleotide, fragment, analog or homologue thereof within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9 or HighFive cell). Examples of suitable mammalian cells include various prostate cancer cell lines such as DU145 and TsuPr1, other transfectable or transducible prostate cancer cell lines, primary cells (PrEC), as well as a number of mammalian cells routinely used for the expression of recombinant proteins (e.g., COS, CHO, 293, 293T cells). More particularly, a polynucleotide comprising the coding sequence of 161P2F10B or a fragment, analog or homolog thereof can be used to generate 161P2F10B proteins or fragments thereof using any number of host-vector systems routinely used and widely known in the art.

A wide range of host-vector systems suitable for the expression of 161P2F10B proteins or fragments thereof are available, see for example, Sambrook et al., 1989, supra; Current Protocols in Molecular Biology, 1995, supra). Preferred vectors for mammalian expression include but are not limited to pcDNA 3.1 myc-His-tag (Invitrogen) and the retroviral vector pSRαtkneo (Muller et al., 1991, MCB 11:1785). Using these expression vectors, 161P2F10B can be expressed in several prostate cancer and non-prostate cell lines, including for example 293, 293T, rat-1, NIH 3T3 and TsuPr1. The host-vector systems of the invention are useful for the production of a 161P2F10B protein or fragment thereof. Such host-vector systems can be employed to study the functional properties of 161P2F10B and 161P2F10B mutations or analogs.

Recombinant human 161P2F10B protein or an analog or homolog or fragment thereof can be produced by mammalian cells tranfected with a construct encoding a 161P2F10B-related nucleotide. For example, 293T cells can be transfected with an expression plasmid encoding 161P2F10B or fragment, analog or homolog thereof, the 161P2F10B or related protein is expressed in the 293T cells, and the recombinant 161P2F10B protein is isolated using standard purification mehtods (e.g., affinity purificaiton using anti-161P2F10B antibodies). In another embodiment, a 161P2F10B coding sequences is subcloned into the retroviral vector pSRαMSVtkneo and used to infect various mammalian cell lines, such as NIH 3T3, TsuPr1, 293 and rat-1 in order to establish 161P2F10B expressing cell lines. Various other expression systems well known in the art can also be employed. Expression constructs encoding a leader peptide joined in frame to the 161P2F10B coding sequence can be used for the generation of a secreted form of recombinant 161P2F10B protein.

As discussed herein, redundancy in the genetic code permits variation in 161P2F10B gene sequences. In particular, it is knowhn in the art that specific host species often have specific codon preferences, and thus one can adapt the disclosed sequence as preferred for a desired host. For example, preferred analog codon sequences typically have rare codons (i.e., codons having a usage frquency of less than about 20% in known sequences of the desired host) replaced with higher frequency codons. Codon preferences for a specific speices are calculated, for example, by utilizing codon uage tables available on the INTERNET.

Additional sequence modifications are known to enhance protein expression in a cellular host. These include elimination of sequences encoding spurious polyadenylation signals, exon/intron splice site signals, transposon-like repeats, and/or other such well-characterized sequences that are deleterious to gene expression. The GC content of the sequence is adjusted to levels average for a given cellular host, as calculated by reference to known genes expressed in the host cell. Where possible, the sequence is modified to avoid predicted hairpin secondary mRNA structures. Other useful modifications include the addition of a translation initiation consensus sequence at the start of the open reading frame, as described in Kozak, *Mol. Cell Biol.* 9:5073–5080 (1989). Skilled artisans understand that the general rule that eukaryotic ribosomes initiate translation exclusively at the 5' proximal UD codon is abrogated only under rare conditions (see, e.g., Kozak PNAS 92(7): 2662–2666, (1995) and Kozak NAR 15(20): 8125–8148 (1987)).

III.). 161P2F10B-related Proteins

Another aspect of the present invention provides 161P2F10B-related proteins. Specific embodiments of 161P2F10B proteins comprise a polypeptide having all or part of the amino acid sequence of human 161P2F10B as shown in FIG. 2 or FIG. 3. Alternatively, embodiments of 161P2F10B proteins comprise variant, homolog or analog polypeptides that have alterations in the amino acid sequence of 161P2F10B shown in FIG. 2 or FIG. 3.

In general, naturally occurring allelic variants of human 161P2F10B share a high degree of structural identity and homology (e.g., 90% or more homology). Typically, allelic variants of the 161P2F10B protein contain conservative amino acid substitutions within the 161P2F10B sequences described herein or contain a substitution of an amino acid from a corresponding position in a homologous of 161P2F10B. One class of 161P2F10B allelic variants are proteins that share a high degree of homology with at least a small region of a particular 161P2F10B amino acid sequence, but further contain a radial departure from the sequence, such as a non-conservative substitution, truncation, insertion or frame shift. In comparisons of protein sequences, the terms, similarity, identity, and homology each have a distinct meaning as appreciated in the field of genetics. Moreover, orthology and paralogy can be important concepts describing the relationship of members of a given protein family in one organism to the members of the same family in other organisms.

Amino acid abbreviations are provided in Table II. Conservative amino acid substitutions can frequently be made in a protein without altering either the conformation or the function of the protein. Proteins of the invention can comprise 1, 2, 3, 4, 5, 6, 7, 8, 9, 10, 11, 12, 13, 14, 15 conservative substitutions. Such changes includes substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with luecine and isoleucine, and sometimes with valine. Lysine (K) and arigine (R) are frequently interchangeable in locations in which the significant feature of the amino acid residue is its charge and the differing pK's of these two amino acid residues are not significant. Still other changes can be considered "conservative" in particular environments (see, e.g., Table III herein; pages 13–15; "Biochemistry" 2$^{nd}$ ED. Luber Stryer ed (Stanford University); Henikoff et al., PNAS 1992 Vol 89 10915–10919; Lei et al., J Biol Chem 1995 May 19; 270(20):11882–6).

Embodiments of the invention disclosed herein include a wide variety of art-accepted variants or analogs of 161P2F10B proteins such as polypeptides having amino acid insertions, deletions and substitutions. 161P2F10B variants can be made using methods known in the art such as site-directed mutagenesis, alanine scanning, and PCR mutagenesis. Site-directed mutagenesis (Carter et al., *Nucl. Acads Res.* 13:4331 (1986); Zoller et al., *Nucl. Acids Res.* 10:6487 (1987)), cassette mutagenesis (Wells et al., Gene, 34:315 (1985)), restriction selection mutagenesis (Wells et al., *Philos. Trans R. Soc. London SerA*, 317:415 (1986)) or other known techniques can be performed on the cloned DNA to produce the 161P2F10B variant DNA.

Scanning amino acid analysis can also be employed to identify one or more amino acids along a contiguous sequence that is involved in a specific biological activity such as a protein-protein interaction. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions (Creighton, *The Proteins,* (W.H. Freeman & Co., N.Y.); Chothia, J. Mol. Biol., 150:1 (1976)). If alanine substitution doe not yield adequate amounts of variant, an isosteric amino acid can be used.

As defined herein, 161P2F10B variants, analogs or homologs, have the distinguishing attribute of having at least one epitope that is "cross reactive" with a 161P2F10B protein having the amino acid sequence of SEQ ID NO: 703. As used in this sentence, "cross reactive" menas that an antibody or T cell that specifically binds to an 161P2F10B variant also specifically binds to the 161P2F10B protein having the amino acid sequence of SEQ ID NO: 703. A polypeptide ceases to be variant of the protein shown in SEQ ID NO: 703 when it no longer contains any epitope capable of being recognized by an antibody or T cell that specifically binds to the 161P2F10B protein. Those skilled in the art understand that antibodies that recognize proteins bind to epitopes of varying size, and a grouping of the order of about four or five amino acids, contiguous or not, is regarded as a typical number of amino acids in a minimal epitope. See, e.g., Nair et al., J. Immunol 2000 165(12):6949–6955; Hebbes et al., Mol Immunol (1989) 26(9):865–73; Schwartz et al., J Immunol (1985) 135(4):2598–608.

Another class of 161P2F10B-related protein variants share 70% , 75%, 80%, 85% or 90% or some similarity with the amino acid sequence of FIG. 2 or a fragment thereof. Another specific class of 161P2F10B protein variants or analogs comprise one or more of the 161P2F10B biological motifs described herein or presently known in the art. Thus, encompassed by the present invention are analogs of 161P2F10B fragments (nucleic or amino acid) that have altered functional (e.g. immunogenic) properties relative to the starting fragment. It is to be appreciated that motifs now or which become part of the art are to be applied to the nucleic or amino acid sequences of FIG. 2 or FIG. 3.

As discussed herein, embodiments of the claimed invention include polypeptides containing less than the full amino acid sequence of the 161P2F10B protein shown in FIG. 2 or FIG. 3. For example, representative embodiments of the invention comprise peptides/proteins having any 4, 5, 6, 7, 8, 9, 10, 11, 12, 13, 14, 15 or more contiguous amino acids of the 161P2F10B protein shown in FIG. 2 or FIG. 3.

Moreover, representative embodiments of the invention disclosed herein include polypeptides consisting of about amino acid 1 to about amino acid 10 of the 161P2F10B protein shown in FIG. 2 or FIG. 3, polypeptides consisting of about amino acid 10 to about amino acid 20 of the 161P2F10B protein shown in FIG. 2 or FIG. 3, polypeptides consisting of about amino acid 20 to about amino acid 30 of the 161P2F10B protein shown in FIG. 2 or FIG. 3, polypeptides consisting of about amino acid 30 to about amino acid 40 of the 161P2F10B protein shown in FIG. 2 or FIG. 3, polypeptides consisting of about amino acid 40 to about amino acid 50 of the 161P2F10B protein shown in FIG. 2 or FIG. 3, polypeptides consisting of about amino acid 50 to about amino acid 60 of the 161P2F10B protein shown in FIG. 2 or FIG. 3, polypeptides consisting of about amino acid 60 to about amino acid 70 of the 161P2F10B protein shown in FIG. 2 or FIG. 3, polypeptides consisting of about amino acid 70 to about amino acid 80 of the 161P2F10B protein shown in FIG. 2 or FIG. 3, polypeptide consisting of about amino acid 80 to about amino acid 90 of the 161P2F10B protein shown in FIG. 2 or FIG. 3, polypeptides consisting of about amino acid 90 to about amino acid 100 of the 161P2F10B protein shown in FIG. 2 or FIG. 3, etc. throughout the entirety of the 161P2F10B amino acid sequence. Moreover, polypeptides consisting of about amino acid 1 (or 20 or 30 or 40 etc.) to about amino acid 20, (or 130, or 140 or 150 etc.) of the 161P2F10B protein shown in FIG. 2 or FIG. 3 are embodiments of the invention. It is be appreciated that the starting and stopping positions in this paragraph refers to the specified position as well as that position plus or minus 5 residues.

161P2F10B-related proteins are generated using standard peptide synthesis technology or using chemical cleavage methods well known in the art. Alternatively, recombinant methods can be used to generate nucleic acid molecules that encode a 161P2F10B-related protein. In one embodiment, nucleic acid molecules provide a means to generate defined fragments of the 161P2F10B protein (or variants, homologs or analogs thereof).

III.A.) Motif-bearing Protein Embodiments

Additional illustrative embodiments of the invention disclosed herein include 161P2F10B polypeptides comprising the amino acid residues of one or more of the biological motifs contained within the 161P2F10B polypeptide sequence set forth in FIG. 2 or FIG. 3. Various motifs are known in the art, and a protein can be evaluated for the presence of such motifs by a number of publicly available Internet sites (see, e.g., Epimatrix™ and Epimer™, Brown University, and BIMAS).

Motif bearing subsequences of the 161P2F10B protein are set forth and identified in Table XIX.

Table XX sets forth several frequency occurring motifs based on pfam searches (see URL address pfam.waustl.edu/). The columns of Table XX list (1) motif name abbreviation, (2) percent identity found amongst the different member of the motif family, (3) motif name or description and (4) most common function; location information is included if the motif is relevant for location.

Polypeptides comprising one or more of the 161P2F10B motifs discussed above are useful in elucidating the specific characteristics of a malignant phenotype in view of the observation that the 161P2F10B motifs discussed above are associated with growth dysregulation and because 161P2F10B is overexpressed in certain cancers (See, e.g., Table I). Casein kinase II, cAMP and camp-dependent protein kinase, and Protein Kinase C, for example, are enzymes known to be associated with the development of the malignant phenotype (see e.g. Chen et al., Lab Invest., 78(2): 165–174 (1998); Gaiddon et al. Endodrinology 136 (10): 4331–4338 (1995); Hall et al., Nucleic Acids Research 24(6): 1119–1126 (1996); Peterziel et al., Oncogene 18(46): 6322–6329 (1999) and O'Brian, Oncol. Rep. 5(2): 305–309 (1998)). Moreover, both glycosylation and myristoylation are protein modifications also associated with cancer and cancer progression (see e.g. Dennis et al., Biochem. Biophys. Acta 1473(1):21–34 (1999); Raju et al., Exp. Cell Res. 235(1): 145–154 (1997)). Amidation is another protein modification also associated with cancer and cancer progression (see e.g., Treston et al., J. Natl. Cancer Inst. Monogr. (13): 169–175 (1992)).

In another embodiment, proteins of the invention comprise one or more of the immunoreactive epitopes identified in accordance with art-accepted methods, such as the peptides set forth in Tables V–XVIII. CTL epitopes can be determined using specific algorithms to identify peptides within an 161P2F10B protein that are capable of optimally binding to specified HLA alleles (e.g., Table IV; Epimatrix™ and Epimer™, Brown University, and BIMAS.) Moreover, processes for identifying peptides that have sufficient binding affinity for HLA molecules and which are correlated with being immunogenic eptiopes, are well known in the art, and are carried out without undue experimentation. In addition, processes for identifying peptides that are immunogenic epitopes, are well known in the art, and are carried out without undue experimentation either in vitro or in vivo.

Also known in the art are principles for creating analogs of such epitopes in order to modulate imunogenicity. For example, one begins with an epitope that bears a CTL or HTL motif (see, e.g., the HLA Class I and HLA Class II motifs/supermotifs of Table IV). The epitope is analoged by substituting out an amino acid at one of the specified positions, and replacing it with another amino acid specified for that position. For example, one can substitute out a deleterious residue in favor of any other residue, such as a preferred residue as defined in Table IV; substitute a less-preferred residue with a preferred residue as defined in Table IV; or substitute an originally-occurring preferred residue with another preferred residue as defined in Table IV. Substitutions can occur at primary anchor positions or at other positions in a peptide; see, e.g., Table IV.

A variety of references reflect the art regarding the identification and generation of epitopes in a protein of interest as well as analogs thereof. See, for example, WO 9733602 to Chestnut et al.; Settle, Immunogenetics 1999 50(3–4): 201–212; Sette et al., J. Immunol. 2001 166(2): 1389–1397; Sidney et al., Hum. Immunol. 1997 58(1): 12–20; Kondo et al., Immunogenetics 1997 45(4): 249–258; Sidney et al., J. Immunol. 1996 157(8): 3480–90; and Falk et al., Nature 351:290–6 (1991); Hunt et al., Science 255:1261–3 (1992); Parker et al., J. Immunol. 149:3580–7 (1992); Parker et al., J. Immunol. 152:163–75 (1994)); Kast et al., 1994 152(8): 3094–12; Borras-Cuesta et al., Hum. Immunol. 2000 6(3): 266–278; Alexander et al., J. Immunol. 2000 164(3); 164(3); 1625–1663; Alexander et al., PMID: 7895164, UI: 95202582; O'Sullivan et al., J. Immunol. 1991 147(8): 2663–2669; Alexande, et al., Immunity 1994 1(9): 751–761 and Alexnader et al., Immunol. Res. 1998 18(2): 79–92.

Related embodiments of the inventions include polypeptides comprising combinations of the different motifs set forth in Table XIX, and/or, one or more of the predicted CTL epitopes of Table V through Table XVIII, and/or, one or more of the T cell binding motifs known in the art. Preferred embodiments contain no insertions, deletions or substitutions either within the motifs or the intervening sequences of the polypeptides. In addition, embodiments which include a number of either N-terminal and/or C-terminal amino acid residues on either side of these motifs may be desirable (to, for example, include a greater portion of the polypeptide architecture in which the motif is located). Typically the number of N-terminal and/or C-terminal amino acid residues on either side of a motif is between about 1 to about 100 amino acid residues, preferably 5 to about 50 amino acid residues.

161P2F10B-related protein are embodied in many forms, preferably in isolated form. A purified 161P2F10B protein molecule will be substantially free of other proteins or molecules that impair the binding of 161P2F10B to antibody, T cell or other ligand. The nature and degree of isolation and purification will depend on the intended use. Embodiments of a 161P2F10B-related proteins include purified 161P2F10B-related proteins and functional, soluble 161P2F10B-related proteins. In one embodiment, a functional, soluble 161P2F10B protein or fragment thereof retains the ability to be bound by antibody; T cell or other ligand.

The invention also provides 161P2F10B protein comprising biologically active fragments of the 161P2F10B amino acid sequence shown in FIG. 2 or FIG. 3. Such proteins exhibit properties of the 161P2F10B protein, such as the ability to elicit the generation of antibodies that specifically bind an epitope associated with the 161P2F10B protein; to be bound by such antibodies; to elicit the activation of HTL or CTL; and/or, to be recognized by HTL or CTL.

161P2F10B-related polypeptides that contain particularly intersecting structures can be predicted and/or identified using various analytical techniques well known in the art, including, for example, the methods of Chou-Fasman, Garrier-Robson, Kyte-Doolittle, Eisenberg, Karplus-Schulz or Jameson-Wolf analysis, or on the basis of immunogenicity. Fragments that contain such structures are particularly useful in generating subunit-specific anti-161P2F10B antibodies, or T cells or in identifying cellular factors that bind to 161P2F10B.

CTL eptiopes can be determined using specific algorithms to identify peptides within an 161P2F10B protein that are capable of optimally binding to specified HLA alleles (e.g., by using the SYFPEITHI website; the listings in Table IV(A)–(E); Epimatrix™ and EPIMER™, Brown University website; and BIMAS. Illustrating this, peptide epitopes from 161P2F10B that are presented in the context of human MHC class I molecules HLA-A1, A2, A3, A11, A24, B7 and B35 were predicted (Tables V–XVIII). Specifically, the complete amino acid sequence of the 161P2F10B protein was entered into the HLA Peptide Motif Search algorithm found in the Bioinformatics and Molecular Analysis Section (BIMAS) web site listed above. The HLA peptide motif search algorithm was developed by Dr. Ken Parker based on binding of specific peptide sequences in the groove of HLA Class I molecules, in particular HLA-A2 (see, e.g., Falk et al., Nature 351: 290–6 (1991); Hunt et al., Science 255:1261–3 (1992); Parker et al., J. Immunol. 149:3580–7 (1992); Parker et al., J. Immunol. 152:163–75 (1994)). This algorithm allows location and ranking of 8-mer, 9-mer and 10-mer peptides from a complete protein sequence for predicted binding to HLA-A2 as well as numerous other HLA Class I molecules. Many HLA class I binding peptides are 8-, 9-, 10 or 11-mers. For example, for class I HLA-A2, the epitopes preferably contain a leucine (L) or methionine (M) at position 2 and a valine (V) or leucine (L) at the C-terminus (see, e.g., Parker et al., J. Imunol. 149:3580–7 (1992)). Selected results of 161P2F10B predicted binding peptides are shown in Tables V–XVIII herein. In Tables X–XVIII, the top 50 ranking candidates, 9-mers and 10-mers, for each family member are shown along with their location, the amino acid sequence of each specific peptide, and an estimated binding score. The binding score corresponds to the estimated half time of dissociation of complexes containing the peptides at 37° C. at pH 6.5. Peptides with the highest building score are predicted to be the most tightly bound to HLA Class I on the cell surface for the greatest period of time and thus represent the best immunogenic targets for T-cell recognition.

Actual binding of peptides to an HLA allele can be evaluated by stabilization of HLA expression on the antigen-processing defective cell line T2 (see, e.g., Xue et al., Prostate 30:73–8 (1997) and Peshwa et al., Prostate 36:129–38 (1998). Immunogenicity of specific peptides can be evaluated in vitro by stimulation of CD8+ cytotoxic T lymphocytes (CTL) in the presence of antigen presenting cells such as dendritic cells.

It is to be appreciated that every epitope predicted by the BIMAS site, Epimer™ and Epimatrix™ sites, or specified by the HLA class I or class II motifs available in the art or which become part of the art such as set forth in Table IV (or determined using World Wide Web site URL syfpeithi.bmi-heidelberg.com/) are to be "applied" to the 161P2F10B protein. As used in this context "applied" means that the 161P2F10B protein is evaluated, e.g., visually or by computer-based patterns finding methods, as appreciated by those of skill in the relevant art. Every subsequence of the 161P2F10B of 8, 9, 10, or 11 amino acid residues that bears an HLA Class I motif, or a subsequence of 9 or more amino acid residues that bear an HLA Class II motif are within the scope of the invention.

III.B.) Expression of 161P2F10B-related Proteins

In an embodiment described in the examples that follow, 161P2F10B can be conveniently expressed in cells (such as 293T cells) transfected with a commercially available expression vector such as a CMV-driven expression vector encoding 161P2F10B with a C-terminus 6×His and MYC tag (pcDNA3.1/mycHIS, Invitrogen or Tag5, GenHunter Corporation, Nashville, Tenn.). The Tag5 vector provides an IgGK secretion signal that can be used to facilitate the production of a secreted 161P2F10B protein in transfected cells. The secreted HIS-tagged 161P2F10B in the culture media can be purified, e.g., using a nickel column using standard techniques.

III.C.) Modifications of 161P2F10B-related Proteins

Modifications of 161P2F10B-related proteins such as covalent modifications are included within the scope of this invention. One type of covalent modification includes reacting targeted amino acid residues of a 161P2F10B polypeptide with an organic derivatizing agent that is capable of reacting with selected side chains or the N- or C-terminal residues of the 161P2F10B. Another type of covalent modification of the 161P2F10B polypeptide included within the scope of this invention comprises altering the native glycosylation pattern of a protein of the invention. Another type of covalent modification of 161P2F10B comprises linking the 161P2F10B polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The 161P2F10B-related proteins of the present invention can also be modified to form a chimeric molecule comprising 161P2F10B fused to another, heterologous polypeptide or amino acid sequence. Such a chimeric molecule can be synthesized chemically or recombinantly. A chimeric molecule can have a protein of the invention fused to another tumor-associated antigen or fragment thereof. Alternatively, a protein in accordance with the invention can comprise a fusion of fragments of the 161P2F10B sequence (amino or nucleic acid) such that a molecule is created that is not, through its length, directly homologous to the amino acid or nucleic acid sequences shown in FIG. 2 or FIG. 3. Such a chimeric molecule can comprise multiples of the same subsequence of 161P2F10B. A chimeric molecule can comprise a fusion of a 161P2F10B-related protein with a polyhistidine eptiope tag, which provides an eptiope to which immobilized nickel can selectively bind, with cytokines or with growth factors. The epitope tag is generally placed at the amino- or carboxy-terminus of the 161P2F10B. In an alternative embodiment, the chimeric molecule can comprise a fusion of a 161P2F10B-related protein with an immunoglobulin or a particular region of an immunoglobulin. For a bivalent form of the chimeric molecule (also referred to as "immunoadhesin"), such a fusion could be to the Fc region of an IgG molecule. The Ig fusions preferably include the substitution of a soluble (transmembranes domain deleted or inactivated) form a 161P2F10B polypeptide in place of at least one variable region within an Ig molecule. In a preferred embodiment, the immunoglobulin fusion includes the hinge, CH2 and CH3, or the hinge, CH1, CH2 and CH3 regions of an IgGI molecule. For the production of immunoglobulin fusions, see, e.g., U.S. Pat. No. 5,428,130 issued Jun. 27, 1995.

III.D.) uses of 161P2F10B-related Proteins

The proteins of the invention have a number of different specific uses. As is highly expressed in prostate and other, 161P2F10B-related proteins are used in methods that assess the status of 161P2F10B gene products in normal versus cancerous tissues, thereby elucidating the malignant phenotype. Typically, polypeptides from specific regions of the 161P2F10B protein are used to assess the presence of perturbations (such as deletions, insertions, point mutations etc.) in those regions (such as regions containing one or more motifs). Exemplary assays utilize antibodies or T cells targeting 161P2F10B-related proteins comprising the amino acid residues of one or more of the biological motifs contained within the 161P2F10B polypeptide sequence in order to evaluate the characteristics of this region in normal versus cancerous tissues or to elicit an immune response to the epitope. Alternatively, 161P2F10B-related proteins that contain the amino acid residues of one or more of the biological motifs in the 161P2F10B protein are used to screen for factors that interact with that region of 161P2F10B.

161P2F10B protein fragments/subsequences are particularly useful in generating and characterizing domain-specific antibodies (e.g., antibodies recognizing an extracellular or intracellular epitope of an 161P2F10B protein), for identifying agents or cellular factors that bind to 161P2F10B or a particular structural domain thereof, and in vacuo therapeutic and diagnostic contexts, including but not limited to diagnostic assays, cancer vaccines and methods of preparing such vaccines.

Proteins encoded by the 161P2F10B genes, or by analogs, homologs or fragments thereof, have a variety of uses, including but not limited to generating antibodies and in methods for identifying ligands and other agents and cellular constituents that bind to an 161P2F10B gene product. Antibodies raised against an 161P2F10B protein or fragment thereof are useful in diagnostic and prognostic and prognostic assays, and imaging methodologies in the management of human cancers characterized by expression of 161P2F10B protein, such as those listed in Table I. Such antibodies can be expressed intracellularly and used in methods of treating patients with such cancers. 161P2F10B-related nucleic acids or proteins are also used in generating HTL or CTL responses.

Various immunological assays useful for the detection of 161P2F10B proteins are used, including but not limited to various types of radioimmunoassays, enzyme-linked immunosorbent assays (ELISA), enzyme-linked immunofluorescent assays (ELIFA), immunocytochemical methods, and the like. Antibodies can be labeled and used as immunological imaging reagents capable of detecting 161P2F10B-expressing cells (e.g., in radioscintigraphic imaging methods). 161P2F10B proteins are also particularly useful in generating cancer vaccines, as further described herein.

IV.) 161P2F10B Antibodies

Another aspect of the invention provides antibodies that bind to 161P2F10B-related proteins. Preferred antibodies specifically bind to a 161P2F10B-related protein and do not bind (or bind weakly) to peptides or proteins that are not 116P2F10B-related proteins. For example, antibodies that bind 161P2F10B can bind 161P2F10B-related proteins such as the homologs or analogs thereof.

161P2F10B antibodies of the invention are particularly useful in cancer (see, e.g., Table I) diagnostic and prognostic assays, and imaging methodologies. Similarly, such antibodies are useful in the treatment, diagnosis, and/or prognosis of other cancers, to the extent 161P2F10B is also expressed or overexpressed in these other cancers. Moreover, intracellularly expressed antibodies (e.g., single chain antibodies) are therapeutically useful in treating cancers in which the expression of 161P2F10B is involved, such as advanced or metastatic prostate cancers.

The invention also provides various immunological assays useful for the detection and quantification of 161P2F10B and mutant 161P2F10B-related proteins. Such assays can comprise one or more 161P2F10B antibodies capable of recognizing and binding a 161P2F10B-related protein, as appropriate. These assays are performed within various immunological assay formats well known in the art, including but not limited to various types of radioimmunoassays, enzyme-linked immunosorbent assays (ELISA), enzyme-linked immunofluorescent assays (ELIFA), and the like.

Immunological non-antibody assays of the invention also comprise T cell immunogenicity assays (unhibitory or stimulatory) as well as major histocompatibility complex (MHC) binding assays.

In addition, immunological imaging methods capable of detecting prostate cancer and other cancers expressing 161P2F10B are also provided by the invention, including but not limited to radioscintigraphic imaging methods using labeled 161P2F10B antibodies. Such assays are clinically useful in the detection, monitoring, and prognosis of 161P2F10B expressing cancers such as prostate cancer.

161P2F10B antibodies are also used in methods for purifying a 161P2F10B-related protein and for isolating 161P2F10B homologues and related molecules. For example, a method of purifying a 161P2F10B-related protein comprises incubating an 161P2F10B antibody, which has been coupled to a solid matrix, with a lysate or other solution containing a 161P2F10B-related protein under conditions that permit the 161P2F10B antibody to bind to the 161P2F10B-related protein, washing the solid matrix to eliminate impurities; and eluting the 161P2F10B-related protein from the coupled antibody. Other uses of the 161P2F10B antibodies of the invention include generating anti-idiotypic antibodies that mimic the 161P2F10B protein.

Various methods for the preparation of antibodies are well known in the art. For example, antibodies can be prepared by immunizing a suitable mammalian host using a 161P2F10b-related protein, peptide, or fragment, in isolated or immunoconjugated form (Antibodies: A Laboratory Manual, CSH Press, Eds., Harlow, and Lane (1988); Harlow, Antibodies, Cold Spring Harbor Press, N.Y. (1989)). In addition, fusion proteins of 161P2F10B can also be used, such as 161P2F10B GST-fusion protein. In a particular embodiment, a GST fusion protein comprising all or most of the amino acid sequence of FIG. 2 or FIG. 3 is produced, then used as an immunogen to generate appropriate antibodies. In another embodiment, a 161P2F10B-related protein is synthesized and used as an immunogen.

In addition, naked DNA immunization techniques known in the art are used (with or without purified 161P2F10B-related protein or 161P2F10B protein expressing cells) to generate response to the encoded immunogen (for review, see Donnelly et al., 1997, Ann. Rev. Immunol. 15:617–648).

The amino acid sequence of 161P2F10B as shown in FIG. 2 or FIG. 3 can be analyzed to select specific regions of the 161P2F10B protein for generating antibodies. For example, hydrophobicity and hydrophophilicity analyses of the 161P2F10B amino acid sequence are used to identify hydrophilic regions in the 161P2F10B structure. Regions of the 161P2F10B gene protein that show immunogenic structure, as well as other regions and domains, can readily be identified using various other methods known in the art, such as Chou-Fasman, Garnier-Robson, Kyle-Doolittle, Eisenberg, Karplus-Schultz or Jameson-Wolf analysis. Thus, each region identified by any of these programs or methods is within the scope of the present invention. Methods for the generation of 161P2F10B antibodies are further illustrated by way of the examples provided herein. Methods for preparing a protein or polypeptide for use as an immunogen are well known in the art. Also well known in the art are methods for preparing immunogenic conjugates of a protein with a carrier, such as BSA, KLH or other carrier protein. In some circumstances, direct conjugation using, for example, carbodiimide reagents are used; in other instances linking reagents such as those supplied by Pierce Chemical Co., Rockford, Ill., are effective. Administration of a 161P2F10B immunogen is often conducted by injection over a suitable time period and with use of a suitable adjuvant, as is understood in the art. During the immunization schedule, titers of antibodies can be taken to determine adequacy of antibody formation.

161P2F10B monoclonal antibodies can be produced by various means well known in the art. For example, immortalized cell lines that secrete a desired monoclonal antibody are prepared using the standard hybridoms technology of Kohler and Milstein or modifications that immortalize antibody-producing B cells, as is generally known. Immortalized cell lines that secrete the desired antibodies are screened by immunoassay in which the antigen is a 161P2F10B-related protein. When the appropriate immortalized cell culture is identified, the cells can be expanded and antibodies produced either from in vitro cultures or from ascites fluid.

The antibodies or fragments of the invention can also be produced, by recombinant means. Regions that bind specifically to the desired regions of the 161P2F10B protein can also be produced in the context of chimeric or complementarity determining region (CDR) grafted antibodies of multiple species origin. Humanized or human 161P2F10B antibodies can also be produced, and are preferred for use in therapeutic contexts. Methods for humanizing murine and other non-human antibodies, by substituting one or more of the non-human antibody CDRs for corresponding human antibody sequences, are well known (see for example, Jones et al., 1986, Nature 321:522–525; Riechmann et al., 1988, Nature 332: 323–327; Verhoeyen et al., 1988, Science 239: 1534–1536). See also, Carter et al., 1993, Proc. Natl. Acad. Sci. USA 89: 4285 and Sims et al, 1993, *J. Immunol.* 151:2296.

Methods for producing fully human monoclonal antibodies include phage display and transgenic methods (for review, see Vaughan et al., 1998, Nature Biotechnology 16: 535–539). Fully human 161P2F10B monoclonal antibodies can be generated using cloning technologies employing large human 1 g gene combinatorial libraries (i.e., phage display) (Griffiths and Hoogenboom, Building an in vitro immune system: human antibodies from phage display libraries. In: Protein Engineering of Antibody Molecules for Prophylactic and Therapeutic Applications in Man, Clark, M. (Ed.), Nottingham Academic, pp 45–64 (1993); Burton and Barbas, Human Antibodies from combinatorial libraries Id., pp 65–82). Fully human 161P2F10B monoclonal antibodies can also be produced using transgenic mice engineered to contain human immunoglobulin gene loci as described in PCT Patent Application WO98/24893, Kucherlapati and Jakobovits et al., published Dec. 3, 1997 (see also, Jakobovits, 1998, Exp. Opin. Invest. Drugs 7(4): 607–614; U.S. Pat. Nos. 6,162,963 issued 19 Dec. 2000; 6,150,584 issued 12 Nov. 2000; and 6,114,598 issued 5 Sep. 2000). This method avoids the in vitro manipulation required with phage display technology and efficiently produces high affinity authentic human antibodies.

Reactivity of 161P2F10B antibodies with an 161P2F10B-related protein can be established by a number of well known means, including Western blot, immunoprecipitation, ELISA, and FACS analyses using, as appropriate, 161P2F10B-related proteins, 161P2F10B-expressing cells or extracts thereof. A 161P2F10B antibody or fragment thereof can be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. Further, bi-specific antibodies specific for two or more 161P2F10B epitopes are generated using methods generally known in the art. Homodimeric antibodies can also be generated by cross-linking techniques known in the art (e.g., Wolff et al., Cancer Res. 53: 2560–2565).

V.) 161P2F10B Cellular Immune Responses

The mechanism by which T cells recognize antigens has been delineated. Efficacious peptide epitope vaccine compositions of the invention induce a therapeutic or prophylactic immune responses in very broad segments of the world-wide population. For an understanding of the value and efficacy of compositions of the invention that induce cellular immune responses, a brief review of immunology-related technology is provided.

A complex of an HLA molecule and a peptidic antigen acts as the ligand recognized by HLA-restricted T cells (Buus, S. et al., *Cell* 47:1071, 1986; Babbitt, B. P. et al., *Nature* 317:359, 1985; Townsend, A. and Bodmer, H., *Annu. Rev. Immunol.* 7:601, 1989; Germain, R. N., *Annu. Rev. Immunol.* 11:403, 1993). Through the study of single amino acid substituted antigen analogs and the sequencing of endogenously bound, naturally processed peptides, critical residues that correspond to motifs required for specific binding to HLA antigen molecules have been identified and are set forth in Table IV (see also, e.g., Southwood, et al., *J. Immunol.* 160:3363, 1998; Rammensee, et al., *Immunogenetics* 41:178, 1995; Rammensee et al., *SYFPEITH*1, access via World Wide Web at URL, syfpeithi.bmi-heidelberg.com/; Sette, A. and Sidney, *J. Curr. Opin. Immunol.* 10:478, 1998; Engelhard, V. H., *Curr. Opin. Immunol.* 6:13, 1994; Sette, A. and Grey, H. M., *Curr. Opin. Immunol.* 4:79, 1992; Sinigaglia, F. and Hammer, *J. Curr. Biol.* 6:52, 1994; Ruppert et al., *Cell* 74:929–937, 1993; Kondo et al. *J. Immunol.* 155:4307–4312, 1995; Sidney et al., *J. Immunol.* 157:3480–3490, 1996; Sidney et al., *Human Immunol.* 45:79–93, 1996; Sette, A. and Sidney, *J. Immunogenetics* 1999 Nov; 50(3–4):201–12, Review).

Furthermore, x-ray crystallographic analyses of HlLA-peptide complexes have revealed pockets within the peptide binding cleft/groove of HLA molecules which accommodate, in an allele-specific mode, residues borne by peptide ligands; these residues in turn determine the HLA binding capacity of the peptides in which they are present (See, e.g., Madden, D. R. *Annu. Rev. Immunol.* 13:587, 1995; Smith, et al., *Immunity* 4:203, 1996; Fremont et al., *Immunity* 8:305, 1998; Stern et al., *Structure* 2:245, 1994; Jones, E. Y. *Curr. Opin. Immunol.* 9:75, 1997; Brown, J. H. et al., *Nature* 364:33, 1993; Guo, H. C. et al., *Proc. Natl. Acad. Sci. USA* 90:8053, 1993; Guo, H. C. et al., *Nature*

360:364, 1992; Silver, M. L. et al., *Nature* 360:367, 1992; Matsumura, M. et al., *Science* 257:927, 1992; Madden et al., *Cell* 70:1035, 1992; Fremont, D. H. et al., *Science* 257:919, 1992; Saper, M. A., Bjorkman, P. J. and Wiley, D. C., *J. Mol. Biol.* 219:277, 1991.)

Accordingly, the definition of class I and class II allele-specific HLA binding motifs, or class I or class II supermotifs allows identification of regions within a protein that are correlated with binding to particular HLA antigen(s).

Thus, by a process of HLA motif identification, candidates for epitope-based vaccines have been identified; such candidates can be further evaluated by HLA-peptide binding assays to determine binding affinity and/or the time period of association of the epitope and its corresponding HLA molecule. Additional confirmatory work can be performed to select, amongst these vaccine candidates, epitopes with preferred characteristics in terms of population coverage, and/or immunogenicity.

Various strategies can be utilized to evaluate cellular immunogenicity, including:

1) Evaluation of primary T-cell cultures from normal individuals (see, e.g., Wentworth, P. A. et al., *Mol. Immunol.* 32:603, 1995; Celis, E. et al., *Proc. Natl. Acad. Sci. USA* 91:2105, 1994; Tsai, V. et al., *J. Immunol.* 158:1796, 1997; Kawashima, I. et al., *Human Immunol.* 59:1, 1998). This procedure involves the stimulation of peripheral blood lymphocytes (PBL) from normal subjects with a test peptide in the presence of antigen processing cells in vitro over a period of several weeks. T cells specific for the peptide become activated during this time and are detected using, e.g., a lymphokine- or $^{51}$Cr-release assay involving peptide sensitized target cells.

2) Immunization of HLA transgenic mice (see, e.g., Wentworth, P. A. et al., *J. Immunol.* 26:97, 1996; Wentworth, P. A. et al., *Int. Immunol.* 8:651, 1996; Alexander, J. et al., *J. Immunol.* 159:4753, 1997). For example, in such methods peptide in incomplete Freund's adjuvant are administered subcutaneously to HLA transgenic mice. Several weeks following immunization, splenocytes are removed and cultured in vitro in the presence of test peptide for approximately one week. Peptide-specific T cells are detected using, e.g., a $^{51}$Cr-release assay involving peptide sensitized target cells and target cells expressing endogenously generated antigen.

3) Demonstration of recall T cell response from immune individuals who have been either effectively vaccinated and/or from chronically ill patients (ee, e.g., Rehermann, B. et al., *J. Exp. Med.* 181:1047, 1995; Doolan, D. L. et al., *Immunity* 7:97, 1997; Bertoni, R. et al., *J. Clin. Invest.* 100:503, 1997; Threlkeld, S. C. et al. *J. Immunol.* 159:1648, 1997; Diepolder, H. M. et al., *J. Virol.* 71:6011, 1997). Accordingly, recall responses are detected by culturing PBL from subjects that have been exposed to the antigen due to disease and thus have generated an immune response "naturally", or from patients who were vaccinated against the antigen. PBL from subjects are cultured in vitro for 1–2 weeks in the presence of test peptide plus antigen presenting cells (APC) to allow activation of "memory" T cells, as compared to "naive" T cells. At the end of the culture period, T cell activity is detected using assays including $^{51}$Cr release involving peptide-sensitized targets, T cell proliferation, or lymphokine release.

VI.) 161P2F10B Transgenic Animals

Nucleic acids that encode a 161P2F10B-related protein can also be used to generate either transgenic animals or "knock out" animals which, in turn, are useful in the development and screening of therapeutically useful reagents. In accordance with established techniques, cDNA encoding 161P2F10B can be used to clone genomic DNA that encodes 161P2F10B. The cloned genomic sequences can then be used to generate transgenic animals containing cells that express DNA that encode 161P2F10B. Methods for generating transgenic animals, particularly animals such as mice or rats, have become conventional in the art and are described, for example, in U.S. Pat. Nos. 4,736,866 issued 12 Apr. 1988, and 4,870,009 issued 26 Sep. 1989. Typically, particular cells would be targeted for 161P2F10B transgene incorporation with tissue-specific enhancers.

Transgenic animals that include a copy of a transgene encoding 161P2F10B can be used to examine the effect of increased expression of DNA that encodes 161P2F10B. Such animals can be used as tester animals for reagents thought to confer protection from, for example, pathological conditions associated with its overexpression. In accordance with this aspect of the invention, an animal is treated with a reagent and a reduced incidence of a pathological condition, compared to untreated animals that bear the transgene, would indicate a potential therapeutic intervention for the pathological condition.

Alternatively, non-human homologues of 161P2F10B can be used to construct a 161P2F10B "knock out" animal that has a defective or altered gene encoding 161P2F10B as a result of homologous recombination between the endogeneous gene encoding 161P2F10B and altered genomic DNA encoding 161P2F10B introduced into an embryonic cell of the animal. For example, cDNA that encodes 161P2F10B can be used to clone genomic DNA encoding 161P2F10B in accordance with established techniques. A portion of the genomic DNA encoding 161P2F10B can be deleted or replaced with another gene, such as a gene encoding a selectable marker that can be used to monitor integration. Typically, several kilobases of unaltered flanking DNA (both at the 5' and 3' ends) are included in the vector (see, e.g., Thomas and Capechhi, *Cell,* 51:503 (1987) for a description of homologous recombination vectors). The vector is introduced into an embryonic stem cell line (e.g., by electroporation) and cells in which the introduced DNA has homologously recombined with the endogenous DNA are selected (see, e.g., Li et al., *Cell,* 69:915 (1992)). The selected cells are then injected into a blastocyst of an animal (e.g., a mouse or rat) to form aggregation chimeras (see, e.g., Bradley, in *Teratocarcinomas and Embryonic Stem Cells: A Practical Approach,* E. J. Robertson, ed. (IRL, Oxford, 1987), pp. 113–152). A chimerci embryo can then be implanted into a suitable pseudopregnant female foster animal, and the embryo brought to term to create a "knock out" animal. Progeny harboring the homologously recombinant DNA in their germ cells can be identified by standard techniques and used to breed animals in which all cells of the animal contain the homologously recombined DNA. Knock out animals can be characterized, for example, for their ability to defend against certain pathological conditions or for their development of pathological conditions due to absence of the 161P2F10B polypeptide.

VII.) Methods for the Detection of 161P2F10B

Another aspect of the present invention relates to methods for detecting 161P2F10B polynucleotides and 161P2F10B-related protein, as well as methods for identifying a cell that expresses 161P2F10B. The expression profile of 161P2F10B makes it a diagnostic marker for metastasized disease. Accordingly, the status of 161P2F10B gene products provides information useful for predicting a variety of factors including susceptibility to advanced stage disease, rate of progression, and/or tumor aggressiveness. As discussed in detail herein, the status of 161P2F10B gene products in patient samples can be analyzed by a variety of protocols that are well known in the art including immunohistochemical analysis, the variety of Northern blotting techniques including in situ hybridization, RT-PCR analysis (for example on laser capture micro-dissected samples), Wester blot analysis and tissue array analysis.

More particularly, the invention provides assays for the detection of 161P2F10B polynucleotides in a biological sample, such as serum, bone, prostate, and other tissues, urine, semen, cell preparation, and the like. Detectable 161P2F10B polynucleotides include, for example, a 161P2F10B gene or fragment thereof, 161P2F10B mRNA, alternative splice variant 161P2F10B mRNAs, and recombinant DNA or RNA molecules that contain a 161P2F10B polynucleotide. A number of methods for amplifying and/or detecting the presence of 161P2F10B polynucleotides are well known in the art and can be employed in the practice of this aspect of the invention.

In one embodiment, a method for detecting an 161P2F10B mRNA in a biological sample comprises producing cDNA from the sample by reverse transcription using at least one primer; amplifying the cDNA so produced using an 161P2F10B polynucleotides as sense and antisense primers to amplify 161P2F10B cDNAs therein; and detecting the presence of the amplified 161P2F10B cDNA. Optionally, the sequence of the amplified 161P2F10B cDNA can be determined.

In another embodiment, a method of detecting a 161P2F10B gene in a biological sample comprises first isolating genomic DNA from the sample; amplifying the isolated genomic DNA using 161P2F10B polynucleotide as sense and antisense primers; and detecting the presence of the amplified 161P2F10B gene. Any number of appropriate sense and antisense probe combinations can be designed from the nucleotide sequence provided for the 161P2F10B (FIG. 2) and used for this purpose.

The invention also provides assays for detecting the presence of an 161P2F10B protein in a tissue or other biological sample such as serum, semen, bone, prostate, urine, cell preparations, and the like. Methods for detecting a 161P2F10B-related protein are also well known and include, for example, immunoprecipitation, immunohistochemical analysis, Western blot analysis, molecular binding assays, ELISA, ELIFA and the like. For example, a method of detecting the presence of a 161P2F10B-related protein in a biological sample comprises first contacting the sample with a 161P2F10B antibody, a 161P2F10B-reactive fragment thereof, or a recombinant protein containing an antigen binding region of a 161P2F10B antibody; and then detecting the binding of 161P2F10B-related protein in the sample.

Methods for identifying a cell that expresses 161P2F10B are also within the scope of the invention. In one embodiment, an assay for identifying a cell that expresses a 161P2F10B gene comprises detecting the presence of 161P2F10B mRNA in the cell. Methods for the detection of particular mRNAs in cells are well known and include, for example, hybridization assays using complementary DNA probes (such as in situ hybridization using labeled 161P2F10B riboprobes, Northern blot and related techniques) and various nucleic acid amplification assays (such as RT-PCR using complementary primers specific for 161P2F10B, and other amplification type detection methods, such as, for example, branched DNA, SISBA, TMA and the like). Alternatively, an assay for identifying a cell that expresses a 161P2F10B gene comprises detecting the presence of 161P2F10B-related protein in the cell or secreted by the cell. Various methods for the detection of proteins are well known in the art and are employed for the detection of 161P2F10B-related proteins and cells that express 161P2F10B-related proteins.

161P2F10B expression analysis is also useful as a tool for identifying and evaluating agents that modulate 161P2F10B gene expression. For example, 161P2F10B expression is significantly upregulated in prostate cancer, and is expressed in cancers of the tissues listed in Table I. Identification of a molecule or biological agent that inhibits 161P2F10B expression or over-expression in cancer cells is a therapeutic value. For example, such an agent can be identified by using a screen that quantifies 161P2F10B expression by RT-PCR, nucleic acid hybridization or antibody binding.

VII.) Methods for Monitoring the Status of 161P2F10B-related Genes and Their Products Oncogenesis is known to be a multistep process where cellular growth becomes progressively dysregulated and cells progress from a normal physiological state to precancerous and then cancerous states (see, e.g., Alers et al., Lab Invest. 77(5): 437–438 (1997) and Issacs et al., Cancer Surv. 23: 19–32 (1995)). In this context, examining a biological sample for evidence of dysregulated cell growth (such as aberrant 161P2F10B expression in cancers) allows for early detection of such aberrant physiology, before a pathologic state such as cancer has progressed to a stage that therapeutic options are more limited and or the prognosis is worse. In such examinations, the status of 161P2F10B in a biological sample of interest can be compared, for example, to the status of 161P2F10B in a corresponding normal sample (e.g. a sample from that individual or alternatively another individual that is not affected by a pathology). An alteration in the status of 161P2F10B in the biological sample (as compared to the normal sample) provides evidence of dysregulated cellular growth. In addition to using a biological sample that is not affected by a pathology as a normal sample, one can also use a predetermined normative value such as a predetermined normal level of mRNA expression (see, e.g., Grever et al., J. Comp. Neurol. 1996 Dec. 9; 376(2):306–14 and U.S. Pat. No. 5,837,501) to compare 161P2F10B status in a sample.

The term "status" in this context is used according to its art accepted meaning and refers to the condition or state of a gene and its products. Typically, skilled artisans use a number of parameters to evaluate the condition or state of a gene and its products. These include, but are not limited to the location of expressed gene products (including the location of 161P2F10B expressing cells) as well as the level, and biological activity of expressed gene products (such as 161P2F10B mRNA, polynucleotides and polypeptides). Typically, an alteration in the status of 161P2F10B comprises a change in the location of 161P2F10B and/or 161P2F10B expressing cells and/or an increase in 161P2F10B mRNA and/or protein expression.

161P2F10B status in a sample can be analyzed by a number of means well known in the art, including without limitation, immunohistochemical analysis, in situ hybridization, RT-PCR analysis on laser capture microdissected samples. Western blot analysis, and tissue array analysis. Typical protocols for evaluating the status of the 161P2F10B gene and gene products are found, for example in Ausubel et al. eds., 1995, Current Protocols In Molecular Biology, Units 2 (Northern Blotting), 4 (Southern Blotting), 15 (Immunoblotting) and 18 (PCR Analysis). Thus, the status of 161P2F10B in a biological sample is evaluated by various methods utilized by skilled artisans including, but not limited to genomic Southern analysis (to examine, for example perturbations in the 161P2F10B gene), Northern analysis and/or PCR analysis of 161P2F10B mRNA (to examine, for example alterations in the polynucleotide sequences or expression levels of 161P2F10B mRNAs), and, Western and/or immunohistochemical analysis (to examine, for example alterations in polypeptide sequences, alterations in polypeptide localization within a sample, alterations in expression levels of 161P2F10B proteins and/or associations of 161P2F10B proteins with polypeptide binding partners). Detectable 161P2F10B polynucleotides include, for example, a 161P2F10B gene or fragment thereof, 161P2F10B mRNA, alternative splice variants, 161P2F10B mRNAs, and recombinant DNA or RNA molecules a 161P2F10B polynucleotide.

The expression profile of 161P2F10B makes it a diagnostic marker for local and/or metastasized disease, and provides information on the growth or oncogenic potential of a biological sample. In particular, the status of 161P2F10B provides information useful for predicting susceptibility to particular disease stages, progression, and/or tumor aggressiveness. The invention provides methods and assays for determining 161P2F10B status and diagnosing cancers that express 161P2F10B, such as cancers of the tissues listed in Table 1. For example, because 161P2F10B mRNA is so highly expressed in prostate and other cancers relative to normal prostate tissue, assays that evaluate the levels of 161P2F10B mRNA transcripts or proteins in a biological sample can be used to diagnose a disease associated with 161P2F10B dysregulation, and can provide prognostic information useful in defining appropriate therapeutic options.

The experience status of 161P2F10B provides information including the presence, stage and locations of dysplastic, precancerous and cancerous cells, predicting susceptibility to various stages of disease, and/or for gauging tumor aggressiveness. Moreover, the expression profile makes it useful as an imaging reagent for metastasized disease. Consequently, an aspect of the invention is directed to the various molecular prognostic and diagnostic methods for examining the status of 161P2F10B in biological samples such as those from individuals suffering from, or suspected of suffering from a pathology characterized by dysregulated cellular growth, such as cancer.

As described above, the status of 161P2F10B in a biological sample can be examined by a number of well-known procedures in the art. For example, the status of 161P2F10B in a biological sample taken from a specific location in the body can be examined by evaluating the sample for the presence or absence of 161P2F10B expressing cells (e.g. those that express 161P2F10B mRNAs or proteins). This examination can provide evidence of dysregulated cellular growth, for example, when 161P2F10B-expressing cells are found in a biological sample that does not normally contain such cells (such as a lymph node), because such alternations in the status of 161P2F10B in a biological sample are often associated with dysregulated cellular growth. Specifically, one indicator of dysregulated cellular growth is the metastases of cancer cells from an organ of origin (such as the prostate) to a different area of the body (such as a lymph node). In this context, evidence of dysregulated cellular growth is important for example because occult lymph metastases can be detected in a substantial proportion of patients with prostate cancer, and such metastases are associated with known predictors of disease progression (see, e.g., Murphy et al. Prostate 42(4): 315–371 (2000); Su et al., Semin. Starg. Oncol. 18(1): 17–28 (2000) and Freeman et al., J Urol 1995 Aug 154(2 Pt 1):474–8).

In one aspect, the invention provides methods for monitoring 161P2F10B gene products by determining the status of 161P2F10B gene products expressed by cells from an individual suspected of having a disease associated with dysregulated cell growth (such as hyperplasia or cancer) and then comparing the status so determined to the status of 161P2F10B gene products in a corresponding normal sample. The presence of aberrant 161P2F10B gene products in the test sample relative to the normal sample provides an indication of the presence of dysregulated cell growth within the cells of the individual.

In another aspect, the invention provides assays useful in determining the presence of cancer in an individual, comprising detecting a significant increase in 161P2F10B mRNA or protein expression in a test cell or tissue sample relative to expression levels in the corresponding normal cell or tissue. The presence of 161P2F10B mRNA can, for example, be evaluated in tissue samples including but not limited to those listed in Table I. The presence of significant 161P2F10B expression in any of these tissues is useful to indicate the emergence, presence and/or severity of a cancer, since the corresponding normal tissues do not express 161P2F10B mRNA or express it at lower levels.

In a related embodiment, 161P2F10B status is determined at the protein level rather than at the nucleic acid level. For example, such a method comprises determining the level of 161P2F10B protein expressed by cells in a test tissue sample and comparing the level so determined to the level of 161P2F10B expressed in a corresponding normal sample. In one embodiment, the presence of 161P2F10B protein is evaluated, for example, using immunohistochemical methods. 161P2F10B antibodies or binding partners capable of detecting 161P2F10B protein expression are used in a variety of assay formats well known in the art for this purpose.

In a further embodiment, one can evaluate the status of 161P2F10B nucleotide and amino acid sequences in a biological sample in order to identify perturbations in the structure of these molecules. These perturbations can include insertions, deletions, substitutions and the like. Such evaluations are useful because perturbations in the nucleotide and amino acid sequences are observed in a large number of proteins associated with a growth dysregulated phenotype (see, e.g., Marrogi et al., 1999, J. Cutan. Pathol. (26(8):369–378). For example, a mutation in the sequence of 161P2F10B may be indicative of the presence or promotion of a tumor. Such assays therefore have diagnostic and predictive value where a mutation in 161P2F10B indicates a potential loss of function or increase in tumor growth.

A wide variety of assays for observing perturbations in nucleotide and amino acid sequences are well known in the art. For example, the size and structure of nucleic acid or amino acid sequences of 161P2F10B gene products are observed by the Northern, Southern, Western, PCR and DNA sequencing protocols discussed herein. In addition, other methods for observing perturbations in nucleotide and amino acid sequences such as single strand conformation polymorphism analysis are well known in the art (see, e.g., U.S. Pat. Nos. 5,382,510 issued 7 Sep. 1999, and 5,952,170 issued 17 Jan. 1995).

Additionally, one can examine the methylation status of the 161P2F10B gene to a biological sample. Aberrant demethylation and/or hypermethylation of CpG islands is gene 5' regulatory regions frequently occurs in immortalized and transformed cells, and can result in altered expression of various genes. For example, promoter hypermethylation of the pi-class glutathione S-transferase (a protein expressed in normal prostate but not expressed in >90% of prostate carcinomas) appears to permanently silence transcription of this gene and is the most frequently detected alteration in prostate carcinomas (De Marzo et al., Am. J. Pathol. 155(6): 1985–1992 (1999)). In addition, this alteration is present in at least 70% of cases of high-grade prostatic intraepithelial neoplasia (PIN) (Brooks et al, Cancer Epidemiol. Biomarkers Prev., 1998, 7:531–536). In another example, expression of the LAGE-1 tumor specific gene (which is not expressed in normal prostate but is expressed in 25–50% of prostate cancers) is induced by deoxy-azacytidine in lymphoblastoid cells, suggesting that tumoral expression is due to demethylation (Lethe et al., Int. J. Cancer 76(6):903–908 (1998)). A variety of assays for examining methylation status of a gene are well known in the art. For example, one can utilize, in Southern hybridization approaches, methylation-sensitive restriction enzymes which cannot cleave sequences that contain methylated CpG sites to assess the methylation status of CpG islands. In addition, MSP (methylation specific PCR) can rapidly profile the methylation status of all the CpG sites present in a CpG island of a given gene. This procedure involves initial modification of DNA by sodium bisulfite (which will convert all unmethylated cytosines to uracil) followed by amplification using primers specific for methylated versus unmethylated DNA. Protocols involving methylation interference can also be found for example in Current Protocols in Molecular Biology, Unit 12, Frederick M. Ausubel et al. eds., 1995.

Gene amplification is an additional method for assessing the status of 161P2F10B. Gene amplification is measured in a sample directly, for example, by conventional Southern blotting or Northern blotting to quantitative the transcription of mRNA. (Thomas, 1980, Proc. Natl. Acad. Sci. USA, 77:5201–5205), dot blotting (DNA analysis), or in situ hybridization, using an appropriately labeled probe, based on the sequences provided herein. Alternatively, antibodies are employed that recognize specific duplexes, including DNA duplexes, RNA duplexes, and DNA-RNA hybrid duplexes or DNA-proteins duplexes. The antibodies in turn are labeled and the assay carried out where the duplex is bound to a surface, so that upon the formation of duplex on the surface, the presence of antibody bound to the duplex can be detected.

Biopsied tissue or peripheral blood can be conveniently assayed for the presence of cancer cells using for example, Northern, dot blot or RT-PCR analysis to detect 161P2F10B expression. The presence of RT-PCR amplifiable 161P2F10B mRNA provides an indication of the presence of cancer. RT-PCR assays are well known in the art. RT-PCR detection assays for tumor cells in peripheral blood are currently being evaluated for use in the diagnosis and management of a number of human solid tumors. In the prostate cancer field, these include RT-PCR assays for the detection of cells expressing PSA and PSM (Verkaik et al., 1997, Urol. Res. 25:373–384; Ghossein et al., 1995, U. Clin. Oncol. 13:1195–2000; Heston et al., 1995, Clin. Chem. 41:1687–1688).

A further aspect of the invention is an assessment of the susceptibility that an individual has for developing cancer. In one embodiment, a method for predicting susceptibility to cancer comprises detecting 161P2F10B mRNA or 161P2F10B protein in a tissue sample, its presence indicating susceptibility to cancer, wherein the degree of 161P2F10B mRNA expression correlates to the degree of susceptibility. In a specific embodiment, the presence of 161P2F10B in prostate or other tissue is examined, with the presence of 161P2F10B in the sample providing an indication of prostate cancer susceptibility (or the emergence or existence of a prostate tumor). Similarly, one can evaluate the integrity 161P2F10B nucleotide and amino acid sequences in a biological sample, in order to identify perturbations in the structure of these molecules such as insertions, deletions, substitutions and the like. The presence of one or more perturbations in 161P2F10B gene products in the sample is an indication of cancer susceptibility (or the emergence or existence of a tumor).

The invention also comprises methods for gauging humor aggressiveness. In one embodiment, a method for gauging aggressiveness of a tumor comprises determining the level of 161P2F10B mRNA or 161P2F10B protein expressed by tumor cells, comparing the level so determined to the level of 161P2F10B mRNA or 161P2F10B protein expressed in a corresponding normal tissue taken from the same individual or a normal tissue reference sample, wherein the degree of 161P2F10B mRNA or 161P2F10B protein expression in the tumor sample relative to the normal sample indicates the degree of aggressiveness. In a specific embodiment, aggressiveness of a tumor is evaluated by determining the extent to which 161P2F10B is expressed in the tumor cells, with higher expression levels indicated more aggressive tumors. "Another embodiment is the evaluation of the integrity of 161P2F10B nucleotide and amino acid sequences in a biological sample, in order to identify perturbations in the structure of these molecules such as insertions, deletions, substitutions and the like. The presence of one or more perturbations indicates more aggressive tumors.

Another embodiment of the invention is directed to methods for observing the progression of a malignancy in an individual over time. In one embodiment, methods for observing the progression of a malignancy in an individual over time comprise determining the level of 161P2F10B mRNA or 161P2F10B protein expressed by cells in a sample of the tumor, comparing the level so determined to be the level of 161P2F10B or 161P2F10B protein expressed in an equivalent tissue sample taken from the same individual at a different time, wherein the degree of 161P2F10B mRNA or 161P2F10B protein expression in the tumor sample over time provides information on the progression of the cancer. In a specific embodiment, the progression of a cancer is evaluated by determining 161P2F10B expression of the tumor cells over time, when increased expression over time indicates a progression of the cancer. Also, one can evaluate the integrity 161P2F10B nucleotide and amino acid sequences in a biological sample in order to identity perturbations in the structure of these molecules such as insertions, deletions, substitutions and the like, where the presence of one or more perturbations indicates a progression of the cancer.

The above diagnostic approaches can be combined with any of a wide variety of prognostic and diagnostic protocols known in the art. For example, another embodiment of the invention is directed to methods for observing a coincidence between the expression of 161P2F10B gene and 161P2F10B gene products (or perturbations in 161P2F10B gene and 161P2F10B gene products) and a factor that is associated with malignancy, as a means for diagnosing and prognosticating the status of a tissue sample. A wide variety of factors associated with malignancy can be utilized, such as the expression of genes associated with malignancy (e.g. PSA, PSCA and PSM expression for prostate cancer etc.) as well as gross cytological observations (see, e.g., Bocking et al., 1984, Anal. Quant. Cytol. 6(2):74–88; Epstein, 1995, Hum. Pathol. 26(2):223–9; Thorson et al., 1998, Mod. Pathol. 11(6):543–51; Baisden et al., 1999, Am. J. Surg. Pathol. 23(8):918–24). Methods for observing a coincidence between the expression of 161P2F10B gene and 161P2F10B gene products (or perturbations in 161P2F10B gene and 161P2F10B gene products) and another factor that is associated with malignancy are useful, for example, because the presence of a set of specific factors that coincide with disease provides information crucial for diagnosing and prognosticating the status of a tissue sample.

In one embodiment, methods for observing a coincidence between the expression of 161P2F10B gene and 161P2F10B gene products (or perturbations in 161P2F10B gene and 161P2F10B gene products) and another factor associated with malignancy entails detecting the overexpression of 161P2F10B mRNA or protein in a tissue sample, detecting the overexpression of PSA mRNA or protein in a tissue sample (or PSCA or PSM expression), and observing a coincidence of 161P2F10B mRNA or protein and PSA mRNA or protein expression (or PSCA or PSM expression). In a specific embodiment, the expression of 161P2F10B and PSA mRNA in prostate tissue is examined, where the coincidence of 161P2F10B and PSA mRNA overexpression in the sample indicates the existence of prostate cancer, prostate cancer susceptibility or the emergence or status of a prostate tumor.

Methods for detecting and quantifying the expression of 161P2F10B mRNA or protein are described herein, and standard nucleic acid and protein detection and quantification technologies are well known in the art. Standard methods for the detection and quantification of 161P2F10B mRNA include in situ hybridization using labeled 161P2F10B riboprobes, Northern blot and related techniques using 161P2F10B polynucleotide probes, RT-PCR analysis using primers specific for 161P2F10B, and other amplification type detection methods, such as, for example, branched DNA, SISBA, TMA and the like. In a specific embodiment, semi-quantitative RT-PCR is used to detect and quantify 161P2F10B mRNA expression. Any number of primers capable of amplifying 161P2F10B can be used for this purpose, including but not limited to the various primer sets specifically described herein. In a specific embodiment, polyclonal or monoclonal antibodies specifically reactive with the wild-type 161P2F10B protein can be used in an immunohistochemical assay of biopsied tissue.

IX.) Identification of Molecules That Interact With 161P2F10B

The 161P2F10B protein and nucleic acid sequences disclosed herein allow a skilled artisan to identify proteins, small molecules and other agents that interact with 161P2F10B, as well as pathways activated by 161P2F10B via any one of a variety of art accepted protocols. For example, one can utilize one of the so-called interaction trap systems (also referred to as the "two-hybrid assay"). In such systems, molecules interact and reconstitute a transcription factor which directs expression of a reporter gene, whereupon the expression of the reporter gene is assayed. Other systems identify protein—protein interactionsin vivo through reconstitution of a eukaryotic transcriptional activator, see, e.g., U.S. Pat. Nos. 5,955,280 issued 21 Sep. 1999, 5,925,523 issued 20 Jul. 1999, 5,846,722 issued 8 Dec. 1998 and 6,004,746 issued 21 Dec. 1999. Algorithms are also available in the art for genome-based predictions of protein functions (see, e.g., Marcotte, et al., Nature 402: 4 Nov. 1999, 83–86).

Alternatively one can screen peptide libraries to identify molecules that interact with 161P2F10B protein sequences. In such methods, peptides that bind to 161P2F10B are identified by screening libraries that encode a random or controlled collection of amino acids. Peptides encoded by the libraries are expressed as fusion proteins of bacteriophage cost proteins, the bacteriophage particles are then screened against the 161P2F10B protein.

Accordingly, peptides having a wide variety of uses, such as therapeutic, prognostic or diagnostic reagents, are thus identified without any prior information on the structure of the expected ligand or receptor molecule. Typical peptide libraries and screening methods that can be used to identify molecules that interact with 161P2F10B protein sequences are disclosed for example in U.S. Pat. Nos. 5,723,286 issued 3 Mar. 1998 and 5,733,731 issued 31 Mar. 1998.

Alternatively, cell lines express 161P2F10B are used to identify protein—protein interactions mediated by 161P2F10B . Such interactions can be examined using immunoprecipitation techniques (see, e.g., Hamilton B. J., et al. Biochem. Biophys. Res. Commun. 1999, 261:646–51). 161P2F10B protein can be immunoprecipitated from 161P2F10B-expressing cell lines using anti-161P2F10B antibodies. Alternatively, antibodies against His-tag can be used in a cell line engineered to express fusions of 161P2F10B and a His-tag (vectors mentioned above). The immunoprecipitated complex can be examined for protein association by procedures such as Western blotting. $^{35}$S-methionine labeling of proteins, protein microsequencing, silver staining and two-dimensional gel electrophoresis.

Small molecules and ligands that interact with 161P2F10B can be identified through related embodiments of such screening assays. For example, small molecules can be identified that interface with protein function, including molecules that interfere with 161P2F10B ability to mediate phosphorylation and de-phosphorylation, interaction with DNA or RNA molecules as an indication of regulation of cell cycles, second messenger signaling or tumorigenesis. Similarly, small molecules that modulate 161P2F10B -related ion channel, protein pump, or cell communication functions are identified and used to treat patients that have a cancer that expresses 161P2F10B (see, e.g., Hille, B., Ionic Channels of Excitable Membranes $2^{nd}$ Ed, Sinauer Assoc., Sunderland, Mass., 1992). Moreover, ligands that regulate 161P2F10B function can be identified based on their ability to bind 161P2F10B and activate a reporter construct. Typical methods are discussed for example in U.S. Pat. No. 5,928, 868 issued 27 Jul. 1999, and include methods for forming hybrid ligands in which at least one ligand is a small molecule. In an illustrative embodiment, cells engineered to express a fusion protein of 161P2F10B and a DNA-binding protein are used to co-express a fusion protein of a hybrid ligand/small molecule and a cDNA library transcriptional activator protein. The cells further contain a reporter gene, the expression of which is conditioned on the proximity of the first and second fusion proteins to each other, an event that occurs only if the hybrid ligand binds to target sites on both hybrid proteins. Those cells that express the reporter gene are selected and the unknown small molecule or the unknown ligand is identified. This method provides a means of identifying modulators which activate or inhibit 161P2F10B.

An embodiment of this invention comprises a method of screening for a molecule that interacts with an 161P2F10B amino acid sequence shown in FIG. 2 or FIG. 3, comprising the steps of contacting a population of molecules with the 161P2F10B amino acid sequence, allowing the population of molecules and the 161P2F10B amino acid sequence to interact under conditions that facilitate an interaction, determining the presence of a molecule that interact with the 161P2F10B amino acid sequence, and then separating molecules that do not interact with the 161P2F10B amino acid sequence from molecules that do. In a specific embodiment, the method further comprises purifying, characterizing and identifying a molecule that interacts with the 161P2F10B amino acid sequence. The identified molecule can be used to modulate a function performed by 161P2F10B . In a preferred embodiment, the 161P2F10B amino acid sequence is contacted with a library of peptides.

X.) Therapeutic Methods and Compositions

The identification of 161P2F10B as a protein that is normally expressed in a restricted set of tissues, but which is also expressed in prostate and other cancers, opens a number of therapeutic approaches to the treatment of such cancers. As contemplated herein, 161P2F10B functions as a transcription factor involved in activating tumor-promoting genes or repressing genes that block tumorigenesis.

Accordingly, therapeutic approaches that inhibit the activity of the 161P2F10B protein are useful for patients suffering from a cancer that expresses 161P2F10B . These therapeutic approaches generally fall into two classes. One class comprises various methods for inhibiting the binding or association of the 161P2F10B protein with its binding partner or with other proteins. Another class comprises a variety of methods for inhibiting the transcription of the 161P2F10B gene or translation of 161P2F10B mRNA.

X.A.) Anti-Cancer Vaccines

The invention provides cancer vaccines comprising a 161P2F10B -related protein or 161P2F10B-related nucleic acid. In view of the expression of 161P2F10B, cancer vaccines prevent and/or treat 161P2F10B -expressing cancers with minimal or no effects on non-target tissues. The use of a tumor antigen in a vaccine that generates humoral and/or cell-mediated immune responses as anti-cancer therapy is well known in the art and has been employed in prostate cancer using human PSMA and rodent PAP immunogens (Hodge et al., 1995, Int. J. Cancer 63:231–237; Fong et al., 1997, J. Immunol. 159:3113–3117).

Such methods can be readily practiced by employing a 161P2F10B -related protein, or an 161P2F10B-encoding nucleic acid molecule and recombinant vectors capable of expressing and presenting the 161P2F10B immunogen (which typically comprises a number of antibody or T cell epitopes). Skilled artisans understand that a wide variety of vaccine systems for delivery of immunoreactive epitopes are known in the art (see, e.g., Herylin et al., Ann Med 1999 Feb 31(1):66–78; Maniyama et al., Cancer Immunol Immunother 2000 Jun. 49(3):123–32) Briefly, such methods of generating an immune response (e.g. humoral and/or cell-mediated) in a mammal, comprise the steps of: exposing the mammal's immune system to an immunoreactive epitope (e.g. an epitope present in the 161P2F10B protein shown in SEQ ID NO:703 or analog or homolog thereof) so that the mammal generates an immune response that is specific for the epitope (e.g. generates antibodies that specifically recognize that epitope). In a preferred method, the 161P2F10B immunogen contains a biological motif, see e.g., Tables V–XVIII, or a peptide of a size range from 161P2F10B indicated in FIG. 5, FIG. 6, FIG. 7, FIG. 8, and FIG. 9.

The entire 161P2F10B protein, immunogenic regions or epitopes thereof can be combined and delivered by various means. Such vaccine compositions can include, for example, lipopeptides (e.g., Vitiello, A. et al., J. Clin. Invest. 95:341, 1995), peptide compositions encapsulated in poly(DL-lactide-co-glycolide) ("PLG") microspheres (see, e.g., Eldridge, et al., Molec. Immunol. 28:287–294, 1991; Alonso et al., Vaccine 12:299–306, 1994; Jones et al., Vaccine 13:675–681, 1994), peptide compositions contained in immune stimulating complexes (ISCOMS) (see, e.g., Takahashi et al., Nature 344:873–875, 1990; Hu et al., Clin Exp Immunol. 113:235–243, 1998), multiple antigen peptide systems (MAPs) (see e.g., Tam, J. P., Proc. Natl. Acad. Sci. U.S.A. 85:5409–5413, 1988; Tam, J. P., J. Immunol. Methods 196:17–32, 1996), peptides formulated as multivalent peptides; peptides for use in ballistic delivery systems, typically crystallized peptides, viral delivery vectors (Perkus, M. E. et al., In: Concepts in vaccine development, Kaufmann, S. H. E., ed., p. 379, 1996; Chakrabarti, S. et al., Nature 320:535, 1986; Hu, S. L. et al., Nature 320:537, 1986; Kieny, M.-P. et al., AIDS Bio/Technology 4:790, 1986; Top, F. H. et al., J. Infect. Dis. 124:148, 1971; Chanda, P. K. et al., Virology 175:535, 1990), particles of viral or synthetic origin (e.g., Kofler, N. et al., J. Immunol. Methods. 192:25, 1996; Eldridge, J. H. et al., Sem. Hematol. 30:16, 1993; Falo, L. D., Jr. et al., Nature Med. 7:649, 1995), adjuvants (Warren, H. S., Vogel, F. R., and Chedid, L. A. Annu. Rev. Immunol. 4:369, 1986; Gupta, R. K. et al., Vaccine 11:293, 1993), liposomes (Reddy, R. et al., J. Immunol. 148:1585, 1992; Rock, K. L. Immunol. Today 17:131, 1996), or, naked or particle absorbed cDNA (Ulmer, J. B. et al., Science 259:1745, 1993; Robinson, H. L., Hunt, L. A., and Webster, R. G., Vaccine 11:957, 1993; Shiver, J. W. et al., In.: Concepts in vaccine development, Kaufmann, S. H. E., ed. p. 423, 1996; Cease, K. B., and Berzofsky, J. A., Annu. Rev. Immunol. 12:923, 1994 and Eldridge, J. H. et al., Sem. Hematol. 30:16, (1993). Toxin-targeted delivery technologies, also known as receptor mediated targeting, such as those of Avant Immunotherapeutics, Inc. (Needham, Mass.) may also be used.

In patients with 161P2F10B-associated cancer, the vaccine compositions of the invention can also be used in conjunction with other treatments used for cancer, e.g., surgery, chemotherapy, drug therapies, radiation therapies, etc. including use in combination with immune adjuvants such as IL-2, IL-12, GM-CSF, and the like.

Cellular Vaccines:

CTL epitopes can be determined using specific algorithms to identify peptides within 161P2F10B protein that bind corresponding HLA alleles (see e.g., Table IV; Epimer™ and Epimatrix™, Brown University website, BIMAS, and SYFPEITHI. In a preferred embodiment, the 161P2F10B immunogen contains one or more amino acid sequences identified using techniques well known in the art, such as the sequences shown in Tables V—XVIII or a peptide of 8, 9, 10 or 11 amino acids specified by an HLA Class I motif/supermotif (e.g., Table IV (A), Table IV (D), or Table IV (E)) and/or a peptide of at least 9 amino acids that comprises an HLA Class II motif/supermotif (e.g., Table IV (B) or Table IV (C)). As is appreciated in the art, the HLA Class I binding groove is essentially closed ended so that peptides of only a particular size range can fit into the groove and be bound, generally HLA Class I epitopes are 8, 9, 10, or 11 amino acids long. In contrast, the HLA Class II binding groove is essentially open ended; therefore a peptide of about 9 or more amino acids can be bound by an HLA Class II molecule. Due to the binding groove differences between HLA Class I and II, HLA Class I motifs are length specific, i.e., position two of a Class I motif is the second amino acid in an amino to carboxyl direction of the peptide. The amino acid positions in a Class II motif are relative only to each other, not the overall peptide, i.e., additional amino acids can be attached to the amino and/or carboxyl termini of a motif-bearing sequence. HLA Class II epitopes are often 9, 10, 11, 12, 13, 14, 15, 16, 17, 18, 19, 20, 21, 22, 23, 24, or 25 amino acids long, or longer than 25 amino acids.

Antibody-based Vaccines

A wide variety of methods for generating an immune response in a mammal are known in the art (for example as the first step in the generation of hybridomas). Methods of generating an immune response in a mammal comprise exposing the mammal's immune system to an immunogenic epitope on a protein (e.g. the 161P2F10B protein) so that an immune response is generated. A typical embodiment consists of a method for generating an immune response to 161P2F10B in a host, by contacting the host with a sufficient amount of at least on 161P2F10B cell or cytotoxic T-cell epitope or analog thereof; and at least on periodic interval thereafter re-contacting the host with the 161P2F10B cell or cytotoxic T-cell epitope or analog thereof. A specific embodiment consists of a method of generating an immune response against a 161P2F10B-related protein or a man-made multiepitopic peptide comprising: administering 161P2F10B immunogen (e.g. the 161P2F10B protein or a peptide fragment thereof, an 161P2F10B fusion protein or analog etc.) in a vaccine preparation to a human or another mammal. Typically, such vaccine preparations further contain a suitable adjuvant (see, e.g., U.S. Pat. No. 6,146,635) or a universal helper epitope such as a PADRE™ peptide (Epimmune Inc., San Diego, Calif.; see, e.g., Alexander et al., J.Immunol. 2000 164(3); 164(3): 1625–1633; Alexander et al., Immunity 1994 1(9): 751–761 and Alexander et al., Immunol. Res. 1998 18(2): 79–92). An alternative method comprises generating an immune response in an individual against a 161P2F10B immunogen by: administering in vivo to muscle or skin of the individual's body a DNA molecule that comprises a DNA sequence that encodes an 161P2F10B immunogen, the DNA sequence operatively linked to regulatory sequences which control the expression of the DNA sequence; wherein the DNA molecule is taken up by cells, the DNA sequence is expressed in the cells and an immune response is generated against the immunogen (see, e.g., U.S. Pat. No. 5,962,428). Optionally a genetic vaccine facilitator such as anionic lipids; saponins; lectins; estrogenic compounds; hydroxylated lower alkyls; dimethyl sulfoxide; and urea is also administered. In addition, an antidiotypic antibody can be administered that mimics 161P2F10B, in order to generate a response to the target antigen.

Nucleic Acid Vaccines:

Vaccine compositions of the invention include nucleic acid-mediated modalities. DNA or RNA that encode protein(s) of the invention can be administered to a patient. Genetic immunization methods can be employed to generate prophylactic or therapeutic humoral and cellular immune responses directed against cancer cells expressing 161P2F10B . Constructs comprising DNA encoding a 161P2F10B-related protein/immunogen and appropriate regulatory sequences can be injected directly into muscle or skin of an individual, such that the cells of the muscle or skin take-up the construct and express the encoded 161P2F10B protein/immunogen. Alternatively, a vaccine comprises a 161P2F10B-related protein. Expression of the 161P2F10B-related protein immunogen results in the generation of prophylactic or therapeutic humoral and cellular immunity against cells that bear 161P2F10B protein. Various prophylactic and therapeutic genetic immunization techniques known in the art can be used. Nucleic acid-based delivery is described, for instance, in Wolff et al., Science 247:1465 (1990) and well as U.S. Pat. Nos. 5,580,859; 5,589,466; 5,804,566; 5,739,118; 5,736,524; 5,679,647; WO 98/04720. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922,687).

For therapeutic or prophylactic immunization purposes, proteins of the invention can be expressed via viral or bacterial vectors. Various viral gene delivery systems that can be used in the practice of the invention include, but are not limited to, vaccinia, fowlpox, canarypox, adenovirus, influenza, poliovirus, adeno-associated virus, lentivirus, and sindbis virus (see, e.g., Restifo, 1996, Curr. Opin. Immunol. 8:658–663; Tsang et al. J. Natl. Cancer Inst. 87:982–990 (1995)). Non-viral delivery systems can be employed by introducing naked DNA encoding a 161P2F10B -related protein into the patient (e.g., intramuscularly or intradermally) to induce an anti-tumor response.

Vaccinia virus is used, for example, as a vector to express nucleotide sequences that encode the peptides of the invention. Upon introduction into a host, the recombinant vaccinia virus expresses the protein immunogenic peptide, and thereby elicits a host immune response. Vaccinia vectors and methods useful in immunization protocols are described in e.g., U.S. Pat. No. 4,722,848. Another vector is BCG (Bacille Calmette Guerin). BCG vectors are described in Stover et al., Nature 351:456–460 (1991). A wide variety of other vectors useful for therapeutic administration or immunization of the peptides of the invention, e.g., adeno and adeno-associated virus vectors, retroviral vectors, Salmonella typhi vectors, detoxified anthrax toxin vectors, and the like, will be apparent to those skilled in the art from the description herein.

Thus, gene delivery systems are used to deliver a 161P2F10B-related nucleic acid molecule. In one embodiment, the full-length human 161P2F10B cDNA is employed. In another embodiment, 161P2F10B nucleic acid molecules encoding specific cytotoxic T lymphocyte (CTL) and/or antibody epitopes are employed.

Ex Vivo Vaccines

Various ex vivo strategies can also be employed to generate an immune response. One approach involves the use of antigen presenting cells (APCs) such as dendritic cells (DC) to present 161P2F10B antigens to a patient's immune system. Dendritic cells expressed MHC class I and II molecules, B7 co-stimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patients' immune system (Tjoa et al., 1996, Prostate 28:65–69; Murphy et al., 1996, Prostate 29:371–380). Thus, denderitic cells can be used to present 161P2F10B peptides to T cells in the context of MHC class I or II molecules. In one embodiment, autologous dendritic cells are pulsed with 161P2F10B peptides capable of binding to MHC class I and/or class II molecules. In another embodiment, dendritic cells are pulsed with the complete 161P2F10B protein. Yet another embodiment involves engineering the overexpression of the 161P2F10B gene in dendritic cells using various implementing vectors known in the art, such as adenovirus (Arthur et al., 1997, Cancer Gene Ther. 4:17–25), retrovirus (Henderson et al., 1996, Cancer Res. 56:3763–3770), lentivirus, adeno-associated virus, DNA transfection (Ribas et al., 1997, Cancer Res. 57:2865–2869), or tumor-derived RNA transfection (Ashley et al., 1997, J. Exp. Med. 186:1177–1182). Cells that express 161P2F10B can also be engineered to express immune modulators, such as GM-CSF, and used as immunizing agents.

X.B.) 161P2F10B as a Target for Antibody-based Therapy

161P2F10B is an attractive target for antibody-based therapeutic strategies. A number of antibody strategies are known to the art for targeting both extracellular and intracellular molecules (see, e.g., complement and ADCC mediated killing as well as the use of intrabodies). Because 161P2F10B is expressed by cancer cells of various lineages relative to corresponding normal cells, systemic administration of 161P2F10B-immunoreactive compositions are prepared that exhibit excellent sensitivity without toxic, non-specific and/or non-target effects caused by binding of the immunoreactive composition to non-target organs and tissues. Antibodies specifically reaction with domains of 161P2F10B are useful to treat 161P2F10B-expressing cancers systemically, either gas conjugates with a toxin or therapeutic agent, or as naked antibodies capable of inhibiting cell proliferation or function.

161P2F10B antibodies can be introduced into a patient such that the antibody binds to 161P2F10B and modulates a function, such as an interaction with a binding partner, and consequently mediates destruction of the tumor cells and/or inhibits the growth of the tumor cells. Mechanisms by which such antibodies exert a therapeutic effect can include complement-mediated cytolysis, antibody-dependent cellular cytotoxicity, modulation of the physiological function of 161P2F10B, inhibition of ligand binding or signal transduction pathways, modulation of tumor cell differentiation, alteration of tumor angiogenesis factor profiles, and/or apoptosis.

Those skilled in the art understand that antibodies can be used to specifically target and bind immunogenic molecules such as an immunogenic region of the 161P2F10B sequence shown in FIG. 2 or FIG. 3. In addition, skilled artisans understand that it is routine to conjugate antibodies to cytotoxic agents (see, e.g., Slevers et al. *Blood* 93:11 3678–3684 (Jun. 1, 1999)). When cytotoxic and/or therapeutic agents are delivered directly to cells, such as by conjugating them to antibodies specific for a molecule expressed by that cell (e.g. 161P2F10B), the cytotoxic agent will exert its known biological effect (i.e. cytotoxicity) on those cells.

A wide variety of compositions and methods for using antibody-cytotoxic agent conjugates to kill cells are known in the art. In the context of cancers, typical methods entail administering to an animal having a tumor a biologically effective amount of a conjugate comprising a selected cytotoxic and/or therapeutic agent linked to a targeting agent (e.g. an anti-161P2F10B antibody) that binds to a marker (e.g. 161P2F10B ) expressed, accessible to binding or localized on the cell surfaces. A typical embodiment is a method of delivery a cytotoxic and/or therapeutic agent to a cell expressing 161P2F10B , comprising conjugating the cytotoxic agent to an antibody that immunospecifically binds to a 161P2F10B epitope, and, exposing the cell to the antibody-agent conjugate. Another illustrative embodiment is a method of treating an individual suspected of suffering from metastasized cancer, comprising a step of administering parenterally to said individual suspected of suffering from metastasized cancer, comprising a step of administering parenterally to said individual a pharmaceutical composition comprising a therapeutically effective amount of an antibody conjugated to a cytotoxic and/or therapeutic agent.

Cancer immunotherapy using anti-161P2F10B antibodies can be done in accordance with various approaches that have been successfully employed in the treatment of other types of cancer, including but not limited to colon cancer (Arlen et al., 1988, *Crit. Rev. Immunol.* 18:133–138), multiple myeloma (Ozaki et al., 1997, Blood 90:3179–3186, Tsunenari et al., 1997, Blood 90:2437–2444), gastric cancer (Kasprzyk et al., 1992, Cancer Res. 52:2771–2776), B-cell lymphoma (Funakoshi et al., 1996, J. Immunother. Emphasis Tumor Immunol. 19:93–101), leukemia (Zhong et al., 1996, Leuk. Res. 20:581–589), colorectal cancer (Moun et al., 1994, Cancer Res. 54:6160–6166; Velders et al., 1995, Cancer Res. 55:4398–4403), and breast cancer (Shepard et al., 1991, J. Clin. Immunol. 11:117–127). Some therapeutic approaches involve conjugation of naked antibody to a toxin, such as the conjugation of $Y^{91}$ of $I^{131}$ to anti-CD20 antibodies (e.g., Zevalin™, IDEC Pharmaceuticals Corp. of Bexxar™, Coulter Pharmaceuticals), while others involve co-administration of antibodies and other therapeutic agents, such as Herceptin™ (trastuzumab) with paclitaxel (Genetech, Inc.). The antibodies can be conjugated to a therapeutic agent. To treat prostate cancer, for example, 161P2F10B antibodies can be administered in conjunction with radiation, chemotherapy or hormone ablation.

Although 161P2F10B antibody therapy is useful for all stages of cancer, antibody therapy can be particularly appropriate in advanced or metastatic cancers. Treatment with the antibody therapy of the invention is indicated for patients who have received one or more rounds of chemotherapy. Alternatively, antibody therapy of the invention is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well.

Cancer patients can be evaluated for the presence and level of 161P2F10B expression, preferably using immunohistochemical assessments of tumor tissue, quantitative 161P2F10B imaging, or other techniques that reliably indicate the presence and degree of 161P2F10B expression. Immunohistochemical analysis of tumor biopsies or surgical specimens is preferred for this purpose. Methods for immunohistochemically analysis of tumor biopsies or surgical specimens is preferred for this purpose. Methods for immunohistochemical analysis of tumor tissues are well known in the art.

Anti-161P2F10B monoclonal antibodies that treat prostate and other cancers include those that initiate a potent immune response against the tumor or those that are directly cytotoxic. In this regard, anti-161P2F10B monoclonal antibodies (mAbs) can elicit tumor cell lysis by either complement-mediated or antibody-dependent cell cytotoxicity (ADCC) mechanisms, both of which require an intact-Fc portion of the immunoglobulin molecule for interaction with effector cell Fc receptor sites on complement proteins. In addition, anti-161P2F10B mAbs that exert a direct biological effect on tumor growth are useful to treat cancers that express 161P2F10B . Mechanisms by which directly cytotoxic mAbs act include: inhibition of cell growth, modulation of cellular differentiation, modulation of tumor angiogenesis factor profiles, and the induction of apoptosis. The mechanism(s) by which a particular anti-161P2F10B mAb exerts an anti-tumor effect is evaluated using any number of in vitro assays that evaluate cell death such as ADCC, ADMMC, complement-mediated cell lysis, and so forth, as is generally known in the art.

In some patients, the use of murine or other non-human monoclonal antibodies, or human/mouse chimeric mAbs can induce moderate to strong immune responses against the non-human antibody. This can result in clearance of the antibody from circulation and reduced efficacy. in the most serve cases, such an immune response can lead to the extensive formation of immune complexes which, potentially, can causer renal failure. Accordingly, preferred monoclonal antibodies used in the therapeutic methods of the invention are those that are either fully human or humanized and that bind specifically to the target 161P2F10B antigen with high affinity but exhibit low or no antigenicity in the patient.

Therapeutic methods of the invention contemplate the administration of single anti-161P2F10B mAbs as well as combinations, or cocktails, of different mAbs. Such mAb cocktails can have certain advantages inasmuch as they contain mAbs that target different epitopes, exploit different effector mechanisms or combine directly cytotoxic mAbs with mAbs that rely on immune effector functionality. Such mAbs in combination can exhibit synergistic therapeutic effects. In addition, anti-161P2F10B mAbs can be administered concomitantly with other therapeutics modalities, including but not limited to various chemotherapeutic agents, androgen-blockers, immune modulators (e.g., IL-2, GM-CSF), surgery or radiation. The anti-161P2F10B mAbs are administered in their "naked" or unconjugated form, or can have a therapeutic agent(s) conjugated to them.

Anti-161P2F10B antibody formulations are administered via any route capable of delivering the antibodies to a tumor cell. Routes of administration include, but are not limited to, intravenous, intraperitoneal, intramuscular, intratumor, intradermal, and the like. Treatment generally involves repeated administration of the anti-161P2F10B antibody preparation, via an acceptable route of administration such as intravenous injection (IV), typically at a dose in the range of about 0.1, .2, .3, .4, .5, .6, .7, .8, .9., 1, 2, 3, 4, 5, 6, 7, 8, 9, 10, 15, 20, or 25 mg/kg body weight. In general, doses in the range of 10–1000 mg mAb per week are effective and well tolerated.

Based on clinical experience with the Herceptin™ mAb in the treatment of metastic breast cancer, an initial loading dose of approximately 4 mg/kg patient body weight IV, followed by weekly doses of about 2 mg/kg IV of the anti-161P2F10B mAb preparation represents an acceptable dosing regimen. Preferably, the initial loading dose is administered as a 90 minute or longer infusion. The periodic maintenance dose is administered as a 30 minute or longer infusion, provided the initial dose was well tolerated. As appreciated by those of skill in the art, various factors can influence the ideal dose regimen in a particular case. Such factors include, for example, the binding affinity and half life of the Ab or mAbs used, the degree of 161P2F10B expression in the patient, the extent of circulating shed 161P2F10B antigen, the desired steady-state antibody concentration level, frequency of treatment, and the influence of chemotherapeutic or other agents used in combination with the treatment method of the invention, as well as the health status of a particular patient.

Optionally, patients should be evaluated for the levels of 161P2F10B in a given sample (e.g. the levels of circulating 161P2F10B antigen and/or 161P2F10B expressing cells) in order to assist in the determination of the most effective dosing regimen, etc. Such evaluations are also used for monitoring purposes throughout therapy, and are useful to gauge therapeutic success in combination with the evaluation of other parameters (for example, urine cytology and/or ImmunoCyt levels in bladder cancer therapy, or by analogy, serum PSA levels in prostate cancer therapy).

Anti-idiotypic anti-161P2F10B antibodies can also be used in anti-cancer therapy as a vaccine for inducing an immune response to cells expressing a 161P2F10B-related protein. In particular, the generation of anti-idiotypic antibodies is well known in the art; that is methodology can readily be adapted to generate anti-idiotypic anti-161P2F10B antibodies that mimic an epitope on a 161P2F10B-related protein (see, for example, Wagner, et al., 1997, Hybridoma 16:33–40; Foon et al., 1995, J. Clin. Invest. 96:334–342; Herlyn et al., 1996, Cancer Immunol. Immunother. 43:65–76). Such an anti-idiotypic antibody can be used in cancer vaccine strategies.

X.C.) 161P2F10B as a Target for Cellular Immune Responses

Vaccines and methods of preparing vaccines that contain an immunogenically effective amount of one or more HLA-binding peptides as described herein are further embodiments of the invention. Furthermore, vaccines in accordance with the invention encompass compositions of one or more of the claimed peptides. A peptide can be present in a vaccine individually. Alternatively, the peptide can exist as a homopolymer comprising multiple copies of the same peptide, or as a heteropolymer of various peptides. Polymers have the advantage of increased immunological reaction and, where different peptide epitopes are used to make up the polymer, the additional ability to induce antibodies and/or CTLs that react with different antigenic determinants of the pathogenic organism or tumor-related peptide targeted for an immune response. The composition can be a naturally occurring region of an antigen or can be prepared, e.g., recombinantly or by chemical synthesis.

Carriers that can be used with vaccines of the invention are well known in the art, and include, e.g., thyroglobulin, albumins such as human serum albumin, tetanus toxoid, polyamino acids such as poly L-lysine, poly L-glutamic acid, influenza, hepatitis B virus core protein, and the like. The vaccines can contain a physiologically tolerable (i.e., acceptable) diluent such as water, or saline, preferably phosphate buffered saline. The vaccines also typically include an adjuvant. Adjuvants such as incomplete Freund's adjuvant, aluminum phosphate, aluminum hydroxide, or alum are examples of materials well known in the art. Additionally, as disclosed herein, CTL responses can be primed by conjugation peptides of the invention to lipids, such as tripalmitoyl-S-glycerylcysteinlyseryl-serine ($P_3CSS$). Moreover, an adjuvant such as a synthetic cytosine-phosphorothiolated-guanine-containing (CpG) oligonucleotides has been found to increase CTL responses 10- to 100-fold. (see, e.g. Davila and Celis *J. Immunol.* 165:539–547 (2000))

Upon immunization with a peptide composition in accordance with the invention, via injection, aerosol oral, transdermal, transmucosal, intrapleural, intrathecal, or other suitable routes, the immune system of the host responds to the vaccine by producing large amounts of CTLs and/or HTLS specific for the desired antigen. Consequently, the host becomes at least partially immune to later development of cells that express or overexpress 161P2F10B antigen, or derives at least some therapeutic benefit when the antigen was tumor-associated.

In some embodiments, it may be desirable to combine the class I peptide components with components that induce or facilitate neutralizing antibody and or helper T cell responses directed to the target antigen. A preferred embodiment of such a composition comprised class I and class II epitopes in accordance with the invention. An alternative embodiment of such a composition comprises a class I and/or class II epitope in accordance with the invention, along with a cross reactive HTL epitope such as PADRE™ (Epimmune, San Diego, Calif.) molecule (described e.g., in U.S. Pat. No. 5,736,142).

A vaccine of the invention can also include antigen-presenting cells (APC), such as dendritic cells (DC), as a vehicle to present peptides of the invention. Vaccine compositions can be created in vivo, following dendtritic cell mobilization and harvesting, whereby loading of denderitic cells occurs in vitro. For example, dendritic cells are transfected, e.g., with a minigene in accordance with the invention, or are pulsed with peptides. The dentritic cell can then be administered to a patient to elicit immune response in vivo. Vaccine compositions, either DNA- or peptide-based, can also be administered in vivo in combination with dendritic cell mobilization whereby loading of dendritic cells occurs in vivo.

Preferably, the following principles are utilized when selecting an array of epitopes for inclusion in a polyepitopic composition for use in a vaccine, or for selecting discrete epitopes to be included in a vaccine and/or to be encoded by nucleic acids such as a minigene. It is preferred that each of the following principles be balanced in order to make the selection. The multiple epitopes to be incorporated in a given vaccine composition may be, but need not be, contiguous in sequence in the native antigen from which the epitopes are derived.

1.). Epitopes are selected which, upon administration, mimic immune responses that have been observed to be correlated with tumor clearance. For HLA Class I this includes 3–4 epitopes that come from at least one tumor associated antigen (TAA). For HLA Class II a similar rationale is employed; again 3–4 epitopes are selected from at least on TAA (see, e.g., Rosenberg et al., *Science* 278:1447–1450). Epitopes from one TAA may be used in combination with epitopes from one or more additional TAAs to produce a vaccine that targets tumors with varying expression patterns of frequently-expressed TAAs.

2.) Epitopes are selected that have the requisite binding affinity established to be correlated with immunogenicity: for HLA Class I an $IC_{50}$ of 500 nM or less, of the 200 nM or less; and for Class II an $IC_{50}$ of 1000 nM or less.

3.) Sufficient supermotif bearing-peptides, or a sufficient array of allele-specific motif-bearing peptides, are selected to give broad population coverage. For example, it is preferable to have at least 80% population coverage. A Monte Carlo analysis, a statistical evaluation known in the art, can be employed to assess the breadth, or redundancy of, population coverage.

4.) When selecting epitopes from cancer-related antigens it is often useful to select analogs because the patient may have developed tolerance to the native epitope.

5.) Of particular relevance are epitopes referred to as "nested epitopes." Nested epitopes occur where at least two epitopes overlap in a given peptide sequence. A nested peptide sequence can comprise B cell, HLA class I and/or HLA class II epitopes. When providing nested epitopes, a general objective is to provide the greatest number of epitopes per sequence. Thus, an aspect is to avoid providing a peptide that is any longer than the amino terminus of the amino terminal epitope and the carboxyl terminus of the carboxyl terminal epitope in the peptide. When providing a multi-epitopic sequence, such as a sequence comprising nested epitopes, it is generally important to screen the sequence in order to insure that it does not have pathological or other deleterious biological properties.

6.) If a polyepitopic protein is created, or when creating a minigene, an objective is to generate the smallest peptide that encompasses the epitopes of interest. This principle is similar, if not the same as that employed when selecting a peptide comprising nested epitopes. However, with an artificial polypepitopic peptide, the size minimization objective is balanced against the need to integrate any spacer sequences between epitopes in the polyepitopic protein. Spacer amino acid residues can, for example, be introduced to avoid junctional epitopes (an epitope recognized by the immune system, not present in the target antigen, and only created by the man-made juxtaposition of epitopes), or to facilitate cleavage between epitopes and thereby enhance epitope presentation. Junctional epitopes are generally to be avoided because the recipient may generate an immune response to that non-native epitope. Of particular concern is a junctional epitope that is a "dominant epitope." A dominant epitope may lead to such a zealous response that immune responses to other epitopes are diminished or suppressed.

7.) Where the sequences of multiple variants of the same target protein are present, potential peptide epitopes can also be selected on the basis of their conservancy. For example, a criterion for conservancy may define that the entire sequence of an HLA class I binding peptide or the entire 9-mer core of a class II binding peptide be conserved in a designated percentage of the sequences evaluated for a specific protein antigen.

X.C.I. Minigene Vaccines

A number of different approaches are available which allow simultaneous delivery of multiple epitopes. Nucleic acids encoding the peptides of the invention are a particularly useful embodiment of the invention. Epitopes for inclusion in a minigene are preferably selected according to the guidelines set forth in the previous section. A preferred means of administering nucleic acids encoding the peptides of the invention uses minigene constructs encoding a peptide comprising one or multiple epitopes of the invention.

The use of multi-epitope minigenes as described below and in, Ishioka et al., *J. Immunol.* 162:3915–3925, 1999; An, L. and Whitton, J. L. *J. Virol.* 71:2292, 1997; Thomson, S. A. et al., *J. Immunol.* 157:822, 1996; Whitton, J. L. et al., *J. Virol.* 67:348, 1993; Hanke, R. et al., *Vaccine* 16:426, 1998. For example, a multi-epitope DNA plasmid encoding supermotif- and/or motif-bearing epitopes derived 161P2F10B, the PADRE® universal helper T cell epitope (or multiple HTL epitopes from 161P2F10B), and an endoplasmic reticulum-translocating signal sequence can be engineered. A vaccine may also comprise epitopes that are derived from other TAAs.

The immunogenicity of a multi-epitopic minigene can be confirmed in transgenic mice to evaluate the magnitude of CTL induction responses against the epitopes tested. Further, the immunogenicity of DNA-encoded epitopes in vivo can be correlated with the in vitro responses of specific CTL lines against target cells transfected with the DNA plasmid. Thus, these experiments can show that the minigene serves to both: 1.) generate a CTL response and 2.) that the induced CTLs recognized cells expressing the encoded epitopes.

For example, to create a DNA sequence encoding the selected epitopes (minigene) for expression in human cells, the amino acid sequences of the epitopes may be reversed translated. A human codon usage table can be used to guide the codon choice for each amino acid. Thee epitope-encoding DNA sequences may be directly adjoined, so that when translated, a continuous polypeptide sequence is created. To optimize expression and/or immunogenicity, additional elements can be incorporated into the minigene design. Examples of amino acid sequences that can be reverse translated and included in the minigene sequence include: HLA class I epitopes, HLA class II epitopes, antibody epitopes, a ubiquitination signal sequence, and/or an endoplasmic reticulum targeting signal. In addition, HLA presentation of CTL and HTL epitopes may be improved by including synthetic (e.g. poly-alanine) or naturally-occurring financing sequences adjacent to the CTL or HTL epitopes, these larger peptides comprising the epitope(s) are within the scope of the invention.

The minigene sequence may be converted to DNA by assembling oligonucleotides that encode the plus and minus strands of the minigene. Overlapping oligonucleotides (30–100 bases long) may be synthesized, phosphorylated, purified and annealed under appropriate conditions using well known techniques. The ends of the oligonucleotides can be joined, for example, using T4 DNA ligase. This synthetic minigene, encoding the epitope polypeptide, can then be cloned in to a desired expression vector.

Standard regulatory sequences well known of those of skill in the art are preferably included in the vector to ensure expression in the target cells. Several vector elements are desirable: a promoter with a down-stream cloning site for minigene insertion: a polyadenylation signal for efficient transcription termination; an *E. coli* origin or replication; and an *E. coli* selectable marker (e.g. ampicillin or kanamycin resistance). Numerous promoters can be used for this purpose, e.g., the human cytomegalovirus (hCMV) promoter. See, e.g., U.S. Pat. Nos. 5,580,859 and 5,589,466 for other suitable promoter sequences.

Additional vector modifications may be desired to optimize minigene expression and immunogenicity. In some cases, introns are required for efficient gene expression, and one or more synthetic or naturally-occurring introns could be incorporated into the transcribed region of the minigene. The inclusion of mRNA stabilization sequences and sequences for replication in mammalian cells may also be considered for increasing minigene expression.

Once an expression vector is selected, the minigene is cloned into the polylinker region downstream of the promoter. This plasmid is transformed into an appropriate *E. coli* strain, and DNA is prepared using standard techniques. The orientation and DNA sequence of the minigene, as well as other elements included in the vector, are confirmed using restriction mapping and DNA sequence analysis. Bacterial cells harboring the correct plasmid can be stored as a master cell bank and a working cell bank.

In addition, immunostimulatory sequences (ISSs or CpGs) appear to play a role in the immunogenicity of DNA vaccines. These sequences may be included in the vector, outside the minigene coding sequence, if desired to enhance immunogenicity.

In some embodiments, a bi-cistronic expression vector which allows production of both the minigene-encoded epitopes and a second protein (included to enhance or decrease immunogenicity) can be used. Examples of proteins or polypeptides that could beneficially enhance the immune response if co-expressed include cytokines (e.g., IL-2, IL-12, GM-CSF), cytokine-inducing molecules (e.g., LeIF), costimulatory molecules, or for HTL responses, pan-DR binding proteins (PADRE™, Epimmune, San Diego, Calif.). Helper (HTL) epitopes can be joined to intracellular targeting signals and expressed separately from expressed CTL epitopes; this allows direction of the HTL epitopes to a cell compartment different than that of the CTL epitopes. If required, this could facilitate more efficient entry of HTL epitopes into the HLA class II pathway, thereby improving HTL induction. In contrast to HTL or CTL induction, specifically decreasing the immune response by co-expression of immunosuppressive molecules (e.g. TGF-β) may be beneficial in certain diseases.

Therapeutic quantities of plasmid DNA can be produced for example, by fermentation in *E. coli*, followed by purification. Aliquots from the working cell bank are used to inoculate growth medium, and grown to saturation in shaker flasks or a bioreactor according to well-known techniques. Plasmid DNA can be purified using standard bioseparation technologies such as solid phase anion-exchange resins supplied by QIAGEN, Inc. (Valenica, Calif.). If required, supercoiled DNA can be isolated from the open circular and linear forms using gel electrophoresis or other methods.

Purified plasmid DNA can be prepared for injection using a variety of formulations. The simplest of these is reconstitution of lyophilized DNA in sterile phosphate-buffer saline (PBS). This approach, known as "naked DNA," is currently being used for intramuscular (IM) administration in clinical trials. To maximize the immunotherapeutic effects of minigene DNA vaccines, an alternative method for formulating purified plasmid DNA may be desirable. A variety of methods have been described, and new techniques may become available. Cationic lipids, glycolipids, and fusogenic liposomes can also be used in the formation (see, e.g., as described by WO 93/24640; Mannino & Gould-Fogerite, *BioTechniques* 6(7): 682 (1988); U.S. Pat. No. 5,279,833; WO 91/06309; and Felgner, et al., *Proc. Nat'l Acad. Sci. USA* 84:7413 (1987). In addition, peptides and compounds referred to collectively as protective, interactive, non-condensing compounds (PINC) could also be complexed to purified plasmid DNA to influence variables such as stability, intramuscular dispersion, or trafficking to specific organs or cell types.

Target cell sensitization can be used as a functional assay for expression and HLA class I presentation of minigene-encoded CTL epitopes. For example, the plasmid DNA is introduced into a mammalian cell line that is suitable as a target for standard CTL chromium release assays. The transfection method used will be dependent on the final formulation. Electroporation can be used for "naked" DNA, whereas cationic lipids allow direct in vitro transfection. A plasmid expressing green fluorescent protein (GFP) can be co-transfected to allow enrichment of transfected cells using fluorescence activated cell sorting (FACS). These cells are then chromium-51 ($^{51}$Cr) labeled and used as target cells for epitope-specific CTL lines; cytolysis, detected by $^{51}$Cr release, indicates both production of, and HLA presentation of minigene-encoded CTL epitopes. Expression of HTL epitopes may be evaluated in an analogous manner using assays to assess HTL activity.

In vivo immunogenicity is a second approach for functional testing of minigene DNA formulations. Transgenic mice expressing appropriate human HLA proteins are immunized with the DNA product. The dose and route of administration are formulation dependent (e.g., IM for DNA in PBS, intraperitoneal (i.p.) for lipid-complexed DNA). Twenty-one days after immunization, splenocytes are harvested and restimulated for one week in the presence of peptides encoding each epitope being tested. Thereafter, for CTL effector cells, assays are conducted for cytolysis of peptide-loaded, $^{51}$Cr-labeled target cells using standard techniques. Lysis of target cells that were sensitized by HLA loaded with peptide epitopes, corresponding to minigene-encoded epitopes, demonstrates DNA vaccine function for in vivo induction of CTLs. Immunogenicity of HTL epitopes is confirmed in transgenic mice in an analogous manner.

Alternatively, the nucleic acids can be administered using ballistic delivery as described, for instance, in U.S. Pat. No. 5,204,253. Using this technique, particles comprised solely of DNA are administered. In a further alternative embodiment, DNA can be adhered to particles, such as gold particles.

Minigenes can also be delivered using other bacterial or viral delivery systems well known in the art, e.g., an expression construct encoding epitopes of the invention can be incorporated into a viral vector such as vaccinia.

X.C.2. Combinations of CTL Peptides with Helper Peptides

Vaccine compositions comprising CTL peptides of the invention can be modified, e.g., analoged to provide desired attributes, such as improved serum half life, broadened population coverage or enhanced immunogenicity.

For instance, the ability of a peptide to induce CTL activity can be enhanced by linking the peptide to a sequence which contains at least one epitope that is capable of inducing a T helper cell response. Although a CTL peptide can be directly linked to a T helper peptide, often CTL epitope/HTL epitope conjugates are linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus may be a hetero- or homo-oligomer. When present, the spacer will usually be at least one or two residues, more usually three to six residues and sometimes 10 or more residues. The CTL peptide epitope can be linked to the T helper peptide either directly or via a spacer either at the amino or carboxy terminus of the CTL peptide. The amino terminus of either the immunogenic peptide or the T helper peptide may be acylated.

In certain embodiments, the T helper peptide is one that is recognized by T helper cells present in a majority of a genetically diverse population. This can be accomplished by selecting peptides that bind to many, most, or all of the HLA class II molecules. Examples of such amino acid bind may HLA Class II molecules include sequences from antigens such as tetanus toxoid at positions 830–843 (QYIKANSKFIGITE; SEQ ID NO: 760), *Plasmodium falciparum* circumsporozoite (CS) protein or positions 378–398 (DIEKKIAKMEKASSVFNVVNS; SEQ ID NO: 761), and *Streptococcus* 18 kD protein at positions 116–131 (GAVDSILGGVATYGAA; SEQ ID NO: 762). Other examples include peptides bearing a DR 1-4-7 supermotif, or either of the DR3 motifs.

Alternatively, it is possible to prepare synthetic peptides capable of stimulating T helper lymphocytes, in a loosely HLA-restricted fashion, using amino acid sequences not found in nature (see, e.g., PCT publication WO 95/07707). These synthetic compounds called Pan-DR-binding epitopes (e.g., PLADRE™, Epimmune, Inc., San Diego, Calif.) are designed to most preferably bind most HLA-DR (human HLA class II) molecules. For instance, a pan-DR-binding epitope peptide having the formula: aKXVAAWTLKAAa (SEQ ID NO: 763), where "X" is either cyclohexylalanine, phenylalanine, or tyrosine, and a is either D-alanine or L-alanine, has been found to bind to most HLA-DR alleles, and to stimulate the response of T helper lymphocytes from most individuals, regardless of their HLA type. An alternative of a pan-DR binding epitope comprises all "L" natural amino acids and can be provided in the form of nucleic acids that encode the epitope.

HTL peptide epitopes can also be modified to alter their biological properties. For example, they can be modified to include D-amino acids to increase their resistance to proteases and thus extend their serum half life, or they can be conjugated to other molecules such as lipids, proteins, carbohydrates, and the like to increase their biological activity. For example, a T helper peptide can be conjugated to one or more palmitic acid chains at either the amino or carboxyl termini.

X.C.3. Combinations of CTL Peptides with T Cell Priming Agents

In some embodiments it may be desirable to include in the pharmaceutical compositions of the inventions at least one component which primes B lymphocytes or T lymphocytes. Lipids have been identified as agents capable or priming CTL invivo. For example, palmitic acid residues can be attached to the ε-and α-amino groups of a lysine residue and then linked, e.g., via one or more linking residues such as Gly, Gly—Gly-, Ser, Ser—Ser, or the like, to an immunogenic peptide. The lipidated peptide can then be administered either directly in a micelle or particle, incorporated into a liposome, or emulsified in an adjuvant, e.g., incomplete Freund's adjuvant. In a preferred embodiment, a particularly effective immunogenic composition comprises palmitic acid attached to ε- and α-amino groups of Lys, which is attached via linkage, e.g. Ser—Ser, to the amino terminus of the immunogenic peptide.

As another example of lipid priming of CTL responses, *E. coli* lipoproteins, such as tripalmitoyl-S-glycerylcysteinlyseryl-serine ($P_3CSS$) can be used to prime virus specific CTL when covalently attached to an appropriate peptide (see, e.g., Deres, et al., *Nature* 342:561, 1989). Peptides of the invention can be coupled to $P_3CSS$, for example, and the lipopeptide administered to an individual to specifically prime an immune response to the target antigen. Moreover, because the induction of neutralizing antibodies can also be primed with $P_3CSS$-conjugated epitopes, two such compositions can be combined to more effectively elicit both humoral and cell-mediated responses.

X.C.4. Vaccine Compositions Comprising DC Pulsed with CTL and/or HTL Peptides

An embodiment of a vaccine composition in accordance with the invention comprises ex vivo administration of a cocktail of epitope-bearing peptides to PBMC, or isolated DC therefrom, from the patient's blood. A pharmaceutical to facilitate harvesting of DC can be used, such as Progenipoietin™ (Pharmacia-Monsanto, St. Louis, Mo.) or GM-CSF/IL-4. After pulsing the DC with peptides and prior to reinfusion into patients, the DC are washed to remove unbound peptides. In this embodiment, a vaccine comprises peptide-pulsed DCs which present the pulsed peptide epitopes complexed with HLA molecules on their surfaces.

The DC can be pulsed ex vivo with a cocktail of peptides, some of which stimulate CTL responses to 161P2F10B. Optionally, a helper T cell (HTL) peptide, such as a natural or artificial loosely restricted HLA Class II peptide, can be included to facilitate the CTL response. Thus, a vaccine in accordance with the invention is used to treat a cancer which expresses or overexpresses 161P2F10B.

X.D. Adoptive Immunotherapy

Antigenic 161P2F10B-related peptides are used to elicit a CTL and/or HTL response ex vivo, as well. The resulting CTL or HTL cells, can be used to treat tumors in patients that do not respond to other conventional forms of therapy, or will not respond to a therapeutic vaccine peptide or nucleic acid in accordance with the invention. Ex vivo CTL or HTL responses to a particular antigen are induced by incubating in tissue culture the patient's or genetically compatible, CTL or HTL precursor cells together with a source of antigen-presenting cells (APC), such as dendritic cells, and the appropriate immunogenic peptide. After an appropriate incubation time (typically about 7–28 days), in which the precursor cells are activated and expanded into effector cells, the cells are infused back into the patient, where they will destroy (CTL) or facilitate destruction (HTL) of their specific target cell (e.g., a tumor cell). Transfected dendritic cells may also be used as antigen presenting cells.

X.E. Administrative of Vaccines for Therapeutic or Prophylactic Purposes

Pharmaceutical and vaccine compositions of the invention are typically used to treat and/or prevent a cancer that expresses or overexpresses 161P2F10B. In therapeutic applications, peptide and/or nucleic acid compositions are administered to a patient in an amount sufficient to elicit an effective B cell, CTL and/or HTL response to the antigen and to cure or at least partially arrest or slow symptoms and/or complications. An amount adequate to accomplish this is defined as "therapeutically effective dose." Amounts effective for this use will depend on, e.g., the particular composition administered, the manner of administration, the stage and severity of the disease being treated, the weight and general state of health of the patient, and the judgment of the prescribing physician.

For pharmaceutical compositions, the immunogenic peptides of the invention, or DNA encoding them, are generally administered to an individual already being a tumor that expresses 161P2F10B. The peptides or DNA encoding then can be administered individually or as fusions of one or more peptide sequences. Patients can be treated with the immunogenic peptides separately or in conjunction with other treatments, such as surgery, as appropriate.

For therapeutic use, administration should generally begin at the first diagnosis of 161P2F10B-associated cancer. This is followed by boosting doses until at least symptoms are substantially abated and for a period thereafter. The embodiment of the vaccine composition (i.e., including, but not limited to embodiments such as peptide cocktails, polyepitopic polypeptides, minigenes, or TAA-specific CTLs or pulsed dendritic cells) delivered to the patient may vary according to the stage of the disease or the patient's health status. For example, in a patient with a tumor that expresses 161P2F10B, a vaccine comprising 161P2F10B -specific CTL may be more efficacious in killing tumor cells in patient with advanced disease than alternative embodiments.

It is generally important to provide an amount of the peptide epitope delivered by a mode of administration sufficient to effectively stimulate a cytotoxic T cell response; compositions which stimulate helper T cell responses can also be given in accordance with this embodiment of the invention.

The dosage for an initial therapeutic immunization generally occurs in a unit dosage range where the lower value is about 1, 5, 50, 500, or 1,000 µg and the higher value is about 10,000; 20,000; 30,000; and 50,000 µg. Dosage values for a human typically range from about 50 µg to about 50,000 µg per 70 kilogram patient. Boosting dosages of between about 0.1 µg to about 50,000 µg of peptide pursuant to a boosting regimen over weeks to months may be administered depending upon the patient's response and condition as determined by measuring the specific activity of CTL and HTL obtained from the patient's blood. Administration should continue until at least clinical symptoms or laboratory tests indicate that the neoplasia, has been eliminated or reduced and for a period thereafter. The dosages, routes of administration, and dose schedules are adjusted in accordance with methodologies known in the art.

In certain embodiments, the peptides and compositions of the present invention are employed in serious disease states, that is, life-threatening or potentially life threatening situations. In such cases, as a result of the minimal amounts of extraneous substances and the relative nontoxic nature of the peptides in preferred compositions of the invention, it is possible and may be felt desirable by the treating physician to administer substantial excesses of these peptides compositions relative to these stated dosage amounts.

The vaccine compositions of the invention can also be sued purely as prophylactic agents. Generally the dosage for an initial prophylactic immunization generally occurs in a unit dosage range where the lower value is about 1, 5, 50, 500, or 1000 µg and the higher value is about 10,000; 20,000; 30,000; or 50,000 µg. Dosage values for a human typically range from about 500 µg to about 50,000 µg per 70 kilogram patient. This is followed by boosting dosages of between about 1.0 µg to about 50,000 µg of peptide administered at defined intervals from about four weeks to six months after the initial administration of vaccine. The immunogenicity of the vaccine can be assessed by measuring the specific activity of CTL and HTL obtained from a sample of the patient's blood.

The pharmaceutical composition for therapeutic treatment are intended for parenteral, topical, oral, nasal, intrahecal, or local (e.g. as a cream or topical ointment) administration. Preferably, the pharmaceutical compositions are administered parentally, e.g., intravenously, subcutaneously, intradermally, or intramuscularly. Thus, the invention provides compositions for parenteral administration which comprise a solution of the immunogenic peptides dissolved or suspended in an acceptable carrier, preferably an aqueous carrier.

A variety of aqueous carriers may be used, e.g., water, buffered water, 0.8% saline, 0.3% glycine, hyaluronic acid and the like. These compositions may be sterilized by conventional, well-known sterilization techniques, or may be sterile filtered. The resulting aqueous solutions may be packaged for use as is, or lyophilized, the lyophilized preparation being combined with a sterile solution prior to administration.

The compositions may contain pharmaceutically acceptable auxiliary substances as required to approximate physiological conditions, such as pH-adjusting and buffering agents, tonicity adjusting agents, wetting agents, preservations, and the like, for example, sodium acetate, sodium lactate, sodium chloride, potassium chloride, calcium chloride, sorbitan monolaurate, triethanolamine oleate, etc.

The concentration of peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

A human unit dose form of a composition is typically included in a pharmaceutical composition that comprises a human unit dose of an acceptable carrier, in one embodiment an aqueous carrier, and is administered in a volume/quantity that is known by those of skill in the art to be used for administration of such compositions to humans (see, e.g., Remington's Pharmaceutical Sciences, 17$^{th}$ Edition, A. Gennaro, Editor, Mack Publishing Co., Easton, Pa., 1985). For example a peptide dose for initial immunization can be from about 1 to about 50,000 µg, generally 100–5,000 µg, for a 70 kg patient. For example, for nucleic acids an initial immunization may be performed using an expression vector in form of naked nucleic acid administered IM (or SC or ID) in the amounts of 0.5–5 mg at multiple sites. The nucleic acid (0.1 to 1000 µg) can also be administered using a gene gun. Following an incubation period of 3–4 weeks, a booster dose is then administered. The booster can be recombinant fowlpox virus administered at a dose of $5-10^7$ to $5 \times 10^9$ pfu.

For antibodies, a treatment generally involves repeated administration of the anti-161P2F10B antibody preparation, via an acceptable route of administration such as intravenous injection (IV), typically at a dose in the range of about 0.1 to about 10 mg/kg body weight. In general doses in the range of 10–500 mg mAb per week are effective and well tolerated. Moreover, an initial loading dose of approximately 4 mg/kg patient body weight TV, followed by weekly doses of about 2 mg/kg IV of the anti161P2F10B mAb preparation represents an acceptable dosing regimen. As appreciated by those of skill in the art, various factors can influence the ideal dose in a particular case. Such factors include, for example, half life of a composition, the binding affinity of an Ab, the immunogenicity of a substance, the degree of 161P2F10B expression in the patient, the extent of circulating shed 161P2F10B antigen, the desired steady-state concentration level, frequency of treatment, and the influence of chemotherapeutic or other agents used in combination with the treatment of the invention, as well as the death status of a particular patient. Non-limiting preferred human unit doses are, for example, 500 µg–1 mg, 1 mg–50 mg, 50 mg–100 mg, 100 mg–200 mg, 200 mg–300 mg, 300 mg–400 mg, 400 mg–500 mg, 500 mg–600 mg, 600 mg–700 mg, 700 mg–800 mg, 800 mg–900 mg, 900 mg–1 g, or 1 mg–700 mg. In certain embodiments, the dose is in a range of 2–5 mg/kg body weight, e.g., with follow on weekly doses of 1–3 mg/kg; 0.5 mg, 1, 2, 3, 4, 5, 6, 7, 8, 9, 10 mg/kg body weight followed, e.g., in two, three or four weeks by weekly doses; 0.5–10 mg/kg body weight, e.g., followed in two, three or four weeks by weekly doses; 225, 250, 275, 300, 325, 350, 375, 400 mg m$^2$ of body area weekly; 1–600 mg m$^2$ of body area weekly; 225–400 mg m$^2$ of body area weekly; these does can be followed by weekly doses for 2, 3, 4, 5, 6, 7, 8, 9, 19, 11, 12 or more weeks.

In one embodiment, human unit dose forms of polynucleotide comprises a suitable dosage range or effective amount that provides any therapeutic effect. As appreciated by one of ordinary skill in the art a therapeutic effect depends on a number of factors, including the sequence of the polynucleotide, molecular weight of the polynucleotide and route of administration. Dosages are generally selected by the physician or other health care professional in accordance with a variety of parameters known in the art, such as severity of symptoms, history of the patient and the like. Generally, for a polynucleotide of about 20 bases, a dosage range may be selected from, for example, an independently selected lower limit such as about 0.1, 0.25, 0.5, 1, 2, 5, 10, 20, 30, 40, 50, 60, 70, 80, 90, 100, 200, 300, 400 or 500 mg/kg up to an independently selected upper limit, greater than the lower limit, of about 60, 80, 100, 200, 300, 400, 500, 750, 1000, 1500, 2000, 3000, 4000, 5000, 6000, 7000, 8000, 9000 or 10,000 mg/kg. For example, a dose may be about any of the following: 0.1 to 100 mg/kg, 0.1 to 50 mg/kg, 0.1 to 25 mg/kg, 0.1 to 10 mg/kg, 1 to 500 mg/kg, 100 to 400 mg/kg, 200 to 300 mg/kg, 1 to 100 mg/kg, 100 to 200 mg/kg, 300 to 400 mg/kg, 400 to 500 mg/kg, 500 to 1000 mg/kg, 500 to 5000 mg/kg, or 500 to 10,000 mg/kg. Generally, parenteral routes of administration may require higher doses of polynucleotide compared to more direct application to the nucleotide to diseased tissue, as do polynucleotides of increasing length.

In one embodiment, human unit dose forms of T-cells comprise a suitable dosage range or effective amount that provides any therapeutic effect. As appreciated by one of ordinary skill in the art, a therapeutic effect depends on a number of factors. Dosages are generally selected by the physician or other health care professional in accordance with a variety of parameters known in the art, such as severity of symptoms, history of the patient and the like. A dose may be about $10^4$ cells to about $10^6$ cells, about $10^6$ cells to about $10^8$ cells, about $10^8$ to about $10^{11}$ cells, or about $10^8$ to about $5 \times 10^{10}$ cells. A dose may also about $10^6$ cells/m$^2$ to about $10^{10}$ cells/m$^2$, or about $10^6$ cells/m$^2$ to about $10^8$ cells/m$^2$.

Protein(s) of the invention, and/or nucleic acids encoding the protein(s), can also be administered via liposomes, which may also serve to: 1) target the protein(s) to a particular tissue, such as lymphoid tissue; 2) to target selectively to diseases cells; or, 3) to increase the half-life of the peptide composition. Liposomes include emulsions, foams, micelles, insoluble monolayers, liquid crystals, phospholipid dispersions, lamellar layers and the like. In these preparations, the peptide to be delivered is incorporated as part of a liposome, alone or in conjunction with a molecule which binds to a receptor prevalent among lymphoid cells, such as monoclonal antibodies which bind to the CD45 antigen, or with other therapeutic or immunogenic compositions. Thus, liposomes either filled or decorated with a desired peptide of the invention can be directed to the site of lymphoid cells, where the liposomes then deliver the peptide compositions. Liposomes for use in accordance with the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka, et al., *Ann. Rev. Biophys. Bioeng.* 9:467 (1980), and U.S. Pat. Nos. 4,235,871, 4,501,728, 4,837,028, and 5,019,369.

For targeting cells of the immune system, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more peptides of the invention, and more preferably at a concentration of 25%–75%.

For aerosol administration, immunogenic peptides are preferably supplied in finely divided form along with a surfactant and propellant. Typical percentages of peptides are about 0.01%–20% by weight, preferably about 1%–10%. The surfactant must, of course, be nontoxic, and preferably soluble in the propellant. Representative of such agents are the esters or partial esters of fatty acids containing from about 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute about 0.1%–20% by weight of the composition, preferably about 0.25–5%. The balance of the composition is ordinarily propellant. A carrier can also be included, as desired, as with, e.g., lecithin for intranasal delivery.

XI.) Diagnostic and Prognostic Embodiments of 161P2F10B

As disclosed herein, 161P2F10B polynucleotides, polypeptides, reactive cytotoxic T cells (CTL), reactive helper T cells (HTL) and anti-polypeptide antibodies are used in well known diagnostic, prognostic and therapeutic assays that examine conditions associated with dysregulated cell growth such as cancer, in particular the cancers listed in Table I (see, e.g., both its specific pattern of tissue expression as well as its overexpression in certain cancers as described for example in Example 4).

161P2F10B can be analogized to a prostate associated antigen PSA, the archetypal marker that has been used by medical practitioners for years to identify and monitor the presence of prostate cancer (see, e.g., Merrill et al., J. Urol. 163(2): 503–5120 (2000); Polascik et al., J. Urol. August; 162(2):293–306 (1999) and Fortier et al., J. Nat. Cancer Inst. 91(19): 1635–1640(1999)). A variety of other diagnostic markers are also used in similar contexts including p53 and K-ras (see, e.g., Tulchinsky et al., Int J Mol Med 1999 July 4(1):99–102 and Minimoto et al., Cancer Detect Prev 2000;24(1):1–12). Therefore, this disclosure of the 161P2F10B polynucleotides and polypeptides (as well as the 161P2F10B polynucleotide probes and anti-161P2F10B antibodies used to identify the presence of these molecules) and their properties allows skilled artisans to utilize these molecules in methods that are analogous to those used, for example, in a variety of diagnostic assays directed to examining conditions associated with cancer.

Typical embodiments of diagnostic methods which utilize the 161P2F10B polynucleotides, polypeptides, reactive T cells and antibodies are analogous to those methods from well-established diagnostic assays which employ, e.g., PSA polynucleotides, polypeptides, reactive T cells and antibodies. For example, just as PSA polynucleotides are used as probes (for example in Northern analysis, see, e.g., Sharief et al., Biochem. Mol. Biol. Int. 33(3):567–74(1994)) and primers (for example in PCR analysis, see, e.g., Okegawa et al., J. Urol. 163(4): 1189–1190 (2000)) to observe the presence and/or the level of PSA mRNAs in methods of monitoring PSA overexpression or the metastasis of prostate cancers, the 161P2F10B polynucleotides described herein can be utilized in the same way to detect 161P2F10B overexpression or the metastasis of prostate and other cancers expressing this gene. Alternatively, just as PSA polypeptides are used to generate antibodies specific for PSA which can then be used to observe the presence and/or the level of PSA proteins in methods to monitor PSA protein overexpression (see, e.g., Stephan et al., Urology 55(4) :560–3 (2000)) or the metastasis of prostate cells (see, e.g., Alanen et al., Pathol. Res. Pract. 192(3):233–7 (1996)), the 161P2F10B polypeptides described herein can be utilized to generate antibodies for use in detecting 161P2F10B overexpression or the metastasis of prostate cells and cells of other cancers expressing this gene.

Specifically, because metastases involves the movement of cancer cells from an organ of origin (such as the lung or prostate gland etc.) to a different area of the body (such as a lymph node), assays which examine a biological sample for the presence of cells expressing 161P2F10B polynucleotides and/or polypeptides can be used to provide evidence of metastasis. For example, when a biological sample from tissue that does not normally contain 161P2F10B-expressing cells (lymph node) is found to contain 161P2F10B-expressing cells such as the 161P2F10B expression seen in LAPC4 and LAPC9, xenografts isolated from lymph node and bone metastasis, respectively, this finding is indicative of metastasis.

Alternatively 161P2F10B polynucleotides and/or polypeptides can be used to provide evidence of cancer, for example, when cells in a biological sample that do not normally express 161P2F10B or express 161P2F10B at a different level are found to express 161P2F10B or have an increased expression of 161P2F10B (see, e.g., the 161P2F10B expression in the cancers listed in Table I and in patient samples etc. shown in the accompanying Figures). In such assays, artisans may further wish to generate supplementary evidence of metastasis by testing the biological sample for the presence of a second tissue restricted marker (in addition to 161P2F10B) such as PSA, PSCA etc. (see, e.g., Alanen et al., Pathol. Res. Pract. 192(3): 233–237 (1996)).

Just as PSA polynucleotide fragments and polynucleotide variants are employed by skilled artisans for use in methods of monitoring PSA, 161P2F10B polynucleotide fragments and polynucleotide variants are used in an analogous manner. In particular, typical PSA polynucleotides used in methods of monitoring PSA are probes or primers which consist of fragments of the PSA cDNA sequence. Illustrating this, primers used to PCR amplify a PSA polynucleotide must include less than the whole PSA sequence to function in the polymerase chain reaction. In the context of such PCR reactions, skilled artisans generally create a variety of different polynucleotide fragments that can be used as primers in order to amplify different portions of a polynucleotide of interest or to optimize amplification reactions (see, e.g., Caetano-Anolles, G. Biotechniques 25(3): 472–476, 478–480 (1998); Robertson et al., Methods Mol. Biol. 98:121–154 (1998)). An additional illustration of the use of such fragments is provided in Example 4, where a 161P2F10B polynucleotide fragment is used as a probe to show the expression of 161P2F10B RNAs in cancer cells. In addition, variant polynucleotide sequences are typically used as primers and probes for the corresponding mRNAs in PCR and Northern analyses (see, e.g., Sawai et al., Fetal Diagn. Ther. 1996 November–December 11(6):407–13 and Current Protocols In Molecular Biology, Volume 2, Unit 2, Frederick M. Ausubel et al. eds., 1995)). Polynucleotide fragments and variants are useful in this context where they are capable of binding to a target polynucleotide sequence (e.g. the 161P2F10B polynucleotide shown in SEQ ID NO: 701) under conditions of high stringency.

Furthermore, PSA polypeptides which contain an epitope that can be recognized by an antibody or T cell that specifically binds to that epitope are used in methods of monitoring PSA. 161P2F10B polypeptide fragments and polypeptide analogs or variants can also be used in an analogous manner. This practice of using polypeptide fragments or polypeptide variants to generate antibodies (such as anti-PSA antibodies or T cells) is typical in the art with a wide variety of systems such as fusion proteins being used by practitioners (see, e.g., Current Protocols In Molecular Biology, Volume 2, Unit 16, Frederick M. Ausubel et al. eds., 1995). In this context, each epitope(s) functions to provide the architecture with which an antibody or T cell is reactive. Typically, skilled artisans create a variety of different polypeptide fragments that can be used in order to generate immune responses specific for different portions of a polypeptide of interest (see, e.g., U.S. Pat. No. 5,840,501 and U.S. Pat. No. 5,939,533). For example it may be preferable to utilize a polypeptide comprising one of the 161P2F10B biological motifs discussed herein or a motif-bearing subsequence which is readily identified by one of skill in the art based on motifs available in the art. Polypeptide fragments, variants or analogs are typically useful in this context as long as they comprise an epitope capable of generating an antibody or T cell specific for a target polypeptide sequence (e.g. the 161P2F10B polypeptide shown in FIG. 2).

As shown herein, the 161P2F10B polynucleotides and polypeptides (as well as the 161P2F10B polynucleotide probes and anti-161P2F10B antibodies or T cells used to identify the presence of these molecules) exhibit specific properties that make them useful in diagnosing cancers such as those listed in Table I. Diagnostic assays that measure the presence of 161P2F10B gene products, in order to evaluate the presence or onset of a disease condition described herein, such as prostate cancer, are used to identify patients for preventive measures or further monitoring, as has been done so successfully with PSA. Moreover, these materials satisfy a need in the art for molecules having similar or complementary characteristics to PSA in situations where, for example, a definite diagnosis of metastasis of prostatic origin cannot be made on the basis of a test for PSA alone (see, e.g., Alanen et al., Pathol. Res. Pract. 192(3): 233–237 (1996)), and consequently, materials such as 161P2F10B polynucleotides and polypeptides (as well as the 161P2F10B polynucleotide probes and anti-161P2F10B antibodies used to identify the presence of these molecules) must be employed to confirm metastases of prostatic origin.

Finally, in addition to their use in diagnostic assays, the 161P2F10B polynucleotides disclosed herein have a number of other utilities such as their use in the identification of oncogenetic associated chromosomal abnormalities in the chromosomal region to which the 161P2F10B gene maps (see Example 3 below). Moreover, in addition to their use in diagnostic assays, the 161P2F10B-related proteins and polynucleotides disclosed herein have other utilities such as their use in the forensic analysis of tissues of unknown origin (see, e.g., Takahama K Forensic Sci Int 1996 June 28;80 (1–2): 63–9).

Additionally, 161P2F10B-related proteins or polynucleotides of the invention can be used to treat a pathologic condition characterized by the over-expression of 161P2F10B. For example, the amino acid or nucleic acid sequence of FIG. 2 or FIG. 3, or fragments of either, can be used to generate an immune response to the 161P2F10B antigen. Antibodies or other molecules that react with 161P2F10B can be used to modulate the function of this molecule, and thereby provide a therapeutic benefit.

XII.) Inhibition of 161P2F10B Protein Function

The invention includes various methods and compositions for inhibiting the binding of 161P2F10B to its binding partner or its association with other protein(s) as well as methods for inhibiting 161P2F10B function.

XII.A.) Inhibition of 161P2F10B with Intracellular Antibodies

In one approach, a recombinant vector that encodes single chain antibodies that specifically bind to 161P2F10B are introduced into 161P2F10B expressing cells via gene transfer technologies. Accordingly, the encoded single chain anti-161P2F10B antibody is expressed intracellularly, binds to 161P2F10B protein, and thereby inhibits its function. Methods for engineering such intracellular single chain antibodies are well known. Such intracellular antibodies, also known as "intrabodies", are specifically targeted to a particular compartment within the cell, providing control over where the inhibitor activity of the treatment is focused. This technology has been successfully applied in the art (for review, see Richardson and Marasco, 1995, TIBTECH vol. 13). Intrabodies have been shown to virtually eliminate the expression of otherwise abundant cell surface receptors (see, e.g., Richardson et al., 1995, Proc. Natl. Acad. Sci. USA 92: 3137–3141; Beerli et al., 1994, J. Biol. Chem. 289: 23931–23936; Deshane et al., 1994, Gene Ther. 1: 332–337).

Single chain antibodies comprise the variable domains of the heavy and light chain joined by a flexible linker polypeptide, and are expressed as a single polypeptide. Optionally, single chain antibodies are expressed as a single chain variable region fragment joined to the light chain constant region. Well-known intracellular trafficking signals are engineered into recombinant polynucleotide vectors encoding such single chain antibodies in order to precisely target the intrabody to the desired intracellular compartment. For example, intrabodies targeted to the endoplasmic reticulum (ER) are engineered to incorporate a leader peptide and, optionally, a C-terminal ER retention signal, such as the KDEL amino acid motif. Intrabodies intended to exert activity in the nucleus are engineered to include a nuclear localization signal. Lipid moieties are joined to intrabodies in order to tether the intrabody to the cytosolic side of the plasma membrane. Intrabodies can also be targeted to exert function in the cytosol. For example, cytosolic intrabodies are used to sequester factors within the cytosol, thereby preventing them from being transported to their natural cellular destination.

In one embodiment, intrabodies are used to capture 161P2F10B in the nucleus, thereby preventing its activity within the nucleus. Nuclear targeting signals are engineered into such 161P2F10B intrabodies in order to achieve the desired targeting. Such 161P2F10B intrabodies are designed to bind specifically to a particular 161P2F10B domain. In another embodiment, cytosolic intrabodies that specifically bind to the 161P2F10B protein are used to prevent 161P2F10B from gaining access to the nucleus, thereby preventing it from exerting any biological activity within the nucleus (e.g., preventing 161P2F10B from forming transcription complexes with other factors).

In order to specifically direct the expression of such intrabodies to particular cells, the transcription of the intrabody is placed under the regulatory control of an appropriate tumor-specific promoter and/or enhancer. In order to target intrabody expression specifically to prostate, for example, the PSA promoter and/or promoter/enhancer can be utilized (See, for example, U.S. Pat. No. 5,919,652 issued 6 Jul. 1999).

XII.B.) Inhibition of 161P2F10B with Recombinant Protein

In another approach, recombinant molecules bind to 161P2F10B and thereby inhibit 161P2F10B function. For example, these recombinant molecules prevent or inhibit 161P2F10B from accessing/binding to its binding partner(s) or associating with other protein(s). Such recombinant molecules can, for example, contain the reactive part(s) of a 161P2F10B specific antibody molecule. In a particular embodiment, the 161P2F10B binding domain of a 161P2F10B binding partner is engineered into a dimeric fusion protein, whereby the fusion protein comprises two 161P2F10B ligand binding domains linked to the Fc portion of a human IgG, such as human IgG1. Such IgG portion can contain, for example, the $C_H2$ and $C_H3$ domains and the hinge region, but not the $C_H1$ domain. Such dimeric fusion proteins are administered in soluble form to patients suffering from a cancer associated with the expression of 161P2F10B, whereby the dimeric fusion protein specifically binds to 161P2F10B and blocks 161P2F10B interaction with a binding partner. Such dimeric fusion proteins are further combined into multimeric proteins using known antibody linking technologies.

XII.C.) Inhibition of 161P2F10B Transcription or Translation

The present invention also comprises various methods and compositions for inhibiting the transcription of the 161P2F10B gene. Similarly, the invention also provides methods and compositions for inhibiting the translation of 161P2F10B mRNA into protein.

In one approach, a method of inhibiting the transcription of the 161P2F10B gene comprises contacting the 161P2F10B gene with a 161P2F10B antisense polynucleotide. In another approach, a method of inhibiting 161P2F10B mRNA translation comprises contacting the 161P2F10B mRNA with an antisense polynucleotide. In another approach, a 161P2F10B specific ribozyme is used to cleave the 161P2F10B message, thereby inhibiting translation. Such antisense and ribozyme based methods can also be directed to the regulatory regions of the 161P2F10B gene, such as the 161P2F10B promoter and/or enhancer elements. Similarly, proteins capable of inhibiting a 161P2F10B gene transcription factor are used to inhibit 161P2F10B mRNA transcription. The various polynucleotides and compositions useful in the aforementioned methods have been described above. The use of antisense and ribozyme molecules to inhibit transcription and translation is well known in the art.

Other factors that inhibit the transcription of 161P2F10B by interfering with 161P2F10B transcriptional activation are also useful to treat cancers expressing 161P2F10B. Similarly, factors that interfere with 161P2F10B processing are useful to treat cancers that express 161P2F10B. Cancer treatment methods utilizing such factors are also within the scope of the invention.

XII.D.) General Considerations for Therapeutic Strategies

Gene transfer and gene therapy technologies can be used to deliver therapeutic polynucleotide molecules to tumor cells synthesizing 161P2F10B (i.e., antisense, ribozyme, polynucleotides encoding intrabodies and other 161P2F10B inhibitory molecules). A number of gene therapy approaches are known in the art. Recombinant vectors encoding 161P2F10B antisense polynucleotides, ribozymes, factors capable of interfering with 161P2F10B transcription, and so forth, can be delivered to target tumor cells using such gene therapy approaches.

The above therapeutic approaches can be combined with any one of a wide variety of surgical, chemotherapy or radiation therapy regimens. The therapeutic approaches of the invention can enable the use of reduced dosages of chemotherapy (or other therapies) and/or less frequent administration, an advantage for all patients and particularly for those that do not tolerate the toxicity of the chemotherapeutic agent well.

The anti-tumor activity of a particular composition (e.g., antisense, ribozyme, intrabody), or a combination of such compositions, can be evaluated using various in vitro and in vivo assay systems. In vitro assays that evaluate therapeutic activity include cell growth assays, soft agar assays and other assays indicative of tumor promoting activity, binding assays capable of determining the extent to which a therapeutic composition will inhibit the binding of 161P2F10B to a binding partner, etc.

In vivo, the effect of a 161P2F10B therapeutic composition can be evaluated in a suitable animal model. For example, xenogenic prostate cancer models can be used, wherein human prostate cancer explants or passaged xenograft tissues are introduced into immune compromised animals, such as nude or SCID mice (Klein et al., 1997, Nature Medicine 3: 402–408). For example, PCT Patent Application WO98/16628 and U.S. Pat. No. 6,107,540, Sawyers et al., published Apr. 23, 1998, describes various xenograft models of human prostate cancer capable of recapitulating the development of primary tumors, micrometastasis, and the formation of osteoblastic metastases characteristic of late stage disease. Efficacy can be predicted using assays that measure inhibition of tumor formation, tumor regression or metastasis, and the like.

In vivo assays that evaluate the promotion of apoptosis are useful in evaluating therapeutic compositions. In one embodiment, xenografts from tumor bearing mice treated with the therapeutic composition can be examined for the presence of apoptotic foci and compared to untreated control xenograft-bearing mice. The extent to which apoptotic foci are found in the tumors of the treated mice provides an indication of the therapeutic efficacy of the composition.

The therapeutic compositions used in the practice of the foregoing methods can be formulated into pharmaceutical compositions comprising a carrier suitable for the desired delivery method. Suitable carriers include any material that when combined with the therapeutic composition retains the anti-tumor function of the therapeutic composition and is generally non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences $16^{th}$ Edition, A. Osal., Ed., 1980).

Therapeutic formulations can be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic protein preparations can be lyophilized and stored as sterile powders, preferably under vacuum, and then reconstituted in bacteriostatic water (containing for example, benzyl alcohol preservative) or in sterile water prior to injection.

Dosages and administration protocols for the treatment of cancers using the foregoing methods will vary with the method and the target cancer, and will generally depend on a number of other factors appreciated in the art.

XIII.) Kits

For use in the diagnostic and therapeutic applications described herein, kits are also within the scope of the invention. Such kits can comprise a carrier, package or container that is compartmentalized to receive one or more containers such as vials, tubes, and the like, each of the container(s) comprising one of the separate elements to be used in the method. For example, the container(s) can comprise a probe that is or can be detectably labeled. Such probe can be an antibody or polynucleotide specific for a 161P2F10B-related protein or a 161P2F10B gene or message, respectively. Where the method utilizes nucleic acid hybridization to detect the target nucleic acid, the kit can also have containers containing nucleotide(s) for amplification of the target nucleic acid sequence and/or a container comprising a reporter-means, such as a biotin-binding protein, such as avidin or streptavidin, bound to a reporter molecule, such as an enzymatic, fluorescent, or radioisotope label. The kit can include all or part of the amino acid sequence of FIG. 2 or FIG. 3 or analogs thereof, or a nucleic acid molecules that encodes such amino acid sequences.

The kit of the invention will typically comprise the container described above and one or more other containers comprising materials desirable from a commercial and user standpoint, including buffers, diluents, filters, needles, syringes, and package inserts with instructions for use.

A label can be present on the container to indicate that the composition is used for a specific therapy or non-therapeutic application, and can also indicate directions for either in vivo or in vitro use, such as those described above. Directions and or other information can also be included on an insert which is included with the kit.

EXAMPLES

Various aspects of the invention are further described and illustrated by way of the several examples that follow, none of which are intended to limit the scope of the invention.

Example 1

SSH-Generated Isolation of a cDNA Fragment of the 161P2F10B Gene

To isolate genes that are over-expressed in kidney cancer we used the Suppression Subtractive Hybridization (SSH) procedure using cDNA derived from kidney cancer patient tissues.

The 161P2F10B SSH cDNA sequence was derived from a subtraction consisting of a kidney cancer minus normal kidney and a mixture of 9 normal tissues: stomach, skeletal muscle, lung, brain, liver, kidney, pancreas, small intestine and heart. By RT-PCR, the 161P2F10B cDNA was identified as highly expressed in kidney cancer pool, with lower expression detected in prostate cancer xenograft pool, prostate cancer pool, colon cancer pool, lung cancer pool, ovary cancer pool, breast cancer pool, metastasis cancer pool, pancreas cancer pool, 2 different prostate cancer metastasis to lymph node, VP1 and VP2. (FIG. 10).

The 161P2F10B SSH cDNA sequence of 182 bp matches the cDNA for phosphodiesterase 1/nucleotide pyrophosphatase 3 (PDNP3). The full length 161P2F10B cDNA and ORF are described in FIG. 2 with the protein sequence listed in FIG. 3.

Materials and Methods

RNA Isolation:

Tumor tissues were homogenized in Trizol reagent (Life Technologies, Gibco BRL) using 10 ml/g tissue or 10 ml/$10^8$ cells to isolate total RNA. Poly A RNA was purified from total RNA using Qiagen's Oligotex mRNA Mini and Midi kits. Total and mRNA were quantified by spectrophotometric analysis (O.D. 260/280 nm) and analyzed by gel electrophoresis.

Oligonucleotides:

The following HPLC purified oligonucleotides were used.

DPNCDN (cDNA Synthesis Primer):
5'TTTTGATCAAGCTT$_{30}$3' (SEQ ID NO: 752)
Adaptor 1:
5'CTAATACGACTCACTATAGGGCTC-
GAGCGGCCGCCCGGGCAG3' (SEQ ID NO: 753)
3'GGCCCGTCCTAG5' (SEQ ID NO: 754)
Adaptor 2:
5'GTAATACGACTCACTATAGGGCAGCGTG-
GTCGCGGCCGAG3' (SEQ ID NO: 755)
3'CGGCTCCTAG5' (SEQ ID NO: 756)
PCR Primer 1:
5'CTAATACGACTCACTATAGGGC3' (SEQ ID NO: 757)
Nested Primer (NP)1:
5'TCGAGCGGCCGCCCGGGCAGGA3' (SEQ ID NO: 758)
Nested Primer (NP)2:
5'AGCGTGGTCGCGGCCGAGGA3' (SEQ ID NO: 759)

Suppression Subtractive Hybridization:

Suppression Subtractive Hybridization (SSH) was used to identify cDNAs corresponding to genes that may be differently expressed in prostate cancer. The SSH reaction utilized cDNA from kidney cancer patient specimens. The gene 161P2F10B was derived from kidney cancer patient tissues minus normal kidney and a mixture of 9 normal tissues: stomach, skeletal muscle, lung, brain, liver, kidney, pancreas, small intestine and heart. The SSH DNA sequence (FIG. 1) was identified.

The cDNA derived from kidney cancer patient tissues was used as the source of the "driver" cDNA, while the cDNA from normal tissues was used as the source of the "tester" cDNA. Double stranded cDNAs corresponding to tester and driver cDNAs were synthesized from 2 μg of poly(A)$^+$ RNA isolated from the relevant tissue, as described above, using CLONTECH's PCR-Select cDNA Subtraction Kit and 1 ng of oligonucleotide DPNCDN as primer. First- and second-strand synthesis were carried out as described in the Kit's user manual protocol (CLONTECH Protocol No. PT1117-1, Catalog No. K1804-1). The resulting cDNA was digested with Dpn II for 3 hrs at 37° C. Digested cDNA was extracted with phenol/chloroform (1:1) and ethanol precipitated.

Tester cDNA was generated by diluting 1 μl of Dpn II digested cDNA from the relevant tissue source (see above) (400 ng) in 5 μl of water. The diluted cDNA (2 μl, 160 ng) was then ligated to 2 μl of Adaptor 1 and Adaptor 2 (10 μM), in separate ligation reactions, in a total volume of 10 μl of 16° C. overnight, using 400 u of T4 DNA ligase (CLONTECH). Ligation was terminated with 1 μl of 0.2 M EDTA and heating at 72° C. for 5 min.

The first hybridization was performed by adding 1.5 μl (600 ng) of driver cDNA to each of two tubes containing 1.5 μl (20 ng) Adaptor 1- and Adaptor 2-ligated tester cDNA. In a final volume of 4 μl, the samples were overlaid with mineral oil, denatured in an MJ Research thermal cycler at 98° C. for 1.5 minutes, and then were allowed to hybridize for 8 hrs at 68° C. The two hybridizations were then mixed together with an additional 1 μl of fresh denatured driver cDNA and were allowed to hybridize overnight at 68° C. The second hybridization was then diluted in 200 μl of 20 mM Hepes, pH 8.3, 50 mM NaCl, 0.2 mM EDTA, heated at 70° C. for 7 min. and stored at −20° C.

PCR Amplification, Cloning and Sequencing of Gene Fragments Generated from SSH:

To amplify gene fragments resulting from SSH reactions, two PCR amplifications were performed. In the primary PCR reaction 1 μl of the diluted final hybridization mix was added to 1 μl of PCR primer 1 (10 μM), 0.5 μl dNTP mix (10 μM), 2.5 μl 10× reaction buffer (CLONTECH) and 0.5 μl 50× Advantage cDNA polymerase Mix (CLONTECH) in a final volume of 25 μl. PCR 1 was conducted using the following conditions: 75° C. for 5 min., 94° C. for 25 sec., then 27 cycles of 94° C. for 10 sec, 66° C. for 30 sec, 72° C. for 1.5 min. Five separate primary PCR reactions were performed for each experiment. The products were pooled and diluted 1:10 with water. For the secondary PCR reaction, 1 μl from the pooled and diluted primary PCR reaction was added to the same reaction mix as used for PCR 1, except that primers NP1 and NP2 (10 μM) were used instead of PCR primer 1. PCR 2 was performed using 10–12 cycles of 94° C. for 10 sec, 68° C. for 30 sec, and 72° C. for 1.5 minutes. The PCR products were analyzed using 2% agarose gel electrophoresis.

The PCR products were inserted into pCR2.1 using the T/A vector cloning kit (Invitrogen). Transformed E. coli were subjected to blue/white and ampicillin selection. White colonies were picked and arrayed into 96 well plates and were grown in liquid culture overnight. To identify inserts, PCR amplification was performed on 1 ml of bacterial culture using the conditions of PCR1 and NP1 and NP2 as primers. PCR products were analyzed using 2% agarose gel electrophoresis.

Bacterial clones were stored in 20% glycerol in a 96 well format. Plasmid DNA was prepared, sequenced, and subjected to nucleic acid homology searches of the GenBank, dBest, and NCI-CGAP databases.

RT-PCR Expression Analysis:

First strand cDNAs can be generated from 1 µg of mRNA with oligo (dT)12–18 priming using the Gibco-BRL Superscript Preamplification system. The manufacturer's protocol was used which included an incubation for 50 min at 42° C. with reverse transcriptase followed by RNAse H treatment at 37° C. for 20 min. After completing the reaction, the volume can be increased to 200 µl with water prior to normalization. First strand cDNAs from 16 different normal human tissues can be obtained from Clontech.

Normalization of the first strand cDNAs from multiple tissues was performed by using the primers 5'atatcgc-cgcgctcgtcgtcgacaa3' (SEQ ID NO: 722) and 5'agccacacg-cagctcattgtagaagg 3' (SEQ ID NO: 723) to amplify β-actin. First strand cDNA (5 µl) were amplified in a total volume of 50 µl containing 0.4 µM primers, 0.2 µM each dNTPs, 1×PCR buffer (Clontech, 10 mM Tris-HCl, 1.5 mM $MgCl_2$, 50 mM KCl, pH 8.3) and 1× Klentaq DNA polymerase (Clontech). Five µl of the PCR reaction can be removed at 18, 20, and 22 cycles and used for agarose gel electrophoresis. PCR was performed using an MJ Research thermal cycler under the following conditions: Initial denaturation can be at 94° C. for 15 sec, followed by a 18, 20, and 22 cycles of 94° C. for 15, 65° C. for 2 min, 72° C. for 5 sec. A final extension at 72° C. was carried out for 2 min. After agarose gel electrophoresis, the band intensities of the 283 bp β-actin bands from multiple tissues were compared by visual inspection. Dilution factors for the first strand cDNAs were calculated to result in equal β-actin band intensities in all tissues after 22 cycles of PCR. Three rounds of normalization can be required to achieve equal band intensities in all tissues after 22 cycles of PCR.

To determine expression levels of the 161P2F10B gene, 5 µl of normalized first strand cDNA were analyzed by PCR using 26, and 30 cycles of amplification. Semi-quantitative expression analysis can be achieved by comparing the PCR products at cycle numbers that give light band intensities.

A typical RT-PCR expression analysis is shown in FIG. 10. RT-PCR expression analysis was performed on first strand cDNAs generated using pools of tissues from multiple samples. The cDNAs were shown to be normalized using beta-actin PCR. Strong expression of 161P2F10B was observed in kidney cancer pool. Expression was also detected in VP1, prostate cancer xenograft pool, prostate cancer pool and colon cancer pool. Low expression was observed in VP2, lung cancer pool, ovary cancer pool, breast cancer pool, metastasis pool, pancreas cancer pool, and in the 2 different prostate cancer metastasis to lymph node.

Example 2

Full Length Cloning of 161P2F10B

Figures 4B, 4B-1:
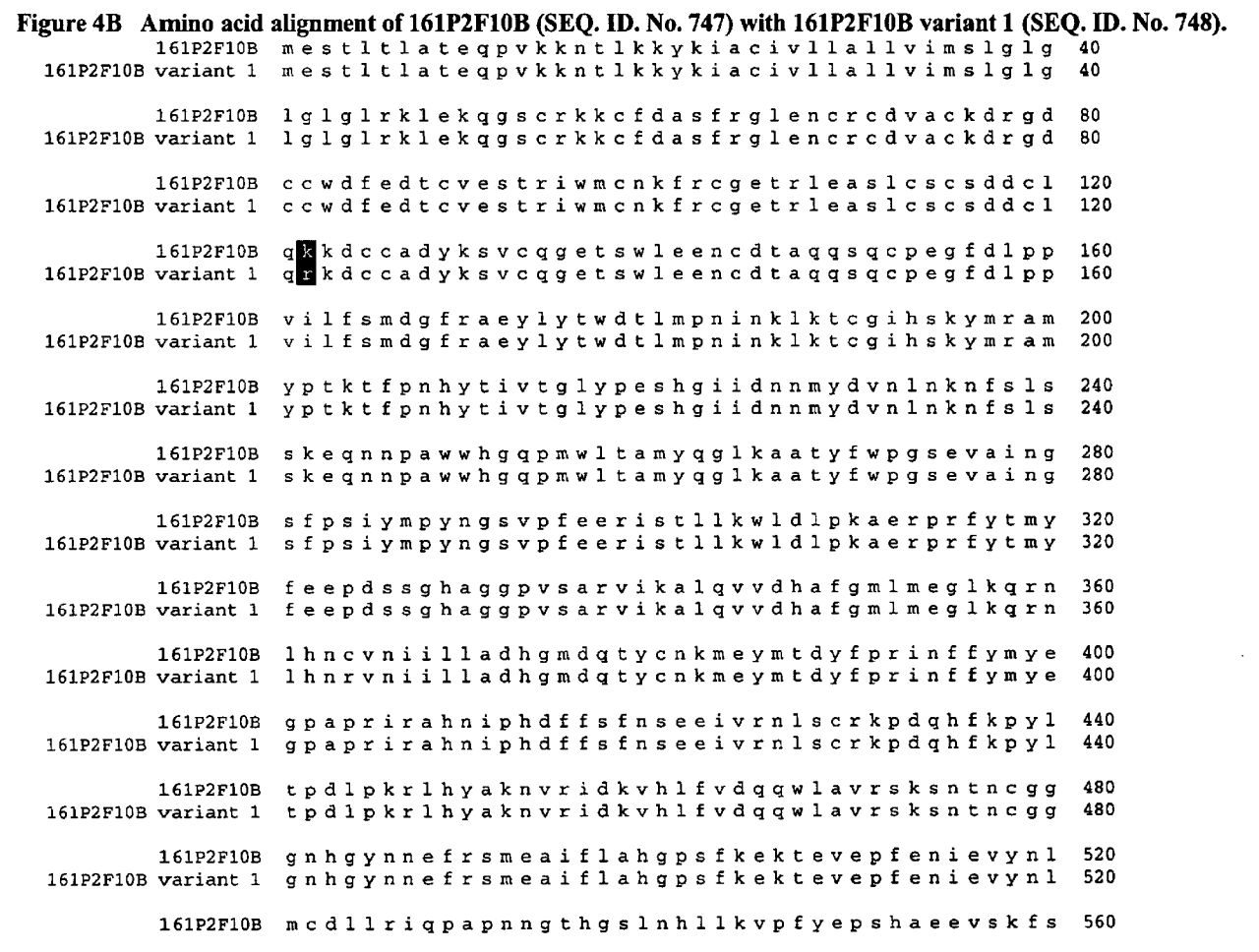

To isolate genes that are involved in kidney cancer, an experiment was conducted using kidney cancer patient specimens. The gene 161P2F10B was derived from a subtraction consisting of kidney cancer specimens, minus normal kidney mixed with a cocktail of 9 normal tissues: stomach, skeletal muscle, lung, brain, liver, kidney, pancreas, small intestine and heart. The SSH DNA sequence (FIG. 1) was designated 161P2F10B. cDNA clone 161P2F10B was cloned from kidney cancer specimens (FIG. 2 and FIG. 3). 161P2F10B showed homology to the gene ENPP3. The amino acid alignment of 161P2F10B with ENPP3 is shown in FIG. 4 (also, see, e.g., Buhring, et al., Blood 97:3303–3305 (2001)).

161P2F10B variant 1 was identified with a single base pair variation at nucleotide position 408 with a G instead of an A when compared to the published ENPP3 sequence (FIG. 2B, FIG. 3B). This nucleotide variation coded for amino acid Lysine in variant 1, compared to amino acid arginine in ENPP3.

Example 3

Chromosomal Localization of 161P2F10B

Chromosomal localization can implicate genes in disease pathogenesis. Several chromosome mapping approaches are available including fluroescent in situ hybridization (FISH), human/hamster radiation hybrid (RH) panels (Walter et al., 1994; Nature Genetics 7:22, Research Genetics, Huntsville, Ala.), human-rodent somatic cell hybrid panels such as is available from the Coriell Institute (Camden, N.J.), and genomic viewers utilizing BLAST homologies to sequenced and mapped genomic clones (NCBI, Bethesda, Md.).

161P2F10B maps to chromosome 6q22, using 161P2F10B sequence and the NCBI BLAST tool.

Example 4

Expression Analysis of 161P2F10B in Normal Tissues and Patient Specimens

Expression of 161P2F10B was analyzed as illustrated in FIG. 10. First strand cDNA was prepared from vital pool 1 (VP1: liver, lung and kidney), vital pool 2 (VP2, pancreas, colon and stomach), prostate xenograft pool (LAPC-4AD, LAPC-4AI, LAPC-9AD, LAPC-9AI), prostate cancer pool, bladder cancer pool, kidney cancer pool, colon cancer pool, lung cancer pool, ovary cancer pool, breast cancer pool, metastasis cancer pool, pancreas cancer pool, and from prostate cancer metastasis to lymph node from 2 different patients. Normalization was performed by PCR using primers to actin and GAPDH. Semi-quantitative PCR, using primers to 161P2F10B, was performed at 26 and 30 cycles of amplification. Strong expression of 161P2F10B was observed in kidney cancer pool. Expression was also detected in VP1, prostate cancer xenograft pool, prostate cancer pool and colon cancer pool. Low expression was observed in VP2, lung cancer pool, ovary cancer pool, breast cancer pool, metastasis pool, pancreas cancer pool, and in the 2 different prostate cancer metastasis to lymph node.

Extensive northern blot analysis of 161P2F10B in 16 human normal tissues confirms the expression observed by RT-PCR (FIG. 11). Two transcripts of 161P2F10B comigrating at approximately 4 kb, were detected in kidney, prostate and colon, and to lower levels, in thymus.

FIG. 12 shows expression of 161P2F10B in kidney cancer xenografts. RNA was extracted from normal kidney (N), prostate cancer xenografts, LAPC-4AD, LAPC-4AI, LAPC-9Ad, and LAPC-9AI, and 2 kidney cancer xenografts (Ki Xeno-1 and Ki Xeno-2). Northern blot with 10 µg of total RNA/lane was probed with 161P2F10B sequence. The results show expression of 161P2F10B in both kidney xenografts, LAPC-4AI, LAPC-9AI, but not in normal kidney. The expression detected in normal kidney after long exposure of the northern blot in FIG. 11, but not in FIG. 12 suggests that 161P2F10B is expressed at low levels in normal kidney, but is upregulated in kidney cancer.

To test expression of 161P2F10B in patient cancer specimens, RNA was extracted from a pool of three kidney cancer patients, as well as from normal prostate (NP), normal bladder (NB), normal kidney (NK), normal colon (NC). Northern blots with 10 µg of total RNA/lane were probed with 161P2F10B sequence (FIG. 13). Results show expression of 161P2F10B in kidney cancer pool, but not in any of the normal tissues tested.

Analysis of individual kidney cancer tissues by northern blot shows expression of 161P2F10B in all 4 clear cell carcinoma kidney tumors, but not in papillary carcinoma, kidney cancer cell lines, nor in normal kidney tissues (FIG. 14).

Expression of 161P2F10B was also analyzed on kidney cancer metastasis samples (FIG. 15). RNA was extracted from kidney cancer metastasis to lung, kidney cancer metastasis to lymph node, normal bladder (NB), normal kidney (NK), and normal lung (NL), normal breast (NBr), normal ovary (NO), and normal pancreas (NPa). Northern blots with 10 µg of total RNA/lane were probed with 161P2F10B sequence. Results show strong expression of 161P2F10B in both kidney cancer metastasis tissues tested. Weak expression is detected in normal kidney and normal breast but not in other normal tissues.

The restricted expression of 161P2F10B in normal tissues and the upregulation detected in kidney cancer, in kidney cancer metastasis, as well as in other cancers, suggest that 161P2F10B is a potential therapeutic target and a diagnostic marker for human cancers.

Example 5

Production of Recombinant 161P2F10B in Prokaryotic Systems

To express recombinant 161P2F10B in prokaryotic cells, the full or partial length 161P2F10B cDNA sequences can be cloned into any one of a variety of expression vectors known in the art. One or more of the following regions of 161P2F10B are expressed in these contructs, amino acids 1 to 875; or any 8, 9, 10, 11, 12, 13, 14, 15, 16, 17, 18, 19, 20, 21, 22, 23, 24, 25, 26, 27, 28, 29, 30 or more contiguous amino acids from 161P2F10B, variants, or analogs thereof.

A. In vitro Transcription and Translation Constructs:

pCRII: To generate 161P2F10B sense and anti-sense RNA probes for RNA in situ investigations, pCRII constructs (Invitrogen, Carlsbad, Calif.) are generated encoding either all or fragments of the 161P2F10B cDNA. The pCRII vector has Sp6 and T7 promoters flanking the insert to drive the transcription of 161P2F10B RNA for use as probes in RNA in situ hybridization experiments. These probes are used to analyze the cell and tissue expression of 161P2F10B at the RNA level. Transcribed 161P2F10B RNA representing the cDNA amino acid coding region of the 161P2F10B gene is used in in vitro translation systems such as the TnT™ Coupled Reticulolysate System (Promega, Corp., Madison, Wis.) to synthesize 161P2F10B protein.

B. Bacterial Constructs:

pGEX Constructs: To generate recombinant 161P2F10B proteins in bacteria that are fused to the Glutathione S-transferase (GST) protein, all or parts of the 161P2F10B cDNA proteins coding sequence are fused to the GST gene by cloning into pGEX-6P-1 or any other GST-fusion vector of the pGEX family (Amersham Pharmacia Biotech, Piscataway, N.J.). These constructs allow controlled expression of recombinant 161P2F10B protein sequences with GST fused at the amino-terminus and a six histidine epitope (6×His) at the carboxyl-terminus. The GST and 6×His tags permit purification of the recombinant fusion protein from induced bacteria with the appropriate affinity matrix and allow recognition of the fusion protein with anti-GST and anti-His antibodies. The 6×His tag is generated by adding 6 histidine codons to the cloning primer at the 3' end, e.g., of the open reading frame (ORF). A proteolytic cleavage site, such as the PreScission™ recognition site in pGEX-6P-1, may be employed such that it permits cleavage of the GST tag from 161P2F10B-related protein. The ampicillin resistance gene and pBR322 origin permits selection and maintenance of the pGEX plasmids in E. coli.

pMAL Constructs: To generate, in bacteria, recombinant 161P2F10B proteins that are fused to maltose-binding protein (MBP), all or parts of the 161P2F10B cDNA protein coding sequence are fused to the MBP gene by cloning into the pMAL-c2X and pMAL-p2X vectors (New England Biolabs, Beverly, Mass.). These constructs allow controlled expression of recombinant 161P2F10B protein sequences with MBP fused at the amino-terminus and a 6×His epitope tag at the carboxyl-terminus. The MBP and 6×His tags permit purification of the recombinant protein from induced bacteria with the appropriate affinity matrix and allow recognition of the fusion protein with anti-MBP and anti-His antibodies. The 6×His epitope tag is generated by adding 6 histidine codons to the 3' cloning primer. A Factor Xa recognition site permits cleavage of the pMAL tag from 161P2F10B. The pMAL-c2X and pMAL-p2X are optimized to express the recombinant protein in the cytoplasm or periplasm respectively. Periplasm expression enhances folding of proteins with disulfide bonds.

pET Constructs: To expression 161P2F10B in bacterial cells, all or parts of the 161P2F10B cDNA protein coding sequence are cloned into the pET family of vectors (Novagen, Madison, Wis.). These vectors allow tightly controlled expression of recombinant 161P2F10B protein in bacteria with and without fusion to proteins that enhance solubility, such as NusA and thioredoxin (Trx), and epitope tags, such as 6×His and S-Tag™ that aid purification and detection of the recombinant protein. For example, constructs are made utilizing pET NusA fusion system 43.1 such that regions of the 161P2F10B protein are expressed as amino-terminal fusions to NusA.

C. Yeast Constructs:

pESC Constructs: To express 161P2F10B in the yeast species Saccharomyces cerevisiae for generation of recombinant protein and functional studies, all or parts of the 161P2F10B cDNA protein coding sequence are cloned into the pESC family of vectors each of which contain 1 of 4 selectable markers, HIS3, TRP1, LEU2, and URA3 (Stratagene, La Jolla, Calif.). These vectors allow controlled expression from the same plasmid of up to 2 different genes or cloned sequences containing either Flag™ or Myc epitope tags in the same yeast cell. This system is useful to confirm protein—protein interactions of 161P2F10B. In addition, expression in yeast yields similar post-translational modifications, such as glycosylations and phosphorylations, that are found when expressed in eukaryotic cells.

pESP Constructs: To express 161P2F10B in the yeast species Saccharomyces pombe, all or parts of the 161P2F10B cDNA protein coding sequence are cloned into the pESP family of vectors. These vectors allow controlled high level of expression of a 161P2F10B protein sequence that is fused at either the amino terminus or at the carboxyl terminus to GST which aids purification of the recombinant protein. A Flag™ epitope tag allows detection of the recombinant protein with anti-Flag™ antibody.

Example 6

Production of Recombinant 161P2F10B in Eukaryotic Systems

A. Mammalian Constructs:

To express recombinant 161P2F10B in eukaryotic cells, the full or partial length 161P2F10B cDNA sequences can be cloned into any one of a variety of expression vectors known in the art. One or more of the following regions of 161P2F10B are expressed in these constructs, amino acids 1 to 875; or any 8, 9, 10, 11, 12, 13, 14, 15, 16, 17, 18, 19, 20, 21, 22, 23, 24, 25, 26, 27, 28, 29, 30 or more contiguous amino acids from 161P2F10B, variants, or analogs thereof.

The constructs can be transfected into any one of a wide variety of mammalian cells such as 293T cells. Transfected 293T cell lysates can be probed with the anti-161P2F10B polyclonal serum, described herein.

pcDNA4/HisMax Constructs: To express 161P2F10B in mammalian cells, the 161P2F10B ORF, or portions thereof, of 161P2F10B are cloned into pcDNA4/HisMax Version A (Invitrogen, Carlsbad, Calif.). Protein expression is driven from the cytomegalovirus (CMV) promoter and the SP16 translational enhancer. The recombinant protein has Xpress™ and six histidine (6×His) epitopes fused to the amino-terminus. The pcDNA4/HisMax vector also contains the bovine growth hormone (BGH) polyadenylation signal and transcription termination sequence to enhance mRNA stability along with the SV40 origin for episomal replication and simple vector rescue in cell lines expressing the large T antigen. The Zeocin resistance gene allows for selection of mammalian cells expressing the protein and the ampicillin resistance gene and ColE1 origin permits selection and maintenance of the plasmid in E. coli.

pcDNA3.1/MycHis Constructs: To express 161P2F10B in mammalian cells, the 161P2F10B ORF, or portions thereof, of 161P2F10B with a consensus Kozak translation initiation site are cloned into pcDNA3.1/MycHis Version A (Invitrogen, Carlsbad, Calif.). Protein expression is driven from the cytomegalovirus (CMV) promoter. The recombinant proteins have the myc epitope and 6×His epitope fused to the carboxyl-terminus. The pcDNA3.1/MycHis vector also contains the bovine growth hormone (BGH) polyadenylation signal and transcription termination sequence to enhance mRNA stability, along with the SV40 origin for episomal replication and simple vector rescue in cell lines expressing the large T antigen. The Neomycin resistance gene can be used, as it allows for selection of mammalian cells expressing the protein and the ampicillin resistance gene and ColE1 origin permits selection and maintenance of the plasmid in E. coli.

pcDNA3.1/CT-GFP-TOPO Construct: To express 161P2F10B in mammalian cells and to allow detection of the recombinant proteins using fluorescence, the 161P2F10B ORF, or portions thereof, of 161P2F10B with a consensus Kozak translation site are cloned into pcDNA3.1/CT-GFP-TOPO (Invitrogen, CA). Protein expression is driven from the cytomegalovirus (CMV) promoter. The recombinant proteins have the Green Fluorescent Protein (GFP) fused to the carboxyl-terminus facilitating non-invasive, in vivo detection and cell biology studies. The pcDNA3.1CT-GFP-TOPO vector also contains the bovine growth hormone (BGH) polyadenylation signal and transcription termination sequence to enhance mRNA stability along with the SV40 origin for episomal replication and simple vector rescue in cell lines expressing the large T antigen. The Neomycin resistance gene allows for selection of mammalian cells that express the protein, and the ampicillin resistance gene and ColE1 origin permits selection and maintenance of the plasmid in E. coli. Additional constructs with an amino-terminal GFP fusion are made in pcDNA3.1/NT-GFP-TOPO spanning the entire length of the 161P2F10B proteins.

PAPtag: The 161P2F10B ORF, or portions thereof, of 161P2F10B are cloned into pAPtag-5 (GenHunter Corp. Nashville, Tenn.). This construct generates an alkaline phosphatase fusion at the carboxyl-terminus of the 161P2F10B proteins while fusing the IgGκ signal sequence to the amino-terminus. Constructs are also generated in which alkaline phosphatase with an amino-terminal IgGκ signal sequence is fused to the amino-terminus of 161P2F10B proteins. The resulting recombinant 161P2F10B proteins are optimized for secretion into the media of transfected mammalian cells and can be used to identify proteins such as ligands or receptors that interact with the 161P2F10B proteins. Protein expression is driven from the CMV promoter and the recombinant proteins also contain myc and 6×His epitopes fused at the carboxyl-terminus that facilitates detection and purification. The Zeocin resistance gene present in the vector allows for selection of mammalian cells expressing the recombinant protein and the ampicillin resistance gene permits selection of the plasmid in E. coli.

ptag5: The 161P2F10B ORF, or portions thereof, of 161P2F10B are cloned into pTag-5. This vector is similar to pAPtag but without the alkaline phosphatase fusion. This construct generates 161P2F10B protein with an amino-terminal IgGκ signal sequence and myc and 6×His epitope tags at the carboxyl-terminus that facilitate detection and affinity purification. The resulting recombinant 161P2F10B protein is optimized for secretion into the media of transfected mammalian cells, and is used as immunogen or ligand to identify proteins such as ligands or receptors that interact with the 161P2F10B proteins. Protein expression is driven from the CMV promoter. The Zeocin resistance gene present in the vector allows for selection of mammalian cells expressing the protein, and the ampicillin resistance gene permits selection of the plasmid in E. coli.

PsecFc: The 161P2F10B ORF, or portions thereof, of 161P2F10B were cloned into psecFc. The psecFc vector was assembled by cloning the human immunoglobulin G1 (IgG) Fc (hinge, CH2, CH3 regions) into pSecTag2 (Invitrogen, California). This construct generates an IgG1 Fc fusion at the amino-terminus of the 161P2F10B proteins. 161P2F10B fusions utilizing the murine IgG1 Fc region are also used. The resulting recombinant 161P2F10B proteins are optimized for secretion into the media of transfected mammalian cells, and can be used as immunogens or to identify proteins such as ligands or receptors that interact with the 161P2F10B protein. Protein expression is driven from the CMV promoter. The hygromycin resistance gene present in the vector allows for selection of mammalian cells that express the recombinant protein, and the ampicillin resistance gene permits selection of the plasmid in E. coli.

pSRα Constructs: To generate mammalian cell lines that express 161P2F10B constitutively, 161P2F10B ORF, or portions thereof, of 161P2F10B are cloned into pSRα constructs. Amphotropic and ecotropic retroviruses are generated by transfection of pSRα constructs into the 293T-10A1 packaging line or co-transfection of pSRα and a helper plasmid (containing deleted packaging sequences) into the 293 cells, respectively. The retrovirus is used to infect a variety of mammalian cell lines, resulting in the integration of the cloned gene, 161P2F10B, into the host cell-lines. Protein expression is driven from a long terminal repeat (LTR). The Neomycin resistance gene present in the vector allows for selection of mammalian cells that express the protein, and the ampicillin resistance gene and ColE1 origin permit selection and maintenance of the plasmid in E. coli. The retroviral vectors can therefore be used for infection and generation of various cell lines using, for example, PC3, NIH 3T3, TsuPr1, 293 or rat-1 cells.

Additional pSRα constructs are made that fuse an epitope tag such as the FLAG™ tag to the carboxyl-terminus of 161P2F10B sequences to allow detection using anti-Flag antibodies. For example, the FLAG™ sequence 5' gat tac aag gat gac gac gat aag 3' (SEQ ID No. 764) is added to cloning primer at the 3' end of the ORF. Additional pSRα constructs are made to produce both amino-terminal and carboxyl-terminal GFP and myc/6xHis fusion proteins of the full-length 161P2F10B proteins.

Additional Viral Vectors: Additional constructs are made for viral-mediated delivery and expression of 161P2F10B. High virus titer leading to high level expression of 161P2F10B is achieved in viral delivery systems such as adenoviral vectors and herpes amplicon vectors. The 161P2F10B coding sequences or fragments thereof are amplified by PCR and subcloned into the AdEasy shuttle vector (Stratagene). Recombination and virus packaging are performed according to the manufacturer's instructions to generate adenoviral vectors. Alternatively, 161P2F10B coding sequences or fragments thereof are cloned into the HSV-1 vector (Imgenex) to generate herpes viral vectors. The viral vectors are thereafter used for infection of various cell lines such as PC3, NIH 3T3, 293 or rat-1 cells.

Regulated Expression Systems: To control expression of 161P2F10B in mammalian cells, coding sequences of 161P2F10B, or portions thereof, are cloned into regulated mammalian expression systems such as the T-Rex System (Invitrogen), the GeneSwitch System (Invitrogen) and the tightly-regulated Ecdysone System (Sratagene). These systems allow the study of the temporal and concentration dependent effects of recombinant 161P2F10B. These vectors are thereafter used to control expression of 161P2F10B in various cell lines such as PC3, NIH 3T3, 293 or rat-1 cells.

B. Baculovirus Expression Systems

To generate recombinant 161P2F10B proteins in a Baculovirus expression system, 161P2F10B ORF, or portions thereof, are cloned into the Baculovirus transfer vector pBlueBac 4.5 (Invitrogen), which provides a His-tag at the N-terminus. Specifically, pBlueBac-161P2F10B is co-transfected with helper plasmid pBac-N-Blue (Invitrogen) into SF9 (Spodoptera frugiperda) insect cells to generate recombinant Baculovirus (see Invitrogen instruction manual for details). Baculovirus is then collected from cell supernatant and purified by plaque assay.

Recombinant 161P2F10B protein is then generated by infection of HighFive insect cells (Invitrogen) with purified Baculovirus. Recombinant 161P2F10B protein can be detected using anti-161P2F10B or anti-His-tag antibody. 161P2F10B protein can be purified and used in various cell-based assays or as immunogen to generate polyclonal and monoclonal antibodies specific for 161P2F10B.

Example 7

Antigenicity Profiles and Secondary Structure

FIG. 5, FIG. 6, FIG. 7, FIG. 8, and FIG. 9 depict graphically five amino acid profiles of the 161P2F10B amino acid sequence, each assessment available by accessing the ProtScale website on the ExPasy molecular biology server.

These profiles: FIG. 5, Hydrophilicity, (Hopp T. P., Woods K. R., 1981. Proc. Natl. Acad. Sci. U.S.A. 78:3824–3828); FIG. 6, Hydropathicity, (Kyte J., Doolittle R. F., 1982. J. Mol. Biol. 157:105–132); FIG. 7, Percentage Accessible Residues (Janin J., 1979 Nature 277:491–492); FIG. 8, Average Flexibility, (Bhaskaran R., and Ponnuswamy P. K., 1988. Int. J. Pept. Protein Res. 32:242–255), FIG. 9, Beta-turn (Deleage, G., Roux B. 1987 Protein Engineering 1:289–294); and optionally others available in the art, such as on the ProtScale website, were used to identify antigenic regions of the 161P2F10B protein. Each of the above amino acid profiles of 161P2F10B were generated using the following ProtScale parameters for analysis: 1) A window size of 9; 2) 100% weight of the window edges compared to the window center; and, 3) amino acid profile values normalized to lie between 0 and 1.

Hydrophilicity (FIG. 5), Hydropathicity (FIG. 6) and Percentage Accessible Residues (FIG. 7) profiles were used to determine stretches of hydrophilic amino acids (i.e., values greater than 0.5 on the Hydrophilicity and Percentage Accessible Residues profile, and values less than 0.5 on the Hydropathicity profile). Such regions are likely to be exposed to the aqueous environment, be present on the surface of the protein, and thus available for immune recognition, such as by antibodies.

Average Flexibility (FIG. 8) and Beta-turn (FIG. 9) profiles determine stretches of amino acids (i.e., values greater than 0.5 on the Beta-turn profile and the Average Flexibility profile) that are not constrained in secondary structures such as beta sheets and alpha helices. Such regions are also more likely to be exposed on the protein and thus accessible to immune recognition, such as by antibodies.

Antigenic sequences of the 161P2F10B protein indicated, e.g., by the profiles set forth in FIG. 5, FIG. 6, FIG. 7, FIG. 8 and/or FIG. 9 are used to prepare immunogens, either peptides or nucleic acids that encode them, to generate therapeutic and diagnostic anti-161P2F10B antibodies. The immunogen can be any 5, 6, 7, 8, 9, 10, 11, 12, 13, 14, 15, 16, 17, 18, 19, 20, 21, 22, 23, 24, 25, 30, 35, 40, 45, 50 or more than 50 contiguous amino acids, or the corresponding nucleic acids that encode them, from the 161P2F10B protein. In particular, peptide immunogens of the invention can comprise, a peptide region of at least 5 amino acids of FIG. 2 in any whole number increment up to 875 that includes an amino acid position having a value greater than 0.5 in the Hydrophilicity profile of FIG. 5; a peptide region of at least 5 amino acids of FIG. 2 in any whole number increment up to 875 that includes an amino acid position having a value less than 0.5 in the Hydropathicity profile of FIG. 6; a peptide region of at least 5 amino acids of FIG. 2 in any whole number increment up to 875 that includes an amino acid position having a value greater than 0.5 in the Percent Accessible Residues profile of FIG. 7; a peptide region of at least 5 amino acids of FIG. 2 in any whole number increment up to 875 that includes an amino acid position having a value greater than 0.5 in the Average Flexibility profile on FIG. 8; and a peptide region of at least 5 amino acids of FIG. 2 in any whole number increment up to 875 that includes an amino acid position having a value greater than 0.5 in the Beta-turn profile of FIG. 9. Peptide immunogens of the invention can also comprise nucleic acids that encode any of the forgoing.

All immunogens of the invention, peptide or nucleic acid, can be embodied in human unit dose form, or comprised by a composition that includes a pharmaceutical excipient compatible with human physiology.

The secondary structure of 161P2F10B, namely the predicted presence and location of alpha helices, extended strands, and random coils, is predicted from the primary amino acid sequence using the HNN—Hierarchical Neural Network method (Guermeur, 1997), accessed from the ExPasy molecular biology server. The analysis indicates that 161P2F10B is composed 31.31% alpha helix, 11.31% extended strand, and 57.37% random coil (FIG. 19A).

Figure 19C:
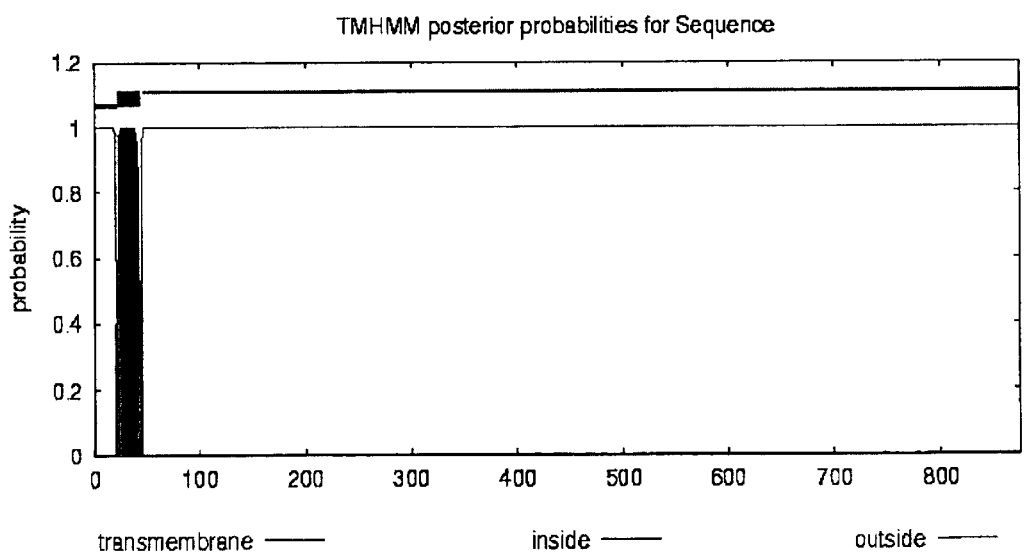

Analysis for the potential presence of transmembrane domains in 161P2F10B was carried out using a variety of transmembrane prediction algorithms accessed from the ExPasy molecular biology server. The programs predict the presence of 1 transmembrane domain in 161P2F10B, consistent with that of a Type II cell surface protein. Shown graphically in FIG. 19 are the results of analysis using the TMpred (FIG. 19B) and TMHMM (FIG. 19C) prediction programs depicting the location of the transmembrane domain. The results of each program, namely the amino acids encoding the transmembrane domain are summarized in Table XXI.

Example 8

Generation of 161P2F10B Polyclonal Antibodies

Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. In addition to immunizing with the full length 161P2F10B protein, computer algorithms are employed in design of immunogens that, based on amino acid sequence analysis contain characteristics of being antigenic and available for recognition by the immune system of the immunized host (see the Example entitled "Antigenicity Profiles"). Such regions would be predicted to be hydrophilic, flexible, in beta-turn conformations, and be exposed on the surface of the protein (see, e.g., FIG. 5, FIG. 6, FIG. 7, FIG. 8, or FIG. 9 for amino acid profiles that indicate such regions of 161P2F10B).

For example, 161P2F10B recombinant bacterial fusion proteins or peptides containing hydrophilic, flexible, beta-turn regions of the 161P2F10B, in which numerous regions are found in the predicted extracellular domain coded by amino acids 45–870, are used as antigens to generate polyclonal antibodies in New Zealand White rabbits. For example, such regions include, but are not limited to, amino acids 43–93, 100–134, 211–246, 467–492, 500–517, and amino acids 810–870. In addition, recombinant proteins are made that encode the whole extracellular domain, amino acids 45–870, or halves of the domain, such as amino acids 45–450 and amino acids 451–870. Antigens are also created encoding the Somatomedin-B-like domain (amino acids 53–133), the catalytic domain (amino acids 158–538), and the nuclease like domain (amino acids 609–875) of 161P2F10B (Bollen et. al., 2000. Crit. Rev. Biochem. Mol. Biol., 35: 393–432), in order to generate antibodies specific to these regions. Ideally antibodies are raised to non-conserved regions of these domains such that they do not crossreact with other homologous nucleotide pyrophosphatases/phosphodiesterases. It is useful to conjugate the immunizing agent to a protein known to be immunogenic in the mammal being immunized. Examples of such immunogenic proteins include, but are not limited to, keyhole limpet hemocyanin (KLH), serum albumin, bovine thyroglobulin, and soybean trypsin inhibitor. In one embodiment, a peptide encoding amino acids 500–517 of 161P2F10B is conjugated to KLH and used to immunize the rabbit. Alternatively the immunizing agent may include all or portions of the 161P2F10B protein, analogs or fusion proteins thereof. For example, the 161P2F10B amino acid sequence can be fused using recombinant DNA techniques to any one of a variety of fusion protein partners that are well known in the art, such as glutathione-S-transferase (GST) and HIS tagged fusion proteins. Such fusion proteins are purified from induced bacteria using the appropriate affinity matrix.

In one embodiment, a GST-fusion protein encoding amino acids 45–875 is produced and purified and used as immunogen. Other recombinant bacterial fusion proteins that may be employed include maltose binding protein, LacZ, thioredoxin, NusA, or an immunoglobulin constant region (see the section entitled "Production of 161P2F10B in Prokaryotic Systems" and Current Protocols In Molecular Biology, Volume 2, Unit 16, Frederick M. Ausubul et al. eds., 1995; Linsley, P. S., Brady, W., Urnes, M., Grosmaire, L., Damle, N., and Ledbetter, L. (1991) J. Exp. Med. 174, 561–566).

In addition to bacterial derived fusion proteins, mammalian expressed protein antigens are also used. These antigens are expressed from mammalian expression vectors such as the Tag5 and Fc-fusion vectors (see the section entitled "Production of Recombinant 161P2F10B in Eukaryotic Systems"), and retain post-translational modifications such as glycosylations found in native protein. In one embodiment, amino acids 45–875 is cloned into the Tag5 mammalian secretion vector. The recombinant protein is purified by metal chelate chromatography from tissue culture supernatants of 293T cells stably expressing the recombinant vector. The purified Tag5 161P2F10B protein is then used as immunogen.

During the immunization protocol, it is useful to mix or emulsify the antigen in adjuvants that enhance the immune response of the host animal. Examples of adjuvants include, but are not limited to, complete Freund's adjuvant (CFA) and MPL-TDM adjuvant (monophosphoryl Lipid A, synthetic trehalose dicorynomycolate).

In a typical protocol, rabbits are initially immunized subcutaneously with up to 200 μg, typically 100–200 μg, of fusion protein or peptide conjugated to KLH mixed in complete Freund's adjuvant (CFA). Rabbits are then injected subcutaneously every two weeks with up to 200 μg, typically 100–200 μg, of the immunogen in incomplete Freund's adjuvant (IFA). Test bleeds are taken approximately 7–10 days following each immunization and used to monitor the titer of the antiserum by ELISA.

To test reactivity and specificity of immune serum, such as the rabbit serum derived from immunization with Tag5 161P2F10B encoding amino acids 58–538, the full-length 161P2F10B cDNA is cloned into pCDNA 3.1 myc-his expression vector (Invitrogen, see the Example entitled "Production of Recombinant 161P2F10B in Eukaryotic Systems"). After transfection of the constructs into 293T cells, cell lysates are probed with the anti-161P2F10B serum and with anti-His antibody (Santa Cruz Biotechnologies, Santa Cruz, Calif.) to determine specific reactivity to denatured 161P2F10B protein using the Western blot technique. Immunoprecipitation and flow cytometric analyses of 293T and other recombinant 161P2F10B-expressing cells determine recognition of native protein by the antiserum. In addition, Western blot, immunoprecipitation, fluorescent microscopy, and flow cytometric techniques using cells that endogenously express 161P2F10B are carried out to test specificity.

The anti-serum from the Tag5 161P2F10B immunized rabbit is affinity purified by passage over a column composed of the Tag5 antigen covalently coupled to Affigel matrix (BioRad, Hercules, Calif.). The serum is then further purified by protein G affinity chromatography to isolate the IgG fraction. Serum from rabbits immunized with fusion proteins, such as GST and MBP fusion proteins, are purified by depletion of antibodies reactive to the fusion partner sequence by passage over an affinity column containing the fusion partner either alone or in the context of an irrelevant fusion protein. Sera from other His-tagged antigens and peptide immunized rabbits as well as fusion partner depleted sera are affinity purified by passage over a column matrix composed of the original protein immunogen or free peptide.

Example 9

Generation of 161P2F10B Monoclonal Antibodies (mAbs)

In one embodiment, therapeutic mAbs to 161P2F10B comprise those that react with epitopes of the protein that would disrupt or modulate the biological function of 161P2F10B, for example those that would disrupt its catalytic activity or its interaction with ligands or proteins that mediate its biological activity. Therapeutic mAbs also comprise those that specifically bind epitopes of 161P2F10B exposed on the cell surface and thus are useful in targeting mAb-toxin conjugates. Immunogens for generation of such mAbs include those designed to encode or contain the entire 161P2F10B protein, the predicted extracellular domain (amino acids 45–875), predicted functional domains such as the somatomedin-B-like domain (amino acids 53–133), the catalytic domain (amino acids 158–538), or the nuclease-like domain (amino acids 609–875), or regions of the 161P2F10B protein predicted to be antigenic from computer analysis of the amino acid sequence (see, e.g., FIG. 5, FIG. 6, FIG. 7, FIG. 8, or FIG. 8, and the Example entitled "Antigenicity Profiles"). Immunogens include peptides, recombinant bacterial proteins, and mammalian expressed Tag 5 proteins and human and murine IgG FC fusion proteins. In addition, cells expressing high levels of 161P2F10B, such as 293T-161P2F10B or 300.19-161P2F10B murine Pre-B cells, are used to immunize mice.

To generate mAbs to 161P2F10B, mice are first immunized intraperitoneally (IP) with, typically, 10–50 µg of protein immunogen or $10^7$ 161P2F10B-expressing cells mixed in complete Freund's adjuvant. Alternatively, mice are immunized intradermally for lymph node fusions. Mice are then subsequently immunized IP every 2–4 weeks with, typically, 10–50 µg of protein immunogen or $10^7$ cells mixed in incomplete Freund's adjuvant. Alternatively, MPL-TDM adjuvant is used in immunizations. In addition to the above protein and cell-based immunization strategies, a DNA-based immunization protocol is employed in which a mammalian expression vector encoding 161P2F10B sequence is used to immunize mice by direct injection of the plasmid DNA. For example, the catalytic domain of 161P2F10B, amino acids 158–538, is cloned into the Tag5 mammalian secretion vector and the recombinant vector is used as immunogen. In another example the same amino acids are cloned into an Fc-fusion secretion vector in which the 161P2F10B sequence is fused at the amino-terminus to an IgK leader sequence and at the carboxyl-terminus to the coding sequence of the human or murine IgG Fc region. This recombinant vector is then used as immunogen. The plasmid immunization protocols are used in combination with purified proteins expressed from the same vector and with cells expressing 161P2F10B.

During the immunization protocol, test bleeds are taken 7–10 days following an injection to monitor titer and specificity of the immune response. Once appropriate reactivity and specificity is obtained as determined by ELISA, Western blotting, immunoprecipitation, fluorescence microscopy, and flow cytometric analyses, fusion and hybridoma generation is then carried out with established procedures well known in the art (see, e.g., Harlow and Lane, 1988).

In one embodiment for generating 161P2F10B monoclonal antibodies, a Tag5-161P2F10B antigen encoding amino acids 158–538 is expressed and purified from stably transfected 293T cells. Balb C mice are initially immunized intraperitoneally with 25 µg of the Tag5-161P2F10B protein mixed in complete Freund's adjuvant. Mice are subsequently immunized every two weeks with 25 µg of the antigen mixed in incomplete Freund's adjuvant for a total of three immunizations. ELISA using the Tag5 antigen determines the titer of serum from immunized mice. Reactivity and specificity of serum to full length 161P2F10B protein is monitored by Western blotting, immunoprecipitation and flow cytometry using 293T cells transfected with an expression vector encoding the 161P2F10B cDNA (see e.g., the Example entitled "Production of Recombinant 161P2F10B in Eukaryotic Systems"). Other recombinant 161P2F10B-expressing cells or cells endogenously expressing 161P2F10B are also used. Mice showing the strongest reactivity are rested and given a final injection of Tag5 antigen in PBS and then sacrificed four days later. The spleens of the sacrificed mice are harvested and fused to SPO/2 myeloma cells using standard procedures (Harlow and Lane, 1988). Supernatants from HAT selected growth wells are screened by ELISA, Western blot, immunoprecipitation, fluorescent microscopy, and flow cytometry to identify 161P2F10B specific antibody-producing clones.

The binding affinity of a 161P2F10B monoclonal antibody is determined using standard technologies. Affinity measurements quantify the strength of antibody to epitope binding and are used to help define which 161P2F10B monoclonal antibodies preferred for diagnostic or therapeutic use, as appreciated by one of skill in the art. The BIAcore system (Uppsala, Sweden) is a preferred method for determining binding affinity. The BIAcore system uses surface plasmon resonance (SPR, Welford K. 1991, Opt. Quant. Elect. 23:1; Morton and Myszka, 1998, Methods in Enzymology 295: 268) to monitor biomolecular interactions in real time. BIAcore analysis conveniently generates association rate constants, dissociation rate constants, equilibrium dissociation constants, and affinity constants.

Example 10

HLA Class I and Class II Binding Assays

HLA class I and class II binding assays using purified HLA molecules are performed in accordance with disclosed protocols (e.g., PCT publications WO 94/20127 and WO 94/03205; Sidney et al., *Current Protocols in Immunology* 18.3.1 (1998); Sidney, et al., *J. Immunol.* 154:247 (1995); Sette, et al., *Mol. Immunol.* 31:813 (1994)). Briefly, purified MHC molecules (5 to 500 nM) are incubated with various unlabeled peptide inhibitors and 1–10 nM $^{125}$I-radiolabeled probe peptides as described. Following incubation, MHC-peptide complexes are separated from free peptide by gel filtration and the fraction of peptide bound is determined. Typically, in preliminary experiments, each MHC preparation is titered in the presence of fixed amounts of radiolabeled peptides to determine the concentration of HLA molecules necessary to bind 10–20% of the total radioactivity. All subsequent inhibition and direct binding assays are performed using these HLA concentrations.

Since under these conditions [label]<[HLA] and $IC_{50} \geq$ [HLA], the measured $IC_{50}$ values are reasonable approximations of the true $K_D$ values. Peptide inhibitors are typically tested at concentrations ranging from 120 µg/ml to 1.2 ng/ml, and are tested in two to four completely independent experiments. To allow comparison of the data obtained in different experiments, a relative binding figure is calculated for each peptide by dividing the $IC_{50}$ of a positive control for inhibition by the $IC_{50}$ for each tested peptide (typically unlabeled versions of the radiolabeled probe peptide). For database purposes, and inter-experiment comparisons, relative binding values are compiled. These values can subsequently be converted back into $IC_{50}$ nM values by dividing the $IC_{50}$ nM of the positive controls for inhibition by the relative binding of the peptide of interest. This method of data compilation is accurate and consistent for comparing peptides that have been tested on different days, or with different lots of purified MHC.

Binding assays as outlined above may be used to analyze HLA supermotif and/or HLA motif-bearing peptides.

Example 11

Identification of HLA Supermotif- and Motif-Bearing CTL Candidate Epitopes

HLA vaccine compositions of the invention can include multiple epitopes. The multiple epitopes can comprise multiple HLA supermotifs or motifs to achieve broad population coverage. This example illustrates the identification and confirmation of supermotif- and motif-bearing epitopes for the inclusion in such a vaccine composition. Calculation of population coverage is performed using the strategy described below.

Computer Searches and Algorithms for Identification of Supermotif and/or Motif-bearing Epitopes The searches performed to identify the motif-bearing peptide sequences in the Example entitled "Antigenicity Profiles" and Tables V–XVIII employ the protein sequence data from the gene product of 161P2F10B set forth in FIGS. 2 and 3.

Computer searches for epitopes bearing HLA Class I or Class II supermotifs or motifs are performed as follows. All translated 161P2F10B protein sequences are analyzed using a text string search software program to identify potential peptide sequences containing appropriate HLA binding motifs; such programs are readily produced in accordance with information in the art in view of known motif/supermotif disclosures. Furthermore, such calculations can be made mentally.

Identified A2-, A3-, and DR-supermotif sequences are scored using polynomial algorithms to predict their capacity to bind to specific HLA-Class I or Class II molecules. These polynomial algorithms account for the impact of different amino acids at different positions, and are essentially based on the premise that the overall affinity (or $\Delta G$) of peptide-HLA molecule interactions can be approximated as a linear polynomial function of the type:

$$\text{``}\Delta G\text{''} = a_{1i} \times a_{2i} \times a_{3i} \ldots \times a_{mi}$$

where $a_{ji}$ is a coefficient which represents the effect of the presence of a given amino acid (j) at a given position (i) along the sequence of a peptide of n amino acids. The crucial assumption of this method is that the effects at each position are essentially independent of each other (i.e., independent binding of individual side-chains). When residue j occurs at position i in the peptide, it is assumed to contribute a constant amount j, to the free energy of binding of the peptide irrespective of the sequence of the rest of the peptide.

The method of derivation of specific algorithm coefficients has been described in Gulukota et al., *J. Mol. Biol.* 267:1258–126, 1997; (see also Sidney et al., *Human Immunol.* 45:79–93, 1996; and Southwood et al., *J. Immunol.* 160:3363–3373, 1998). Briefly, for all i positions, anchor and non-anchor alike, the geometric mean of the average relative binding (ARB) of all peptides carrying j is calculated relative to the remainder of the group, and used as the estimate of $j_i$. For Class II peptides, if multiple alignments are possible, only the highest scoring alignment is utilized, following an iterative procedure. To calculate an algorithm score of a given peptide in a test set, the ARB values corresponding to the sequence of the peptide are multiplied. If this product exceeds a chosen threshold, the peptide is predicted to bind. Appropriate thresholds are chosen as a function of the degree of stringency of prediction desired.

Selection of HLA-A2 Supertype Cross-reactive Peptides

Complete protein sequences from 161P2F10B are scanned utilizing motif identification software, to identify 8-, 9- 10- and 11-mer sequences containing the HLA-A2-supermotif main anchor specificity. Typically, these sequences are then scored using the protocol described above and the peptides corresponding to the positive-scoring sequences are synthesized and tested for their capacity to bind purified HLA-A*0201 molecules in vitro (HLA-A*0201 is considered a prototype A2 supertype molecule).

These peptides are then tested for the capacity to bind to additional A2-supertype molecules (A*0202, A*0203, A*0206, and A*6802). Peptides that bind to at least three of the five A2-supertype alleles tested are typically deemed A2-supertype cross-reactive binders. Preferred peptides bind at an affinity equal to or less than 500 nM to three or more HLA-A2 supertype molecules.

Selection of HLA-A3 Supermotif-bearing Epitopes

The 161P2F10B protein sequence scanned above is also examined for the presence of peptides with the HLA-A3-supermotif primary anchors. Peptide corresponding to the HLA A3 supermotif-bearing sequences are then synthesized and tested for binding to HLA-A*0301 and HLA-A*1101 molecules, the molecules encoded by the two most prevalent A3-supertype alleles. The peptides that bind at least one of the two alleles with binding affinities of ≦500 nM, often ≦200 nM, are then tested for binding cross-reactivity to the other common A3-supertype alleles (e.g., A*3101, A*3301, and A*6801) to identify those that can bind at least three of the five HLA-A3-supertype molecules tested.

Selection of HLA-B7 Supermotif Bearing Epitopes

The 161P2F10B protein is also analyzed for the presence of 8-, 9- 10-, or 11-mer peptides with the HLA-B7- supermotif. Corresponding peptides are synthesized and tested for binding to HLA-B*0702, the molecule encoded by the most common B7-supertype allele (i.e., the prototype B7 supertype allele). Peptides binding B*0702 with $IC_{50}$ of $\leq 500$ nM are identified using standard methods. These peptides are then tested for binding to other common B7-supertype molecules (e.g., B*3501, B*5101, B*5301, and B*5401). Peptides capable of binding to three or more of the five B7-supertype alleles tested are thereby identified.

Selection of A1 and A24 Motif-bearing Epitopes

To further increase population coverage, HLA-A1 and -A24 epitopes can also be incorporated into vaccine compositions. An analysis of the 161P2F10B protein can also be performed to identify HLA-A1- and A24-motif-containing sequences.

High affinity and/or cross-reactive binding epitopes that bear other motif and/or supermotifs are identified using analogous methodology.

Example 12

Confirmation of Immunogenicity

Cross-reactive candidate CTL A2-supermotif-bearing peptides that are identified as described herein are selected to confirm in vitro immunogenicity. Confirmation is performed using the following methodology:

Target Cell Lines for Cellular Screening:

The .221A2.1 cell line, produced by transferring the HLA-A2.1 gene into the HLA-A, -B, -C null mutant human B-lymphoblastoid cell line 721.221, is used as the peptide-loaded target to measure activity of HLA-A2.1-restricted CTL. This cell line is grown in RPMI-1640 medium supplemented with antibiotics, sodium pyruvate, nonessential amino acids and 10% (v/v) heat inactivated FCS. Cells that express an antigen of interest, or transfectants comprising the gene encoding the antigen of interest, can be used as target cells to confirm the ability of peptide-specific CTLs to recognize endogenous antigen.

Primary CTL Induction Cultures:

Generation of Dendritic Cells (DC): PBMCs are thawed in RPMI with 30 µg/ml DNAse, washed twice and resuspended in complete medium (RPMI-1640 plus 5% AB human serum, non-essential amino acids, sodium pyruvate, L-glutamine and penicillin/streptomycin). The monocytes are purified by plating $10 \times 10^6$ PBMC/well in a 6-well plate. After 2 hours at 37° C., the non-adherent cells are removed by gently shaking the plates and aspirating the supernatants. The wells are washed a total of three times with 3 ml RPMI to remove most of the non-adherent and loosely adherent cells. Three ml of complete medium containing 50 ng/ml of GM-CSF and 1,000 U/ml of IL-4 are then added to each well. TNFα is added to the DCs on day 6 at 75 ng/ml and the cells are used for CTL induction cultures on day 7.

Induction of CTL with DC and Peptide: CD8+ T-cells are isolated by positive selection with Dynal immunomagnetic beads (Dynabeads® M-450) and the detacha-bead® reagent. Typically about $200-250 \times 10^6$ PBMC are processed to obtain $24 \times 10^6$ CD8+ T-cells (enough for a 48-well plate culture). Briefly, the PBMCs are thawed in RPMI with 30 µg/ml DNAse, washed once with PBS containing 1% human AB serum and resuspended in PBS/1% AB serum at a concentration of $20 \times 10^6$ cells/ml. The magnetic beads are washed 3 times with PBS/AB serum, added to the cells (140 µl beads/$20 \times 10^6$ cells) and incubated for 1 hour at 4° C. with continuous mixing. The beads and cells are washed 4× with PBS/AB serum to remove the nonadherent cells and resuspended at $100 \times 10^6$ cells/ml (based on the original cell number) in PBS/AB serum containing 100 µl/ml detacha-bead® reagent and 30 µg/ml DNAse. The mixture is incubated for 1 hour at room temperature with continuous mixing. The beads are washed again with PBS/AB/DNAse to collect the CD8+ T-cells. The DC are collected and centrifuged at 1300 rpm for 5–7 minutes, washed once with PBS with 1% BSA, counted and pulsed with 40 µg/ml of peptide at a cell concentration of $1-2 \times 10^6$/ml in the presence of 3 µg/ml $\beta_2$-microglobulin for 4 hours at 20° C. The DC are then irradiated (4,200 rads), washed 1 time with medium and counted again.

Setting up induction cultures: 0.25 ml cytokine-generated DC (at $1 \times 10^5$ cells/ml) are co-cultured with 0.25 ml of CD8+ T-cells (at $2 \times 10^6$ cell/ml) in each well of a 48-well plate in the presence of 10 ng/ml of IL-7. Recombinant human IL-10 is added the next day at a final concentration of 10 ng/ml and rhuman IL-2 is added 48 hours later at 10 IU/ml.

Restimulation of the induction cultures with peptide-pulsed adherent cells: Seven and fourteen days after the primary induction, the cells are restimulated with peptide-pulsed adherent cells. The PBMCs are thawed and washed twice with RPMI and DNAse. The cells are resuspended at $5 \times 10^6$ cells/ml and irradiated at ~4200 rads. The PBMCs are plated at $2 \times 10^6$ in 0.5 ml complete medium per well and incubated for 2 hours at 37° C. The plates are washed twice with RPMI by tapping the plate gently to remove the nonadherent cells and the adherent cells pulsed with 10 µg/ml of peptide in the presence of 3 µg/ml $\beta_2$ microglobulin in 0.25 ml RPMI/5% AB per well for 2 hours at 37° C. Peptide solution from each well is aspirated and the wells are washed once with RPMI. Most of the media is aspirated from the induction cultures (CD8+ cells) and brought to 0.5 ml with fresh media. The cells are then transferred to the wells containing the peptide-pulsed adherent cells. Twenty four hours later recombinant human IL-10 is added at a final concentration of 10 ng/ml and recombinant human IL2 is added the next day and again 2–3 days later at 50 IU/ml (Tsai et al., *Critical Reviews in Immunology* 18(1–2):65–75, 1998). Seven days later, the cultures are assayed for CTL activity in a $^{51}$Cr release assay. In some experiments the cultures are assayed for peptide-specific recognition in the in situ IFNγELISA at the time of the second restimulation followed by assay of endogenous recognition 7 days later. After expansion, activity is measured in both assays for a side-by-side comparison.

Measurement of CTL Lytic Activity by $^{51}$Cr Release.

Seven days after the second restimulation, cytotoxicity is determined in a standard (5 hr) $^{51}$Cr release assay by assaying individual wells at a single E:T. Peptide-pulsed targets are prepared by incubating the cells with 10 µg/ml peptide overnight at 37° C.

Adherent target cells are removed from culture flasks with trypsin-EDTA. Target cells are labeled with 200 µCi of $^{51}$Cr sodium chromate (Dupont, Wilmington, Del.) for 1 hour at 37° C. Labeled target cells are resuspended at $10^6$ per ml and diluted 1:10 with K562 cells at a concentration of $3.3 \times 10^6$/ml (an NK-sensitive erythroblastoma cell line used to reduce non-specific lysis). Target cells (100 µl) and effectors (100 µl) are plated in 96 well round-bottom plates and incubated for 5 hours at 37° C. At that time, 100 µl of supernatant are collected from each well and percent lysis is determined according to the formula:

[(cpm of the test sample-cpm of the spontaneous $^{51}$Cr release sample)/(cpm of the maximal $^{51}$Cr release sample-cpm of the spontaneous $^{51}$Cr release sample)]×100.

Maximum and spontaneous release are determined by incubating the labeled targets with 1% Triton X-100 and media alone, respectively. A positive culture is defined as one in which the specific lysis (sample-background) is 10% or higher in the case of individual wells and is 15% or more at the two highest E:T ratios when expanded cultures are assayed.

In Situ Measurement of Human IFNγ Production as an Indicator of Peptide-specific and Endogenous Recognition Immulon 2 plates are coated with mouse anti-human IFNγ monoclonal antibody (4 μg/ml 0.1M NaHCO$_3$, pH 8.2) overnight at 4° C. The plates are washed with Ca$^{2+}$, Mg$^{2+}$-free PBS/0.05% Tween 20 and blocked with PBS/10% FCS for two hours, after which the CTLs (100 μl/well) and targets (100 μl/well) are added to each well, leaving empty wells for the standards and blanks (which received media only). The target cells, either peptide-pulsed or endogenous targets, are used at a concentration of 1×10$^6$ cells/ml. The plates are incubated for 48 hours at 37° C. with 5% CO$_2$.

Recombinant human IFN-gamma is added to the standard wells starting at 400 pg or 1200 pg/100 microliter/well and the plate incubated for two hours at 37° C. The plates are washed and 100 μl of biotinylated mouse anti-human IFN-gamma monoclonal antibody (2 microgram/ml in PBS/3% FCS/0.05% Tween 20) are added and incubated for 2 hours at room temperature. After washing again, 100 microliter HRP-streptavidin (1:4000) are added and the plates incubated for one hour at room temperature. The plates are then washed 6× with wash buffer, 100 microliter/well developing solution (TMB 1:1) are added, and the plates allowed to develop for 5–15 minutes. The reaction is stopped with 50 microliter/well 1M H$_3$PO$_4$ and read at OD450. A culture is considered positive if it measured at least 50 pg of IFN-gamma/well above background and is twice the background level of expression.

CTL Expansion.

Those cultures that demonstrate specific lytic activity against peptide-pulsed targets and/or tumor targets are expanded over a two week period with anti-CD3. Briefly, 5×10$^4$ CD8+ cells are added to a T25 flask containing the following: 1×10$^6$ irradiated (4,200 rad) PBMC (autologous or allogeneic) per ml, 2×10$^5$ irradiated (8,000 rad) EBV-transformed cells per ml, and OKT3 (anti-CD3) at 30 ng per ml in RPMI-1640 containing 10% (v/v) human AB serum, non-essential amino acids, sodium pyruvate, 25 μM 2-mercaptoethanol, L-glutamine and penicillin/streptomycin. Recombinant human IL2 is added 24 hours later at a final concentration of 200 IU/ml and every three days thereafter with fresh media at 50 IU/ml. The cells are split if the cell concentration exceeds 1×10$^6$/ml and the cultures are assayed between days 13 and 15 at E:T ratios of 30, 10, 3 and 1:1 in the $^{51}$Cr release assay or at 1×10$^6$/ml in the in situ IFNγ assay using the same targets as before the expansion.

Cultures are expanded in the absence of anti-CD3$^+$ as follows. Those cultures that demonstrate specific lytic activity against peptide and endogenous targets are selected and 5×10$^4$ CD8$^+$ cells are added to a T25 flask containing the following: 1×10$^6$ autologous PBMC per ml which have been peptide-pulsed with 10 μg/ml peptide for two hours at 37° C. and irradiated (4,200 rad); 2×10$^5$ irradiated (8,000 rad) EBV-transformed cells per ml RPMI-1640 containing 10% (v/v) human AB serum, non-essential AA, sodium pyruvate, 25 mM 2-ME, L-glutamine and gentamicin.

Immunogenicity of A2 Supermotif-bearing Peptides

A2-supermotif cross-reactive binding peptides are tested in the cellular assay for the ability to induce peptide-specific CTL in normal individuals. In this analysis, a peptide is typically considered to be an epitope if it induces peptide-specific CTLs in at least individuals, and preferably, also recognizes the endogenously expressed peptide.

Immunogenicity can also be confirmed using PBMCs isolated from patients bearing a tumor that expresses 161P2F10B. Briefly, PBMCs are isolated from patients, re-stimulated with peptide-pulsed monocytes and assayed for the ability to recognize peptide-pulsed target cells as well as transfected cells endogenously expressing the antigen.

Evaluation of A*03/A11 Immunogenicity

HLA-A3 supermotif-bearing cross-reactive binding peptides are also evaluated for immunogenicity using methodology analogous for that used to evaluate the immunogenicity of the HLA-A2 supermotif peptides.

Evaluation of B7 Immunogenicity

Immunogenicity screening of the B7-supertype cross-reactive binding peptides identified as set forth herein are confirmed in a manner analogous to the confirmation of A2- and A3-supermotif-bearing peptides.

Peptides bearing other supermotifs/motifs, e.g., HLA-A1, HLA-A24 etc. are also confirmed using similar methodology.

Example 13

Implementation of the Extended Supermotif to Improve the Binding Capacity of Native Epitopes by Creating Analogs HLA motifs and supermotifs (comprising primary and/or secondary residues) are useful in the identification and preparation of highly cross-reactive native peptides, as demonstrated herein. Moreover, the definition of HLA motifs and supermotifs also allows one to engineer highly cross-reactive epitopes by identifying residues within a native peptide sequence which can be analoged to confer upon the peptide certain characteristics, e.g. greater cross-reactivity within the group of HLA molecules that comprise a supertype, and/or greater binding affinity for some or all of those HLA molecules. Examples of analoging peptides to exhibit modulated binding affinity are set forth in this example.

Analoging at Primary Anchor Residues

Peptide engineering strategies are implemented to further increase the cross-reactivity of the epitopes. For example, the main anchors of A2-supermotif-bearing peptides are altered, for example, to introduce a preferred L, I, V, or M at position 2, and I or V at the C-terminus.

To analyze the cross-reactivity of the analog peptides, each engineered analog is initially tested for binding to the prototype A2 supertype allele A*0201, then, if A*0201 binding capacity is maintained, for A2-supertype cross-reactivity.

Alternatively, a peptide is confirmed as binding one or all supertype members and then analoged to modulate binding affinity to any one (or more) of the supertype members to add population coverage.

The selection of analogs for immunogenicity in a cellular screening analysis is typically further restricted by the capacity of the parent wild type (WT) peptide to bind at least weakly, i.e., bind at an IC$_{50}$ of 5000 nM or less, to three of more A2 supertype alleles. The rationale for this requirement is that the WT peptides must be present endogenously in sufficient quantity to be biologically relevant. Analoged peptides have been shown to have increased immunogenicity and cross-reactivity by T cells specific for the parent epitope (see, e.g., Parkhurst et al., *J. Immunol.* 157:2539, 1996; and Pogue et al., *Proc. Natl. Acad. Sci. USA* 92:8166, 1995).

In the cellular screening of these peptide analogs, it is important to confirm that analog-specific CTLs are also able to recognize the wild-type peptide and, when possible, target cells that endogenously express the epitope.

Analoging of HLA-A3 and B7-supermotif-bearing Peptides

Analogs of HLA-A3 supermotif-bearing epitopes are generated using strategies similar to those employed in analoging HLA-A2 supermotif-bearing peptides. For example, peptides binding to ⅗ of the A3-supertype molecules are engineered at primary anchor residues to possess a preferred residue (V, S, M, or A) at position 2.

The analog peptides are then tested for the ability to bind A*03 and A*11 (prototype A3 supertype alleles). Those peptides that demonstrate ≦500 nM binding capacity are then confirmed as having A3-supertype cross-reactivity.

Similarly to the A2- and A3-motif bearing peptides, peptides binding 3 or more B7-supertype alleles can be improved, where possible, to achieve increased cross-reactive binding or greater binding affinity or binding half life. B7 supermotif-bearing peptides are, for example, engineered to possess a preferred residue (V, I. L, or F) at the C-terminal primary anchor position, as demonstrated by Sidney et al. (*J. Immunol.* 157:3480–3490, 1996).

Analoging at primary anchor residues of other motif and/or supermotif-bearing epitopes is performed in a like manner.

The analog peptides are then be confirmed for immunogenicity, typically in a cellular screening assay. Again, it is generally important to demonstrate that analog-specific CTLs are also able to recognize the wild-type peptide and, when possible, targets that endogenously express the epitope.

Analoging at Secondary Anchor Residues

Moreover, HLA supermotifs are of value in engineering highly cross-reactive peptides and/or peptides that bind HLA molecules with increased affinity by identifying particular residues at secondary anchor positions that are associated with such properties. For example, the binding capacity of a B7 supermotif-bearing peptide with an F residue at position 1 is analyzed. The peptide is then analoged to, for example, substitute L for F at position 1. The analoged peptide is evaluated for increased binding affinity, binding half life and/or increased cross-reactivity. Such a procedure identifies analoged peptides with enhanced properties.

Engineered analogs with sufficiently improved binding capacity or cross-reactivity can also be tested for immunogenicity in HLA-B7-transgenic mice, following for example, IFA immunization or lipopeptide immunization. Analoged peptides are additionally tested for the ability to stimulate a recall response using PBMC from patients with 161P2F10B-expressing tumors.

Other Analoging Strategies

Another form of peptide analoging, unrelated to anchor positions, involves the substitution of a cysteine with α-amino butyric acid. Due to its chemical nature, cysteine has the propensity to form disulfide bridges and sufficiently alter the peptide structurally so as to reduce binding capacity. Substitutions of α-amino butyric acid for cysteine not only alleviates this problem, but has been shown to improve binding and crossbinding capabilities in some instances (see, e.g., the review by Sette et al., In: Persistent Viral Infections, Eds. R. Ahmed and I. Chen, John Wiley & Sons, England, 1999).

Thus, by the use of single amino acid substitutions, the binding properties and/or cross-reactivity of peptide ligands for HLA supertype molecules can be modulated.

Example 14

Identification and Confirmation of 161P2F10B-derived Sequences with HLA-DR Binding Motifs Peptide epitopes bearing an HLA class II supermotif or motif are identified and confirmed as outlined below using methodology similar to that described for HLA Class I peptides.

Selection of HLA-DR-supermotif-bearing Epitopes

To identify 161P2F10B-derived, HLA class II HTL epitopes, the 161P2F10B antigen is analyzed for the presence of sequences bearing an HLA-DR-motif or supermotif. Specifically, 15-mer sequences are selected comprising a DR-supermotif, comprising a 9-mer core, and three-residue N- and C-terminal flanking regions (15 amino acids total).

Protocols for predicting peptide binding to DR molecules have been developed (Southwood et al., *J. Immunol.* 160:3363–3373, 1998). These protocols, specific for individual DR molecules, allow the scoring, and ranking, of 9-mer core regions. Each protocol not only scores peptide sequences for the presence of DR-supermotif primary anchors (i.e., at position 1 and position 6) within a 9-mer core, but additionally evaluates sequences for the presence of secondary anchors. Using allele-specific selection tables (see, e.g., Southwood et al., ibid.), it has been found that these protocols efficiently select peptide sequences with a high probability of binding a particular DR molecule. Additionally, it has been found that performing these protocols in tandem, specifically those for DR1, DR4w4, and DR7, can efficiently select DR cross-reactive peptides.

The 161P2F10B-derived peptides identified above are tested for their binding capacity for various common HLA-DR molecules. All peptides are initially tested for binding to the DR molecules in the primary panel: DR1, DR4w4, and DR7. Peptides binding at least two of these three DR molecules are then tested for binding to DR2w2 β1, DR2w2 β2, DR6w19, and DR9 molecules in secondary assays. Finally, peptides binding at least two of the four secondary panel DR molecules, and thus cumulatively at least four of seven different DR molecules, are screened for binding to DR4w15, DR5w11, and DR8w2 molecules in tertiary assays. Peptides binding at least seven of the ten DR molecules comprising the primary, secondary, and tertiary screening assays are considered cross-reactive DR binders. 161P2F10B-derived peptides found to bind common HLA-DR alleles are of particular interest.

Selection of DR3 Motif Peptides

Because HLA-DR3 is an allele that is prevalent in Caucasian, Black, and Hispanic populations, DR3 binding capacity is a relevant criterion in the selection of HTL epitopes. Thus, peptides shown to be candidates may also be assayed for their DR3 binding capacity. However, in view of the binding specificity of the DR3 motif, peptides binding only to DR3 can also be considered as candidates for inclusion in a vaccine formulation.

To efficiently identify peptides that bind DR3, target 161P2F10B antigens are analyzed for sequences carrying one of the two DR3-specific binding motifs reported by Geluk et al. (*J. Immunol.* 152:5742–5748, 1994). The corresponding peptides are then synthesized and confirmed as having the ability to bind DR3 with an affinity of 1 μM or better, i.e., less than 1 μM. Peptides are found that meet this binding criterion and qualify as HLA class II high affinity binders.

DR3 binding epitopes identified in this manner are included in vaccine compositions with DR supermotif-bearing peptide epitopes.

Similarly to the case of HLA class I motif-bearing peptides, the class II motif-bearing peptides are analoged to improve affinity or cross-reactivity. For example, aspartic acid at position 4 of the 9-mer core sequence is an optimal residue for DR3 binding, and substitution for that residue often improves DR 3 binding.

Example 15

Immunogenicity of 161P2F10B-derived HTL Epitopes

This example determines immunogenic DR supermotif- and DR3 motif-bearing epitopes among those identified using the methodology set forth herein.

Immunogenicity of HTL epitopes are confirmed in a manner analogous to the determination of immunogenicity of CTL epitopes, by assessing the ability to stimulate HTL responses and/or by using appropriate transgenic mouse models. Immunogenicity is determined by screening for: 1.) in vitro primary induction using normal PBMC or 2.) recall responses from patients who have 161P2F10B-expressing tumors.

Example 16

Calculation of Phenotypic Frequencies of HLA-supertypes in Various Ethnic Backgrounds to Determine Breadth of Population Coverage This example illustrates the assessment of the breadth of population coverage of a vaccine composition comprised of multiple epitopes comprising multiple supermotifs and/or motifs.

In order to analyze population coverage, gene frequencies of HLA alleles are determined. Gene frequencies for each HLA allele are calculated from antigen or allele frequencies utilizing the binomial distribution formulae $gf=1-(SQRT(1-af))$ (see, e.g., Sidney et al., *Human Immunol.* 45:79–93, 1996). To obtain overall phenotypic frequencies, cumulative gene frequencies are calculated, and the cumulative antigen frequencies derived by the use of the inverse formula $[af=1-(1-Cgf)^2]$.

Where frequency data is not available at the level of DNA typing, correspondence to the serologically defined antigen frequencies is assumed. To obtain total potential supertype population coverage no linkage disequilibrium is assumed, and only alleles confirmed to belong to each of the supertypes are included (minimal estimates). Estimates of total potential coverage achieved by inter-loci combinations are made by adding to the A coverage the proportion of the non-A covered population that could be expected to be covered by the B alleles considered (e.g., $total=A+B*(1-A)$). Confirmed members of the A3-like supertype are A3, A11, A31, and A*3301, and A*6801. Although the A3-like supertype may also include A34, A66, and A*7401, these alleles were not included in overall frequency calculations. Likewise, confirmed members of the A2-like supertype family are A*0201, A*0202, A*0203, A*0204, A*0205, A*0206, A*0207, A*6802, and A*6901. Finally, the B7-like supertype-confirmed alleles are: B7, B*3501-03, B51, B*5301, B*5401, B*5501-2, B*5601, B*6701, and B*7801 (potentially also B*1401, B*3504-06, B*4201, and B*5602).

Population coverage achieved by combining the A2-, A3- and B7-supertypes is approximately 86% in five major ethnic groups. Coverage may be extended by including peptides bearing the A1 and A24 motifs. On average, A1 is present in 12% and A24 in 29% of the population across five different major ethnic groups (Caucasian, North American Black, Chinese, Japanese, and Hispanic). Together, these alleles are represented with an average frequencey of 39% in the same ethnic populations. The total coverage across the major ethnicities when A1 and A24 are combined with the coverage of the A2-, A3- and B7-supertype alleles is >95%. An analogous approach can be used to estimate population coverage achieved with combinations of class II motif-bearing epitopes.

Immunogenicity studies in humans (e.g., Bertoni et al., *J. Clin. Invest.* 100:503, 1997; Doolan et al., *Immunity* 7:97, 1997; and Threlkeld et al., *J. Immunol.* 159:1648, 1997) have shown that highly cross-reactive binding peptides are almost always recognized as epitopes. The use of highly cross-reactive binding peptides is an important selection criterion in identifying candidate epitopes for inclusion in a vaccine that is immunogenic in a diverse population.

With a sufficient number of epitopes (as disclosed herein and from the art), an average population coverage is predicted to be greater than 95% in each of five major ethnic populations. The game theory Monte Carlo stimulation analysis, which is known in the art (see e.g., Osborne, M. J. and Rubinstein, A. "A course in game theory" MIT Press, 1994), can be used to estimate what percentage of the individuals in a population comprised of the Caucasian, North American Black, Japanese, Chinese, and Hispanic ethnic groups would recognize the vaccine epitopes described herein. A preferred percentage is 90%. A more preferred percentage is 95%.

Example 17

CTL Recognition Of Endogenously Processed Antigens After Priming

This example confirms that CTL induced by native or analoged peptide epitopes identified and selected as described herein recognize endogenously synthesized, i.e., native antigens.

Effector cells isolated from transgenic mice that are immunized with peptide epitopes, for example HLA-A2 supermotif-bearing epitopes, are re-stimulated in vitro using peptide-coated stimulator cells. Six days later, effector cells are assayed for cytotoxicity and the cell lines that contain peptide-specific cytotoxic activity are further re-stimulated. An additional six days later, these cell lines are tested for cytotoxic activity on $^{51}Cr$ labeled Jurak-A2.1/$K^b$ target cells in the absence or presence of peptide, and also tested on $^{51}Cr$ labeled target cells bearing the endogenously synthesized antigen, i.e. cells that are stably transfected with 161P2F10B expression vectors.

The results demonstrate that CTL lines obtained from animals primed with peptide epitope recognize endogenously synthesized 161P2F10B antigen. The choice of transgenic mouse model to be used for such an analysis depends upon the epitope(s) that are being evaluated. In addition to HLA-A*0201/$K^b$ transgenic mice, several other transgenic mouse models including mice with human A11, which may also be used to evaluate A3 epitopes, and B7 alleles have been characterized and others (e.g., transgenic mice for HLA-A1 and A24) are being developed. HLA-DR1 and HLA-DR3 mouse models have also been developed, which may be used to evaluate HTL epitopes.

Example 18

Activity of CTL-HTL Conjugated Epitope in Transgenic Mice

This example illustrates the induction of CTLs and HTLs in transgenic mice, by use of a 161P2F10B-drived CTL and HTL peptide vaccine compositions. The vaccine composition used herein comprise peptides to be administered to a patient with a 161P2F10B-expressing tumor. The peptide composition can comprise multiple CTL and/or HTL epitopes. The epitopes are identified using methodology as described herein. This example also illustrates that enhanced immunogenicity can be achieved by inclusion of one or more HTL epitopes in a CTL vaccine composition; such as peptide composition can comprise an HTL epitope conjugated to a CTL epitope. The CTL epitope can be one that binds to multiple HLA family members at an affinity of 500 nM less, or analogs of that epitope. The peptides may be lipidated, if desired.

Immunization procedures: Immunization of transgenic mice is performed as described (Alexander et al., J. Immunol. 159:4753–4761, 1997). For example, A2K$^b$ mice, which are transgenic for the human HLA A2.1 allele and are used to confirm the immunogenicity of HLA-A*0201 motif- or HLA-A2 supermotif -bearing epitopes, and are primed subcutaneously (base of the tail) with a 0.1 ml of peptide in Incomplete Freund's Adjuvant, or if the peptide composition is a lipidated CTL/HTL conjugate, in DMSO/saline, or if the peptide composition is a polypeptide, in PBS or Incomplete Freund's Adjuvant. Seven days after priming, splenocytes obtained from these animals are restimulated with syngenic irradiated LPS-activated lymphoblasts coated with peptide.

Cell lines: Target cells for peptide-specific cytotoxicity assays are jukat cells transfected with the HLA-A2.1/K$^b$ chimeric gene (e.g., Vitiello et al., *J. Exp. Med.* 173:1007, 1991)

In vitro CTL activation: One week after priming, spleen cells (30×10$^6$ cells/flask) are co-cultured at 37° C. with syngeneic, irradiated (3000 rads), peptide coated lymphoblasts (10×10$^6$ cells/flask) in 10 ml of culture medium/T25 flask. After six days, effector cells are harvested and assayed for cytotoxic activity.

Assay for cytotoxic activity: Target cells (1.0 to 1.5×10$^6$) are incubated at 37° C. in the presence of 200 µl of $^{51}$Cr. After 60 minutes, cells are washed three times and resuspended in R10 medium. Peptide is added where required at a concentration of 1 µg/ml. For the assay, 10$^4$ $^{51}$Cr-labeled target cells are added to different concentrations of effector cells (final volume of 200 µl) in U-bottom 96-well plates. After a six hour incubation period at 37° C., a 0.1 ml aliquot of supernatant is removed from each well and radioactivity is determined in a Micromedic automatic gamma counter. The percent specific lysis is determined by the formula: percent specific release–100×(experimental release—spontaneous release)/(maximum release—spontaneous release). To facilitate comparison between separate CTL assays run under the same conditions, % $^{51}$Cr release data is expressed as lytic units/10$^6$ cells. One lytic unit is arbitrarily defined as the number of effector cells required to achieve 30% lysis of 10,000 target cells in a six hour $^{51}$Cr release assay. To obtain specific lytic units/10$^6$, the lytic units/10$^6$ obtained in the absence of peptide is subtracted from the lytic units/10$^6$ obtained in the presence of peptide. For example, if 30% $^{51}$Cr release is obtained at the effector(E): target (T) ratio of 50:1 (i.e., 5×10$^5$ effector cells for 10,000 targets) in the absence of peptide and 5:1 (i.e., 5×10$^4$ effector cells for 10,000 targets) in the presence of peptide, the specific lytic units would be: [(1/50,000)–(1/500,000)]×10$^6$=18 LU.

The results are analyzed to assess the magnitude of the CTL responses of animals injected with the immunogenic CTL/HTL conjugate vaccine preparation and are compared to the magnitude of the CTL response achieved using, for example, CTL epitopes as outlined above in the Example entitled "Confirmation of Immunogenicity". Analysis similar to this may be performed to confirm the immunogenicity of peptide conjugates containing multiple CTL epitopes and/or multiple HTL epitopes. In accordance with these procedures, it is found that a CTL response is induced, and concomitantly that an HTL response is induced upon administration of such compositions.

Example 19

Selection of CTL and HTL epitopes for inclusion in an 161P2F10B-specific vaccine This example illustrates a procedure for selecting peptide epitopes for vaccines compositions of the invention. The peptides in the composition can be in the form of a nucleic acid sequence, either single or one or more sequences (i.e., minigene) that encodes peptide(s), or can be single and/or polyepitopic peptides.

The following principles are utilized when selecting a plurality of epitopes for inclusion in a vaccine composition. Each of the following principles is balanced in order to make the selection.

Epitopes are selected which, upon administration, mimic immune responses that are correlated with 161P2F10B clearance. The number of epitopes used depends on observations of patients who spontaneously clear 161P2F10B. For example, if it has been observed that patients who spontaneously clear 161P2F10B generate an immune response to at least three (3) from 161P2F10B antigen, then three or four (3–4) epitopes. should be included for HLA class I. A similar rationale is used to determine HLA class II epitopes.

Epitopes are often selected that have a binding affinity of an IC$_{50}$ of 500 nM or less for an HLA class I molecule, or for class II, an IC$_{50}$ of 1000 nM or less; or HLA Class I peptides with high binding scores from the BIMAS web site, at URL bimas.dcrt.nih.gov/.

In order to achieve broad coverage of the vaccine through out a diverse population, sufficient supermotif bearing peptides, or a sufficient array of allele-specific motif bearing peptides, are selected to give broad population coverage. In one embodiment, epitopes are selected to provide at least 80% population coverage. A Monte Carlo analysis, a statistical evaluation known in the art, can be employed to assess breadth, or redundancy, or population coverage.

When creating polyepitopic composition, or a minigene that encodes same, it is typically desirable to generate the smallest peptide possible that encompasses the epitopes of interest. The principles employed are similar, if not the same, as those employed when selecting a peptide comprising nested epitopes. For example, a protein sequence for the vaccine composition is selected because it has maximal number of epitopes contained within the sequence, i.e., it has a high concentration of epitopes. Epitopes may be nested or overlapping (i.e., frame shifted relative to one another). For example, with overlapping epitopes, two 9-mer epitopes and one 10-mer epitope can be present in a 10 amino acid peptide. Each epitope can be exposed and bound by an HLA molecule upon administration of such a peptide. A multi-epitopic, peptide can be generated synthetically; recombinantly, or via cleavage from the native source. Alternatively, an analog can be made of this native sequence, whereby one or more of the epitopes comprise substitutions that alter the cross-reactivity and/or binding affinity properties of the polyepitopic peptide. Such a vaccine composition is administered for therapeutic or prophylactic purposes. This embodiment provides for the possibility that an as yet undiscovered aspect of immune system processing will apply to the native nested sequence and thereby facilitate the production of therapeutic or prophylactic immune response-inducing vaccine compositions. Additionally such an embodiment provides for the possibility of motif-bearing epitopes for an HLA makeup that is presently unknown. Furthermore, this embodiment (absent the creating of any analogs) directs the immune response to multiple peptide sequences that are actually present in 161P2F10B, thus avoiding the need to evaluate any junctional epitopes. Lastly, the embodiment provides an economy of scale when producing nucleic acid vaccine compositions. Related to this embodiment, computer programs can be derived in accordance with principles in the art, which identify in a target sequence, the greatest number of epitopes per sequence length.

A vaccine composition comprised of selected peptides, when administered, is safe, efficacious, and elicits an immune response similar in magnitude to an immune response that controls or clears cells that bear or overexpress 161P2F10B.

Example 20

Construction of "Minigene" Multi-Epitope DNA Plasmids

This example discusses the construction of a minigene expression plasmid. Minigene plasmids may, of course, contain various configurations of B cell, CTL and/or HTL epitopes or epitope analogs as described herein.

A minigene expression plasmid typically includes multiple CTL and HTL peptide epitopes. In the present example, HLA-A2-A2, -A3, -B7 supermotif-bearing peptide epitope and HLA-A1 and -A24 motif-bearing peptide epitopes are used in conjunction with DR supermotif-bearing epitopes and/or Dr3 epitopes. HLA class 1 supermotif or motif-bearing peptide epitopes derived 161P2F10B, are selected such that multiple supermotifs/motifs are represented to ensure broad population coverage. Similarly, HLA class II epitopes are selected from 161P2F10B to provide broad population coverage, i.e. both BLA DR-1-4-7 supermotif-bearing epitopes and HLA DR-3 motif-bearing epitopes are selected for inclusion in the minigene construct. The selected CTL and HTL epitopes are then incorporated into a minigene for expression in an expression vector.

Such a construct may additionally include sequences that direct the HTL epitopes to the endoplasmic reticulum. For example, the Ii protein may be fused to one or more HTL epitopes as described in the art, wherein the CLIP sequence of the Ii protein is removed and replaced with an HLA class II epitope sequence so that HLA class II epitope is directed to the endoplasmic reticulum, where the epitope binds to an HLA class II molecules.

This example illustrates the methods to be used for construction of a minigene-bearing expression plasmid. Other expression vectors that may be used for minigene compositions are available and known to those of skill in the art.

The minigene DNA plasmid of this example contains a consensus Kozak sequence and a consensus murine kappa Ig-light chain signal sequence followed by CTL and/or HTl epitopes selected in accordance with principles disclosed herein. The sequence encodes an open frame fused to the Myc and His antibody epitope tag coded for by the pcDNA 3.1 Myc-His vector.

Overlapping oligonucleotides that can, for example, average about 70 nucleotides in length with 15 nucleotide overlaps, are synthesized and HPLC-purified. The oligonucleotide encode the selected peptide epitopes as well as appropriate linker nucleotides, Kozak sequence, and signal sequence. The final multiepitope minigene is assembled by extending the overlapping oligonucleotides in three sets of reactions using PCR. A Perkin/Elmer 9600 PCR machine is used and a total of 30 cycles are performed using the following conditions: 95° C. for 15 sec, annealing temperature (5° below the lowest calculated Tm of each primer pair) for 30 sec, and 72° C. for 1 min.

For example, a minigene is prepared as follows. For a first PCR reaction, 5 µg of each of two oligonucleotides are annealed and extended: In an example using eight oligonucleotides, i.e., four pairs of primers, oligonucleotides 1+2, 3+4, 5+6, and 7+8 are combined in 100 µl reactions containing Pfu polymerase buffer (1×=10 mM KCL, 10 mM (NH4)$_2$SO$_4$, 20 mM Tris-chloride, pH 8.75, 2 mM MgSO$_4$, 0.1% Triton X-100, 100 µg/ml BSA), 0.25 mM each dNTP, and 2.5 U of Pfu polymerase. The full-length dimer products are gel-purified, and two reactions containing the product of 1+2 and 3+4, and the product of 5+6 and 7+8 are mixed, annealed, and extended for 10 cycles. Half of the two reactions are then mixed, and 5 cycles of annealing and extension carried out before flanking primers are added to amplify the full length product. The full-length product is gel-purified and cloned into pCR-blunt (Invitrogen) and individual clones are screened by sequencing.

Example 21

The Plasmid Construct and the Degree to Which it Induces Immunogenicity

The degree to which a plasmid construct, for example a plasmid constructed in accordance with the previous Example, is able to induce immunogenicty is confirmed in vitro by determining epitope presentation by APC following transduction or transfection of the APC with an epitope-expressing nucleic acid construct. Such a study determines "antigenicity" and allows the use of human APC. The assay determines the ability of the epitope to be presented by the APC in a context that is recognized by a T cell by quantifying the density of epitope-HLA class I complexes on the cell surface. Quantitation can be performed by directly measuring the amount of peptide eluted from the APC (see, e.g., Sijts et al., *J. Immunol.* 156:683–692, 1996; Dernotz et al., *Nature* 342:682–684, 1989); or the number of peptide-HLA class I complexes can be estimated by measuring the amount of lysis or lymphline release induced by disease or transfected target cells, and then determining the concentration of peptide necessary to obtain equivalent levels of lysis or lymphokine release (ee, e.g., Kageyama et al., *J. Immunol.* 154:567–576, 1995).

Alternatively, immunogenicity is confirmed through in vivo injections into mice and subsequent in vitro assessment of CTL and HTL activity, which are analyzed using cytotoxicity and proliferation assays, respectively, as detailed, e.g., in Alexander et al., *Immunity* 1:751–761, 1994.

For example, to confirm the capacity of a DNA minigene construct containing at least one HLA-A2 supermotif peptide to induce CTLs in vivo, HLA-A2.1/K$^b$ transgenic mice, for example, are immunized intramuscularly with 100 µg of naked cDNA. As a means of comparing the level of CTLs induced by cDNA immunization, a control group of animals is also immunized with an actual peptide composition that comprises multiple epitopes synthesized as a single polypeptide as they would be encoded by the minigene.

Splenocytes from immunized animals are stimulated twice with each of the respective compositions (peptide epitopes encoded in the minigene or the polyepitopic peptide), then assayed for peptide-specific cytotoxic activity in a $^{51}$Cr release assay. The results indicate the magnitude of the CTL response directed against the A2-restricted epitope, thus indicating the in vivo immunogenicity of the minigene vaccine and polyepitopic vaccine.

It is, therefore, found that the minigene elicits immune responses directed toward the HLA-A2 supermotif peptide epitopes as does the polyepitopic peptide vaccine. A similar analysis is also performed using other HLA-A3 and HLA-7 transgenic mouse models to access CTL induction by HLA-A3 and HLA-B7 motif or supermotif epitopes, whereby it is also found that the minigene elicits appropriate immune responses directed toward the provided epitopes.

To confirm the capacity of a class II epitope-encoding minigene to induce HTLs in vivo, DR transgenic mice, or for those epitopes that cross react with the appropriate mouse MHC molecule, I-A$^b$-restricted mice, for example, are immunized intramuscularly with 100 μg of plasmid DNA. As a means of comparing the level of HTLs induced by DNA immunization, a group of control animals is also immunized with an actual peptide composition emulsified in complete Freund's adjuvant. CD4+T cells, i.e. HTLs, are purified from splenocytes of immunized animals and stimulated with each of the respective compositions (peptides encoded in the minigene). The HTL response is measured using a $^3$H-thymidine incorporation proliferation assay, (see, e.g., Alexander et al. Immunity 1:751–761, 1994). The results indicate the magnitude of the HTL response, thus demonstrating the in vivo immunogenicity of the minigene.

DNA minigenes, constructed as described in the previous Example, can also be confirmed as a vaccine in combination with a boosting agent using a prime boost protocol. The boosting agent can consist of recombinant protein (e.g., Barnett et al., *Aids Res. and Human Retroviruses* 14, Supplement 3:S299–S309, 1998) or recombinant vaccinia, for example, expressing a minigene or DNA encoding the complete protein of interest (see, e.g., Hanke et al., *Vaccine* 16:439–445, 1998; Sedegah et al., *Proc. Natl. Acad. Sci USA* 95:7648–53, 1998; Hanke and McMichael, *Immunol. Letters* 66:177–181, 1999; and Robinson et al., *Nature Med.* 5:526–34, 1999).

For example, the efficacy of the DNA minigene used in a prime boost protocol is initially evaluated in transgenic mice. In this example, A2.1/K$^b$ transgenic mice are immunized IM with 100 μg of a DNA minigene encoding the immunogenic peptides including at least one HLA-A2 supermotif-bearing people. After an incubation period (ranging from 3–9 weeks), the mice are boosted IP with 10$^7$ pfu/mouse of a recombinant vaccinia virus expressing the same sequence encoded by the DNA minigene. Control mice are immunized with 100 μg, of DNA or recombinant vaccinia without the minigene sequence, or with DNA encoding the minigene, but without the vaccinia boost. After an additional incubation period of two weeks, splenocytes from the mice are immediately assayed for peptide-specific activity in an ELISPOT assay. Additionally, splenocytes are stimulated in vitro with A2-restricted peptide epitopes encoded in the minigene and recombinant vaccinia, then assayed for peptide-specific activity in an alpha, beta and/or gamma IFN ELISA.

It is found that the minigene utilized in a prime-boost protocol elicits greater immune responses toward the HLA-A2 supermotif peptides than with DNA alone. Such an analysis can also be performed using HLA-A11 or HLA-B7 transgenic mouse models to assess CTL induction by HLA-A3 or HLA-B7 motif or supermotif epitopes. The use of prime boost protocols in humans is described below in the Example entitled "Induction of CTL Responses Using a Prime Boost Protocol."

Example 22

Peptide Composition for Prophylactic Uses

Vaccine compositions of the present invention can be used to prevent 161P2F10B expression in persons who are at risk for tumors that bear this antigen. For example, a polyepitopic peptide epitope composition (or a nucleic acid comprising the same) containing multiple CTL and HTL epitopes such as those selected in the above Examples, which are also selected to target greater than 80% of the population, is administered to individuals at risk for a 161P2F10B-associated tumor.

For example, a peptide-based composition is provided as a single polypeptide that encompasses multiple epitopes. The vaccine is typically administered in a physiological solution that comprises an adjuvant, such as Incomplete Freunds Adjuvant. The dose of peptide for the initial immunization is from about 1 to about 50,000 μg, generally 100–5,000 μg, for a 70 kg patient. The initial administration of vaccine is followed by booster dosages at 4 weeks followed by evaluation of the magnitude of the immune response in the patient, by techniques that determine the presence of epitope-specific CTL populations in a PBMC sample. Additional booster doses are administered as required. The composition is found to be both safe and efficacious as a prophylaxis against 161P2F10B-associated disease.

Alternatively, a composition typically comprising transfecting agents is used for the administration of a nucleic acid-based vaccine in accordance with methodologies known in the art and disclosed herein.

Example 23

Polyepitopic Vaccine Compositions Derived from Native 161P2F10B Sequences

A native 161P2F10B polyprotein sequence is analyzed, preferably using computer algorithms defined for each class I and/or class II supermotif or motif, to identify "relatively short" regions of the polyprotein that comprise multiple epitopes. The "relatively short" regions are preferably less in length than an entire native antigen. This relatively short sequence that contains multiple distinct or overlapping "nested" epitopes is selected; it can be used to generate a minigene construct. The construct is engineered to express the peptide, which corresponds to the native protein sequence. The "relatively short" peptide is generally less than 250 amino acids in length, often less than 100 amino acid in length, preferably less than 75 amino acids in length, and more preferably less than 50 amino acids in length. The protein sequence of the vaccine composition is selected because it has maximal number of epitopes contained within the sequence, i.e., it has a high concentration of epitopes. As noted herein, epitope motifs may be nested or overlapping (i.e., frame shifted relative to one another). For example, with overlapping epitopes, two 9-mer epitopes and one 10-mer epitope can be present in a 10 amino acid peptide. Such a vaccine composition is administered for therapeutic or prophylactic purposes.

The vaccine composition will include, for example, multiple CTL epitopes from 161P2F10B antigen and at least one HTL epitope. This polyepitopic native sequence is administered either as a peptide or as a nucleic acid sequence which encodes the peptide. Alternatively, an analog can be made of this native sequence, whereby one or more of the epitopes comprise substitutions that alter the cross-reactivity and/or binding affinity properties of the polyepitopic peptide.

The embodiment of this example provides for the possibility that an as yet undiscovered aspect of immune system processing will apply to the native nested sequence and thereby facilitate the production of therapeutic or prophylactic immune response-inducing vaccine composition. Additionally such an embodiment provides for the possibility of motif-bearing epitopes for an HLA makeup that is presently unknown. Furthermore, this embodiment (excluding an analoged embodiment) directs the immune response to multiple peptide sequences that are actually present in native 161P2F10B, thus avoiding the need to evaluate any junctional epitopes. Lastly, the embodiment provides an economy of scale when producing peptide or nucleic acid vaccine compositions.

Related to this embodiment, computer programs are available in the art which can be used to identify in a target sequence, the greatest number of epitopes per sequence length.

Example 24

Polyepitopic Vaccine Composition from Multiple Antigens

The 161P2F10B peptide epitopes of the present invention are used in conjunction with epitopes from other target tumor-associated antigens, to create a vaccine composition that is useful for the prevention or treatment of cancer that expresses 161P2F10B and such other antigens. For example, a vaccine composition can be provided as a single polypeptide that incorporates multiple epitopes from 161P2F10B as well as tumor-associated antigens that are often expressed with a target cancer associated with 161P2F10B expression, or can be administered as a composition comprising a cocktail of one or more discrete epitopes. Alternatively, the vaccine can be administered as a minigene construct or as dendritic cells which have been loaded with the peptide epitopes in vitro.

Example 25

Use of Peptides to Evaluate an Immune Response

Peptides of the invention may be used to analyze an immune response for the presence of specific antibodies, CTL or HTL directed to 161P2F10B. Such an analysis can be performed in a manner described by Ogg et al., Science 279:2103–2106, 1998. In this Example, peptides in accordance with the invention are used as a reagent for diagnostic or prognostic purposes, not as an immunogen.

In this example highly sensitive human leukocyte antigen tetrametic complexes ("tetramers") are used for a cross-sectional analysis of, for example, 161P2F10B HLA-A*0201-specific CTL frequences from HLA A*0201-positive individuals at different stages of disease or following immunization comprising an 161P2F10B peptide containing an A*0201 motif. Tetrameric complexes are synthesized as described (Musey et all, N. Engl. J. Med. 337:1267, 1997). Briefly, purified HLA heavy chain (A*0201 in this example) and β2-microglobulin are synthesized by means of a prokaryotic expression system. The heavy chain is modified by deletion of the transmembrane-cytosolic tail and COOH-terminal addition of a sequence containing a BirA enzymatic biotinylation site. The heavy chain, β2-microglobulin, and peptide are refolded by dilution. The 45-kD refolded product is isolated by fast protein liquid chromatography and then biotinylated by BirA in the presence of biotin (Sigma, St. Louis, Mo.), adenosine 5' triphosphate and magnesium. Streptavidin-phycoerythrin conjugate is added in a 1:4 molar ratio, and the tetrameric product is concentrated to 1 mg/ml. The resulting product is referred to as tetramer-phycoerythrin.

For the analysis of patient blood samples, approximately one million PBMCs are centrifuged at 300 g for 5 minutes and resuspended in 50 µl of cold phosphate-buffered saline. Tri-color analysis is performed with the tetramer-phycoerythrin, along with anti-CD8-Tricolor, and anti-CD38. The PBMCs are incubated with tetramer and antibodies on ice for 30 to 60 min and then washed twice before formaldehyde fixation. Gates are applied to contain >99.98% of control samples. Controls for the tetramers include both A*0201-negative individuals and A *0201-positive non-diseased donors. The percentage of cells stained with one tetramer is then determined by flow cytometry. The results indicate the number of cells in the PBMC sample that contain epitope-restricted CTLs, thereby readily indicating the extent of immune response to the 161P2F10B epitope, and thus the status of exposure to 161P2F10B, or exposure to a vaccine that elicits a protective or therapeutic response.

Example 26

Use of Peptide Epitopes to Evaluate Recall Responses

The peptide epitopes of the invention are used as reagents to evaluate T cell responses, such as acute or recall responses, in patients. Such an analysis may be performed on patients who have recovered from 161P2F10B-associated disease or who have been vaccinated with an 161P2F10B vaccine.

For example, the class I restricted CTL responses of persons who have been vaccinated may be analyzed. The vaccine may be any 161P2F10B vaccine. PBMC are collected from vaccinated individuals and HLA typed. Appropriate peptide epitopes of the invention that, optimally, bear supermotifs to provide cross-reactivity with multiple HLA supertype family members, are then used for analysis of samples derived from individuals who bear the HLA type.

PBMC from vaccinated individuals are separated on Ficoll-Histopaque density gradients (Sigma Chemical Co., St. Louis, Mo.), washed three times in HBSS (GIBCO Laboratories), resuspended in RPMI-1640 (GIBCO Laboratories) supplemented with L-glutamine (2 mM), penicillin (50 U/mol), streptomycin (50 µg/ml), and Hepes (10 mM) containing 10% heat-inactivated human AB serum (complete RPMI) and plated using microculture formats. A synthetic peptide comprising an epitope of the invention is added at 10 µg/ml to each well and HBV core 128–140 epitope is added at 1 µg/ml to each well as a source of T cell help during the first week of stimulation.

In the microculture format, $4 \times 10^5$ PBMC are stimulated with peptide in 8 replicate cultures in 96-well round bottom plate in 100 µl/well of complete RPMI. On days 3 and 10, 100 µl of complete RPMI and 20 U/ml final concentration of rIL-2 are added to each well. One day 7 the cultures are transferred into a 96-well flat-bottom plate and restimulated with peptide, rIL-2 and $10^5$ irradiated (3,000 rad) autologous feeder cells. The cultures are tested for cytotoxic activity one day 14. A positive CTL response requires two or more of the eight replicate cultures to display greater than 10% specific $^{31}$Cr release, based on comparison with non-diseased control specific as previously described (Rehermann, et al., Nature Med. 2:1104, 1108, 1996; Rehermann et al., J. Clin. Invest. 97:1655–1665, 1996; and Rehermann et al. J. Clin. Invest. 98:1432–1440, 1996).

Target cell lines are autologous and allogeneic EBV-transformed B-LCL that are either purchased from the American Society for Histocompatibility and Immunogenetics (ASHI, Boston, Mass.) or established from the pool of patients as described (Guilhot, et al., *J. Virol.* 66:2670–2678, 1992).

Cytotoxicity assays are performed in the following manner. Target cells consist of either allogeneic HLA-mediated or autologous EBV-transformed B lymphoblastoid cell line that are incubated overnight with the synthetic peptide epitope of the invention at 10 µM, and labeled with 100 µCi of $^{51}$Cr (Amersham Corp., Arlington Heights, Ill.) for 1 hour after which they are washed four times with HBSS.

Cytolytic activity is determined in a standard 4-h, split well $^{51}$Cr release assay using U-bottomed 96 well plates containing 3,000 targets/well. Stimulated PBMC are tested at effector/target (E/T) ratios of 20–50:1 one day 14. Percent cytotoxicity is determined from the formula: 100× [(experimental release-spontaneous release)/maximum release-spontaneous release)]. Maximum release is determined by lysis of targets by detergent (2% Triton X-100; Sigma Chemical Co., St. Louis, Mo.). Spontaneous release is <25% of maximum release for all experiments.

The results of such an analysis indicate the extent to which HLA-restricted CTL populations have been stimulated by previous exposure to 161P2F10B or an 161P2F10B vaccine.

Similarly, Class II restricted HTL response may also be analyzed. Purified PBMC are cultured in a 96-well flat bottom plate at a density of 1.5×10$^5$ cells/well and are stimulated with 10 µg/ml synthetic peptide of the invention, whole 161P2F10B antigen, or PHA. Cells are routinely plated in replicates of 4–6 wells for each condition. After seven days of culture, the medium is removed and replaced with fresh medium containing 10 U/ml IL-2. Two days later, 1 µCi $^3$H-thymidine is added to each well and incubation is continued for an additional 18 hours. Cellular DNA is then harvested on glass fiber mats and analyzed for $^3$H-thymidine incorporation. Antigen-specific T cell proliferation is calculated as the ratio of $^3$H-thymidine incorporation in the presence of antigen divided by the $^3$H-thymidine incorporation in the absence of antigen.

Example 27

Induction of Specific CTL Response in Humans

A human clinical trial for an immunogenic composition comprising CTL and HTL epitopes of the invention is set up as an IND Phase I, dose escalation study and carried out as a randomized, double-blind, placebo-controlled trial. Such a trial is designed, for example, as follows:

A total of about 27 individuals are enrolled and divided into 3 groups;

Group I: 3 subjects are injected with placebo and 6 subjects are injected with 5 µg of peptide composition;

Group II: 3 subjects are injected with placebo and 6 subjects are injected with 50 µg peptide composition;

Group III: 3 subjects are injected with placebo and 6 subjects are injected with 500 µg of peptide composition.

After 4 weeks following the first injection, all subjects receive a booster inoculation at the same dosage.

The endpoints measured in this study relate to the safety and tolerability of the peptide composition as well as its immunogenicity. Cellular immune response to the peptide composition are an index of the intrinsic activity of this the peptide composition, and can therefore be viewed as a measure of biological efficacy. The following summarize the clinical and laboratory data that relate to safety and efficacy endpoints.

Safety: The incidence of adverse events is monitored in the placebo and drug treatment group and assessed in terms of degree and reversibility.

Evaluation of Vaccine Efficacy: For evaluation of vaccine efficacy, subjects are bled before and after injection. Peripheral blood mononuclear cells are isolated from fresh heparinized blood by Ficoll-Hypaque density gradient centrifugation, aliquoted in freezing media and stored frozen. Samples are assayed for CTL and HTL activity.

The vaccine is found to be both safe and efficacious.

Example 28

Phase II Trials in Patients Expressing 161P2F10B

Phase II trials are performed to study the effect of administering for CTL-HTL peptide compositions to patients having cancer that expresses 161P2F10B. The main objective of the trial are to determine an effective dose and regimen for inducing CTLs in cancer patients that express 161P2F10B, to establish the safety of inducing a CTL and HTL response in these patients, and to see to what extent activation of CTLs improves the clinical picture of these patients, as manifested, e.g., by the reduction and/or shrinking of lesions. Such a study is designed for example, as follows:

The studies are performed in multiple centers. The trial design is an open-label, uncontrolled, dose escalation protocol wherein the peptide composition is administered as a single dose followed six weeks later by a single booster shot of the same dose. The dosages are 50, 500 and 5,000 micrograms per injection. Drug-associated adverse effects (severity and reversibility) are recorded.

There are three patient groupings. The first group is injected with 50 micrograms of the peptide composition and the second and third groups with 500 and 5,000 micrograms of peptide composition, respectively. The patients within each group range in age from 21–65 and represent diverse ethnic backgrounds. All of them have a tumor that expresses 161P2F10B.

Clinical manifestations or antigen-specific T-cell responses are monitored to assess the effects of administering the peptide compositions. The vaccine composition is found to be both safe and efficacious in the treatment of 161P2F10B-associated disease.

Example 29

Induction of CTL Responses Using a Prime Boost Protocol

A primer boost protocol similar in its underlying principle to that used to confirm the efficacy of a DNA vaccine in transgenic mice, such as described above in the Example entitled "The Plasmid Construct and the Degree to Which It Induces Immunogenicity," can also be used for the administration of the vaccine to humans. Such a vaccine regimen can include an initial administration of, for example, naked DNA followed by a boost using recombinant virus encoding the vaccine, or recombinant protein/polypeptide or a peptide mixture administered in an adjuvant.

For example, the initial immunization may be performed using an expression vector, such as that constructed in the Example entitled "Construction of 'Minigene' Multi-Epitope DNA Plasmids" in the form of naked nucleic acid administered IM (or SC or ID) in the amounts of 0.5–5 mg at multiple sites. The nucleic acid (0.1 to 1000 µg) can also be administered using a gene gun. Following an incubation period of 3–4 weeks, a booster dose is then administered. The booster can be recombinant fowlpox virus administered at a dose of $5–10^7$ to $5\times10^9$ pfu. An alternative recombinant virus, such as an MVA, canarypox, adenovirus, or adeno-associated virus, can also be used for the booster, or the polypeptide protein or a mixture of the peptides can be administered. For evaluation of vaccine efficacy, patient blood samples are obtained before immunizations as well as at intervals following administration of the initial vaccine and booster doses of the vaccine. Peripheral blood mononuclear cells are isolated from fresh heparinized blood by Ficoll-Hypaque density gradient centrifugation, aliquoted in freezing media and stored frozen. Samples are assayed for CTL and HTL activity. Analysis of the results indicates that a magnitude of response sufficient to achieve a therapeutic or protective immunity against 161P2F10B is generated.

Example 30

Administration of Vaccine Compositions Using Dendritic Cells (DC)

Vaccines comprising peptides epitopes of the invention can be administered using APCs, or "professional" APCs such as DC. In this example, peptide-pulsed DC are administered to a patient to stimulate a CTL response in vivo. In this method, dendritic cells are isolated, expanded, and pulsed with a vaccine comprising peptide CTL and HTL epitopes of the invention. The dentritic cells are infused back into the patient to elicit CTL and HTL responses in vivo. The induced CTL and HTL then destroy or facilitate destruction, respectively, of the target cells that bear the 161P2F10B protein from which the epitopes in the vaccine are derived.

For example, a cocktail of epitope-comprising peptides is administered ex vivo to PBMC, or isolated DC therefrom. A pharmaceutical to facilitate harvesting of DC can be used, such as Progenipoietin™ (Monsanta, St. Louis, Mo.) or GM-CSF/IL-4. After pulsing the DC with peptides, and prior to reinfusion into patients, the DC are washed to remove unbound peptides.

As appreciated clinically, and readily determined by one of skill based on clinical outcomes, the number of DC reinfused into the patient can vary (see, e.g., Nature Med. 4:328, 1998; Nature Med. 2:52, 1996 and Prostate 32:272, 1997). Although $2–50\times10^6$ DC per patient are typically administered, larger number of DC, such as $10^7$ or $10^8$ can also be provided. Such cell populations typically contain between 50–90% DC.

In some embodiments, peptide-loaded PBMC are injected into patients without purification of the DC. For example, PBMC generated after treatment with an agent such as Progenipoietin™ are injected into patients without purification of the DC. The total number of PBMC that are administered often ranges from $10^8$ to $10^{10}$. Generally, the cell doses injected into patients is based on the percentage of DC in the blood of each patient, as determined, for example, by immunofluorescence analysis with specific anti-DC antibodies. Thus, for example, if Progenipoietin™ mobilizes 2% DC in the peripheral blood of a given patient, and that patient is to receive $5\times10^6$ DC, then the patient will be injected with a total of $2.5\times10^8$ peptide-loaded PBMC. The percent DC mobilized by an agent such as Progenipoietin™ is typically estimated to be between 2–10%, but can vary as appreciated by one of the skill in the art.

Ex vivo activation of CTL/HTL responses

Alternatively, ex vivo CTL or HTL responses to 161P2F10B can be induced by incubating, in tissue culture, the patient's, or genetically compatible, CTL or HTL precursor cells together with a source of APC, such as DC, and immunogenic peptides. After an appropriate incubation time (typically about 7–28 days), in which the precursor cells are activated and expanded into effector cells, the cells are infused into the patient, where they will destroy (CTL) or facilitate destruction (HTL), of their specific target cells, i.e., tumor cells.

Example 31

An Alternative Method of Identifying and Confirming Motif-Bearing Peptides

Another method of identifying and confirming motif-bearing peptides is to eluted them from cells bearing defined MHC molecules. For example, EBV transformed B cell lines used for tissue typing have been extensively characterized to determine which HLA molecules they express. In certain cases these cells express only a single type of HLA molecule. These cells can be transfected with nucleic acids that express the antigen of interest, e.g. 161P2F10B. Peptides produced by endogenous antigen processing of peptides produced as a result of transfection will then bind to HLA molecules within the cell and be transported and displayed on the cell's surface. Peptides are then eluted from the HLA molecules by exposure to mild acid conditions and their amino acid sequence determined, e.g., by mass spectral analysis (e.g., Kubo et al., J. Immunol. 152:3913, 1994). Because of majority of peptides that bind a particular HLA molecule are motif-bearing, this is an alternative modality for obtaining the motif-bearing peptides correlated with the particular HLA molecule expressed on the cell.

Alternatively, cell lines that do not express endogenous HLA molecules can be transfected with an expression construct encoding a single HLA allele. These cells can then be used as described, i.e., they can then be transfected with nucleic acids that encode 161P2F10B to isolate peptides corresponding to 161P2F10B that have been presented on the cell surface. Peptides obtained from such an analysis will bear motif(s) that correspond to binding to the single HLA allele that is expressed in the cell.

As appreciated by one in the art, one can perform a similar analysis on a cell bearing more than one HLA allele and subsequently determines peptides specific for each HLA allele expressed. Moreover, one of skill would also recognize that means other than transfection, such as loading with a protein antigen, can be used to provide a source of antigen to the cell.

Example 32

Complementary Polynucleotides

Sequences complementary to the 161P2F10B-encoding sequences, or any parts thereof, are used to detect, decrease, or inhibit expression of naturally occurring 161P2F10B. Although use of oligonucleotides comprising from about 15 to 30 base pairs is described, essentially the same procedure is used with smaller or with larger sequence fragments. Appropriate oligonucleotides are designed using, e.g., OLIGO 4.06 software (National Biosciences) and the coding sequence of 161P2F10B. To inhibit transcription, a complementary oligonucleotide is designed from the most unique 5' sequence and used to prevent promoter binding to the coding sequence. To inhibit translation, a complementary oligonucleotide is designed to prevent ribosomal binding to the 161P2F10B-encoding transcript.

Example 33

Purification of Naturally-occurring or Recombinant 161P2F10B Using 161P2F10B Specific Antibodies Naturally occurring or recombinant 161P2F10B is substantially purified by immunoaffinity chromatography using antibodies specific for 161P2F10B. An immunoaffinity column is constructed by covalently coupling anti-161P2F10B antibody to an activated chromatographic resin, such as CNBr-activated SEPHAROSE (Amersham Pharmacia is Biotech). After the coupling, the resin is blocked and washed according to the manufacturer's instructions.

Media containing 161P2F10B are passed over the immunoaffinity column, and the column is washed under conditions that allow the preferential absorbance of 161P2F10B (e.g., high ionic strength buffers in the presence of detergent). The column is eluted under conditions that disrupt antibody/161P2F10B binding (e.g., a buffer of pH 2 to pH 3, or a high concentration of a chaotrope, such as urea or thiocyanate ion), and GCR.P is collected.

Example 34

Identification of Molecules which Interact with 161P2F10B

161P2F10B, or biologically active fragments thereof, are labeled with 121 I Bolton-Hunter reagent. (See, e.g., Bolton et al. (1973) Biochem J. 133:529). Candidate molecules previously arrayed in the wells of a multi-well plate are incubated with the labeled 161P2F10B, washed, and any wells with labeled 161P2F10B complex are assayed. Data obtained using different concentrations of 161P2F10B are used to calculate values for the number, affinity, and association of 161P2F10B with the candidate molecules.

Example 35

In Vivo Assay for 161P2F10B Tumor Growth Promotion

The effect of the 161P2F10B protein on tumor cell growth is evaluated in vivo by gene overexpression in tumor-bearing mice. For example, SCI mice are injected subcutaneously on each flank with $1\times10^6$ of either PC3, TSUPR1, or DU145 cells containing (tkNeo empty vector or 161P2F10B. At least two strategies may be used: (1) Constitutive 161P2F10B expression under regulation of a promoter such as a constitutive promoter obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian, Virus 40 (SV40), or from heterologous mammalian promoters, e.g., the actin promoter or an immunoglobulin promoter, provided such promoters are compatible with the host cell systems, and (2) regulated expression under control of an inducible vector system, such as ecdysone, tet, etc., provided such promoters are compatible with the host cell systems. Tumor volume is then monitored at the appearance of palpable tumors and followed over time to determines that 161P2F10B-expressing cells grow at a faster rate and/or tumors produced by 161P2F10B-expressing cells demonstrate characteristics of altered aggressiveness (e.g. enhanced metastasis, vascularization, reduced responsiveness or chemotherapeutic drugs).

Additionally, mice can be implanted with $1\times10^5$ of the same cells orthotopically to determine that 161P2F10B has an effect on local growth in the prostate and/or on the ability of the cells to metastasize, e.g., to lungs, lymph nodes, and bone marrow.

The assay is also useful to determine the 161P2F10B-inhibitory effect of candidate therapeutic compositions, such as for example, small molecule drugs, 161P2F10B intrabodies, 161P2F10B antisense molecules and ribozymes.

Example 36

161P2F10B Monoclonal Antibody-mediated Inhibition of Prostate Tumors In Vivo The significant expression of 161P2F10B, in cancer tissues, together with its restricted expression in normal tissues along with its cell surface expression makes 161P2F10B an excellent target for antibody therapy. Similarly, 161P2F10B is a target for T cell-based immunotherapy. Thus, the therapeutic efficacy of anti-161P2F10B mAbs is evaluated, e.g., in human prostate cancer xenograft mouse models using androgen-independent LAPC-4 and LAPC-9 xenografts (Craft, N., et al., Cancer Res, 1999. 59(19): p. 5030–6), kidney cancer xenografts (AGS -K3, AGS-K6), kidney cancer metastases to lymph node (AGS-K6 met) xenografts, and kidney cancer cell lines transfected with 161P2F10B, such as 769P-161P2F10B, A498-161P2F10B.

Antibody efficacy on tumor growth and metastasis formation is studied, e.g., in mouse orthotopic prostate cancer xenograft models and mouse kidney xenograft models. The antibodies can be unconjugated, as discussed in this Example, or can be conjugated to a therapeutic modality, as appreciated in the art. Anti-161P2F10B mAbs inhibit formation of both the androgen-dependent LAPC-9 and androgen-independent PC3-161P2F10B tumor xenografts. Anti-161P2F10B mAbs also retard the growth of established orthotopic tumors and prolonged survival of tumor-bearing mice. These results indicate the utility of anti-161P2F10B mAbs in the treatment of local and advanced stages of prostate cancer. (See, e.g., Saffran, D., et al., PNAS 10:1073–1078. Similarly, anti-161P2F10B mAbs can inhibit formation of AGS-K3 and AGS-K6 tumors in SCID mice, and prevent on retard the growth A498-161P2F10B tumor xenografts. These results indicate the use of anti-161P2F10B mAbs in the treatment of prostate and/or kidney cancer.

Administration of the anti-161P2F10B mAbs leads to retardation of established orthotopic tumor growth and inhibition of metastasis to distant sites, resulting in a significant prolongation in the survival of tumor-bearing mice. These studies indicate that 161P2F10B is an attractive target for immunotherapy and demonstrate the therapeutic use of anti-161P2F10B mAbs for the treatment of local and metastatic prostate cancer. This example demonstrates that unconjugated 161P2F10B monoclonal antibodies are effective to inhibit the growth of human prostate tumor xenografts and human kidney xenografts grown in SCID mice.

Tumor inhibition using multiple unconjugated 161P2F10B mAbs

Materials and Methods

161P2F10B Monoclonal Antibodies:

Monoclonal antibodies are raised against 161P2F10B as described in the Example entitled "Generation of 161P2F10B Monoclonal Antibodies (mAbs)" or are obtained commercially, e.g., 97A6 (Coulter Immunotech). The antibodies are characterized by ELISA, Western blot, FACS, and immunoprecipitation for their capacity to bind 161P2F10B. Epitope mapping data for the anti-161P2F10B mAbs, as determined by ELISA and Western analysis, recognize epitopes on the 161P2F10B protein. The 97A6 antibody binds to amino acids 393–405 of the 161P2F10B protein shown in FIG. 2. Immunohistochemical analysis of cancer tissues and cells is performed with these antibodies.

The monoclonal antibodies are purified from ascites or hybridoma tissue culture supernatants by Protein-G Sepharose chromatography, dialyzed against PBS, filter sterilized, and stored at −20° C. Protein determinations are performed by a Bradford assay (Bio-Rad, Hercules, Calif.). A therapeutic monoclonal antibody or a cocktail comprising a mixture of individual monoclonal antibodies is prepared and used for the treatment of mice receiving subcutaneous or orthotopic injections of LAPC-9 prostate tumor xenografts.

Cancer Xenografts and Cell Lines

The LAPC-9 xenograft, which expresses a wild-type androgen receptor and produces prostate-specific antigen (PSA), is passaged in 6- to 8-week-old male ICR-severe combined immunodeficient (SCID) mice (Taconic Farms) by s.c. trocar implant (Craft, N., et al., supra). The AGS-K3 and AGS-K6 kidney xenografts are also passaged by subcutaneous implants in 6- to 8-week old SCID mice. Single-cell suspensions of tumor cells are prepared as described in Craft, et al. The prostate carcinoma cell line PC3 (American Type Culture Collection) is maintained in RPMI supplemented with L-glutamine and 10% FBS, and the kidney carcinoma line A498 (American Type Culture Collection) is maintained in DMEM supplemented with L-glutamine and 10% FBS.

PC3-161P2F10B and A498--161P2F10B cell populations are generated by retroviral gene transfer as described in Hubert, R. S., et al., STEAP: A Prostate-specific Cell-surface Antigen Highly Expressed in Human Prostate Tumors, Proc. Natl Acad Sci U S A, 1999. 96(25): p 14523–8. Anti-161P2F10B staining is detected by using an FITC-conjugate goat anti-mouse antibody (Southern Biotechnology Associates) followed by analysis on a Coulter Epics-XL flow cytometer.

Xenograft Mouse Models

Subcutaneous (s.c.) tumors are generated by injection of $1\times10^6$ LAPC-9, AGS-K3, AGS-K6, PC3, PC3-161P2F10B, A498 or A498-161P2F10B cells mixed at a 1:1 dilution with Matrigel (Collaborative Research) in the right flank of male SCID mice. To test antibody efficacy on tumor formation, i.p. antibody injections are started on the same day as tumor-cell injections. As a control, mice are injected with either purified mouse IgG (ICN) or PBS; or a purified monoclonal antibody that recognizes an irrelevant antigen not expressed in human cells. In preliminary studies, no difference is found between mouse IgG or PBS or tumor growth. Tumor sizes are determined by vernier caliper measurements, and the tumor volume is calculated as length×width×height. Mice with s.c. tumors greater than 1.5 cm in diameter are sacrificed. PSA levels are determined by using a PSA ELISA kit (Anogen, Missisauga, Ontario). Circulating levels of anti-161P2F10B mAbs are determined by a capture ELISA kit (Bethyl Laboratories, Montgomery, Tex.). (See, e.g., (Saffran, D., et al., PNAS 10:1073–1078.

Orthotopic prostate injections are performed under anesthesia by using ketamine/xylazine. For prostate orthotopic studies, an incision is made through the abdominal muscles to expose the bladder and seminal vesicles, which then are delivered through the incision to expose the dorsal prostate. LAPC-9 cells ($5\times10^5$) mixed with Matrigel are injected into each dorsal lobe in a 10-μl volume. To monitor tumor growth, mice are bled on a weekly basis for determination of PSA levels. For kidney orthopotic models, an incision is made through the abdominal muscles to expose the kidney. AGS-K3 or AGS-K6 celsl mixed with Matrigel are injected under the kidney capsule. The mice are segregated into groups for the appropriate treatments, with anti-161P2F10B or control mAbs being injected i.p.

Anti-161P2F10B mAbs Inhibit Growth of 161P2F10B-Expressing Xenograft-Cancer Tumors The effect of anti-161P2F10B mAbs on tumor formation is tested by using LAPC-9 and/or AGS-K3 orthotopic models. As compared with the s.c. tumor model, the orthotopic model, which requires injection of tumor cells directly in the mouse prostate or kidney, respectively, results in a local tumor growth, development of metastasis in distal sites, deterioration of mouse health, and subsequent death (Saffran, D., et al., PNAS supra; Fu, X., et al., Int. J. Cancer, 1992, 52(6): p. 987–90; Kubota, T., J Cell Biochem, 1994 56(1): p. 4–8). The features make the orthotopic model more representative of human disease progression and allowed for tracking of the therapeutic effect of mAbs on clinically relevant end points.

Accordingly, tumor cells are injected into the mouse prostate or kidney, and 2 days later, the mice are segregated into two groups and treated with either: a) 200–500 μg, of anti-161P2F10B Ab, or b) PBS three times per week for two to five weeks.

A major advantage of the orthotopic prostate-cancer model is the ability to study the development of metastases. Formation of metastasis in mice bearing established orthotopic tumors is studies by IHC analysis on lung sections using an antibody against a prostate-specific cell-surface protein STEAP expressed at high levels in LAPC-9 xenografts (Hubert, R. S. et al., Proc. Natl Acad Sci U S A, 1999 96(25): p. 14523-8) or anti-G250 antibody for kidney cancer models.

Mice bearing established orthotopic LAPC-9 tumors are administered 1000 μg injections of either anti-161P2F10B mAb or PBS over a 4-week period. Mice in both groups are allowed to establish a high tumor burden (PSA levels greater than 300 ng/ml), to ensure a high frequency of metastasis formation in mouse lungs. Mice then are killed and their prostate/kidney and lungs are analyzed for the presence of tumor cells by IHC analysis.

These studies demonstrate a broad anti-tumor efficacy of anti-161P2F10B antibodies on initiation and progression of prostate and kidney cancer in xenograft mouse models. Anti-161P2F10B antibodies inhibit tumor formation of both androgen-dependent and androgen-independent prostate tumors as well as retarding the growth of already established tumors and prolong the survival of treated mice. Moreover, anti-161P2F10B mAbs demonstrate a dramatic inhibitory effect on the spread of local prostate tumor to distal sites, even in the presence of a large tumor burden. Similar therapeutic effects are seen in the kidney cancer model. Thus, anti-161P2F10B mAbs are efficacious on major clinically relevant end points (tumor growth), prolongation of survival, and health.

Example 37

Inhibition of 161P2F10B Phosphodiesterase Activity

A number of phosphodiesterase inhibitors are currently in clinical trials to investigate their use as vasodilators, antiinflammatory, anti-asthmatic, anti-thrombotic and anti-depressant agents. Some of these inhibitors are non-selective, such as Theophylline used for the treatment of asthma, whereas others exhibit substrate specificity. For example, the phosphodiesterase V inhibitor sildenafil showed great success for the treatment of male erectile dysfunction. The phosphodiesterase I inhibitor vinpocetine is currently being investigated for the treatment of urge incontinence and low compliance bladder. KF-119514 is a phosphodiesterase I/IV inhibitor shown to protect against asthma by virtue of its anti-allergic and bronchodilator activities (Fujimura et al. European Journal of Pharmacology 327:57, 1997). Metforman is another phosphodiesterase I inhibitor that has been shown to reduce lymphocyte PC-1 activity after 3-months administration to Type 2 diabetic patients, corresponding to an improvement in insulin sensitivity (Stefanovic et al. Diabetes/ Metabolism Research and Reviews 15:400, 1999).

The significant expression of 161P2F10B in cancer tissues, together with its restricted expression in normal tissues, makes 161P2F10B an excellent target for phosphodiesterase inhibitor therapy. Accordingly, the efficacy of the phosphodiesterase inhibitors in human cancer mouse models is modeled in 161P2F10B-expressing kidney, bladder or prostate cancer xenografts or cancer cell lines, either expressing 161P2F10B endogenously, or have been engineered to express 161P2F10B as discussed in Example 6 above. Such studies performed on human pancreatic cancer cells have demonstrated the utility of phosphodiesterase inhibitors in preventing cell cycle progression of cancer cells (Boucher M et al, Biochem. Biophys. Res. Commun. 2001, 13:285). Moreover, studies performed in SCID mice demonstrate that phosphodiesterase inhibitors such as Zaprinast decrease tumor weight in neuroblastoma bearing mice (Giorgi M et al., J. Neurooncol. 2001, 51:25).

Administration of phosphodiesterase inhibitors retard established tumor growth and inhibit metastasis to distant sites, resulting in a significant prolongation in the survival of tumor-bearing mice. These studies show that 161P2F10B is an attractive target for cancer therapy and demonstrate the therapeutic efficacy of phosphodiesterase inhibitors for the treatment of local and metastatic cancers, e.g., kidney, bladder and prostate cancers.

This example demonstrates that phosphodieterase inhibitors effectively inhibit the growth of human tumors grown in SCID mice. Accordingly, in one embodiment it is also seen that a combination of such efficacious phosphodiesterase inhibitors and/or derivatives thereof are also effective.

Example 38

"ENPP Activity": Detection of 161P2F10B Phosphodiesterase Activity in Human Cancer Cells 161P2F10B is identical to ENPP3 phosphodieterase (also called CD203C or PD-1 beta). ENPP3 is an ecto-enzyme belonging to a family of ectonucleotide phosphodiesterases and pyrophospahatases. ENPP3 is a phosphodiesterase I ecto-enzyme. It is expressed in normal prostate and uterus, as well as on basophils and mast cells. Expression on the hematopoietic cells is upregulated in presence of allergen or by cross-linking with IgE (Buring et al., 1999, Blood 94: 2343).

Members of the ENPP family posses ATPase and ATP pytophosphatase activities. They hydrolize extracellular nucleotides, nucleoside phosphates, and NAD. They are involved in extracellular nucleotide metabolism, nucleotide signaling, and recycling of extracellular nucleotides. They are also involved in cell—cell and cell-matrix interactions. ENPP enzymes differ in their substrate specificity and tissue distribution.

ENPP enzymes also play a role in recycling extracellular nucleotides. It has been demonstrated that ENNP1 allows activated T-cells to use NAD+ from dying cells as a source of adenosine. ENPP3 expressed in the intensine may also be involved in the hydrolysis of nucleotides derived from food (Byrd et al 1985, Scott et al. 1997).

To assess phosphodiesterase I activity of 161P2F10B, cell lysates or purified protein are prepared from human normal and cancer tissues, and incubated for 5 hr at 37 degrees in 20 mM Tris/HCL, pH 9.6 containing 5 mM $MgCl_2$ and 1 mM p-nitrophenyl thymidine-5'-L-monophosphate. The reaction is terminated by the addition of 0.1 N NaOH and the reaction product quantified by reading absorbance at 410 nm (A410×64=nmol p-nitrophenol). Thus, the phosphodiesterase I activity of 161P2F10B in cancer tissues is confirmed. When 161P2F10B shows phosphodiesterase activity, it is used as a target for diagnostic, prognostic, preventative and/or therapeutic purposes.

Example 39

Detection of 161P2F10B protein in kidney cancer patient specimens

To confirm the expression of 161P2F10B protein, kidney cancer specimens were obtained from kidney cancer patients, and stained using the commercially available antibody 97A6 specific for ENPP3 protein (also called anti-CD203e) (Immunotech, Marseilles, France). Briefly, frozen tissues were cut into 4 micron sections and fixed in acetone for 10 minutes. The sections were then incubated with PE-labeled mouse monoclonal anti-ENPP3 antibody for 3 hours (FIG. 16A–F), or isotype control antibody (FIG. 16G–I). The slides were washed three times in buffer, and either analyzed by fluorescence microscopy (FIGS. 16A, B and C), or further incubated with DAKO EnVision+™ peroxidase-conjugated goat anti-mouse antibody (DAKO Corporation, Carpenteria, Calif.) for 1 hour (FIGS. 16D, E, and F). The sections were then washed in buffer, developed using the DAB kit (SIGMA Chemicals), counterstained using hematoxylin, and analyzed by bright field microscopy (FIGS. 16D, E and F). The results showed strong expression of 161P2F10B in the renal carcinoma patient tissue (FIGS. 16A and D) and the kidney cancer metastatis to lymph node tissue (FIGS. 16C and F), but weekly in normal kidney (FIGS. 16B and E). The expression was detected mostly around the cell membrane indicating that 161P2F10B is membraned associated in kidney cancer tissues. The weak expression detected in normal kidney was localized to the kidney tubules. The sections stained with the isotype control antibody were negative showing the specificity of the anti-ENPP3 antibody (FIG. 16G–J).

FIG. 20 shows expression of 161P2F10B in human patient cancers by Western blot analysis. Cell lysates from kidney cancer tissues (KiCa), kidney cancer metastatis to lymph node (KiCa Met), as well as normal kidney (NK) were subjected to western analysis using an anti-161P2F10B mouse monoclonal antibody. Briefly, tissues (~25 g total protein) were solubilized in SDS-PAGE sample buffer and separated on a 10–20% SDS-PAGE gel and transferred to nitrocellulose. Blots were blocked in Tris-buffered saline (TBS)+3% non-fat milk and then probed with purified anti-161P2F10B antibody in TBS+0.15% Tween-20+1% milk. Blots were then washed and incubated with a 1:4,000 dilution of anti-mouse IgG-HRP conjugated secondary antibody. Following washing anti-161P2F10B immunoreactive bands were developed and visualized by enhanced chemiluminescence and exposure to autoradiographic film. The specific anti-161P2F10B immunoreactive bands represent a monomeric form of the 161P2F10B protein, which runs at approximately 130 kDa. These results demonstrate that 161P2F10B is useful as a diagnostic and therapeutic target for kidney cancers, metastic cancers and other human cancers that express this protein.

The strong expression of 161P2F10B in kidney cancer tissues and is restricted expression in normal kidney as well as its membrane localization show that 161P2F10B is a target, e.g., for kidney cancer diagnosis and therapy. The expression detected in kidney cancer metastic tissue indicates that 161P2F10B is also a target for metastatic disease.

Example 40

Expression of 161P2F10B Protein in Kidney Cancer Xenograft tissues

Cancer xenographs were established from patient renal clear cell carcinoma and from its metastatic tissue to lymph node. Xenograft tissues were harvested from animals and dispersed into single cell suspension. The cells were stained with the using the commercially available antibody 97A6 specific for ENPP3 protein (also called anti-CD203c) (Immunotech, Marseilles, France). They were then washed in PBS and analyzed by flow cytometry as shown in FIG. 17. Results show strong expression of 161P2F10B in both renal cell carcinoma xenograft (FIG. 17A) as well as renal cancer metasis xenograft (FIG. 17B). These data demonstrate that 161P2F10B is expressed on the cell surface of the kidney cancer and kidney cancer metastasis xenograft cells.

FIG. 18 shows expression of 161P2F10B in xenograft tissue by immunohistochemistry. Renal cell carcinoma (FIG. 18, A, D, G), renal cell carcinoma metastatis to lymph node (FIG. 18 B, E, H), and prostate cance LAPC-4AI (FIG. 18, C, F, I) xenografts were grown in SCID mice. Xenograft tissues were harvested, frozen sections were cut into 4 micron sections and fixed in acetone for 10 minutes. The sections were then incubated with PE-labeled mouse monoclonal anti-ENPP3 antibody (Immunotech, Marseilles, France) for 3 hours (FIG. 18 A–F), or isotype control antibody (FIG. 18 G–I). The slides were washed three times in buffer, and either analyzed by fluorescence microscopy (FIG. 18 A–C), or further incubated with DAKO EnVision+™ peroxidase-conjugated goat anti-mouse secondary antibody (DAKO Corporation, Carpenterai, Calif.) for 1 hour (FIG. 18 D–I). The sections were then washed in buffer, developed using the DAB kit (SIGMA Chemicals), counterstained using hematoxylin, and analyzed by bright field microscopy (FIG. 17 C–F). The results showed strong expression of 161P2F10B in the renal cell carcinoma xenograft tissue (FIGS. 17A and D), in the kidney cancer metastasis to lymph node, as well as in the LAPC-4AI prostate xenograft, but not in the negative isotype control sections (FIG. 17 G, H, I). The expression was detected mostly around the cell membrane indicating that 161P2F10B is membrane-associated in these tissues.

FIG. 21 shows expression of 161P2F10B in human xenograft tissues by Western blot analysis. Cell lysates from kidney cancer xenograft (KiCa Xeno), kidney cancer metastasis to lymph node xenograft (Met Xeno), as well as normal kidney (NK) were subjected to Western analysis using an anti-161P2F10B mouse monoclonal antibody. Briefly, tissues (~25 μg total protein) were solubilized in SDS-PAGE sample buffer and separated on a 10–20% SDS-PAGE gel and transferred to nitrocellulose. Blots were blocked in Tris-buffered saline (TBS)+3% non-fat milk and then probed with purified anti-161P2F10B antibody in Tris-buffered Tween-20+1% milk. Blots were then washed and incubated with a 1:4,000 dilution of anti-mouse IgG-HRP conjugated secondary antibody. Following washing, anti-161P2F10B immunoreactive bands were developed and visualized by enhanced chemuluminescence and exposure to autoradiographic film. The specific anti-161P2F10B immunoreactive bands represent a monomeric form of the 161P2F10B protein, which runs at approximately 130 kDa, and a multi mer of approximately 260 kDa. The results demonstrate that the human cancer xenograft mouse models can be used to study the diagnostic and therapeutic effects of 161P2F10B.

The strong expression of 161P2F10B detected bin kidney and prostate cancer xenograft tissues show that 161P2F10B is a cell surface target, e.g., for cancer diagnosis and therapy; these features can be modeled in human cancer xenograft mouse models.

Example 41

Therapeutic and Diagnostic Use of Anti-161P2F10B Antibodies (such as monoclonal antibody 97A6) in Humans Anti-161P2F10B monoclonal antibodies are safely and effectively used for diagnostic, prophylactic, prognostic and/or therapeutic purposes in humans. In one embodiments, the anti-161P2F10B monoclonal antibody is 97A6 (Coulter-Immunotech). The monoclonal antibody 97A6 was generated through immunization of mice with erythro-megakaryoblastic cell line UT-7 and screening for monoclonal hybridomas that specifically react with only a small subset of mononuclear peripheral blood cells and bone marrow cells. Further characterization of the recognized population demonstrated that the mAb specifically identifies mature basophils and mast cells (Buhring, H. J. et al. 1999. Blood 94:2343–2356). The antigen specifically recognized by mAb 97A6 was later identified as ectonucleotide pyrophosphatase/phosphodiesterase 3 (ENPP3) (see, e.g., Buhring, H. J. et al. 2001. Blood 97:3303–3305). The antibody specifically binds ENPP3 under native non-denatured conditions such as those used in flow cytometric and therapeutic applications in which it is useful to bind to live cancer cells. The 97A6mAb also specifically binds ENPP3 under denatured/fixed conditions such as those used in diagnostic applications such as immunohistochemistry and Western blotting.

As disclosed herein, Wester blot and immunohistochemical analysis of kidney cancer tissues and kidney cancer xenografts with mAb97A6 showed strong extensive staining of ENPP3 in clear cell kidney carcinoma but significantly lower or undetectable levels in normal kidney (FIG. 16, 18, 20, 21). Detection of 161P2F10B (ENPP3) in high grade cell carcinoma and in metastatic disease demonstrates the usefulness of the mAb as a diagnostic and/or prognostic indicator. 97A6 is therefore used in diagnostic applications such as immunohistochemistry of kidney biopsy specimens to detect cancer from suspect patients. ENPP3 exhibits polarized apical surface expression in normal cells (Meerson, N. R., et al. 2000. J. Cell Sci. 113 Pt 23:4193–4202). Detection of a redistribution of ENPP3 from apical surface expression in normal cells to high level contiguous surface expression in advanced cancer or a change in expression levels of ENPP3 among grades of cancer by mA97A6 also demonstrates the usefulness in diagnostic and/or prognostic applications.

As determined by blow cytometry (FIG. 18), mAb97A6 specifically binds to the surface of clear cell kidney carcinoma cells. Thus, anti-161P2F10B antibodies, such as mAb 97A7 is used in diagnostic whole body imaging applications, such as radioimmunoscintigraphy and radioimmunotherapy, (see, e.g., Potamianos S., et. al. Anti-cancer Res 20(2A):925–948 (2000)) for the detection of localized and metastatic kidney cancers and other cancers that exhibit expression of 161P2F10B (ENPP3). Shedding or release of the extracellular domain of ENPP3 into the extracellular millieu, such as that seen for alkaline phosphodiesterase B10 (Meerson, N. R., Hepatology 27:563–568 (1998)), allows diagnostic detection of ENPP3 by mAb 97A6 in serum and urine samples from suspect patients.

MAb97A6, due to its ability to specifically bind cell surface ENPP3, is used in therapeutic applications for the treatment of cancers that express ENPP3, such as clear cell kidney carcinoma. MAb 97A6 is used as an unconjugated medality and as conjugated form in which it is attached to one of various therapeutic or imaging modalities well known in the art, such as a prodrugs, enzymes or radioisotopes. In preclinical studies, unconjugated and conjugated 97A6 is tested for efficacy of tumor prevention and growth inhibition in the SCID mouse kidney cancer xenograft models AGS-K3 and AGS-K6, (see, e.g., the Example entitled "Monoclonal Antibody-mediated Inhibition of Prostate and Kidney Tumors in Vivo". Conjugated and unconjugated 97A6 is used as a therapeutic modality in human clinical trials either alone or in combination with other treatments as described in Examples 42–45.

Example 42

Human Clinical Trials for the Treatment and Diagnosis of Human Carcinomas through Use of Human Anti-161P2F10B Antibodies In Vivo Antibodies are used in accordance with the present invention, such as 97A6 antibody (Coulter) which recognizes the following epitope on 161P2F10B (amino acids 393–405): are used in the treatment of certain solid tumors. Based upon a number of factors, including 161P2F10B expression levels among other criteria, tumors, such as those listed in Table 1, e.g., breast, colon, kidney, lung, ovary, pancreas and prostate, are present preferred indications. In connection with each of these indications, three clinical approaches are successfully pursued.

I.) Adjunctive therapy: In adjunctive therapy, patients are treated with anti-161P2F10B antibodies in combination with a chemotherapeutic or antineoplastic agent and/or radiation therapy. Primary targets, such as those listed above, are treated under standard protocols by the addition anti-161P2F10B antibodies to standard first and second line therapy. Protocol designs address effectiveness as assessed by reduction in tumor mass as well as the ability to reduce usual doses of standard chemotherapy. These dosage reductions allow additional and/or prolonged therapy by reducing dose-related toxicity of the chemotherapeutic agent. Anti-161P2F10B antibodies are utilized in several adjunctive clinical trials in combination with the chemotherapeutic or antineoplastic agents adriamycin (advanced prostrate-carcinoma), cisplatin (advanced head and neck and lung carcinomas), taxol (breast cancer), and doxorubicin (preclinical).

II.) Montherapy: In connection with the use of anti-161P2F10B antibodies in monotherapy of tumors, the antibodies are administered to patients without a chemotherapeutic or antineoplastic agent. In one embodiment, monotherapy is conducted clinically in end stage cancer patients with extensive metastatic disease. Patients show some disease stabilization. Trials demonstrate an effect in refractory patients with (cancer) tumor.

III.) Imaging Agent: Through binding a radionuclide (e.g., yttrium ($^{90}$Y)) to anti-161P2F10B antibodies, the radiolabeled antibodies are utilized as a diagnostic and/or imaging agent. In such a role, the labeled antibodies localize to both solid tumors, as well as, metastatic lesions of cells expressing 161P2F10B. In connection with the use of the anti-161P2F10B antibodies as imaging agents, the antibodies are used in assisting surgical treatment of solid tumors, as both a pre-surgical screen as well as a post-operative follow-up to determine what tumor remains and/or returns. In one embodiment, a ($^{111}$In)-161P2F10B antibody is used as an imaging agent in a Phase I human clinical trial in patients having a carcinoma that expresses 161P2F10B (by analogy see, e.g., Divgi et al. *J. Natl. Cancer Inst.* 83:97–104 (1991)). Patents are followed with standard anterior and posterior gamma camera. Initial data indicates that all primary lesions and metastatic lesions are identified.

Dose and Route of Administration

As appreciated by those of ordinary skill in the art, dosing considerations can be determined through comparison with the analogous products that are in the clinic. Thus, anti-161P2F10B antibodies can be administered with doses in the range of 5 to 400 mg/m$^2$, with the lower doses used, e.g., in connections with safety studies. The affinity of anti-161P2F10B antibodies relative to the affinity of a known antibody for its target is one parameter used by those of skill in the art for determining analgous dose regimens. Further, anti-161P2F10B antibodies that are fully human antibodies, as compared to the chimeric antibody, have slower clearance; accordingly, dosing in patients with such fully human anti-161P2F10B antibodies can be lower, perhaps in the range of 50 to 300 mg/m$^2$, and still remain efficacious. Dosing in mg/m$^2$, as opposed to the conventional measurement of dose in mg/kg, is a measurement based on surface area and is a convenient dosing measurement that is designed to include patients of all sizes from infants to adults.

Three distinct delivery approaches are useful for delivery of the anti-161P2F10B antibodies. Conventional intravenous delivery is one standard delivery technique for many tumors. However, in connection with tumors in the peritoneal cavity, such as tumors of the ovaries, biliary duct, other ducts, and the like, intraperitoneal administration may prove favorable for obtaining high dose of antibody of the tumor and to also minimize antibody clearance. In a similar manner certain solid tumors possess vasculature that is appropriate for regional perfusion. Regional perfusion allow the obtention of a high dose of the antibody at the site of a tumor and minimizes short term clearance of the antibody.

Clinical Development Plan (CDP)

Overview: The CDP follows and develops treatments of anti-161P2F10B in connection with adjunctive therapy, monotherapy, and as an imaging agent. Trials initially demonstrate safety and thereafter confirm efficacy in repeat doses. Trials are open label comparing standard chemotherapy with standard therapy plus anti-161P2F10B antibodies. As will be appreciated, one criteria that can be utilized in connection with enrollment of patients as 161P2F10B expression levels of patient tumors as determined in biopsy.

As with any protein or antibody infusion based therapeutic, safety concerns are related primarily to (i) cytokine release syndrome, i.e., hypotension, fever, shaking, chills, (ii) the development of an immunogenic response to the material (i.e., development of human antibodies by the patient to the antibody therapeutic, or HAHA response), and (iii) toxicity to normal cells that express 161P2F10B. Standard tests and follow-up are utilized to monitor each of these safety concerns. Anti-161P2F10B antibodies are found to be safe upon human administration.

Example 43

Human Clinical Trial Adjunctive Therapy with Human Anti-161P2F10B Antibody and Chemotherapeutic Agent A phase I human clinical trial is initiated to assess the safety of six intravenous doses of a human anti-161P2F10B antibody in connection with the treatment of a solid tumor, e.g., breast cancer. In the study, the safety of single doses of anti-161P2F10B antibodies when utilized as an adjunctive therapy to an antineoplastic or chemotherapeutic agent, such as cisplatin, topotecan, doxorubicin, adriamycin, taxol, or the like, is assessed. The trial design includes delivery of six single doses of an anti-161P2F10B antibody with dosage of antibody escalating from approximately about 25 mg/m$^2$ to about 275 mg/m$^2$ over the course of the treatment in accordance with the following schedule.

|  | Day 0 | Day 7 | Day 14 | Day 21 | Day 28 | Day 35 |
|---|---|---|---|---|---|---|
| mAb Dose | 25 mg/m$^2$ | 75 mg/m$^2$ | 125 mg/m$^2$ | 175 mg/m$^2$ | 225 mg/m$^2$ | 275 mg/m$^2$ |
| Chemotherapy (standard dose) | + | + | + | + | + | + |

Patients are closely followed for one-week following each administration of antibody and chemotherapy. In particular, patients are assessed for the safety concerns mentioned above: (i) cytoline release syndrome, i.e., hypotension, fever, shaking, chills, (ii) the development of an immunogenic response to the material (i.e., development of human antibodies by the patient to the human antibody therapeutic, or HAHA response), and (iii) toxicity to normal cells that express 161P2F10B. Standard tests and follow-up are utilized to monitor each of these salary concerns. Patients are also assessed for clinical outcome, and particularly reduction in tumor mass or evidenced by MRI or other imaging.

The anti-161P2F10B antibodies are demonstrated to be safe and efficacious, Phase II trials confirm the efficacy and refine optimum dosing.

Example 44

Human Clinical Trial: Monotherapy with Human Anti-161P2F10B Antibody

Anti-161P2F10B antibodies are safe in connection with the above-discussed adjunctive trial, a Phase II human clinical trial confirms the efficacy and optimum dosing for monotherapy. Such trial is accomplished, and entails the same safety and outcome analyses, to the above-described adjunctive trial with the exception being that patients do not receive chemotherapy concurrently with the receipt of doses of anti-161P2F10B antibodies.

Example 45

Human Clinical Trial: Diagnostic Imaging with Anti-161P2F10B Antibody

Once again, as the adjunctive therapy discussed above is safe within the safety criteria discussed above, a human clinical trial is conducted concerning the use of anti-161P2F10B antibodies as a diagnostic imaging agent. The protocol is designed in a substantially similar manner to those described in the art, such as in Divgi et al. *J. Natl. Cancer Inst.* 83:97–104 (1991).

Example 46

Homology Comparison of 161P2F10B to Known Sequences

The 161P2F10B gene is identical to a previously cloned and sequenced gene, namely ectonucleotide pyrophosphatase/phosphodiesterase 3 (gi 4826896) (Jin-Hua P et al, Genomics 1997, 45:412), also known as phosphodiesterase-I beta; gp130RB13-6; E-NPP3 (ENPP3), PDNP3 and CD203c. The 161P2F10B protein shows 100% identity to human ectonucleotide pyrophosphatase/phosphodiesterase 3 (gi 4826896), and 81% homology and 89% identity to rat alkaline phosphodiesterase (gi 1699034). The 161P2F10B protein consists of 875 amino acids, with calculated molecular weight of 100.09 kDa, and pI of 6.12. 161P2F10B is a cell surface protein as shown by immunostaining in basophils (Buhring HJ et al, Blood 2001, 97:3303) and in epithelial tumor cells as shown in the example entitled "Expression of 161P2F10B protein in kidney cancer xenograft tissues". Some localization to the golgi-endoplasmic fraction has also been observed (Geoffrey V et al, Arch Biochem Biophys. 2001, 387:154). Two isoforms of phosphodiesterase 3 have been identified, with one protein containing an additional 145 aa at its amino-terminus (Choi YH et al, Biochem J. 2001, 353:41). In addition, a single nucleotide polymorphisms has also been identified at position 383, resulting in a change in amino acid from thronine to proline at that position.

Motif analysis revealed the presence of several known motifs, including 2–3 somatostatin B domains located at the amino terminus of the 161P2F10B protein, a phosphodiesterase domain and an endonuclease domain at the C-teminus. 161P2F10B belongs to a family of closely related phosphodiesterases, consisting of PDNP1, -2, and -3 (Bollen M et al, Crit. Rev. Biochem Mol. Biol. 2000, 35:393). All three members of this family are type II proteins, with a short N-terminus domain located intracellularly. They contain one transmembrane domain, a catalytic phosphodiesterase domain and a C-terminal nuclease domain.

Phosphodiesterase 3 expression has been detected in human neoplatic submandibular cells, glioma cells, and transformed lymphocytes (Murata T et al, Anticancer Drugs 2001, 12:79; Andoh K et al, Biochim Biophys Acta 1999, 1446:213; Ekholm D et al, Biochem Pharmacol 1999, 58: 935).

Phosphodiesterase 3 plays an important role in several biological processes, including release of nucleotides, cell differentiation, metabolism, cell growth, survival, angiogenesis and cell motility (Bollen M et al, Crit. Rev. Biochem Mol. Biol. 2000, 35: 393; Rawadi G et al, Endocrinol 2001, 142:4673; DeFouw L et al, Microvasc Res 2001, 62:263). In addition, Phosphodiesterase 3 regulates gene expression in epithelial cells, including the expression of key adhesion molecules such as VCAM-1 (Blease K et al, Br J Pharmacol. 1998, 124:229).

This information indicates that 161P2F10B plays a role in the growth of mammalian cells, supports cell survival and motility, and regulate gene transcription by regulating events in the nucleus.

Accordingly, when 161P2F10B functions as a regulator of cell transformation, tumor formation, or as a modulator of transcription involved in activating genes associated with inflammation, tumorigenesis or proliferation, 161P2F10B is used for therapeutic, diagnostic, prognostic and/or preventative purposes. In addition, when a molecule, such as a variant, polymorphism or SNP of 161P2F10B is expressed in cancerous tissues, such as those listed in Table 1, they are used for therapeutic, diagnostic, prognostic and/or preventative purposes.

Example 47

Identification and Confirmation of Potential Signal Transduction Pathways

Many mammalian proteins have been reported to interact with signaling molecules and to participate in regulating signaling pathways. (J Neurochem. 2001; 217–223). In particular, GPCRs have been reported to activate MAK cascades as well as G proteins, and been associated with the EGFR pathway in epithelial cells (Naor, Z., et al, Trends Endocrinol Metab. 2000, 11:91; Vacca F et al, Cancer Res. 2000, 60:5310; Della Rocca G J et al, J Biol Chem. 1999, 274:13978). Using immunoprecipitation and Western blotting techniques, proteins are identified that associate with 161P2F10B and mediate signaling events. Several pathways known to play a role in cancer biology can be regulated by 161P2F10B, including phospholipid pathways such as PI3K, AKT, etc, adhesion and migration pathways, including FAK, Rho, Rac-1, etc, as well as mutogenic/survival cascades such as ERK, p38, etc (Cell Growth Differ. 2000, 11:279; J Biol Chem. 1999, 274:801; Oncogene. 2000, 19:3003, J. Cell Biol. 1997, 138:913).

To confirm that 161P2F10B directly or indirectly activates known signal transduction pathways in cells, luciferase (luc) based transcriptional reporter assays are carried out in cells expressing individual genes. These transcriptional reporters contain consensus-binding sites for known transcription factors that lie downstream of well-characterized signal transduction pathways. The reporters and examples of these associated transcription factors, signal transduction pathways, and activation stimuli are listed below.

1. NFkB-luc, NFkB/Rel; Ik-kinase/SAPK; growth/apoptosis/stress
2. SKE-luc, SRF/TCF/ELK1; MAPK/SAPK; growth/differentiation
3. AP-1-luc, FOS/JUN; MAPK/SAPK/PKC; growth/apoptosis/stress
4. ARE-luc, androgen receptor; steroids/MAPK; growth/differentiation/apoptosis
5. p53-luc, p53; SAPK; growth/differentation/apoptosis
6. CRE-luc, CREB/AT2; PKA/p38; growth/apoptosis/stress Gene-mediated effects can be assayed in cells showing mRNA expression. Luciferase reporter plasmids can be introduced by lipid-mediated transfection (TFX-50, Promega). Luciferase activity, an indicator of relative transcriptional activity, is measured by incubation of cell extracts with luciferin substrate and luminescence of the reaction is monitored in a luminometer.

Signaling pathways by 161P2F10B is involved in cell signaling, it is used as target for diagnostic, prognostic, preventative and/or therapeutic purposes.

Example 48

Involvement in Tumor Progression

The 161P2F10B gene contributes to the growth of cancer cells. The role of 161P2F10B in tumor growth is confirmed in a variety of primary and transfected cell lines including prostate, colon, bladder and kidney cell lines, as well as NIH 3T3 cells engineered to stably express 161P2F10B. Parental cells lacking 161P2F10B and cells expressing 161P2F10B are evaluated for cell growth using a well-documented proliferation assay (Fraser, S. P., et al., Prostate, 2000, 44:61, Johnson, D. E., et al., Anticancer Drugs, 1996, 7:228).

To confirm the role of 161P2F10B in the transformation process, its effect in colony forming assays is investigated. Parental NIH-3T3 cells lacking 161P2F10B are compared to NIH-3T3cells expressing 161P2F10B, using a soft agar assay under stringent and more permissive conditions (Song Z. et al., Cancer Res. 2000:60:6730).

To conform the role of 161P2F10B in invasion and metastasis of cancer cells, a well-establishing assay to used, e.g., a TRANSWELL Insert System assay (Becton Dickinson)(Cancer Res. 1999; 59:6010). Control cells, including prostate, colon, bladder and kidney cell lines lacking 161P2F10B are compared to cells expressing 161P2F10B. Cells are loaded with the fluorescent dye calcein, and plated in the top well of the TRANSWELL insert coated with a basement membrane analog. Invasion is determined by fluorescence of cells in the lower chamber relative to the fluorescence of the entire cell population.

161P2F10B can also play a role in cell and apoptosis. Parental cells and cells expressing 161P2F10B are compared for differences in cell cycle regulation using a well-established BrdU assay (Abdel-Malek, Z. A., J. Cell Physiol. 1988, 136:247). In short, cells are grown under both optimal (full serum) and limiting (low serum) conditions are labeled with BrdU and stained with anti-BrdU Ab and propidium iodide. Cells are analyzed for entry into the G1, S, and G2M phases of the cell cycle. Alternatively, the effect of stress on apoptosis is evaluated in control parental cells and cells expressing 161P2F10B, including normal and tumor prostate, colon and lung cells. Engineered and parental cells are treated with various chemotherapeutic agents, such as etoposide, flutamide, etc, and protein synthesis inhibitors, such as cycloheximide. Cells are stained with annexin V-FITC and cell death is measured by FACS analysis. The modulation of cell death of 161P2F10B can play a critical role in regulating tumor progression and tumor load.

When 161P2F10B plays a role in cell growth, transformation, invasion or apoptosis, it is used as a target for diagnostic, prognostic, preventative and/or therapeutic purposes.

Example 49

Involvement in Angiogenesis

Angiogenesis or new capillary blood vessel formation is necessary for tumorgrowth (Hanahan D, Folkman J. Cell, 1996, 86:353; Folkman, J. Endocrinology, 1998 139:441). Based on the effect of phsophodieseterase inhibitors on endothelial cells, 161P2F10B plays a role in angiogenesis (DeFouw L. et al, Microvasc Res 2001, 62:263). Several assays have been developed to measure angiogenesis in vitro and in vivo, such as the tissue culture assays endothelial cell tube formation and endothelial cell proliferation. Using these assays as well as in vitro neo-vacularization, the role of 161P2F10B in angiogenesis, enhancement or inhibition, is confirmed.

For example, endothelial cells engineered to express 161P2F10B are evaluated using tube formation and proliferation assays. The effect of 161P2F10B is also confirmed in animal models in vivo. For example, cells either expressing or lacking 161P2F10B are implanted subcutaneously in immunocompromised mice. Endothelial cell migration and angiogenesis are evaluated 5–15 days later using immunohistochemistry techniques. 161P2F10B affects angiogenesis, and it is used as a target for diagnostic, prognostic, preventative and/or therapeutic purposes.

Example 50

Regulation of Transcription

The cell surface localization of 161P2F10B and ability to regulate VCAM expression indicate that 161P2F10B is effectively used as a modulator of the transcriptional regulation of eukaryotic genes. Regulation of gene expression is confirmed, e.g., by studying gene expression in cells expressing or lacking 161P2F10B. For this purpose, two types of experiments are performed.

In the first set of experiments, RNA from parental and 161P2F10B-expressing cells are extracted and hybridized to commercially available gene arrays (Clontech) (Smid-Koopman E et al. Br J Cancer, 2000. 83:246). Resting cells as well as cells treated with FBS or androgen are compared. Differentially expressed genes are identified in accordance with procedures known in the art. The differentially expressed genes are then mapped to biological pathways (Chen, K., et al., Thyroid, 2001 11:41).

In a second set of expression, specific transcriptional pathway activation is evaluated using commercially available (Stratagene) luciferase reporter constructs including: NFkB-luc, SRE-luc, ELK1-luc, ARE-luc, p53-luc, and CRE-luc. These transcriptional reporters contain consensus binding sites for known transcription factors that lie downstream of well-characterized signal transduction pathways, and represent a good tool to ascertain pathway activation and screen for positive and negative modulators of pathway activation.

Thus, it is found that 161P2F10B plays a role in gene regulation, and it is used as a target for diagnostic, prognostic, preventative and/or therapeutic purposes.

Example 51

Involvement in Cell Adhesion

Cell adhesion plays a critical role in tissue colonization and metastasis. 161P2F10B can participate in cellular organization, and as a consequence cell adhesion and motility. To confirm the 161P2F10B regulates cell adhesion, control cells lacking 161P2F10B are compared to cells expressing 161P2F10B, using techniques previously described (see, e.g., Haier, et al., Br. J. Cancer, 1999, 80:1867; Lehr and Pienta, J. Natl. Cancer Inst., 1998, 90:118). Briefly, in one embodiment, cells labeled with a fluorescent indicator, such as calcein, are incubated on tissue culture wells coated with media alone or with matrix proteins. Adherent cells are detected by fluorimetric analysis and percent adhesion is calculated. In another embodiment, cells lacking or expressing 161P2F10B are analyzed for their ability to mediate cell—cell adhesion using similar experimental techniques as described above. Both of these experimental systems are used to identify proteins, antibodies and/or small molecules the modulate cell adhesion to extracellular matrix and cell—cell interaction. Cell adhesion plays a critical role in tumor growth, progression, and, colonization, and 161P2F10B is involved in these processes. Thus, 161P2F10B serves in diagnostic, prognostic, preventative and/or therapeutic modalities.

Example 52

Protein—Protein Association

Several phosophodiesterases have been shown to interact with other proteins, thereby regulating gene transcription as well as cell growth (Butt E et al, Mol Pharmacol. 1995, 47:340). Using immunoprecipitation techniques as well as two yeast hybrid systems, proteins are identified that associate with 161P2F10B. Immunoprecipitates from cells expressing 161P2F10B and cells lacking 161P2F10B are compared for specific protein—protein associations.

Studies are performed to confirm the extent of association of 161P2F10B with effector molecules, such as nuclear proteins, transcription factors, kinases, phosphates etc. Studies comparing 161P2F10B positive and 161P2F10B negative cells as well as studies comparing unstimulated/resting cells and cells treated with epithelial cell activators, such as cytokines, growth factors, androgen and anti-integrin Ab reveal unique interactions.

In addition, protein—protein interactions are confirmed using two yeast hybrid methodology (Curr Opin Chem Biol., 1999, 3:64). A vector carrying a library of proteins fused to the activation domain of a transcription factor is introduced into yeast expressing a 161P2F10B-DNA-binding domain fusion protein and a reporter construct. Protein-protein interaction is detected by colorimetric reporter activity. Specific association with effector molecules and transcription factors directs one of skill to the mode of action of 161P2F10B, and thus identifies therapeutic, prognostic, preventative and/or diagnostic targets for cancer. This and similar assays are also used to identify and screen for small molecules that interact with 161P2F10B.

Thus it is found that 161P2F10B associates with proteins and small molecules. Accordingly, 161P2F10B and these proteins and small molecules are used for diagnostic, prognostic, preventative and/or therapeutic purposes.

Throughout this application various website data content, publications, patent applications and patents are referenced (Web sties are referenced by their Uniform Resource Locator, or URL, addresses on the World Wide Web.) The disclosures of each of these references are hereby incorporated by reference herein in their entireties.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

TABLE I

Tissues that Express 161P2F10B When Malignant

Breast
Colon
Kidney
Lung
Ovary
Pancreas
Prostate

TABLE II

AMINO ACID ABBREVIATIONS

| SINGLE LETTER | THREE LETTER | FULL NAME |
|---|---|---|
| F | Phe | phenylalanine |
| L | Leu | leucine |
| S | Ser | serine |
| Y | Tyr | tyrosine |
| C | Cys | cysteine |
| W | Trp | tryptophan |
| P | Pro | proline |
| H | His | histidine |
| Q | Gln | glutamine |
| R | Arg | arginine |
| I | Ile | isoleucine |
| M | Met | methionine |
| T | Thr | threonine |
| N | Asn | asparagine |
| K | Lys | lysine |
| V | Val | valine |
| A | Ala | alanine |
| D | Asp | aspartic acid |
| E | Glu | glutamic acid |
| G | Gly | glycine |

TABLE IV

A

| | POSITION 2 (Primary Anchor) | POSITION 3 (Primary Anchor) | POSITION C Terminus (Primary Anchor) |
|---|---|---|---|
| SUPERMOTIFS | | | |
| A1 | TILVMS | | FWY |
| A2 | LIVMATQ | | IVMATL |
| A3 | VSMATLI | | RK |
| A24 | YFWIVLMT | | FIYWLM |
| B7 | P | | VILFMWYA |
| B27 | RHK | | FYLWMIVA |
| B44 | ED | | FWYLIMVA |
| B58 | ATS | | FWYLIVMVA |
| B62 | QLIVMP | | FWYMIVLA |
| MOTIFS | | | |
| A1 | TSM | | Y |
| A1 | | DEAS | Y |
| A2.1 | LMVQIAT | | VLIMAT |
| A3 | LMVISATFCGD | | KYRHFA |
| A11 | VTMLISAGNCDF | | KRYH |
| A24 | YFWM | | FLIW |
| A*3101 | MVTALIS | | RK |
| A*3301 | MVALFIST | | RK |
| A*6801 | AVTMSLI | | RK |
| B*0702 | P | | LMFWYAIV |
| B*3501 | P | | LMFWYIVA |
| B51 | P | | LIVFWYAM |
| B*5301 | P | | IMFWYALV |
| B*5401 | P | | ATIVLMFWY |

Bolded residues are preferred, italicized residues are less preferred: A peptide is considered motif-bearing if it has primary anchors at each primary anchor position for a motif or supermotif as specified in the above table.

TABLE III

AMINO ACID SUBSTITUTION MATRIX
Adapted from the GCG Software 9.0 BLOSUM62 amino acid substitution matrix (block substitution matrix). The higher the value, the more likely a substitution is found in related, natural proteins. (See URL www.ikp.unibe.ch/manual/blosum62.html)

| A | C | D | E | F | G | H | I | K | L | M | N | P | Q | R | S | T | V | W | Y | . |
|---|---|---|---|---|---|---|---|---|---|---|---|---|---|---|---|---|---|---|---|---|
| 4 | 0 | -2 | -1 | -2 | 0 | -2 | -1 | -1 | -1 | -1 | -2 | -1 | -1 | -1 | 1 | 0 | 0 | -3 | -2 | A |
| | 9 | -3 | -4 | -2 | -3 | -3 | -1 | -3 | -1 | -1 | -3 | -3 | -3 | -3 | -1 | -1 | -1 | -2 | -2 | C |
| | | 6 | 2 | -3 | -1 | -1 | -3 | -1 | -4 | -3 | 1 | -1 | 0 | -2 | 0 | -1 | -3 | -4 | -3 | D |
| | | | 5 | -3 | -2 | 0 | -3 | 1 | -3 | -2 | 0 | -1 | 2 | 0 | 0 | -1 | -2 | -3 | -2 | E |
| | | | | 6 | -3 | -1 | 0 | -3 | 0 | 0 | -3 | -4 | -3 | -3 | -2 | -2 | -1 | 1 | 3 | F |
| | | | | | 6 | -2 | -4 | -2 | -4 | -3 | 0 | -2 | -2 | -2 | 0 | -2 | -3 | -2 | -3 | G |
| | | | | | | 8 | -3 | -1 | -3 | -2 | 1 | -2 | 0 | 0 | -1 | -2 | -3 | -2 | 2 | H |
| | | | | | | | 4 | -3 | 2 | 1 | -3 | -3 | -3 | -3 | -2 | -1 | 3 | -3 | -1 | I |
| | | | | | | | | 5 | -2 | -1 | 0 | -1 | 1 | 2 | 0 | -1 | -2 | -3 | -2 | K |
| | | | | | | | | | 4 | 2 | -3 | -3 | -2 | -2 | -2 | -1 | 1 | -2 | -1 | L |
| | | | | | | | | | | 5 | -2 | -2 | 0 | -1 | -1 | -1 | 1 | -1 | -1 | M |
| | | | | | | | | | | | 6 | -2 | 0 | 0 | 1 | 0 | -3 | -4 | -2 | N |
| | | | | | | | | | | | | 7 | -1 | -2 | -1 | -1 | -2 | -4 | -3 | P |
| | | | | | | | | | | | | | 5 | 1 | 0 | -1 | -2 | -2 | -1 | Q |
| | | | | | | | | | | | | | | 5 | -1 | -1 | -3 | -3 | -2 | R |
| | | | | | | | | | | | | | | | 4 | 1 | -2 | -3 | -2 | S |
| | | | | | | | | | | | | | | | | 5 | 0 | -2 | -2 | T |
| | | | | | | | | | | | | | | | | | 4 | -3 | -1 | V |
| | | | | | | | | | | | | | | | | | | 11 | 2 | W |
| | | | | | | | | | | | | | | | | | | | 7 | Y |

TABLE IV

(B): HLA CLASS II SUPERMOTIF

| 1 | 6 | 9 | 5 |
|---|---|---|---|
| W, F, Y, V, I, L | A, V, I, L, P, C, S, T | A, V, I, L, C, S, T, M, Y | |

TABLE IV

C

| MOTIFS | | 1° anchor 1 | 2 | 3 | 4 | 5 | 1° anchor 6 | 7 | 8 | 9 |
|---|---|---|---|---|---|---|---|---|---|---|
| DR4 | preferred | FMY*LIVW* | M | T | | I | VST*CPALIM* | MH | | MH |
| | deleterious | | | | W | | | R | | WDE |
| DR1 | preferred | MF*LIVWY* | | | PAMQ | | VMAT*SPLIC* | M | | AVM |
| | deleterious | | C | CH | FD | CWD | | GDE | D | |
| DR7 | preferred | MF*LIVWY* | M | W | A | | IVMSA*CTPL* | M | | IV |
| | deleterious | | C | | G | | | GRD | N | G |

| | MOTIFS | 1° anchor 1 | 2 | 3 | 1° anchor 4 | 5 | 1° anchor 6 |
|---|---|---|---|---|---|---|---|
| DR3 | | | | | | | |
| motif a preferred | | LIVMFY | | | D | | |
| motif b preferred | | LIVMFAY | | | DNQEST | | KRH |
| DR Supermotif | | MF*LIVWY* | | | | | VMSTA*CPLI* |

Italicized residues indicate less preferred or "tolerated" residues.

TABLE IV

D

| | | POSITION | | | | | | | |
|---|---|---|---|---|---|---|---|---|---|
| SUPER-MOTIFS | | 1 | 2 | 3 | 4 | 5 | 6 | 7 | 8 | C-terminus |
| A1 | | | 1° Anchor TI*LVMS* | | | | | | | 1° Anchor FWY |
| A2 | | | 1° Anchor LIVMA*TQ* | | | | | | | 1° Anchor LIVMAT |
| A3 | preferred | | 1° Anchor VSMA*TLI* | YFW (4/5) | | YFW (3/5) | YFW (4/5) | P (4/5) | | 1° Anchor RK |
| | deleterious | DE (3/5); P (5/5) | | DE (4/5) | | | | | | |
| A24 | | | 1° Anchor YF*WIVLMT* | | | | | | | 1° Anchor FIY*WLM* |
| B7 | preferred | FWY (5/5) LIVM (3/5) | 1° Anchor P | FWY (4/5) | | | | FWY (3/5) | | 1° Anchor VILF*MWYA* |
| | deleterious | DE (3/5); P(5/5); G(4/5); A(3/5); QN(3/5) | | | | DE (3/5) | G(4/5) | QN(4/5) | DE(4/5) | |
| B27 | | | 1° Anchor RHK | | | | | | | 1° Anchor FYL*WMIVA* |
| B44 | | | 1° Anchor E*D* | | | | | | | 1° Anchor FWYLIMVA |
| B58 | | | 1° Anchor ATS | | | | | | | 1° Anchor FWY*LIVMA* |
| B62 | | | 1° Anchor Q*LIVMP* | | | | | | | 1° Anchor FWY*MIVLA* |

TABLE IV

| | | | | | | E | | | | | |
|---|---|---|---|---|---|---|---|---|---|---|---|
| | | 1 | 2 | 3 | 4 | 5 | 6 | 7 | 8 | 9 or C-terminus | C-terminus |
| A1 9-mer | preferred | GFYW | 1° Anchor STM | DEA | YFW | | P | DEQN | YFW | 1° Anchor Y | |
| | deleterious | DE | | RHKLWMP | A | G | A | | | | |
| A1 9-mer | preferred | GRHK | ASTCLIVM | 1° Anchor DEAS | GSTC | | ASTC | LIVM | DE | 1° Anchor Y | |
| | deleterious | A | RHKDEPY FW | | DE | PQN | RHK | PG | GP | | |
| A1 10-mer | preferred | YFW | 1° Anchor STM | DEAQN | A | YFW QN | | PASTC | GDE | P | 1° Anchor Y |
| | deleterious | GP | | RHKGLIVM | DE | RHK | QNA | RHKYFW | RHK | A | |
| A1 10-mer | preferred | YFW | STCLIVM | 1° Anchor DEAS | A | YFW | | PG | G | YFW | 1° Anchor Y |
| | deleterious | RHK | RHKDEPY FW | | | P | G | | PRHK | QN | |
| A2.1 9-mer | preferred | YFW | 1° Anchor L M _IVQAT_ | YFW | STC | YFW | | A | P | 1° Anchor V _LIMAT_ | |
| | deleterious | DEP | | DERKH | | | RKH | DERKH | | | |
| A2.1 10-mer | preferred | AYFW | 1° Anchor L M _IVQAT_ | LVIM | G | | G | | FYWL VIM | 1° Anchor V _LIMAT_ | |
| | deleterious | DEP | | DE | RKHA | P | | RKH | DERKH | RKH | |
| A3 | preferred | RHK | 1° Anchor L M V I S A T F C G D | YFW | PRHK YFW | A | YFW | | P | 1° Anchor KYR _HFA_ | |
| | deleterious | DEP | | DE | | | | | | | |
| A11 | preferred | A | 1° Anchor V T L M I S A G N _CDF_ | YFW | YFW | A | YFW | YFW | P | 1° Anchor K _RYH_ | |
| | deleterious | DEP | | | | | | A | G | | |
| A24 9-mer | preferred | YFWRHK | 1° Anchor YFW _M_ | | STC | | | YFW | YFW | 1° Anchor FLIW | |
| | deleterious | DEG | | DE | G | QNP | DERHK | G | AQN | | |
| A24 10-mer | preferred | | 1° Anchor YFW _M_ | | P | YFWP | | P | | | 1° Anchor FLIW |
| | deleterious | | | GDE | QN | RHK | DE | A | QN | DEA | |
| A3101 | prefrrred | RHK | 1° Anchor MVT _ALIS_ | YFW | P | | YFW | YFW | AP | 1° Anchor R _K_ | |
| | deleterious | DEP | | DE | ADE | DE | DE | DE | | | |
| A3301 | preferred | | 1° Anchor MVALF _IST_ | YFW | | | | AYFW | | 1° Anchor RK | |
| | deleterious | GP | | DE | | | | | | | |
| A6801 | preferred | YFWSTC | 1° Anchor AVT _MSLI_ | | | YFWL IVM | | YFW | P | 1° Anchor RK | |
| | deleterious | GP | | DEG | RHK | | | | A | | |
| B0702 | preferred | RHKFW Y | 1° Anchor P | RHK | | RHK | RHK | RHK | PA | 1° Anchor LMF _WYAI V_ | |
| | deleterious | DEQNP | | DEP | DE | DE | GDE | QN | DE | | |
| B3501 | preferred | FWYLIV M | 1° Anchor P | FWY | | | | FWY | | 1° Anchor LMFWY _IV A_ | |
| | deleterious | AGP | | | | G | G | | | | |
| B51 | preferred | LIVMFW Y | 1° Anchor P | FWY | STC | FWY | | G | FWY | 1° Anchor LIVF _WYA M_ | |
| | deleterious | AGPDER HKSTC | | | | DE | G | DEQN | GDE | | |
| B5301 | preferred | LIVMFW Y | 1° Anchor P | FWY | STC | FWY | | LIVMFW Y | FWY | 1° Anchor IMFWY _AL V_ | |
| | deleterious | AGPQN | | | | | G | RHKQN | DE | | |
| B5401 | preferred | FWY | 1° Anchor P | FWYLIVM | | LIVM | | ALIVM | FWYAP | 1° Anchor ATIV _LMF WY_ | |
| | deleterious | GPQNDE | | GDESTC | | RHKDE | DE | QNDGE | DE | | |

Italicized residues indicate less preferred or "tolerated" residues. The inforrtiation in this Table is specific for 9-mers unless otherwise specified.

TABLE V

HLA PEPTIDE SCORING RESULTS 161P2F10B - A1,9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 1 | 165 | SMDGFRAEY | 25.000 | 1. |
| 2 | 814 | NVESCPEGK | 18.000 | 2. |
| 3 | 115 | CSDDCLQKK | 15.000 | 3. |
| 4 | 506 | KTEVEPFEN | 11.250 | 4. |
| 5 | 305 | WLDLPKAER | 10.000 | 5. |
| 6 | 858 | VSEILQLKT | 6.750 | 6. |
| 7 | 431 | KPDQHFKPY | 6.250 | 7. |
| 8 | 377 | QTYCNKMEY | 6.250 | 8. |
| 9 | 374 | GMDQTYCNK | 5.000 | 9. |
| 10 | 70 | RCDVACKDR | 5.000 | 10. |
| 11 | 514 | NIEVYNLMC | 4.500 | 11. |
| 12 | 382 | KMEYMTDYF | 4.500 | 12. |
| 13 | 89 | CVESTRIWM | 4.500 | 13. |
| 14 | 800 | WLDVLPFII | 2.500 | 14. |
| 15 | 462 | FVDQQWLAV | 2.500 | 15. |
| 16 | 619 | NYDHCLLYH | 2.500 | 16. |
| 17 | 771 | NTDVPIPTH | 2.500 | 17. |
| 18 | 178 | DTLMPNINK | 2.500 | 18. |
| 19 | 710 | ITSNLVPMY | 2.500 | 19. |
| 20 | 745 | VVSGPIFDY | 2.500 | 20. |
| 21 | 491 | SMEAIFLAH | 2.250 | 21. |
| 22 | 8 | ATEQPVKKN | 2.250 | 22. |
| 23 | 670 | RVPPSESQK | 2.000 | 23. |
| 24 | 439 | YLTPDLPKR | 2.000 | 24. |
| 25 | 673 | PSESQKCSF | 1.350 | 25. |
| 26 | 273 | GSEVAINGS | 1.350 | 26. |
| 27 | 419 | NSEEIVRNL | 1.350 | 27. |
| 28 | 188 | KTCGIHSKY | 1.250 | 28. |
| 29 | 386 | MTDYFPRIN | 1.250 | 29. |
| 30 | 486 | NNEFRSMEA | 1.125 | 30. |
| 31 | 572 | SLDCFCPHL | 1.000 | 31. |
| 32 | 713 | NLVPMYEEF | 1.000 | 32. |
| 33 | 692 | FLYPPASNR | 1.000 | 33. |
| 34 | 42 | GLGLRKLEK | 1.000 | 34. |
| 35 | 114 | SCSDDCLQK | 1.000 | 35. |
| 36 | 126 | CADYKSVCQ | 1.000 | 36. |
| 37 | 223 | IIDNNMYDV | 1.000 | 37. |
| 38 | 666 | RADVRVPPS | 1.000 | 38. |
| 39 | 585 | QLEQVNQML | 0.900 | 39. |
| 40 | 65 | GLENCRCDV | 0.900 | 40. |
| 41 | 827 | WVEERFTAH | 0.900 | 41. |
| 42 | 139 | WLEENCDTA | 0.900 | 42. |
| 43 | 107 | RLEASLCSC | 0.900 | 43. |
| 44 | 508 | EVEPFENIE | 0.900 | 44. |
| 45 | 597 | QEEITATVK | 0.900 | 45. |
| 46 | 47 | KLEKQGSCR | 0.900 | 46. |
| 47 | 552 | HAEEVSKFS | 0.900 | 47. |
| 48 | 701 | TSDSQYDAL | 0.750 | 48. |
| 49 | 686 | KNITHGFLY | 0.625 | 49. |
| 50 | 618 | KNVDHCLLY | 0.625 | 50. |

TABLE VI

HLA PEPTIDE SCORING RESULTS 161P2F10B - A1,10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 1 | 858 | VSEILQLKTY | 67.500 | 51. |
| 2 | 386 | MTDYFPRINF | 62.500 | 52. |
| 3 | 771 | NTDVPIPTHY | 62.500 | 53. |
| 4 | 841 | DVELLTGLDF | 45.000 | 54. |
| 5 | 508 | EVEPFENIEV | 45.000 | 55. |
| 6 | 280 | GSFPSIYMPY | 37.500 | 56. |
| 7 | 441 | TPDLPKRLHY | 31.250 | 57. |
| 8 | 370 | LADHGMDQTY | 25.000 | 58. |
| 9 | 746 | VSGPIFDYNY | 15.000 | 59. |
| 10 | 273 | GSEVAINGSF | 13.500 | 60. |
| 11 | 619 | NVDHCLLYHR | 10.000 | 61. |
| 12 | 462 | FVDQQWLAVR | 10.000 | 62. |
| 13 | 673 | PSESQKCSFY | 6.750 | 63. |

TABLE VI-continued

HLA PEPTIDE SCORING RESULTS 161P2F10B - A1,10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 14 | 552 | HAEEVSKFSV | 4.500 | 64. |
| 15 | 627 | HREYVSGFGK | 4.500 | 65. |
| 16 | 585 | QLEQVNQMLN | 4.500 | 66. |
| 17 | 596 | TQEEITATVK | 2.700 | 67. |
| 18 | 758 | HFDAPDEITK | 2.500 | 68. |
| 19 | 744 | NVVSGPIFDY | 2.500 | 69. |
| 20 | 344 | VVDHAFGMLM | 2.500 | 70. |
| 21 | 506 | KTEVEPFENI | 2.250 | 71. |
| 22 | 8 | ATEQPVKKNT | 2.250 | 72. |
| 23 | 718 | YEEFRKMWDY | 2.250 | 73. |
| 24 | 822 | KPEALWVEER | 2.250 | 74. |
| 25 | 802 | DVLPFIIPHR | 2.000 | 75. |
| 26 | 179 | TLMPNINTKLK | 2.000 | 76. |
| 27 | 827 | WVEERFTAHI | 1.800 | 77. |
| 28 | 47 | KLEKQGSCRK | 1.800 | 78. |
| 29 | 701 | TSDSQYDALI | 1.500 | 79. |
| 30 | 164 | FSMDGFRAEY | 1.500 | 80. |
| 31 | 113 | CSCSDDCLQK | 1.500 | 81. |
| 32 | 419 | NSEEIVRNLS | 1.350 | 82. |
| 33 | 409 | HNIPHDFFSF | 1.250 | 83. |
| 34 | 388 | DYFPRINFFY | 1.250 | 84. |
| 35 | 155 | GFDLPPVILF | 1.250 | 85. |
| 36 | 661 | VPDCLRADVR | 1.250 | 86. |
| 37 | 217 | YPESHGIIDN | 1.125 | 87. |
| 38 | 713 | NLVPMYEEFR | 1.000 | 88. |
| 39 | 714 | LVPMYEEFRK | 1.000 | 89. |
| 40 | 38 | GLGLGLGLRK | 1.000 | 90. |
| 41 | 5 | LTLATEQPVK | 1.000 | 91. |
| 42 | 709 | LITSNLVPMY | 1.000 | 92. |
| 43 | 89 | CVESTRIWMC | 0.900 | 93. |
| 44 | 139 | WLEENCDTAQ | 0.900 | 94. |
| 45 | 170 | RAEYLYTWDT | 0.900 | 95. |
| 46 | 107 | RLEASLCSCS | 0.900 | 96. |
| 47 | 491 | SMEAIFLAHG | 0.900 | 97. |
| 48 | 65 | GLENCRCDVA | 0.900 | 98. |
| 49 | 416 | FSFNSEEIVR | 0.750 | 99. |
| 50 | 572 | SLDCFCPHLQ | 0.500 | 100. |

TABLE VII

HLA PEPTIDE SCORING RESULTS 161P2F10B - A2,9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 1 | 723 | KMWDYFHSV | 11367.476 | 101. |
| 2 | 623 | CLLYHREYV | 693.538 | 102. |
| 3 | 385 | YMTDYFPRI | 270.002 | 103. |
| 4 | 867 | YLPTFETTI | 182.365 | 104. |
| 5 | 179 | TLMPNINKL | 181.794 | 105. |
| 6 | 256 | WLTAMYQGL | 147.401 | 106. |
| 7 | 519 | NLMCDLLRI | 88.783 | 107. |
| 8 | 173 | YLYTWDTLM | 73.129 | 108. |
| 9 | 607 | NLPFGRPRV | 69.552 | 109. |
| 10 | 825 | ALWVEERFT | 68.037 | 110. |
| 11 | 800 | WLDVLPFII | 45.649 | 111. |
| 12 | 298 | RISTLLKWL | 37.157 | 112. |
| 13 | 31 | LLVIMSLGL | 36.316 | 113. |
| 14 | 215 | GLYPESHGI | 33.385 | 114. |
| 15 | 572 | SLDCFCPHL | 32.471 | 115. |
| 16 | 639 | RMPMWSSYT | 29.601 | 116. |
| 17 | 27 | VLLALLVIM | 29.468 | 117. |
| 18 | 259 | AMYQGLKAA | 26.408 | 118. |
| 19 | 455 | RIDKVHLFV | 21.039 | 119. |
| 20 | 462 | FVDQQWLAV | 19.036 | 120. |
| 21 | 33 | VIMSLGLGL | 18.476 | 121. |
| 22 | 584 | TQLEQVNQM | 17.575 | 122. |
| 23 | 807 | IIPHRPTNV | 16.258 | 123. |
| 24 | 223 | IIDNNMYDV | 14.957 | 124. |
| 25 | 460 | HLFVDQQWL | 14.781 | 125. |
| 26 | 847 | GLDPYQDKV | 13.632 | 126. |

TABLE VII-continued

HLA PEPTIDE SCORING RESULTS 161P2F10B - A2,9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 27 | 150 | SQCPEGFDL | 12.562 | 127. |
| 28 | 753 | YNYDGHFDA | 11.352 | 128. |
| 29 | 343 | QVVDHAFGM | 10.337 | 129. |
| 30 | 360 | NLHNCVNII | 9.838 | 130. |
| 31 | 40 | GLGLGLRKL | 9.827 | 131. |
| 32 | 25 | CIVLLALLV | 9.563 | 132. |
| 33 | 615 | VLQKNVDHC | 9.518 | 133. |
| 34 | 592 | MLNLTQEEI | 8.691 | 134. |
| 35 | 630 | YVSGFGKAM | 7.599 | 135. |
| 36 | 862 | LQLKTYLPT | 7.129 | 136. |
| 37 | 560 | SVCGFANPL | 7.103 | 137. |
| 38 | 865 | KTYLPTFET | 6.723 | 138. |
| 39 | 490 | RSMEAIFLA | 6.563 | 139. |
| 40 | 5 | LTLATEQPV | 6.076 | 140. |
| 41 | 337 | RVIKALQVV | 5.739 | 141. |
| 42 | 22 | KIACIVLLA | 5.499 | 142. |
| 43 | 26 | IVLLALLVI | 5.415 | 143. |
| 44 | 231 | VNLNKNFSL | 5.087 | 144. |
| 45 | 594 | NLTQEEITA | 4.968 | 145. |
| 46 | 119 | CLQKKDCCA | 4.968 | 146. |
| 47 | 443 | DLPKRLHYA | 4.713 | 147. |
| 48 | 860 | EILQLKTYL | 4.483 | 148. |
| 49 | 65 | GLENCRCDV | 4.451 | 149. |
| 50 | 512 | FENIEVYNL | 4.395 | 150. |

TABLE VIII

HLA PEPTIDE SCORING RESULTS 161P2F10B - A2,10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 1 | 723 | KMWDYFHSVL | 2862.980 | 151. |
| 2 | 397 | YMYEGPAPRI | 454.740 | 152. |
| 3 | 825 | ALWVEERFTA | 239.160 | 153. |
| 4 | 162 | ILFSMDGFRA | 181.243 | 154. |
| 5 | 692 | FLYPPASNRT | 109.693 | 155. |
| 6 | 439 | YLTPDLPKRL | 98.267 | 156. |
| 7 | 222 | GIIDNNMYDV | 90.183 | 157. |
| 8 | 28 | LLALLVIMSL | 83.527 | 158. |
| 9 | 30 | ALLVIMSLGL | 79.041 | 159. |
| 10 | 4 | TLTLATEQPV | 69.552 | 160. |
| 11 | 369 | LLADHGMDQT | 58.537 | 161. |
| 12 | 175 | YTWDTLMPNI | 52.169 | 162. |
| 13 | 639 | RMPMWSSYTV | 50.232 | 163. |
| 14 | 806 | FIIPHRPTNV | 43.992 | 164. |
| 15 | 615 | VLQKNVDHCL | 36.316 | 165. |
| 16 | 467 | WLAVRSKSNT | 34.279 | 166. |
| 17 | 94 | RIWMCNKFRC | 32.884 | 167. |
| 18 | 584 | TQLEQVNQML | 32.857 | 168. |
| 19 | 34 | IMSLGLGLGL | 26.228 | 169. |
| 20 | 660 | TVPDCLRADV | 24.952 | 170. |
| 21 | 22 | KIACIVLLAL | 23.646 | 171. |
| 22 | 36 | SLGLGLGLGL | 21.362 | 172. |
| 23 | 861 | ILQLKTYLPT | 19.003 | 173. |
| 24 | 259 | AMYQGLKAAT | 17.222 | 174. |
| 25 | 594 | NLTQEEITAT | 17.140 | 175. |
| 26 | 165 | SMDGFRAEYL | 16.632 | 176. |
| 27 | 81 | CCWDFEDTCV | 15.450 | 177. |
| 28 | 591 | QMLNLTQEEI | 13.661 | 178. |
| 29 | 580 | LQNSTQLEQV | 13.511 | 179. |
| 30 | 674 | SESQKCSFYL | 13.251 | 180. |
| 31 | 708 | ALITSNLVPM | 11.426 | 181. |
| 32 | 111 | SLCSCSDDCL | 10.468 | 182. |
| 33 | 447 | RLHYAKNVRI | 10.433 | 183. |
| 34 | 131 | SVCQGETSWL | 10.281 | 184. |
| 35 | 180 | LMPNINKLKT | 9.149 | 185. |
| 36 | 360 | NLHNCVNIIL | 8.759 | 186. |
| 37 | 855 | VQPVSEILQL | 8.469 | 187. |
| 38 | 293 | VPFEERISTL | 8.271 | 188. |
| 39 | 204 | KTFPNHYTIV | 7.693 | 189. |

TABLE VIII-continued

HLA PEPTIDE SCORING RESULTS 161P2F10B - A2,10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 40 | 64  | RGLENCRCDV | 6.887 | 190. |
| 41 | 595 | LTQEEITATV | 6.733 | 191. |
| 42 | 157 | DLPPVILFSM | 4.970 | 192. |
| 43 | 342 | LQVVDHAFGM | 4.966 | 193. |
| 44 | 460 | HLFVDQQWLA | 4.687 | 194. |
| 45 | 827 | WVEERFTAHI | 4.187 | 195. |
| 46 | 431 | KPDQHFKPYL | 4.080 | 196. |
| 47 | 284 | SIYMPYNGSV | 3.978 | 197. |
| 48 | 846 | TGLDFYQDKV | 3.375 | 198. |
| 49 | 682 | YLADKNITHG | 3.233 | 199. |
| 50 | 32  | LVIMSLGLGL | 3.178 | 200. |

TABLE IX

HLA PEPTIDE SCORING RESULTS 161P2F10B - A3,9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 1  | 227 | NMYDVNLNK | 300.000 | 651. |
| 2  | 42  | GLGLRKLEK | 120.000 | 652. |
| 3  | 374 | GMDQTYCNK | 60.000  | 653. |
| 4  | 692 | FLYPPASNR | 45.000  | 654. |
| 5  | 302 | LLKWLDLPK | 40.000  | 655. |
| 6  | 397 | YMYEGPAPR | 30.000  | 656. |
| 7  | 723 | KMWDYFHSV | 27.000  | 657. |
| 8  | 196 | YMRAMYPTK | 20.000  | 658. |
| 9  | 496 | FLAHGPSFK | 20.000  | 659. |
| 10 | 6   | TLATEQPVK | 20.000  | 660. |
| 11 | 165 | SMDGFRAEY | 18.000  | 661. |
| 12 | 180 | LMPNINKLK | 15.000  | 662. |
| 13 | 215 | GLYPESHGI | 13.500  | 663. |
| 14 | 47  | KLEKQGSCR | 12.000  | 664. |
| 15 | 803 | VLPFIIPHR | 9.000   | 665. |
| 16 | 863 | QLKTYLPTF | 9.000   | 666. |
| 17 | 439 | YLTPDLPKR | 9.000   | 667. |
| 18 | 351 | MLMEGLKQR | 6.750   | 668. |
| 19 | 382 | KMEYMTDYF | 6.000   | 669. |
| 20 | 732 | LLIKHATER | 6.000   | 670. |
| 21 | 305 | WLDLPKAER | 6.000   | 671. |
| 22 | 162 | ILFSMDGFR | 6.000   | 672. |
| 23 | 38  | GLGLGLGLR | 5.400   | 673. |
| 24 | 385 | YMTDYFPRI | 5.400   | 674. |
| 25 | 92  | STRIWMCNK | 4.500   | 675. |
| 26 | 713 | NLVPMYEEF | 4.500   | 676. |
| 27 | 745 | VVSGPIFDY | 4.050   | 677. |
| 28 | 447 | RLHYAKNVR | 4.000   | 678. |
| 29 | 173 | YLYTWDTLM | 3.000   | 679. |
| 30 | 341 | ALQVVDHAF | 3.000   | 680. |
| 31 | 670 | RVPPSESQK | 3.000   | 681. |
| 32 | 460 | HLFVDQQWL | 3.000   | 682. |
| 33 | 519 | NLMCDLLRI | 2.700   | 683. |
| 34 | 678 | KCSFYLADK | 2.700   | 684. |
| 35 | 843 | ELLTGLDFY | 2.700   | 685. |
| 36 | 179 | TLMPNINKL | 2.025   | 686. |
| 37 | 204 | KTFPNHYTI | 2.025   | 687. |
| 38 | 377 | QTYCNKMEY | 2.000   | 688. |
| 39 | 423 | IVRNLSCRK | 2.000   | 689. |
| 40 | 814 | NVESCPEGK | 2.000   | 690. |
| 41 | 867 | YLPTFETTI | 1.800   | 691. |
| 42 | 410 | NIPHDFFSF | 1.800   | 692. |
| 43 | 491 | SMEAIFLAH | 1.800   | 693. |
| 44 | 263 | GLKAATYFW | 1.800   | 694. |
| 45 | 847 | GLDFYQDKV | 1.800   | 695. |
| 46 | 31  | LLVIMSLGL | 1.800   | 696. |
| 47 | 360 | NLHNCVNII | 1.800   | 697. |
| 48 | 572 | SLDCFCPHL | 1.800   | 698. |
| 49 | 800 | WLDVLPFII | 1.800   | 699. |
| 50 | 782 | VVLTSCKNK | 1.500   | 700. |

TABLE X

HLA PEPTIDE SCORING RESULTS 161P2F10B - A3,10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 1 | 38 | GLGLGLGLRK | 120.000 | 201. |
| 2 | 186 | KLKTCGIHSK | 90.000 | 202. |
| 3 | 47 | KLEKQGSCRK | 60.000 | 203. |
| 4 | 301 | TLLKWLDLPK | 60.000 | 204. |
| 5 | 179 | TLMPNINKLK | 33.750 | 205. |
| 6 | 713 | NLVPMYEEFR | 27.000 | 206. |
| 7 | 723 | KMWDYFHSVL | 27.000 | 207. |
| 8 | 6 | TLATEQPVKK | 20.000 | 208. |
| 9 | 443 | DLPKRLHYAK | 18.000 | 209. |
| 10 | 256 | WLTAMYQGLK | 18.000 | 210. |
| 11 | 350 | GMLMEGLKQR | 13.500 | 211. |
| 12 | 437 | KPYLTPDLPK | 9.000 | 212. |
| 13 | 397 | YMYEGPAPRI | 6.750 | 213. |
| 14 | 731 | VLLIKHATER | 6.000 | 214. |
| 15 | 714 | LVPMYEEFRK | 6.000 | 215. |
| 16 | 215 | GLYPESHGII | 4.050 | 216. |
| 17 | 744 | NVVSGPIFDY | 4.050 | 217. |
| 18 | 637 | AMRMPMWSSY | 4.000 | 218. |
| 19 | 845 | LTGLDFYQDK | 3.000 | 219. |
| 20 | 460 | HLFVDQQWLA | 3.000 | 220. |
| 21 | 825 | ALWVEERFTA | 3.000 | 221. |
| 22 | 162 | ILFSMDGFRA | 3.000 | 222. |
| 23 | 28 | LLALLVIMSL | 2.700 | 223. |
| 24 | 538 | SLNHLLKVPF | 2.000 | 224. |
| 25 | 286 | YMPYNGSVPF | 2.000 | 225. |
| 26 | 374 | GMDQTYCNKM | 1.800 | 226. |
| 27 | 462 | FVDQQWLAVR | 1.800 | 227. |
| 28 | 30 | ALLVIMSLGL | 1.800 | 228. |
| 29 | 360 | NLHNCVNIIL | 1.800 | 229. |
| 30 | 619 | NVDHCLLYHR | 1.800 | 230. |
| 31 | 277 | AINGSFPSIY | 1.800 | 231. |
| 32 | 781 | FVVLTSCKNK | 1.500 | 232. |
| 33 | 5 | LTLATEQPVK | 1.500 | 233. |
| 34 | 280 | GSFPSIYMPY | 1.350 | 234. |
| 35 | 34 | IMSLGLGLGL | 1.200 | 235. |
| 36 | 603 | TVKVNLPFGR | 1.200 | 236. |
| 37 | 709 | LITSNLVPMY | 1.200 | 237. |
| 38 | 36 | SLGLGLGLGL | 1.200 | 238. |
| 39 | 822 | KPEALWVEER | 1.080 | 239. |
| 40 | 390 | FPRINFFYMY | 1.080 | 240. |
| 41 | 494 | AIFLAHGPSF | 1.000 | 241. |
| 42 | 17 | TLKKYKIACI | 0.900 | 242. |
| 43 | 615 | VLQKNVDHCL | 0.900 | 243. |
| 44 | 165 | SMDGFRAEYL | 0.900 | 244. |
| 45 | 591 | QMLNLTQEEI | 0.900 | 245. |
| 46 | 355 | GLKQRNLHNC | 0.900 | 246. |
| 47 | 422 | EIVRNLSCRK | 0.900 | 247. |
| 48 | 596 | TQEEITATVK | 0.900 | 248. |
| 49 | 22 | KIACIVLLAL | 0.810 | 249. |
| 50 | 692 | FLYPPASNRT | 0.750 | 250. |

TABLE XI

HLA PEPTIDE SCORING RESULTS - 161P2F10B - A11,9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 1 | 670 | RVPPSESQK | 6.000 | 251. |
| 2 | 42 | GLGLRKLEK | 2.400 | 252. |
| 3 | 423 | IVRNLSCRK | 2.000 | 253. |
| 4 | 814 | NVESCPEGK | 2.000 | 254. |
| 5 | 227 | NMYDVNLNK | 1.600 | 255. |
| 6 | 782 | VVLTSCKNK | 1.500 | 256. |
| 7 | 715 | VPMYEEFRK | 1.200 | 257. |
| 8 | 374 | GMDQTYCNK | 1.200 | 258. |
| 9 | 628 | REYVSGFGK | 1.080 | 259. |
| 10 | 92 | STRIWMCNK | 1.000 | 260. |
| 11 | 257 | LTAMYQGLK | 1.000 | 261. |
| 12 | 332 | GPVSARVIK | 0.900 | 262. |
| 13 | 178 | DTLMPNINK | 0.900 | 263. |

TABLE XI-continued

HLA PEPTIDE SCORING RESULTS - 161P2F10B - A11,9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 14 | 302 | LLKWLDLPK | 0.800 | 264. |
| 15 | 678 | KCSFYLADK | 0.600 | 265. |
| 16 | 444 | LPKRLHYAK | 0.400 | 266. |
| 17 | 727 | YFHSVLLIK | 0.400 | 267. |
| 18 | 114 | SCSDDCLQK | 0.400 | 268. |
| 19 | 12 | PVKKNTLKK | 0.400 | 269. |
| 20 | 496 | FLAHGPSFK | 0.400 | 270. |
| 21 | 714 | LVPMYEEFR | 0.400 | 271. |
| 22 | 6 | TLATEQPVK | 0.400 | 272. |
| 23 | 450 | YAKNVRIDK | 0.400 | 273. |
| 24 | 196 | YMRAMYPTK | 0.400 | 274. |
| 25 | 780 | YFVVLTSCK | 0.300 | 275. |
| 26 | 11 | QPVKKNTLK | 0.300 | 276. |
| 27 | 94 | RIWMCNKFR | 0.240 | 277. |
| 28 | 38 | GLGLGLGLR | 0.240 | 278. |
| 29 | 447 | RLHYAKNVR | 0.240 | 279. |
| 30 | 47 | KLEKQGSCR | 0.240 | 280. |
| 31 | 7 | LATEQPVKK | 0.200 | 281. |
| 32 | 857 | PVSEILQLK | 0.200 | 282. |
| 33 | 68 | NCRCDVACK | 0.200 | 283. |
| 34 | 180 | LMPNINKLK | 0.200 | 284. |
| 35 | 162 | ILFSMDGFR | 0.160 | 285. |
| 36 | 397 | YMYEGPAPR | 0.160 | 286. |
| 37 | 692 | FLYPPASNR | 0.160 | 287. |
| 38 | 384 | EYMFDYFPR | 0.144 | 288. |
| 39 | 438 | PYLTPDLPK | 0.120 | 289. |
| 40 | 465 | QQWLAVRSK | 0.120 | 290. |
| 41 | 204 | KTFPNHYTI | 0.120 | 291. |
| 42 | 732 | LLIKHATER | 0.120 | 292. |
| 43 | 343 | QVVDHAFGM | 0.090 | 293. |
| 44 | 337 | RVIKALQVV | 0.090 | 294. |
| 45 | 614 | RVLQKNVDH | 0.090 | 295. |
| 46 | 803 | VLPFIIPHR | 0.080 | 296. |
| 47 | 439 | YLTPDLPKR | 0.080 | 297. |
| 48 | 351 | MLMEGLKQR | 0.080 | 298. |
| 49 | 417 | SFNSEEIVR | 0.080 | 299. |
| 50 | 305 | WLDLPKAER | 0.080 | 300. |

TABLE XII

HLA PEPTIDE SCORING RESULTS - 161P2F10B - A11,10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 1 | 714 | LVPMYEEFRK | 6.000 | 301. |
| 2 | 437 | KPYLTPDLPK | 2.400 | 302. |
| 3 | 195 | KYMRAMYPTK | 2.400 | 303. |
| 4 | 38 | GLGLGLGLRK | 2.400 | 304. |
| 5 | 781 | FVVLTSCKNK | 1.500 | 305. |
| 6 | 5 | LTLATEQPVK | 1.500 | 306. |
| 7 | 301 | TLLKWLDLPK | 1.200 | 307. |
| 8 | 47 | KLEKQGSCRK | 1.200 | 308. |
| 9 | 186 | KLKTCGIHSK | 1.200 | 309. |
| 10 | 603 | TVKVNLPFGR | 1.200 | 310. |
| 11 | 845 | LTGLDFYQDK | 1.000 | 311. |
| 12 | 779 | HYFVVLTSCK | 0.800 | 312. |
| 13 | 619 | NVDHCLLYHR | 0.800 | 313. |
| 14 | 449 | HYAKNVRIDK | 0.800 | 314. |
| 15 | 11 | QPVKKNTLKK | 0.600 | 315. |
| 16 | 596 | TQEEITATVK | 0.600 | 316. |
| 17 | 726 | DYFHSVLLIK | 0.480 | 317. |
| 18 | 462 | FVDQQWLAVR | 0.400 | 318. |
| 19 | 6 | TLATEQPVKK | 0.400 | 319. |
| 20 | 758 | HFDAPDEITK | 0.400 | 320. |
| 21 | 256 | WLTAMYQGLK | 0.400 | 321. |
| 22 | 179 | TLMPNINKLK | 0.400 | 322. |
| 23 | 630 | YVSGFGKAMR | 0.400 | 323. |
| 24 | 856 | QPVSEILQLK | 0.300 | 324. |
| 25 | 495 | IFLAHGPSFK | 0.300 | 325. |
| 26 | 443 | DLPKRLHYAK | 0.240 | 326. |

TABLE XII-continued

HLA PEPTIDE SCORING RESULTS - 161P2F10B - A11,10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 27 | 114 | SCSDDCLQKK | 0.200 | 327. |
| 28 | 428 | SCRKPDQHFK | 0.200 | 328. |
| 29 | 348 | AFGMLMEGLK | 0.200 | 329. |
| 30 | 691 | GFLYPPASNR | 0.180 | 330. |
| 31 | 802 | DVLPFIIPHR | 0.180 | 331. |
| 32 | 350 | GMLMEGLKQR | 0.180 | 332. |
| 33 | 422 | EIVRNLSCRK | 0.180 | 333. |
| 34 | 10 | EQPVKKNTLK | 0.180 | 334. |
| 35 | 396 | FYMYEGPAPR | 0.160 | 335. |
| 36 | 226 | NNMYDVNLNK | 0.160 | 336. |
| 37 | 517 | VYNLMCDLLR | 0.160 | 337. |
| 38 | 161 | VILFSMDGFR | 0.120 | 338. |
| 39 | 822 | KPEALWVEER | 0.120 | 339. |
| 40 | 605 | KVWLPFGRPR | 0.120 | 340. |
| 41 | 713 | NLVPMYEEFR | 0.120 | 341. |
| 42 | 295 | FEERISTLLK | 0.120 | 342. |
| 43 | 731 | VLLIKHATER | 0.120 | 343. |
| 44 | 497 | LAHGPSFKEK | 0.100 | 344. |
| 45 | 744 | NVVSGPIFDY | 0.090 | 345. |
| 46 | 189 | TCGIHSKYMR | 0.080 | 346. |
| 47 | 383 | MEYMTDYFPR | 0.072 | 347. |
| 48 | 41 | LGLGLRKLEK | 0.060 | 348. |
| 49 | 627 | HREYVSGFGK | 0.060 | 349. |
| 50 | 813 | TNVESCPEGK | 0.060 | 350. |

TABLE XIII

HLA PEPTIDE SCORING RESULTS - 161P2F10B - A24,9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 1 | 20 | KYKIACIVL | 400.000 | 351. |
| 2 | 172 | EYLYTWDTL | 300.000 | 352. |
| 3 | 517 | VYNLMCDLL | 300.000 | 353. |
| 4 | 388 | DYFPRINFF | 144.000 | 354. |
| 5 | 216 | LYPESHGII | 90.000 | 355. |
| 6 | 398 | MYEGPAPRI | 75.000 | 356. |
| 7 | 726 | DYFHSVLLI | 50.000 | 357. |
| 8 | 484 | GYNNEFRSM | 45.000 | 358. |
| 9 | 100 | KFRCGETRL | 40.000 | 359. |
| 10 | 378 | TYCNKMEYM | 25.000 | 360. |
| 11 | 58 | CFDASFRGL | 24.000 | 361. |
| 12 | 348 | AFGMLMEGL | 24.000 | 362. |
| 13 | 854 | KVQPVSEIL | 20.160 | 363. |
| 14 | 155 | GFDLPPVIL | 20.000 | 364. |
| 15 | 195 | KYMRAMYPT | 15.000 | 365. |
| 16 | 495 | IFLAHGPSF | 15.000 | 366. |
| 17 | 866 | TYLPTFETT | 10.800 | 367. |
| 18 | 693 | LYPPASNRT | 10.800 | 368. |
| 19 | 850 | FYQDKVQPV | 10.800 | 369. |
| 20 | 585 | QLEQVNQML | 10.080 | 370. |
| 21 | 419 | NSEEIVRNL | 10.080 | 371. |
| 22 | 720 | EFRKMWDYF | 10.000 | 372. |
| 23 | 488 | EFRSMEAIF | 10.000 | 373. |
| 24 | 629 | EYVSGFGKA | 9.900 | 374. |
| 25 | 298 | RISTLLKWL | 9.600 | 375. |
| 26 | 179 | TLMPNINKL | 9.504 | 376. |
| 27 | 260 | MYQGLKAAT | 9.000 | 377. |
| 28 | 681 | FYLADKNIT | 9.000 | 378. |
| 29 | 285 | IYMPYNGSV | 9.000 | 379. |
| 30 | 717 | MYEEFRKMW | 9.000 | 380. |
| 31 | 440 | LTPDLPKRL | 8.640 | 381. |
| 32 | 657 | LPPTVPDCL | 8.400 | 382. |
| 33 | 29 | LALLVIMSL | 8.400 | 383. |
| 34 | 200 | MYPTKTFPN | 7.500 | 384. |
| 35 | 24 | ACIVLLALL | 7.200 | 385. |
| 36 | 10 | EQPVKKNTL | 7.200 | 386. |
| 37 | 37 | LGLGLGLGL | 7.200 | 387. |
| 38 | 860 | EILQLKTYL | 7.200 | 388. |
| 39 | 33 | VIMSLGLGL | 7.200 | 389. |

TABLE XIII-continued

HLA PEPTIDE SCORING RESULTS - 161P2F10B - A24,9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 40 | 35 | MSLGLGLGL | 7.200 | 390. |
| 41 | 209 | HYTIVTGLY | 7.000 | 391. |
| 42 | 779 | HYFVVLTSC | 7.000 | 392. |
| 43 | 761 | APDEITKHL | 6.720 | 393. |
| 44 | 228 | MYDVNLNKN | 6.600 | 394. |
| 45 | 300 | STLLKWLDL | 6.000 | 395. |
| 46 | 856 | QPVSEILQL | 6.000 | 396. |
| 47 | 132 | VCQGETSWL | 6.000 | 397. |
| 48 | 587 | EQVNQMLNL | 6.000 | 398. |
| 49 | 793 | TPENCPGWL | 6.000 | 399. |
| 50 | 382 | KMEYMTDYF | 6.000 | 400. |

TABLE XIV

HLA PEPTIDE SCORING RESULTS - 161P2F10B - A24,10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 1 | 20 | KYKIACIVLL | 400.000 | 401. |
| 2 | 705 | QYDALITSNL | 280.000 | 402. |
| 3 | 228 | MYDVNLNKNF | 120.000 | 403. |
| 4 | 625 | LYHREYVSGF | 100.000 | 404. |
| 5 | 384 | EYMTDYFPRI | 90.000 | 405. |
| 6 | 866 | TYLPTFETTI | 90.000 | 406. |
| 7 | 629 | EYVSGFGKAM | 37.500 | 407. |
| 8 | 172 | EYLYTWDTLM | 37.500 | 408. |
| 9 | 435 | HFKPYLTPDL | 28.800 | 409. |
| 10 | 488 | EFRSMEAIFL | 20.000 | 410. |
| 11 | 850 | FYQDKVQPVS | 12.600 | 411. |
| 12 | 584 | TQLEQVNQML | 12.096 | 412. |
| 13 | 452 | KNVRIDKVHL | 12.000 | 413. |
| 14 | 57 | KCFDASFRGL | 11.520 | 414. |
| 15 | 22 | KIACIVLLAL | 11.200 | 415. |
| 16 | 760 | DAPDEITKHL | 10.080 | 416. |
| 17 | 155 | GFDLPPVILF | 10.000 | 417. |
| 18 | 750 | IFDYNYDGHF | 10.000 | 418. |
| 19 | 547 | FYEPSHAEEV | 9.900 | 419. |
| 20 | 700 | RTSDSQYDAL | 9.600 | 420. |
| 21 | 723 | KMWDYFHSVL | 9.600 | 421. |
| 22 | 693 | LYPPASNRTS | 9.000 | 422. |
| 23 | 343 | QVVDHAFGML | 8.640 | 423. |
| 24 | 388 | DYFPRINFFY | 8.400 | 424. |
| 25 | 615 | VLQKNVDHCL | 8.400 | 425. |
| 26 | 340 | KALQVVDHAF | 8.400 | 426. |
| 27 | 431 | KPDQHFKPYL | 8.000 | 427. |
| 28 | 178 | DTLMPNINKL | 7.920 | 428. |
| 29 | 752 | DYNYDGHFDA | 7.500 | 429. |
| 30 | 260 | MYQGLKAATY | 7.500 | 430. |
| 31 | 817 | SCPEGKPEAL | 7.200 | 431. |
| 32 | 103 | CGETRLEASL | 7.200 | 432. |
| 33 | 571 | ESLDCFCPHL | 7.200 | 433. |
| 34 | 32 | LVIMSLGLGL | 7.200 | 434. |
| 35 | 792 | HTPENCPGWL | 7.200 | 435. |
| 36 | 559 | FSVCGFANPL | 7.200 | 436. |
| 37 | 255 | MWLTAMYQGL | 7.200 | 437. |
| 38 | 564 | FANPLPTESL | 7.200 | 438. |
| 39 | 418 | FNSEEIVRNL | 6.720 | 439. |
| 40 | 39 | LGLGLGLRKL | 6.600 | 440. |
| 41 | 855 | VQPVSEILQL | 6.000 | 441. |
| 42 | 149 | QSQCPEGFDL | 6.000 | 442. |
| 43 | 30 | ALLVIMSLGL | 6.000 | 443. |
| 44 | 352 | LMEGLKQRNL | 6.000 | 444. |
| 45 | 530 | APNNGTHGSL | 6.000 | 445. |
| 46 | 230 | DVNLNKNFSL | 6.000 | 446. |
| 47 | 607 | NLPFGRPRVL | 6.000 | 447. |
| 48 | 269 | YFWPGSEVAI | 6.000 | 448. |
| 49 | 648 | VPQLGDTSPL | 6.000 | 449. |
| 50 | 439 | YLTPDLPKRL | 5.760 | 450. |

TABLE XV

HLA PEPTIDE SCORING RESULTS - 161P2F10B - A7,9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 1 | 403 | APRIRAHNI | 240.000 | 451. |
| 2 | 390 | FPRINFFYM | 200.000 | 452. |
| 3 | 453 | NVRIDKVHL | 200.000 | 453. |
| 4 | 836 | IARVRDVEL | 120.000 | 454. |
| 5 | 856 | QPVSEILQL | 80.000 | 455. |
| 6 | 608 | LPFGRPRVL | 80.000 | 456. |
| 7 | 776 | IPTHYFVVL | 80.000 | 457. |
| 8 | 657 | LPPTVPDCL | 80.000 | 458. |
| 9 | 761 | APDEITKHL | 72.000 | 459. |
| 10 | 612 | RPRVLQKNV | 40.000 | 460. |
| 11 | 818 | CPEGKPEAL | 24.000 | 461. |
| 12 | 793 | TPENCPGWL | 24.000 | 462. |
| 13 | 516 | EVYNLMCDL | 20.000 | 463. |
| 14 | 854 | KVQPVSEIL | 20.000 | 464. |
| 15 | 158 | LPPVILFSM | 20.000 | 465. |
| 16 | 560 | SVCGFANPL | 20.000 | 466. |
| 17 | 565 | ANPLPTESL | 18.000 | 467. |
| 18 | 29 | LALLVIMSL | 12.000 | 468. |
| 19 | 24 | ACIVLLALL | 12.000 | 469. |
| 20 | 179 | TLMPNINKL | 12.000 | 470. |
| 21 | 23 | IACIVLLAL | 12.000 | 471. |
| 22 | 33 | VIMSLGLGL | 12.000 | 472. |
| 23 | 640 | MPMWSSYTV | 12.000 | 473. |
| 24 | 344 | VVDHAFGML | 6.000 | 474. |
| 25 | 838 | RVRDVELLT | 5.000 | 475. |
| 26 | 630 | YVSGFGKAM | 5.000 | 476. |
| 27 | 343 | QVVDHAFGM | 5.000 | 477. |
| 28 | 534 | GTHGSLNHL | 4.000 | 478. |
| 29 | 362 | HNCVNIILL | 4.000 | 479. |
| 30 | 31 | LLVIMSLGL | 4.000 | 480. |
| 31 | 313 | RPRFYTMYF | 4.000 | 481. |
| 32 | 225 | DNNMYDVNL | 4.000 | 482. |
| 33 | 587 | EQYNQMLNL | 4.000 | 483. |
| 34 | 35 | MSLGLGLGL | 4.000 | 484. |
| 35 | 440 | LTPDLPKRL | 4.000 | 485. |
| 36 | 300 | STLLKWLDL | 4.000 | 486. |
| 37 | 643 | WSSYTVPQL | 4.000 | 487. |
| 38 | 675 | ESQKCSFYL | 4.000 | 488. |
| 39 | 334 | VSARVIKAL | 4.000 | 489. |
| 40 | 298 | RISTLLKWL | 4.000 | 490. |
| 41 | 774 | VPIPTHYFV | 4.000 | 491. |
| 42 | 460 | HLFVDQQWL | 4.000 | 492. |
| 43 | 100 | KFRCGETRL | 4.000 | 493. |
| 44 | 796 | NCPGWLDVL | 4.000 | 494. |
| 45 | 860 | EILQLKTYL | 4.000 | 495. |
| 46 | 256 | WLTAMYQGL | 4.000 | 496. |
| 47 | 150 | SQCPEGFDL | 4.000 | 497. |
| 48 | 10 | EQPVKKNTL | 4.000 | 498. |
| 49 | 40 | GLGLGLRKL | 4.000 | 499. |
| 50 | 37 | LGLGLGLGL | 4.000 | 500. |

TABLE XVI

HLA PEPTIDE SCORING RESULTS - 161P2F10B - A7,10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 1 | 530 | APNNGTHGSL | 240.000 | 501. |
| 2 | 836 | IARVRDVELL | 120.000 | 502. |
| 3 | 577 | CPHLQNSTQL | 80.000 | 503. |
| 4 | 648 | VPQLGDTSPL | 80.000 | 504. |
| 5 | 293 | VPFEERISTL | 80.000 | 505. |
| 6 | 715 | VPMYEEFRKM | 60.000 | 506. |
| 7 | 431 | KPDQHFKPYL | 24.000 | 507. |
| 8 | 343 | QVVDHAFGML | 20.000 | 508. |
| 9 | 516 | EVYNLMCDLL | 20.000 | 509. |
| 10 | 32 | LVIMSLGLGL | 20.000 | 510. |
| 11 | 230 | DVNLNKNFSL | 20.000 | 511. |
| 12 | 246 | NPAWWHGQPM | 20.000 | 512. |
| 13 | 131 | SVCQGETSWL | 20.000 | 513. |

TABLE XVI-continued

HLA PEPTIDE SCORING RESULTS - 161P2F10B - A7,10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 14 | 564 | FANPLPTESL | 18.000 | 514. |
| 15 | 469 | AVRSKSNTNC | 15.000 | 515. |
| 16 | 30 | ALLVIMSLGL | 12.000 | 516. |
| 17 | 760 | DAPDEITKHL | 12.000 | 517. |
| 18 | 347 | HAFGMLMEGL | 12.000 | 518. |
| 19 | 23 | IACIVLLALL | 12.000 | 519. |
| 20 | 403 | APRIRAHNIP | 6.000 | 520. |
| 21 | 335 | SARVIKALQV | 6.000 | 521. |
| 22 | 154 | EGFDLPPVIL | 6.000 | 522. |
| 23 | 26 | IVLLALLVIM | 5.000 | 523. |
| 24 | 488 | EFRSMEAIFL | 4.000 | 524. |
| 25 | 584 | TQLEQVNQML | 4.000 | 525. |
| 26 | 452 | KNVRIDKVHL | 4.000 | 526. |
| 27 | 111 | SLCSCSDDCL | 4.000 | 527. |
| 28 | 599 | EITATVKVNL | 4.000 | 528. |
| 29 | 57 | KCFDASFRGL | 4.000 | 529. |
| 30 | 418 | FNSEEIVRNL | 4.000 | 530. |
| 31 | 795 | ENCPGWLDVL | 4.000 | 531. |
| 32 | 149 | QSQCPEGFDL | 4.000 | 532. |
| 33 | 616 | LQKNVDHCLL | 4.000 | 533. |
| 34 | 615 | VLQKNVDHCL | 4.000 | 534. |
| 35 | 700 | RTSDSQYDAL | 4.000 | 535. |
| 36 | 39 | LGLGLGLRKL | 4.000 | 536. |
| 37 | 559 | FSVCGFANPL | 4.000 | 537. |
| 38 | 36 | SLGLGLGLGL | 4.000 | 538. |
| 39 | 28 | LLALLVIMSL | 4.000 | 539. |
| 40 | 835 | HIARVRDVEL | 4.000 | 540. |
| 41 | 22 | KIACIVLLAL | 4.000 | 541. |
| 42 | 607 | NLPFGRPRVL | 4.000 | 542. |
| 43 | 299 | ISTLLKWLDL | 4.000 | 543. |
| 44 | 792 | HTPENCPGWL | 4.000 | 544. |
| 45 | 723 | KMWDYFHSVL | 4.000 | 545. |
| 46 | 774 | VPIPTHYFVV | 4.000 | 546. |
| 47 | 533 | NGTHGSLNHL | 4.000 | 547. |
| 48 | 390 | FPRINFFYMY | 4.000 | 548. |
| 49 | 817 | SCPEGKPEAL | 4.000 | 549. |
| 50 | 34 | IMSLGLGLGL | 4.000 | 550. |

TABLE XVII

HLA PEPTIDE SCORING RESULTS - 161P2F10B - A35,9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 1 | 390 | FPRINFFYM | 120.000 | 551. |
| 2 | 313 | RPRFYTMYF | 120.000 | 552. |
| 3 | 308 | LPKAERPRF | 90.000 | 553. |
| 4 | 510 | EPFENIEVY | 80.000 | 554. |
| 5 | 568 | LPTESLDCF | 40.000 | 555. |
| 6 | 158 | LPPVILFSM | 40.000 | 556. |
| 7 | 253 | QPMWLTAMY | 40.000 | 557. |
| 8 | 856 | QPVSEILQL | 30.000 | 558. |
| 9 | 193 | HSKYMRAMY | 30.000 | 559. |
| 10 | 431 | KPDQHFKPY | 24.000 | 560. |
| 11 | 403 | APRIRAHNI | 24.000 | 561. |
| 12 | 612 | RPRVLQKNV | 24.000 | 562. |
| 13 | 657 | LPPTVPDCL | 20.000 | 563. |
| 14 | 608 | LPFGRPRVL | 20.000 | 564. |
| 15 | 287 | MPYNGSVPF | 20.000 | 565. |
| 16 | 776 | IPTHYFVVL | 20.000 | 566. |
| 17 | 556 | VSKFSVCGF | 15.000 | 567. |
| 18 | 761 | APDEITKHL | 12.000 | 568. |
| 19 | 836 | IARVRDVEL | 9.000 | 569. |
| 20 | 618 | KNVDHCLLY | 8.000 | 570. |
| 21 | 634 | FGKAMRMPM | 6.000 | 571. |
| 22 | 793 | TPENCPGWL | 6.000 | 572. |
| 23 | 198 | RAMYPTKTF | 6.000 | 573. |
| 24 | 818 | CPEGKPEAL | 6.000 | 574. |
| 25 | 293 | VPFEERIST | 6.000 | 575. |
| 26 | 698 | SNRTSDSQY | 6.000 | 576. |

TABLE XVII-continued

HLA PEPTIDE SCORING RESULTS - 161P2F10B - A35,9-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 27 | 407 | RAHNIPHDF | 6.000 | 577. |
| 28 | 35 | MSLGLGLGL | 5.000 | 578. |
| 29 | 675 | ESQKCSFYL | 5.000 | 579. |
| 30 | 643 | WSSYTVPQL | 5.000 | 580. |
| 31 | 334 | VSARVIKAL | 5.000 | 581. |
| 32 | 453 | NVRIDKVHL | 4.500 | 582. |
| 33 | 188 | KTCGIHSKY | 4.000 | 583. |
| 34 | 584 | TQLEQVNQM | 4.000 | 584. |
| 35 | 343 | QVVDHAFGM | 4.000 | 585. |
| 36 | 640 | MPMWSSYTV | 4.000 | 586. |
| 37 | 513 | ENIEVYNLM | 4.000 | 587. |
| 38 | 774 | VPIPTHYFV | 4.000 | 588. |
| 39 | 411 | IPHDFFSFN | 4.000 | 589. |
| 40 | 686 | KNITHGFLY | 4.000 | 590. |
| 41 | 23 | IACIVLLAL | 3.000 | 591. |
| 42 | 616 | LQKNVDHCL | 3.000 | 592. |
| 43 | 240 | SSKEQNNPA | 3.000 | 593. |
| 44 | 29 | LALLVIMSL | 3.000 | 594. |
| 45 | 863 | QLKTYLPTF | 3.000 | 595. |
| 46 | 428 | SCRKPDQHF | 3.000 | 596. |
| 47 | 545 | VPFYEPSHA | 3.000 | 597. |
| 48 | 671 | VPPSESQKC | 3.000 | 598. |
| 49 | 221 | HGIIDNNMY | 3.000 | 599. |
| 50 | 824 | EALWVEERF | 3.000 | 600. |

TABLE XVIII

HLA PEPTIDE SCORING RESULTS 161P2F10B - B35, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 1 | 308 | LPKAERPRFY | 120.000 | 601. |
| 2 | 390 | FPRINFFYMY | 120.000 | 602. |
| 3 | 715 | VPMYEEFRKM | 60.000 | 603. |
| 4 | 246 | NPAWWHGQPM | 40.000 | 604. |
| 5 | 201 | YPTKTFPNHY | 40.000 | 605. |
| 6 | 293 | VPFEERISTL | 40.000 | 606. |
| 7 | 797 | CPGWLDVLPF | 30.000 | 607. |
| 8 | 648 | VPQLGDTSPL | 30.000 | 608. |
| 9 | 530 | APNNGTHGSL | 20.000 | 609. |
| 10 | 577 | CPHLQNSTQL | 20.000 | 610. |
| 11 | 164 | FSMDGFRAEY | 20.000 | 611. |
| 12 | 240 | SSKEQNNPAW | 15.000 | 612. |
| 13 | 836 | IARVRDVELL | 13.500 | 613. |
| 14 | 431 | KPDQHFKPYL | 12.000 | 614. |
| 15 | 441 | TPDLPKRLHY | 12.000 | 615. |
| 16 | 280 | GSFPSIYMPY | 10.000 | 616. |
| 17 | 697 | ASNRTSDSQY | 10.000 | 617. |
| 18 | 631 | VSGFGKAMRM | 10.000 | 618. |
| 19 | 571 | ESLDCFCPHL | 10.000 | 619. |
| 20 | 746 | VSGPIFDYNY | 10.000 | 620. |
| 21 | 219 | ESHGIIDNNM | 10.000 | 621. |
| 22 | 149 | QSQCPEGFDL | 7.500 | 622. |
| 23 | 380 | CNKMEYMTDY | 6.000 | 623. |
| 24 | 637 | AMRMPMWSSY | 6.000 | 624. |
| 25 | 407 | RAHNIPHDFF | 6.000 | 625. |
| 26 | 760 | DAPDEITKHL | 6.000 | 626. |
| 27 | 500 | GPSFKEKTEV | 6.000 | 627. |
| 28 | 444 | LPKRLHYAKN | 6.000 | 628. |
| 29 | 340 | KALQVVDHAF | 6.000 | 629. |
| 30 | 120 | LQKKDCCADY | 6.000 | 630. |
| 31 | 427 | LSCRKPDQHF | 5.000 | 631. |
| 32 | 299 | ISTLLKWLDL | 5.000 | 632. |
| 33 | 130 | KSVCQGETSW | 5.000 | 633. |
| 34 | 559 | FSVCGFANPL | 5.000 | 634. |
| 35 | 616 | LQKNVDHCLL | 4.500 | 635. |
| 36 | 510 | EPFENIEVYN | 4.000 | 636. |
| 37 | 723 | KMWDYFHSVL | 4.000 | 637. |
| 38 | 57 | KCFDASFRGL | 4.000 | 638. |
| 39 | 700 | RTSDSQYDAL | 4.000 | 639. |

TABLE XVIII-continued

HLA PEPTIDE SCORING RESULTS 161P2F10B - B35, 10-MERS

| RANK | START POSITION | SUBSEQUENCE RESIDUE LISTING | SCORE (ESTIMATE OF HALF TIME OF DISASSOCIATION OF A MOLECULE CONTAINING THIS SUBSEQUENCE) | SEQ. ID# |
|---|---|---|---|---|
| 40 | 672 | PPSESQKCSF | 4.000 | 640. |
| 41 | 188 | KTCGIHSKYM | 4.000 | 641. |
| 42 | 88 | TCVESTRIWM | 4.000 | 642. |
| 43 | 411 | IPHDFFSFNS | 4.000 | 643. |
| 44 | 568 | LPTESLDCFC | 4.000 | 644. |
| 45 | 774 | VPIPTHYFVV | 4.000 | 645. |
| 46 | 310 | KAERPRFYTM | 3.600 | 646. |
| 47 | 858 | VSEILQLKTY | 3.000 | 647. |
| 48 | 74 | ACKDRGDCCW | 3.000 | 648. |
| 49 | 452 | KNVRIDKVHL | 3.000 | 649. |
| 50 | 23 | IACIVLLALL | 3.000 | 650. |

TABLE XIX

Motifs and Post-translational Modifications of 161P2F10B

N-glycosylation sites
Number of matches: 10

| | | | |
|---|---|---|---|
| 1 | 236–239 | NFSL | (SEQ. ID. No. 701) |
| 2 | 279–282 | NGSF | (SEQ. ID. No. 702) |
| 3 | 290–293 | NGSV | (SEQ. ID. No. 703) |
| 4 | 426–429 | NLSC | (SEQ. ID. No. 704) |
| 5 | 533–536 | NGTH | (SEQ. ID. No. 705) |
| 6 | 582–585 | NSTQ | (SEQ. ID. No. 706) |
| 7 | 594–597 | NLTQ | (SEQ. ID. No. 707) |
| 8 | 687–690 | NITH | (SEQ. ID. No. 708) |
| 9 | 699–702 | NRTS | (SEQ. ID. No. 709) |
| 10 | 789–792 | NKSH | (SEQ. ID. No. 710) | cAMP- and cGMP-dependent protein kinase phosphorylation site

| | | | |
|---|---|---|---|
| | 14–17 | KKNT | (SEQ. ID. No. 711) |

Protein kinase C phosphorylation sites
Number of matches: 13

| | | |
|---|---|---|
| 1 | 17–19 | TLK |
| 2 | 53–55 | SCR |
| 3 | 428–430 | SCR |
| 4 | 62–64 | SFR |
| 5 | 92–94 | STR |
| 6 | 240–242 | SSK |
| 7 | 335–337 | SAR |
| 8 | 53–55 | SCR |
| 9 | 428–430 | SCR |
| 10 | 502–504 | SFK |
| 11 | 603–605 | TVK |
| 12 | 676–678 | SQK |
| 13 | 698–700 | SNR |

Casein kinase II phosphorylation sites
Number of matches: 15

| | | | |
|---|---|---|---|
| 1 | 88–91 | TCVE | (SEQ. ID. No. 712) |
| 2 | 106–109 | TRLE | (SEQ. ID. No. 713) |
| 3 | 114–117 | SCSD | (SEQ. ID. No. 714) |
| 4 | 138–141 | SWLE | (SEQ. ID. No. 715) |
| 5 | 240–243 | SSKE | (SEQ. ID. No. 716) |
| 6 | 502–505 | SFKE | (SEQ. ID. No. 717) |
| 7 | 507–510 | TEVE | (SEQ. ID. No. 718) |
| 8 | 551–554 | SHAE | (SEQ. ID. No. 719) |
| 9 | 584–587 | TQLE | (SEQ. ID. No. 720) |
| 10 | 596–599 | TQEE | (SEQ. ID. No. 721) |
| 11 | 660–663 | TVPD | (SEQ. ID. No. 722) |
| 12 | 704–707 | SQYD | (SEQ. ID. No. 723) |
| 13 | 813–816 | TNVE | (SEQ. ID. No. 724) |
| 14 | 817–820 | SCPE | (SEQ. iD. No. 725) |
| 15 | 846–849 | TGLD | (SEQ. ID. No. 726) |

TABLE XIX-continued

Motifs and Post-translational Modifications of 161P2F10B

Tyrosine kinase phosphorylation site

| | 700–706 | RTSDSQY | (SEQ. ID. No. 727) |
|---|---|---|---|

N-myristoylation sites
Number of matches: 11

| 1 | 38–43 | GLGLGL | (SEQ. ID. No. 728) |
|---|---|---|---|
| 2 | 40–45 | GLGLGL | (SEQ. ID. No. 729) |
| 3 | 38–43 | GLGLGL | (SEQ. ID. No. 730) |
| 4 | 40–45 | GLGLGL | (SEQ. ID. No. 731) |
| 5 | 65–70 | GLENCR | (SEQ. ID. No. 732) |
| 6 | 222–227 | GIIDNN | (SEQ. ID. No. 733) |
| 7 | 263–268 | GLKAAT | (SEQ. ID. No. 734) |
| 8 | 273–278 | GSEVAI | (SEQ. ID. No. 735) |
| 9 | 280–285 | GSFPSI | (SEQ. ID. No. 736) |
| 10 | 331–336 | GGPVSA | (SEQ. ID. No. 737) |
| 11 | 374–379 | GMDQTY | (SEQ. ID. No. 738) |

Cell attachment sequence

| | 78–80 | RGD | (SEQ. ID. No. 739) |
|---|---|---|---|

Somatomedin B domain signatures
Number of matches: 2

| 1 | 69–89 | CRCDVACKDRGDCCWDFEDTC | (SEQ. ID. No. 740) |
|---|---|---|---|
| 2 | 113–133 | CSCSDDCLQKKDCCADYKSVC | (SEQ. ID. No. 741) |

TABLE XX

Frequently Ocurring Motifs

| Name | avrg. % identity | Description | Potential Function |
|---|---|---|---|
| zf-C2H2 | 34% | Zinc finger, C2H2 type | Nucleic acid-binding protein functions as transcription factor, nuclear location probable |
| cytochrome b N | 68% | Cytochrome b(N-terminal)/b6/petB | membrane bound oxidase, generate superoxide |
| Ig | 19% | Immunoglobulin domain | domains are one hundred amino acids long and include a conserved intradomain disulfide bond. |
| WD40 | 18% | WD domain, G-beta repeat | tandem repeats of about 40 residues, each containing a Trp-Asp motif. Function in signal transduction and protein interaction |
| PDZ | 23% | PDZ domain | may function in targeting signaling molecules to sub-membranous sites |
| LRR | 28% | Leucine Rich Repeat | short sequence motifs involved in protein-protein interactions |
| Pkinase | 23% | Protein kinase domain | conserved catalytic core common to both serine/threonine and tyrosine protein kinases containing an ATP binding site and a catalytic site |
| PH | 16% | PH domain | pleckstrin homology involved in intracellular signaling or as constituents of the cytoskeleton |
| EGF | 34% | EGF-like domain | 30–40 amino-acid long found in the extracellular domain of membrane-bound proteins or in secreted proteins |
| Rvt | 49% | Reverse transcriptase (RNA-dependent DNA polymerase) | |
| Ank | 25% | Ank repeat | Cytoplasmic protein, associates integral membrane proteins to the cytoskeleton |
| Oxidored q1 | 32% | NADH-Ubiquinone/plastoquinone (complex I), various chains | membrane associated. Involved in proton translocation across the membrane |
| Efhand | 24% | EF hand | calcium-binding domain, consists of a 12 residue loop flanked on both sides by a 12 residue alpha-helical domain |
| Rvp | 79% | Retroviral aspartyl protease | Aspartyl or acid proteases, centered on a catalytic aspartyl residue |

TABLE XX-continued

Frequently Ocurring Motifs

| Name | avrg. % identity | Description | Potential Function |
|---|---|---|---|
| Collagen | 42% | Collagen triple helix repeat (20 copies) | extracellular structural proteins involved in formation of connective tissue. The sequence consists of the G-X-Y and the polypeptide chains forms a triple helix. |
| fn3 | 20% | Fibronectin type III domain | Located in the extracellular ligand-binding region of receptors and is about 200 amino acid residues long with two pairs of cysteines involved in disulfide bonds |
| 7tm 1 | 19% | 7 transmembrane receptor (rhodopsin family) | seven hydrophobic transmembrane regions, with the N-terminus located extracellularly while the C-terminus is cytoplasmic. Signal through G proteins |

TABLE XXI

Properties of 161P2F10B

| Feature | Bioinformatic Program | Outcome |
|---|---|---|
| ORF (includes stop codon) | ORF finder | 44–2671 |
| # of amino acids | | 875 |
| Transmembrane region | TM Pred | One TM, aa 23–41 |
| | HMMTop | One TM, aa 23–45 |
| | Sosui | One TM, aa 23–45 |
| | TMHMM | One TM, aa 23–45 |
| Signal Peptide | Signal P | none |
| pI | pI/MW tool | 6.12 |
| Molecular weight | pI/MW tool | 100.09 kDa |
| Localization | PSORT | Plasma membrane 74% Golgi 30% |
| | PSORT II | Endoplasmic 30.4% Golgi 21.7% |
| Motifs | Pfam | Somatomedin B, Type I phosphodiesterase/ nucleotide pyrophosphatase |
| | Prints | Cell Attachement RGD |
| | Blocks | Somatomedin B, DNA/RNA non-specific endonuclease, |
| | Prosite | Somatomedin B |

What is claimed is:

1. A method of inhibiting growth of a tumor cell that expresses SEQ ID NO:743 or SEQ ID NO:745 comprising: contacting said cell with an antibody or fragment thereof specifically binds to a protein having an amino acid sequence of SEQ ID NOS: 743 or 745, wherein the antibody or fragment thereof binds to and inhibits the growth of the tumor cell via the protein.

2. The method of claim 1, wherein the antibody is a monoclonal antibody.

3. The method of claim 1, wherein the antibody is a single chain monoclonal antibody.

4. The method of claim 3, wherein the monoclonal antibody is recombinantly produced.

5. The method of claim 1, wherein the antibody or fragment thereof is labeled with a detectable marker.

6. The method of claim 1, wherein the fragment thereof is selected from the group consisting of Fab, F(ab')2, Fv and sFv fragment.

7. The method of claim 1, wherein the antibody is a human antibody, a humanized antibody or a chimeric antibody.

8. The method of claim 1, wherein the antibody or fragment thereof is labeled with a cytotoxic agent.

9. The method of claim 8, wherein the cytotoxic agent is selected from the group consisting of radioactive isotopes, chemotherapeutic agents and toxins.

10. The method of claim 9, wherein the radioactive isotope is selected from the group consisting of $^{211}$At, $^{131}$I, $^{125}$I, $^{90}$Y, $^{186}$Re, $^{188}$Re, $^{153}$Sm, $^{212}$Bi, $^{32}$P and radioactive isotopes of Lu.

11. The method of claim 9, wherein the chemotherapeutic agent is selected from the group consisting of taxol, actinomycin, mitomycin, etoposide, tenoposide, vincristine, vinblastine, colchicine, gelonin, and calicheamicin.

12. The method of claim 9, wherein the toxin is selected from the group consisting of diphtheria toxin, enomycin, phenomycin, Pseudomonas exotoxin (PE) A, PE40, abrin, abrin A chain, mitogellin, modeccin A chain, and alpha-sarcin.

* * * * *

UNITED STATES PATENT AND TRADEMARK OFFICE
CERTIFICATE OF CORRECTION

PATENT NO. : 7,067,130 B2  Page 1 of 1
APPLICATION NO. : 10/062109
DATED : June 27, 2006
INVENTOR(S) : Pia M. Challita-Eid et al.

It is certified that error appears in the above-identified patent and that said Letters Patent is hereby corrected as shown below:

In the Claims, at column 399, Claim 1, please correct the following:

1. A method of inhibiting growth of a tumor cell that expresses "SEQ ID NO:743 or SEQ ID NO: 734" --161P2F10B (SEQ ID NOS: 743 or 745),-- comprising:

contacting said cell with an antibody or fragment thereof --that-- specifically binds to a protein having an amino acid sequence of SEQ ID NOS: 743 or 745, wherein the antibody or fragment thereof binds to "and inhibits the growth of" the tumor cell via the protein --, wherein the tumor cell is a kidney tumor cell--.

Signed and Sealed this

Twenty-fourth Day of October, 2006

JON W. DUDAS
*Director of the United States Patent and Trademark Office*

SEQUENCE LISTING

```
<160> NUMBER OF SEQ ID NOS: 765

<210> SEQ ID NO 1
<211> LENGTH: 9
<212> TYPE: PRT
<213> ORGANISM: Homo sapiens

<400> SEQUENCE: 1

Ser Met Asp Gly Phe Arg Ala Glu Tyr
 1               5

<210> SEQ ID NO 2
<211> LENGTH: 9
<212> TYPE: PRT
<213> ORGANISM: Homo sapiens

<400> SEQUENCE: 2

Asn Val Glu Ser Cys Pro Glu Gly Lys
 1               5

<210> SEQ ID NO 3
```

```
<211> LENGTH: 9
<212> TYPE: PRT
<213> ORGANISM: Homo sapiens

<400> SEQUENCE: 3

Cys Ser Asp Asp Cys Leu Gln Lys Lys
 1               5

<210> SEQ ID NO 4
<211> LENGTH: 9
<212> TYPE: PRT
<213> ORGANISM: Homo sapiens

<400> SEQUENCE: 4

Lys Thr Glu Val Glu Pro Phe Glu Asn
 1               5

<210> SEQ ID NO 5
<211> LENGTH: 9
<212> TYPE: PRT
<213> ORGANISM: Homo sapiens

<400> SEQUENCE: 5

Trp Leu Asp Leu Pro Lys Ala Glu Arg
 1               5

<210> SEQ ID NO 6
<211> LENGTH: 9
<212> TYPE: PRT
<213> ORGANISM: Homo sapiens

<400> SEQUENCE: 6

Val Ser Glu Ile Leu Gln Leu Lys Thr
 1               5

<210> SEQ ID NO 7
<211> LENGTH: 9
<212> TYPE: PRT
<213> ORGANISM: Homo sapiens

<400> SEQUENCE: 7

Lys Pro Asp Gln His Phe Lys Pro Tyr
 1               5

<210> SEQ ID NO 8
<211> LENGTH: 9
<212> TYPE: PRT
<213> ORGANISM: Homo sapiens

<400> SEQUENCE: 8

Gln Thr Tyr Cys Asn Lys Met Glu Tyr
 1               5

<210> SEQ ID NO 9
<211> LENGTH: 9
<212> TYPE: PRT
<213> ORGANISM: Homo sapiens

<400> SEQUENCE: 9

Gly Met Asp Gln Thr Tyr Cys Asn Lys
 1               5

<210> SEQ ID NO 10
<211> LENGTH: 9
<212> TYPE: PRT
```

```
<213> ORGANISM: Homo sapiens

<400> SEQUENCE: 10

Arg Cys Asp Val Ala Cys Lys Asp Arg
 1               5

<210> SEQ ID NO 11
<211> LENGTH: 9
<212> TYPE: PRT
<213> ORGANISM: Homo sapiens

<400> SEQUENCE: 11

Asn Ile Glu Val Tyr Asn Leu Met Cys
 1               5

<210> SEQ ID NO 12
<211> LENGTH: 9
<212> TYPE: PRT
<213> ORGANISM: Homo sapiens

<400> SEQUENCE: 12

Lys Met Glu Tyr Met Thr Asp Tyr Phe
 1               5

<210> SEQ ID NO 13
<211> LENGTH: 9
<212> TYPE: PRT
<213> ORGANISM: Homo sapiens

<400> SEQUENCE: 13

Cys Val Glu Ser Thr Arg Ile Trp Met
 1               5

<210> SEQ ID NO 14
<211> LENGTH: 9
<212> TYPE: PRT
<213> ORGANISM: Homo sapiens

<400> SEQUENCE: 14

Trp Leu Asp Val Leu Pro Phe Ile Ile
 1               5

<210> SEQ ID NO 15
<211> LENGTH: 9
<212> TYPE: PRT
<213> ORGANISM: Homo sapiens

<400> SEQUENCE: 15

Phe Val Asp Gln Gln Trp Leu Ala Val
 1               5

<210> SEQ ID NO 16
<211> LENGTH: 9
<212> TYPE: PRT
<213> ORGANISM: Homo sapiens

<400> SEQUENCE: 16

Asn Val Asp His Cys Leu Leu Tyr His
 1               5

<210> SEQ ID NO 17
<211> LENGTH: 9
<212> TYPE: PRT
<213> ORGANISM: Homo sapiens
```

```
<400> SEQUENCE: 17

Asn Thr Asp Val Pro Ile Pro Thr His
 1               5

<210> SEQ ID NO 18
<211> LENGTH: 9
<212> TYPE: PRT
<213> ORGANISM: Homo sapiens

<400> SEQUENCE: 18

Asp Thr Leu Met Pro Asn Ile Asn Lys
 1               5

<210> SEQ ID NO 19
<211> LENGTH: 9
<212> TYPE: PRT
<213> ORGANISM: Homo sapiens

<400> SEQUENCE: 19

Ile Thr Ser Asn Leu Val Pro Met Tyr
 1               5

<210> SEQ ID NO 20
<211> LENGTH: 9
<212> TYPE: PRT
<213> ORGANISM: Homo sapiens

<400> SEQUENCE: 20

Val Val Ser Gly Pro Ile Phe Asp Tyr
 1               5

<210> SEQ ID NO 21
<211> LENGTH: 9
<212> TYPE: PRT
<213> ORGANISM: Homo sapiens

<400> SEQUENCE: 21

Ser Met Glu Ala Ile Phe Leu Ala His
 1               5

<210> SEQ ID NO 22
<211> LENGTH: 9
<212> TYPE: PRT
<213> ORGANISM: Homo sapiens

<400> SEQUENCE: 22

Ala Thr Glu Gln Pro Val Lys Lys Asn
 1               5

<210> SEQ ID NO 23
<211> LENGTH: 9
<212> TYPE: PRT
<213> ORGANISM: Homo sapiens

<400> SEQUENCE: 23

Arg Val Pro Pro Ser Glu Ser Gln Lys
 1               5

<210> SEQ ID NO 24
<211> LENGTH: 9
<212> TYPE: PRT
<213> ORGANISM: Homo sapiens

<400> SEQUENCE: 24
```

```
Tyr Leu Thr Pro Asp Leu Pro Lys Arg
 1               5

<210> SEQ ID NO 25
<211> LENGTH: 9
<212> TYPE: PRT
<213> ORGANISM: Homo sapiens

<400> SEQUENCE: 25

Pro Ser Glu Ser Gln Lys Cys Ser Phe
 1               5

<210> SEQ ID NO 26
<211> LENGTH: 9
<212> TYPE: PRT
<213> ORGANISM: Homo sapiens

<400> SEQUENCE: 26

Gly Ser Glu Val Ala Ile Asn Gly Ser
 1               5

<210> SEQ ID NO 27
<211> LENGTH: 9
<212> TYPE: PRT
<213> ORGANISM: Homo sapiens

<400> SEQUENCE: 27

Asn Ser Glu Glu Ile Val Arg Asn Leu
 1               5

<210> SEQ ID NO 28
<211> LENGTH: 9
<212> TYPE: PRT
<213> ORGANISM: Homo sapiens

<400> SEQUENCE: 28

Lys Thr Cys Gly Ile His Ser Lys Tyr
 1               5

<210> SEQ ID NO 29
<211> LENGTH: 9
<212> TYPE: PRT
<213> ORGANISM: Homo sapiens

<400> SEQUENCE: 29

Met Thr Asp Tyr Phe Pro Arg Ile Asn
 1               5

<210> SEQ ID NO 30
<211> LENGTH: 9
<212> TYPE: PRT
<213> ORGANISM: Homo sapiens

<400> SEQUENCE: 30

Asn Asn Glu Phe Arg Ser Met Glu Ala
 1               5

<210> SEQ ID NO 31
<211> LENGTH: 9
<212> TYPE: PRT
<213> ORGANISM: Homo sapiens

<400> SEQUENCE: 31

Ser Leu Asp Cys Phe Cys Pro His Leu
 1               5
```

```
<210> SEQ ID NO 32
<211> LENGTH: 9
<212> TYPE: PRT
<213> ORGANISM: Homo sapiens

<400> SEQUENCE: 32

Asn Leu Val Pro Met Tyr Glu Glu Phe
1               5

<210> SEQ ID NO 33
<211> LENGTH: 9
<212> TYPE: PRT
<213> ORGANISM: Homo sapiens

<400> SEQUENCE: 33

Phe Leu Tyr Pro Pro Ala Ser Asn Arg
1               5

<210> SEQ ID NO 34
<211> LENGTH: 9
<212> TYPE: PRT
<213> ORGANISM: Homo sapiens

<400> SEQUENCE: 34

Gly Leu Gly Leu Arg Lys Leu Glu Lys
1               5

<210> SEQ ID NO 35
<211> LENGTH: 9
<212> TYPE: PRT
<213> ORGANISM: Homo sapiens

<400> SEQUENCE: 35

Ser Cys Ser Asp Asp Cys Leu Gln Lys
1               5

<210> SEQ ID NO 36
<211> LENGTH: 9
<212> TYPE: PRT
<213> ORGANISM: Homo sapiens

<400> SEQUENCE: 36

Cys Ala Asp Tyr Lys Ser Val Cys Gln
1               5

<210> SEQ ID NO 37
<211> LENGTH: 9
<212> TYPE: PRT
<213> ORGANISM: Homo sapiens

<400> SEQUENCE: 37

Ile Ile Asp Asn Asn Met Tyr Asp Val
1               5

<210> SEQ ID NO 38
<211> LENGTH: 9
<212> TYPE: PRT
<213> ORGANISM: Homo sapiens

<400> SEQUENCE: 38

Arg Ala Asp Val Arg Val Pro Pro Ser
1               5
```

```
<210> SEQ ID NO 39
<211> LENGTH: 9
<212> TYPE: PRT
<213> ORGANISM: Homo sapiens

<400> SEQUENCE: 39

Gln Leu Glu Gln Val Asn Gln Met Leu
 1               5

<210> SEQ ID NO 40
<211> LENGTH: 9
<212> TYPE: PRT
<213> ORGANISM: Homo sapiens

<400> SEQUENCE: 40

Gly Leu Glu Asn Cys Arg Cys Asp Val
 1               5

<210> SEQ ID NO 41
<211> LENGTH: 9
<212> TYPE: PRT
<213> ORGANISM: Homo sapiens

<400> SEQUENCE: 41

Trp Val Glu Glu Arg Phe Thr Ala His
 1               5

<210> SEQ ID NO 42
<211> LENGTH: 9
<212> TYPE: PRT
<213> ORGANISM: Homo sapiens

<400> SEQUENCE: 42

Trp Leu Glu Glu Asn Cys Asp Thr Ala
 1               5

<210> SEQ ID NO 43
<211> LENGTH: 9
<212> TYPE: PRT
<213> ORGANISM: Homo sapiens

<400> SEQUENCE: 43

Arg Leu Glu Ala Ser Leu Cys Ser Cys
 1               5

<210> SEQ ID NO 44
<211> LENGTH: 9
<212> TYPE: PRT
<213> ORGANISM: Homo sapiens

<400> SEQUENCE: 44

Glu Val Glu Pro Phe Glu Asn Ile Glu
 1               5

<210> SEQ ID NO 45
<211> LENGTH: 9
<212> TYPE: PRT
<213> ORGANISM: Homo sapiens

<400> SEQUENCE: 45

Gln Glu Glu Ile Thr Ala Thr Val Lys
 1               5

<210> SEQ ID NO 46
<211> LENGTH: 9
```

```
<212> TYPE: PRT
<213> ORGANISM: Homo sapiens

<400> SEQUENCE: 46

Lys Leu Glu Lys Gln Gly Ser Cys Arg
 1               5

<210> SEQ ID NO 47
<211> LENGTH: 9
<212> TYPE: PRT
<213> ORGANISM: Homo sapiens

<400> SEQUENCE: 47

His Ala Glu Glu Val Ser Lys Phe Ser
 1               5

<210> SEQ ID NO 48
<211> LENGTH: 9
<212> TYPE: PRT
<213> ORGANISM: Homo sapiens

<400> SEQUENCE: 48

Thr Ser Asp Ser Gln Tyr Asp Ala Leu
 1               5

<210> SEQ ID NO 49
<211> LENGTH: 9
<212> TYPE: PRT
<213> ORGANISM: Homo sapiens

<400> SEQUENCE: 49

Lys Asn Ile Thr His Gly Phe Leu Tyr
 1               5

<210> SEQ ID NO 50
<211> LENGTH: 9
<212> TYPE: PRT
<213> ORGANISM: Homo sapiens

<400> SEQUENCE: 50

Lys Asn Val Asp His Cys Leu Leu Tyr
 1               5

<210> SEQ ID NO 51
<211> LENGTH: 10
<212> TYPE: PRT
<213> ORGANISM: Homo sapiens

<400> SEQUENCE: 51

Val Ser Glu Ile Leu Gln Leu Lys Thr Tyr
 1               5                  10

<210> SEQ ID NO 52
<211> LENGTH: 10
<212> TYPE: PRT
<213> ORGANISM: Homo sapiens

<400> SEQUENCE: 52

Met Thr Asp Tyr Phe Pro Arg Ile Asn Phe
 1               5                  10

<210> SEQ ID NO 53
<211> LENGTH: 10
<212> TYPE: PRT
<213> ORGANISM: Homo sapiens
```

```
<400> SEQUENCE: 53

Asn Thr Asp Val Pro Ile Pro Thr His Tyr
 1               5                  10

<210> SEQ ID NO 54
<211> LENGTH: 10
<212> TYPE: PRT
<213> ORGANISM: Homo sapiens

<400> SEQUENCE: 54

Asp Val Glu Leu Leu Thr Gly Leu Asp Phe
 1               5                  10

<210> SEQ ID NO 55
<211> LENGTH: 10
<212> TYPE: PRT
<213> ORGANISM: Homo sapiens

<400> SEQUENCE: 55

Glu Val Glu Pro Phe Glu Asn Ile Glu Val
 1               5                  10

<210> SEQ ID NO 56
<211> LENGTH: 10
<212> TYPE: PRT
<213> ORGANISM: Homo sapiens

<400> SEQUENCE: 56

Gly Ser Phe Pro Ser Ile Tyr Met Pro Tyr
 1               5                  10

<210> SEQ ID NO 57
<211> LENGTH: 10
<212> TYPE: PRT
<213> ORGANISM: Homo sapiens

<400> SEQUENCE: 57

Thr Pro Asp Leu Pro Lys Arg Leu His Tyr
 1               5                  10

<210> SEQ ID NO 58
<211> LENGTH: 10
<212> TYPE: PRT
<213> ORGANISM: Homo sapiens

<400> SEQUENCE: 58

Leu Ala Asp His Gly Met Asp Gln Thr Tyr
 1               5                  10

<210> SEQ ID NO 59
<211> LENGTH: 10
<212> TYPE: PRT
<213> ORGANISM: Homo sapiens

<400> SEQUENCE: 59

Val Ser Gly Pro Ile Phe Asp Tyr Asn Tyr
 1               5                  10

<210> SEQ ID NO 60
<211> LENGTH: 10
<212> TYPE: PRT
<213> ORGANISM: Homo sapiens

<400> SEQUENCE: 60
```

```
Gly Ser Glu Val Ala Ile Asn Gly Ser Phe
 1               5                  10
```

<210> SEQ ID NO 61
<211> LENGTH: 10
<212> TYPE: PRT
<213> ORGANISM: Homo sapiens

<400> SEQUENCE: 61

```
Asn Val Asp His Cys Leu Leu Tyr His Arg
 1               5                  10
```

<210> SEQ ID NO 62
<211> LENGTH: 10
<212> TYPE: PRT
<213> ORGANISM: Homo sapiens

<400> SEQUENCE: 62

```
Phe Val Asp Gln Gln Trp Leu Ala Val Arg
 1               5                  10
```

<210> SEQ ID NO 63
<211> LENGTH: 10
<212> TYPE: PRT
<213> ORGANISM: Homo sapiens

<400> SEQUENCE: 63

```
Pro Ser Glu Ser Gln Lys Cys Ser Phe Tyr
 1               5                  10
```

<210> SEQ ID NO 64
<211> LENGTH: 10
<212> TYPE: PRT
<213> ORGANISM: Homo sapiens

<400> SEQUENCE: 64

```
His Ala Glu Glu Val Ser Lys Phe Ser Val
 1               5                  10
```

<210> SEQ ID NO 65
<211> LENGTH: 10
<212> TYPE: PRT
<213> ORGANISM: Homo sapiens

<400> SEQUENCE: 65

```
His Arg Glu Tyr Val Ser Gly Phe Gly Lys
 1               5                  10
```

<210> SEQ ID NO 66
<211> LENGTH: 10
<212> TYPE: PRT
<213> ORGANISM: Homo sapiens

<400> SEQUENCE: 66

```
Gln Leu Glu Gln Val Asn Gln Met Leu Asn
 1               5                  10
```

<210> SEQ ID NO 67
<211> LENGTH: 10
<212> TYPE: PRT
<213> ORGANISM: Homo sapiens

<400> SEQUENCE: 67

Thr Gln Glu Glu Ile Thr Ala Thr Val Lys

```
1               5                   10
```

<210> SEQ ID NO 68
<211> LENGTH: 10
<212> TYPE: PRT
<213> ORGANISM: Homo sapiens

<400> SEQUENCE: 68

```
His Phe Asp Ala Pro Asp Glu Ile Thr Lys
1               5                   10
```

<210> SEQ ID NO 69
<211> LENGTH: 10
<212> TYPE: PRT
<213> ORGANISM: Homo sapiens

<400> SEQUENCE: 69

```
Asn Val Val Ser Gly Pro Ile Phe Asp Tyr
1               5                   10
```

<210> SEQ ID NO 70
<211> LENGTH: 10
<212> TYPE: PRT
<213> ORGANISM: Homo sapiens

<400> SEQUENCE: 70

```
Val Val Asp His Ala Phe Gly Met Leu Met
1               5                   10
```

<210> SEQ ID NO 71
<211> LENGTH: 10
<212> TYPE: PRT
<213> ORGANISM: Homo sapiens

<400> SEQUENCE: 71

```
Lys Thr Glu Val Glu Pro Phe Glu Asn Ile
1               5                   10
```

<210> SEQ ID NO 72
<211> LENGTH: 10
<212> TYPE: PRT
<213> ORGANISM: Homo sapiens

<400> SEQUENCE: 72

```
Ala Thr Glu Gln Pro Val Lys Lys Asn Thr
1               5                   10
```

<210> SEQ ID NO 73
<211> LENGTH: 10
<212> TYPE: PRT
<213> ORGANISM: Homo sapiens

<400> SEQUENCE: 73

```
Tyr Glu Glu Phe Arg Lys Met Trp Asp Tyr
1               5                   10
```

<210> SEQ ID NO 74
<211> LENGTH: 10
<212> TYPE: PRT
<213> ORGANISM: Homo sapiens

<400> SEQUENCE: 74

```
Lys Pro Glu Ala Leu Trp Val Glu Glu Arg
1               5                   10
```

```
<210> SEQ ID NO 75
<211> LENGTH: 10
<212> TYPE: PRT
<213> ORGANISM: Homo sapiens

<400> SEQUENCE: 75

Asp Val Leu Pro Phe Ile Ile Pro His Arg
1               5                   10

<210> SEQ ID NO 76
<211> LENGTH: 10
<212> TYPE: PRT
<213> ORGANISM: Homo sapiens

<400> SEQUENCE: 76

Thr Leu Met Pro Asn Ile Asn Lys Leu Lys
1               5                   10

<210> SEQ ID NO 77
<211> LENGTH: 10
<212> TYPE: PRT
<213> ORGANISM: Homo sapiens

<400> SEQUENCE: 77

Trp Val Glu Glu Arg Phe Thr Ala His Ile
1               5                   10

<210> SEQ ID NO 78
<211> LENGTH: 10
<212> TYPE: PRT
<213> ORGANISM: Homo sapiens

<400> SEQUENCE: 78

Lys Leu Glu Lys Gln Gly Ser Cys Arg Lys
1               5                   10

<210> SEQ ID NO 79
<211> LENGTH: 10
<212> TYPE: PRT
<213> ORGANISM: Homo sapiens

<400> SEQUENCE: 79

Thr Ser Asp Ser Gln Tyr Asp Ala Leu Ile
1               5                   10

<210> SEQ ID NO 80
<211> LENGTH: 10
<212> TYPE: PRT
<213> ORGANISM: Homo sapiens

<400> SEQUENCE: 80

Phe Ser Met Asp Gly Phe Arg Ala Glu Tyr
1               5                   10

<210> SEQ ID NO 81
<211> LENGTH: 10
<212> TYPE: PRT
<213> ORGANISM: Homo sapiens

<400> SEQUENCE: 81

Cys Ser Cys Ser Asp Cys Leu Gln Lys
1               5                   10

<210> SEQ ID NO 82
```

```
<211> LENGTH: 10
<212> TYPE: PRT
<213> ORGANISM: Homo sapiens

<400> SEQUENCE: 82

Asn Ser Glu Glu Ile Val Arg Asn Leu Ser
1               5                   10

<210> SEQ ID NO 83
<211> LENGTH: 10
<212> TYPE: PRT
<213> ORGANISM: Homo sapiens

<400> SEQUENCE: 83

His Asn Ile Pro His Asp Phe Phe Ser Phe
1               5                   10

<210> SEQ ID NO 84
<211> LENGTH: 10
<212> TYPE: PRT
<213> ORGANISM: Homo sapiens

<400> SEQUENCE: 84

Asp Tyr Phe Pro Arg Ile Asn Phe Phe Tyr
1               5                   10

<210> SEQ ID NO 85
<211> LENGTH: 10
<212> TYPE: PRT
<213> ORGANISM: Homo sapiens

<400> SEQUENCE: 85

Gly Phe Asp Leu Pro Pro Val Ile Leu Phe
1               5                   10

<210> SEQ ID NO 86
<211> LENGTH: 10
<212> TYPE: PRT
<213> ORGANISM: Homo sapiens

<400> SEQUENCE: 86

Val Pro Asp Cys Leu Arg Ala Asp Val Arg
1               5                   10

<210> SEQ ID NO 87
<211> LENGTH: 10
<212> TYPE: PRT
<213> ORGANISM: Homo sapiens

<400> SEQUENCE: 87

Tyr Pro Glu Ser His Gly Ile Ile Asp Asn
1               5                   10

<210> SEQ ID NO 88
<211> LENGTH: 10
<212> TYPE: PRT
<213> ORGANISM: Homo sapiens

<400> SEQUENCE: 88

Asn Leu Val Pro Met Tyr Glu Glu Phe Arg
1               5                   10

<210> SEQ ID NO 89
<211> LENGTH: 10
<212> TYPE: PRT
```

<213> ORGANISM: Homo sapiens

<400> SEQUENCE: 89

Leu Val Pro Met Tyr Glu Glu Phe Arg Lys
1               5                   10

<210> SEQ ID NO 90
<211> LENGTH: 10
<212> TYPE: PRT
<213> ORGANISM: Homo sapiens

<400> SEQUENCE: 90

Gly Leu Gly Leu Gly Leu Gly Leu Arg Lys
1               5                   10

<210> SEQ ID NO 91
<211> LENGTH: 10
<212> TYPE: PRT
<213> ORGANISM: Homo sapiens

<400> SEQUENCE: 91

Leu Thr Leu Ala Thr Glu Gln Pro Val Lys
1               5                   10

<210> SEQ ID NO 92
<211> LENGTH: 10
<212> TYPE: PRT
<213> ORGANISM: Homo sapiens

<400> SEQUENCE: 92

Leu Ile Thr Ser Asn Leu Val Pro Met Tyr
1               5                   10

<210> SEQ ID NO 93
<211> LENGTH: 10
<212> TYPE: PRT
<213> ORGANISM: Homo sapiens

<400> SEQUENCE: 93

Cys Val Glu Ser Thr Arg Ile Trp Met Cys
1               5                   10

<210> SEQ ID NO 94
<211> LENGTH: 10
<212> TYPE: PRT
<213> ORGANISM: Homo sapiens

<400> SEQUENCE: 94

Trp Leu Glu Glu Asn Cys Asp Thr Ala Gln
1               5                   10

<210> SEQ ID NO 95
<211> LENGTH: 10
<212> TYPE: PRT
<213> ORGANISM: Homo sapiens

<400> SEQUENCE: 95

Arg Ala Glu Tyr Leu Tyr Thr Trp Asp Thr
1               5                   10

<210> SEQ ID NO 96
<211> LENGTH: 10
<212> TYPE: PRT
<213> ORGANISM: Homo sapiens

```
<400> SEQUENCE: 96

Arg Leu Glu Ala Ser Leu Cys Ser Cys Ser
 1               5                  10

<210> SEQ ID NO 97
<211> LENGTH: 10
<212> TYPE: PRT
<213> ORGANISM: Homo sapiens

<400> SEQUENCE: 97

Ser Met Glu Ala Ile Phe Leu Ala His Gly
 1               5                  10

<210> SEQ ID NO 98
<211> LENGTH: 10
<212> TYPE: PRT
<213> ORGANISM: Homo sapiens

<400> SEQUENCE: 98

Gly Leu Glu Asn Cys Arg Cys Asp Val Ala
 1               5                  10

<210> SEQ ID NO 99
<211> LENGTH: 10
<212> TYPE: PRT
<213> ORGANISM: Homo sapiens

<400> SEQUENCE: 99

Phe Ser Phe Asn Ser Glu Glu Ile Val Arg
 1               5                  10

<210> SEQ ID NO 100
<211> LENGTH: 10
<212> TYPE: PRT
<213> ORGANISM: Homo sapiens

<400> SEQUENCE: 100

Ser Leu Asp Cys Phe Cys Pro His Leu Gln
 1               5                  10

<210> SEQ ID NO 101
<211> LENGTH: 9
<212> TYPE: PRT
<213> ORGANISM: Homo sapiens

<400> SEQUENCE: 101

Lys Met Trp Asp Tyr Phe His Ser Val
 1               5

<210> SEQ ID NO 102
<211> LENGTH: 9
<212> TYPE: PRT
<213> ORGANISM: Homo sapiens

<400> SEQUENCE: 102

Cys Leu Leu Tyr His Arg Glu Tyr Val
 1               5

<210> SEQ ID NO 103
<211> LENGTH: 9
<212> TYPE: PRT
<213> ORGANISM: Homo sapiens

<400> SEQUENCE: 103
```

-continued

Tyr Met Thr Asp Tyr Phe Pro Arg Ile
1               5

<210> SEQ ID NO 104
<211> LENGTH: 9
<212> TYPE: PRT
<213> ORGANISM: Homo sapiens

<400> SEQUENCE: 104

Tyr Leu Pro Thr Phe Glu Thr Thr Ile
1               5

<210> SEQ ID NO 105
<211> LENGTH: 9
<212> TYPE: PRT
<213> ORGANISM: Homo sapiens

<400> SEQUENCE: 105

Thr Leu Met Pro Asn Ile Asn Lys Leu
1               5

<210> SEQ ID NO 106
<211> LENGTH: 9
<212> TYPE: PRT
<213> ORGANISM: Homo sapiens

<400> SEQUENCE: 106

Trp Leu Thr Ala Met Tyr Gln Gly Leu
1               5

<210> SEQ ID NO 107
<211> LENGTH: 9
<212> TYPE: PRT
<213> ORGANISM: Homo sapiens

<400> SEQUENCE: 107

Asn Leu Met Cys Asp Leu Leu Arg Ile
1               5

<210> SEQ ID NO 108
<211> LENGTH: 9
<212> TYPE: PRT
<213> ORGANISM: Homo sapiens

<400> SEQUENCE: 108

Tyr Leu Tyr Thr Trp Asp Thr Leu Met
1               5

<210> SEQ ID NO 109
<211> LENGTH: 9
<212> TYPE: PRT
<213> ORGANISM: Homo sapiens

<400> SEQUENCE: 109

Asn Leu Pro Phe Gly Arg Pro Arg Val
1               5

<210> SEQ ID NO 110
<211> LENGTH: 9
<212> TYPE: PRT
<213> ORGANISM: Homo sapiens

<400> SEQUENCE: 110

Ala Leu Trp Val Glu Glu Arg Phe Thr
1               5

-continued

<210> SEQ ID NO 111
<211> LENGTH: 9
<212> TYPE: PRT
<213> ORGANISM: Homo sapiens

<400> SEQUENCE: 111

Trp Leu Asp Val Leu Pro Phe Ile Ile
1               5

<210> SEQ ID NO 112
<211> LENGTH: 9
<212> TYPE: PRT
<213> ORGANISM: Homo sapiens

<400> SEQUENCE: 112

Arg Ile Ser Thr Leu Leu Lys Trp Leu
1               5

<210> SEQ ID NO 113
<211> LENGTH: 9
<212> TYPE: PRT
<213> ORGANISM: Homo sapiens

<400> SEQUENCE: 113

Leu Leu Val Ile Met Ser Leu Gly Leu
1               5

<210> SEQ ID NO 114
<211> LENGTH: 9
<212> TYPE: PRT
<213> ORGANISM: Homo sapiens

<400> SEQUENCE: 114

Gly Leu Tyr Pro Glu Ser His Gly Ile
1               5

<210> SEQ ID NO 115
<211> LENGTH: 9
<212> TYPE: PRT
<213> ORGANISM: Homo sapiens

<400> SEQUENCE: 115

Ser Leu Asp Cys Phe Cys Pro His Leu
1               5

<210> SEQ ID NO 116
<211> LENGTH: 9
<212> TYPE: PRT
<213> ORGANISM: Homo sapiens

<400> SEQUENCE: 116

Arg Met Pro Met Trp Ser Ser Tyr Thr
1               5

<210> SEQ ID NO 117
<211> LENGTH: 9
<212> TYPE: PRT
<213> ORGANISM: Homo sapiens

<400> SEQUENCE: 117

Val Leu Leu Ala Leu Leu Val Ile Met
1               5

```
<210> SEQ ID NO 118
<211> LENGTH: 9
<212> TYPE: PRT
<213> ORGANISM: Homo sapiens

<400> SEQUENCE: 118

Ala Met Tyr Gln Gly Leu Lys Ala Ala
1               5

<210> SEQ ID NO 119
<211> LENGTH: 9
<212> TYPE: PRT
<213> ORGANISM: Homo sapiens

<400> SEQUENCE: 119

Arg Ile Asp Lys Val His Leu Phe Val
1               5

<210> SEQ ID NO 120
<211> LENGTH: 9
<212> TYPE: PRT
<213> ORGANISM: Homo sapiens

<400> SEQUENCE: 120

Phe Val Asp Gln Gln Trp Leu Ala Val
1               5

<210> SEQ ID NO 121
<211> LENGTH: 9
<212> TYPE: PRT
<213> ORGANISM: Homo sapiens

<400> SEQUENCE: 121

Val Ile Met Ser Leu Gly Leu Gly Leu
1               5

<210> SEQ ID NO 122
<211> LENGTH: 9
<212> TYPE: PRT
<213> ORGANISM: Homo sapiens

<400> SEQUENCE: 122

Thr Gln Leu Glu Gln Val Asn Gln Met
1               5

<210> SEQ ID NO 123
<211> LENGTH: 9
<212> TYPE: PRT
<213> ORGANISM: Homo sapiens

<400> SEQUENCE: 123

Ile Ile Pro His Arg Pro Thr Asn Val
1               5

<210> SEQ ID NO 124
<211> LENGTH: 9
<212> TYPE: PRT
<213> ORGANISM: Homo sapiens

<400> SEQUENCE: 124

Ile Ile Asp Asn Asn Met Tyr Asp Val
1               5

<210> SEQ ID NO 125
<211> LENGTH: 9
```

```
<212> TYPE: PRT
<213> ORGANISM: Homo sapiens

<400> SEQUENCE: 125

His Leu Phe Val Asp Gln Gln Trp Leu
 1               5

<210> SEQ ID NO 126
<211> LENGTH: 9
<212> TYPE: PRT
<213> ORGANISM: Homo sapiens

<400> SEQUENCE: 126

Gly Leu Asp Phe Tyr Gln Asp Lys Val
 1               5

<210> SEQ ID NO 127
<211> LENGTH: 9
<212> TYPE: PRT
<213> ORGANISM: Homo sapiens

<400> SEQUENCE: 127

Ser Gln Cys Pro Glu Gly Phe Asp Leu
 1               5

<210> SEQ ID NO 128
<211> LENGTH: 9
<212> TYPE: PRT
<213> ORGANISM: Homo sapiens

<400> SEQUENCE: 128

Tyr Asn Tyr Asp Gly His Phe Asp Ala
 1               5

<210> SEQ ID NO 129
<211> LENGTH: 9
<212> TYPE: PRT
<213> ORGANISM: Homo sapiens

<400> SEQUENCE: 129

Gln Val Val Asp His Ala Phe Gly Met
 1               5

<210> SEQ ID NO 130
<211> LENGTH: 9
<212> TYPE: PRT
<213> ORGANISM: Homo sapiens

<400> SEQUENCE: 130

Asn Leu His Asn Cys Val Asn Ile Ile
 1               5

<210> SEQ ID NO 131
<211> LENGTH: 9
<212> TYPE: PRT
<213> ORGANISM: Homo sapiens

<400> SEQUENCE: 131

Gly Leu Gly Leu Gly Leu Arg Lys Leu
 1               5

<210> SEQ ID NO 132
<211> LENGTH: 9
<212> TYPE: PRT
<213> ORGANISM: Homo sapiens
```

```
<400> SEQUENCE: 132

Cys Ile Val Leu Leu Ala Leu Leu Val
1               5

<210> SEQ ID NO 133
<211> LENGTH: 9
<212> TYPE: PRT
<213> ORGANISM: Homo sapiens

<400> SEQUENCE: 133

Val Leu Gln Lys Asn Val Asp His Cys
1               5

<210> SEQ ID NO 134
<211> LENGTH: 9
<212> TYPE: PRT
<213> ORGANISM: Homo sapiens

<400> SEQUENCE: 134

Met Leu Asn Leu Thr Gln Glu Glu Ile
1               5

<210> SEQ ID NO 135
<211> LENGTH: 9
<212> TYPE: PRT
<213> ORGANISM: Homo sapiens

<400> SEQUENCE: 135

Tyr Val Ser Gly Phe Gly Lys Ala Met
1               5

<210> SEQ ID NO 136
<211> LENGTH: 9
<212> TYPE: PRT
<213> ORGANISM: Homo sapiens

<400> SEQUENCE: 136

Leu Gln Leu Lys Thr Tyr Leu Pro Thr
1               5

<210> SEQ ID NO 137
<211> LENGTH: 9
<212> TYPE: PRT
<213> ORGANISM: Homo sapiens

<400> SEQUENCE: 137

Ser Val Cys Gly Phe Ala Asn Pro Leu
1               5

<210> SEQ ID NO 138
<211> LENGTH: 9
<212> TYPE: PRT
<213> ORGANISM: Homo sapiens

<400> SEQUENCE: 138

Lys Thr Tyr Leu Pro Thr Phe Glu Thr
1               5

<210> SEQ ID NO 139
<211> LENGTH: 9
<212> TYPE: PRT
<213> ORGANISM: Homo sapiens

<400> SEQUENCE: 139
```

```
Arg Ser Met Glu Ala Ile Phe Leu Ala
  1               5
```

<210> SEQ ID NO 140
<211> LENGTH: 9
<212> TYPE: PRT
<213> ORGANISM: Homo sapiens

<400> SEQUENCE: 140

```
Leu Thr Leu Ala Thr Glu Gln Pro Val
  1               5
```

<210> SEQ ID NO 141
<211> LENGTH: 9
<212> TYPE: PRT
<213> ORGANISM: Homo sapiens

<400> SEQUENCE: 141

```
Arg Val Ile Lys Ala Leu Gln Val Val
  1               5
```

<210> SEQ ID NO 142
<211> LENGTH: 9
<212> TYPE: PRT
<213> ORGANISM: Homo sapiens

<400> SEQUENCE: 142

```
Lys Ile Ala Cys Ile Val Leu Leu Ala
  1               5
```

<210> SEQ ID NO 143
<211> LENGTH: 9
<212> TYPE: PRT
<213> ORGANISM: Homo sapiens

<400> SEQUENCE: 143

```
Ile Val Leu Leu Ala Leu Leu Val Ile
  1               5
```

<210> SEQ ID NO 144
<211> LENGTH: 9
<212> TYPE: PRT
<213> ORGANISM: Homo sapiens

<400> SEQUENCE: 144

```
Val Asn Leu Asn Lys Asn Phe Ser Leu
  1               5
```

<210> SEQ ID NO 145
<211> LENGTH: 9
<212> TYPE: PRT
<213> ORGANISM: Homo sapiens

<400> SEQUENCE: 145

```
Asn Leu Thr Gln Glu Glu Ile Thr Ala
  1               5
```

<210> SEQ ID NO 146
<211> LENGTH: 9
<212> TYPE: PRT
<213> ORGANISM: Homo sapiens

<400> SEQUENCE: 146

```
Cys Leu Gln Lys Lys Asp Cys Cys Ala
```

```
1               5
```

<210> SEQ ID NO 147
<211> LENGTH: 9
<212> TYPE: PRT
<213> ORGANISM: Homo sapiens

<400> SEQUENCE: 147

```
Asp Leu Pro Lys Arg Leu His Tyr Ala
1               5
```

<210> SEQ ID NO 148
<211> LENGTH: 9
<212> TYPE: PRT
<213> ORGANISM: Homo sapiens

<400> SEQUENCE: 148

```
Glu Ile Leu Gln Leu Lys Thr Tyr Leu
1               5
```

<210> SEQ ID NO 149
<211> LENGTH: 9
<212> TYPE: PRT
<213> ORGANISM: Homo sapiens

<400> SEQUENCE: 149

```
Gly Leu Glu Asn Cys Arg Cys Asp Val
1               5
```

<210> SEQ ID NO 150
<211> LENGTH: 9
<212> TYPE: PRT
<213> ORGANISM: Homo sapiens

<400> SEQUENCE: 150

```
Phe Glu Asn Ile Glu Val Tyr Asn Leu
1               5
```

<210> SEQ ID NO 151
<211> LENGTH: 10
<212> TYPE: PRT
<213> ORGANISM: Homo sapiens

<400> SEQUENCE: 151

```
Lys Met Trp Asp Tyr Phe His Ser Val Leu
1               5                   10
```

<210> SEQ ID NO 152
<211> LENGTH: 10
<212> TYPE: PRT
<213> ORGANISM: Homo sapiens

<400> SEQUENCE: 152

```
Tyr Met Tyr Glu Gly Pro Ala Pro Arg Ile
1               5                   10
```

<210> SEQ ID NO 153
<211> LENGTH: 10
<212> TYPE: PRT
<213> ORGANISM: Homo sapiens

<400> SEQUENCE: 153

```
Ala Leu Trp Val Glu Glu Arg Phe Thr Ala
1               5                   10
```

```
<210> SEQ ID NO 154
<211> LENGTH: 10
<212> TYPE: PRT
<213> ORGANISM: Homo sapiens

<400> SEQUENCE: 154

Ile Leu Phe Ser Met Asp Gly Phe Arg Ala
1               5                   10

<210> SEQ ID NO 155
<211> LENGTH: 10
<212> TYPE: PRT
<213> ORGANISM: Homo sapiens

<400> SEQUENCE: 155

Phe Leu Tyr Pro Pro Ala Ser Asn Arg Thr
1               5                   10

<210> SEQ ID NO 156
<211> LENGTH: 10
<212> TYPE: PRT
<213> ORGANISM: Homo sapiens

<400> SEQUENCE: 156

Tyr Leu Thr Pro Asp Leu Pro Lys Arg Leu
1               5                   10

<210> SEQ ID NO 157
<211> LENGTH: 10
<212> TYPE: PRT
<213> ORGANISM: Homo sapiens

<400> SEQUENCE: 157

Gly Ile Ile Asp Asn Asn Met Tyr Asp Val
1               5                   10

<210> SEQ ID NO 158
<211> LENGTH: 10
<212> TYPE: PRT
<213> ORGANISM: Homo sapiens

<400> SEQUENCE: 158

Leu Leu Ala Leu Leu Val Ile Met Ser Leu
1               5                   10

<210> SEQ ID NO 159
<211> LENGTH: 10
<212> TYPE: PRT
<213> ORGANISM: Homo sapiens

<400> SEQUENCE: 159

Ala Leu Leu Val Ile Met Ser Leu Gly Leu
1               5                   10

<210> SEQ ID NO 160
<211> LENGTH: 10
<212> TYPE: PRT
<213> ORGANISM: Homo sapiens

<400> SEQUENCE: 160

Thr Leu Thr Leu Ala Thr Glu Gln Pro Val
1               5                   10

<210> SEQ ID NO 161
```

-continued

<211> LENGTH: 10
<212> TYPE: PRT
<213> ORGANISM: Homo sapiens

<400> SEQUENCE: 161

Leu Leu Ala Asp His Gly Met Asp Gln Thr
1               5                   10

<210> SEQ ID NO 162
<211> LENGTH: 10
<212> TYPE: PRT
<213> ORGANISM: Homo sapiens

<400> SEQUENCE: 162

Tyr Thr Trp Asp Thr Leu Met Pro Asn Ile
1               5                   10

<210> SEQ ID NO 163
<211> LENGTH: 10
<212> TYPE: PRT
<213> ORGANISM: Homo sapiens

<400> SEQUENCE: 163

Arg Met Pro Met Trp Ser Ser Tyr Thr Val
1               5                   10

<210> SEQ ID NO 164
<211> LENGTH: 10
<212> TYPE: PRT
<213> ORGANISM: Homo sapiens

<400> SEQUENCE: 164

Phe Ile Ile Pro His Arg Pro Thr Asn Val
1               5                   10

<210> SEQ ID NO 165
<211> LENGTH: 10
<212> TYPE: PRT
<213> ORGANISM: Homo sapiens

<400> SEQUENCE: 165

Val Leu Gln Lys Asn Val Asp His Cys Leu
1               5                   10

<210> SEQ ID NO 166
<211> LENGTH: 10
<212> TYPE: PRT
<213> ORGANISM: Homo sapiens

<400> SEQUENCE: 166

Trp Leu Ala Val Arg Ser Lys Ser Asn Thr
1               5                   10

<210> SEQ ID NO 167
<211> LENGTH: 10
<212> TYPE: PRT
<213> ORGANISM: Homo sapiens

<400> SEQUENCE: 167

Arg Ile Trp Met Cys Asn Lys Phe Arg Cys
1               5                   10

<210> SEQ ID NO 168
<211> LENGTH: 10
<212> TYPE: PRT

<213> ORGANISM: Homo sapiens

<400> SEQUENCE: 168

Thr Gln Leu Glu Gln Val Asn Gln Met Leu
 1               5                  10

<210> SEQ ID NO 169
<211> LENGTH: 10
<212> TYPE: PRT
<213> ORGANISM: Homo sapiens

<400> SEQUENCE: 169

Ile Met Ser Leu Gly Leu Gly Leu Gly Leu
 1               5                  10

<210> SEQ ID NO 170
<211> LENGTH: 10
<212> TYPE: PRT
<213> ORGANISM: Homo sapiens

<400> SEQUENCE: 170

Thr Val Pro Asp Cys Leu Arg Ala Asp Val
 1               5                  10

<210> SEQ ID NO 171
<211> LENGTH: 10
<212> TYPE: PRT
<213> ORGANISM: Homo sapiens

<400> SEQUENCE: 171

Lys Ile Ala Cys Ile Val Leu Leu Ala Leu
 1               5                  10

<210> SEQ ID NO 172
<211> LENGTH: 10
<212> TYPE: PRT
<213> ORGANISM: Homo sapiens

<400> SEQUENCE: 172

Ser Leu Gly Leu Gly Leu Gly Leu Gly Leu
 1               5                  10

<210> SEQ ID NO 173
<211> LENGTH: 10
<212> TYPE: PRT
<213> ORGANISM: Homo sapiens

<400> SEQUENCE: 173

Ile Leu Gln Leu Lys Thr Tyr Leu Pro Thr
 1               5                  10

<210> SEQ ID NO 174
<211> LENGTH: 10
<212> TYPE: PRT
<213> ORGANISM: Homo sapiens

<400> SEQUENCE: 174

Ala Met Tyr Gln Gly Leu Lys Ala Ala Thr
 1               5                  10

<210> SEQ ID NO 175
<211> LENGTH: 10
<212> TYPE: PRT
<213> ORGANISM: Homo sapiens -continued

```
<400> SEQUENCE: 175

Asn Leu Thr Gln Glu Glu Ile Thr Ala Thr
1               5                   10

<210> SEQ ID NO 176
<211> LENGTH: 10
<212> TYPE: PRT
<213> ORGANISM: Homo sapiens

<400> SEQUENCE: 176

Ser Met Asp Gly Phe Arg Ala Glu Tyr Leu
1               5                   10

<210> SEQ ID NO 177
<211> LENGTH: 10
<212> TYPE: PRT
<213> ORGANISM: Homo sapiens

<400> SEQUENCE: 177

Cys Cys Trp Asp Phe Glu Asp Thr Cys Val
1               5                   10

<210> SEQ ID NO 178
<211> LENGTH: 10
<212> TYPE: PRT
<213> ORGANISM: Homo sapiens

<400> SEQUENCE: 178

Gln Met Leu Asn Leu Thr Gln Glu Glu Ile
1               5                   10

<210> SEQ ID NO 179
<211> LENGTH: 10
<212> TYPE: PRT
<213> ORGANISM: Homo sapiens

<400> SEQUENCE: 179

Leu Gln Asn Ser Thr Gln Leu Glu Gln Val
1               5                   10

<210> SEQ ID NO 180
<211> LENGTH: 10
<212> TYPE: PRT
<213> ORGANISM: Homo sapiens

<400> SEQUENCE: 180

Ser Glu Ser Gln Lys Cys Ser Phe Tyr Leu
1               5                   10

<210> SEQ ID NO 181
<211> LENGTH: 10
<212> TYPE: PRT
<213> ORGANISM: Homo sapiens

<400> SEQUENCE: 181

Ala Leu Ile Thr Ser Asn Leu Val Pro Met
1               5                   10

<210> SEQ ID NO 182
<211> LENGTH: 10
<212> TYPE: PRT
<213> ORGANISM: Homo sapiens

<400> SEQUENCE: 182
```

-continued

Ser Leu Cys Ser Cys Ser Asp Asp Cys Leu
1               5                   10

<210> SEQ ID NO 183
<211> LENGTH: 10
<212> TYPE: PRT
<213> ORGANISM: Homo sapiens

<400> SEQUENCE: 183

Arg Leu His Tyr Ala Lys Asn Val Arg Ile
1               5                   10

<210> SEQ ID NO 184
<211> LENGTH: 10
<212> TYPE: PRT
<213> ORGANISM: Homo sapiens

<400> SEQUENCE: 184

Ser Val Cys Gln Gly Glu Thr Ser Trp Leu
1               5                   10

<210> SEQ ID NO 185
<211> LENGTH: 10
<212> TYPE: PRT
<213> ORGANISM: Homo sapiens

<400> SEQUENCE: 185

Leu Met Pro Asn Ile Asn Lys Leu Lys Thr
1               5                   10

<210> SEQ ID NO 186
<211> LENGTH: 10
<212> TYPE: PRT
<213> ORGANISM: Homo sapiens

<400> SEQUENCE: 186

Asn Leu His Asn Cys Val Asn Ile Ile Leu
1               5                   10

<210> SEQ ID NO 187
<211> LENGTH: 10
<212> TYPE: PRT
<213> ORGANISM: Homo sapiens

<400> SEQUENCE: 187

Val Gln Pro Val Ser Glu Ile Leu Gln Leu
1               5                   10

<210> SEQ ID NO 188
<211> LENGTH: 10
<212> TYPE: PRT
<213> ORGANISM: Homo sapiens

<400> SEQUENCE: 188

Val Pro Phe Glu Glu Arg Ile Ser Thr Leu
1               5                   10

<210> SEQ ID NO 189
<211> LENGTH: 10
<212> TYPE: PRT
<213> ORGANISM: Homo sapiens

<400> SEQUENCE: 189

Lys Thr Phe Pro Asn His Tyr Thr Ile Val
1               5                   10

<210> SEQ ID NO 190
<211> LENGTH: 10
<212> TYPE: PRT
<213> ORGANISM: Homo sapiens

<400> SEQUENCE: 190

Arg Gly Leu Glu Asn Cys Arg Cys Asp Val
1               5                   10

<210> SEQ ID NO 191
<211> LENGTH: 10
<212> TYPE: PRT
<213> ORGANISM: Homo sapiens

<400> SEQUENCE: 191

Leu Thr Gln Glu Glu Ile Thr Ala Thr Val
1               5                   10

<210> SEQ ID NO 192
<211> LENGTH: 10
<212> TYPE: PRT
<213> ORGANISM: Homo sapiens

<400> SEQUENCE: 192

Asp Leu Pro Pro Val Ile Leu Phe Ser Met
1               5                   10

<210> SEQ ID NO 193
<211> LENGTH: 10
<212> TYPE: PRT
<213> ORGANISM: Homo sapiens

<400> SEQUENCE: 193

Leu Gln Val Val Asp His Ala Phe Gly Met
1               5                   10

<210> SEQ ID NO 194
<211> LENGTH: 10
<212> TYPE: PRT
<213> ORGANISM: Homo sapiens

<400> SEQUENCE: 194

His Leu Phe Val Asp Gln Gln Trp Leu Ala
1               5                   10

<210> SEQ ID NO 195
<211> LENGTH: 10
<212> TYPE: PRT
<213> ORGANISM: Homo sapiens

<400> SEQUENCE: 195

Trp Val Glu Glu Arg Phe Thr Ala His Ile
1               5                   10

<210> SEQ ID NO 196
<211> LENGTH: 10
<212> TYPE: PRT
<213> ORGANISM: Homo sapiens

<400> SEQUENCE: 196

Lys Pro Asp Gln His Phe Lys Pro Tyr Leu
1               5                   10

```
<210> SEQ ID NO 197
<211> LENGTH: 10
<212> TYPE: PRT
<213> ORGANISM: Homo sapiens

<400> SEQUENCE: 197

Ser Ile Tyr Met Pro Tyr Asn Gly Ser Val
1               5                   10

<210> SEQ ID NO 198
<211> LENGTH: 10
<212> TYPE: PRT
<213> ORGANISM: Homo sapiens

<400> SEQUENCE: 198

Thr Gly Leu Asp Phe Tyr Gln Asp Lys Val
1               5                   10

<210> SEQ ID NO 199
<211> LENGTH: 10
<212> TYPE: PRT
<213> ORGANISM: Homo sapiens

<400> SEQUENCE: 199

Tyr Leu Ala Asp Lys Asn Ile Thr His Gly
1               5                   10

<210> SEQ ID NO 200
<211> LENGTH: 10
<212> TYPE: PRT
<213> ORGANISM: Homo sapiens

<400> SEQUENCE: 200

Leu Val Ile Met Ser Leu Gly Leu Gly Leu
1               5                   10

<210> SEQ ID NO 201
<211> LENGTH: 10
<212> TYPE: PRT
<213> ORGANISM: Homo sapiens

<400> SEQUENCE: 201

Gly Leu Gly Leu Gly Leu Gly Leu Arg Lys
1               5                   10

<210> SEQ ID NO 202
<211> LENGTH: 10
<212> TYPE: PRT
<213> ORGANISM: Homo sapiens

<400> SEQUENCE: 202

Lys Leu Lys Thr Cys Gly Ile His Ser Lys
1               5                   10

<210> SEQ ID NO 203
<211> LENGTH: 10
<212> TYPE: PRT
<213> ORGANISM: Homo sapiens

<400> SEQUENCE: 203

Lys Leu Glu Lys Gln Gly Ser Cys Arg Lys
1               5                   10

<210> SEQ ID NO 204
<211> LENGTH: 10
```

<212> TYPE: PRT
<213> ORGANISM: Homo sapiens

<400> SEQUENCE: 204

Thr Leu Leu Lys Trp Leu Asp Leu Pro Lys
 1               5                  10

<210> SEQ ID NO 205
<211> LENGTH: 10
<212> TYPE: PRT
<213> ORGANISM: Homo sapiens

<400> SEQUENCE: 205

Thr Leu Met Pro Asn Ile Asn Lys Leu Lys
 1               5                  10

<210> SEQ ID NO 206
<211> LENGTH: 10
<212> TYPE: PRT
<213> ORGANISM: Homo sapiens

<400> SEQUENCE: 206

Asn Leu Val Pro Met Tyr Glu Glu Phe Arg
 1               5                  10

<210> SEQ ID NO 207
<211> LENGTH: 10
<212> TYPE: PRT
<213> ORGANISM: Homo sapiens

<400> SEQUENCE: 207

Lys Met Trp Asp Tyr Phe His Ser Val Leu
 1               5                  10

<210> SEQ ID NO 208
<211> LENGTH: 10
<212> TYPE: PRT
<213> ORGANISM: Homo sapiens

<400> SEQUENCE: 208

Thr Leu Ala Thr Glu Gln Pro Val Lys Lys
 1               5                  10

<210> SEQ ID NO 209
<211> LENGTH: 10
<212> TYPE: PRT
<213> ORGANISM: Homo sapiens

<400> SEQUENCE: 209

Asp Leu Pro Lys Arg Leu His Tyr Ala Lys
 1               5                  10

<210> SEQ ID NO 210
<211> LENGTH: 10
<212> TYPE: PRT
<213> ORGANISM: Homo sapiens

<400> SEQUENCE: 210

Trp Leu Thr Ala Met Tyr Gln Gly Leu Lys
 1               5                  10

<210> SEQ ID NO 211
<211> LENGTH: 10
<212> TYPE: PRT
<213> ORGANISM: Homo sapiens

```
<400> SEQUENCE: 211

Gly Met Leu Met Glu Gly Leu Lys Gln Arg
1               5                   10

<210> SEQ ID NO 212
<211> LENGTH: 10
<212> TYPE: PRT
<213> ORGANISM: Homo sapiens

<400> SEQUENCE: 212

Lys Pro Tyr Leu Thr Pro Asp Leu Pro Lys
1               5                   10

<210> SEQ ID NO 213
<211> LENGTH: 10
<212> TYPE: PRT
<213> ORGANISM: Homo sapiens

<400> SEQUENCE: 213

Tyr Met Tyr Glu Gly Pro Ala Pro Arg Ile
1               5                   10

<210> SEQ ID NO 214
<211> LENGTH: 10
<212> TYPE: PRT
<213> ORGANISM: Homo sapiens

<400> SEQUENCE: 214

Val Leu Leu Ile Lys His Ala Thr Glu Arg
1               5                   10

<210> SEQ ID NO 215
<211> LENGTH: 10
<212> TYPE: PRT
<213> ORGANISM: Homo sapiens

<400> SEQUENCE: 215

Leu Val Pro Met Tyr Glu Glu Phe Arg Lys
1               5                   10

<210> SEQ ID NO 216
<211> LENGTH: 10
<212> TYPE: PRT
<213> ORGANISM: Homo sapiens

<400> SEQUENCE: 216

Gly Leu Tyr Pro Glu Ser His Gly Ile Ile
1               5                   10

<210> SEQ ID NO 217
<211> LENGTH: 10
<212> TYPE: PRT
<213> ORGANISM: Homo sapiens

<400> SEQUENCE: 217

Asn Val Val Ser Gly Pro Ile Phe Asp Tyr
1               5                   10

<210> SEQ ID NO 218
<211> LENGTH: 10
<212> TYPE: PRT
<213> ORGANISM: Homo sapiens

<400> SEQUENCE: 218
```

Ala Met Arg Met Pro Met Trp Ser Ser Tyr
1               5                   10

<210> SEQ ID NO 219
<211> LENGTH: 10
<212> TYPE: PRT
<213> ORGANISM: Homo sapiens

<400> SEQUENCE: 219

Leu Thr Gly Leu Asp Phe Tyr Gln Asp Lys
1               5                   10

<210> SEQ ID NO 220
<211> LENGTH: 10
<212> TYPE: PRT
<213> ORGANISM: Homo sapiens

<400> SEQUENCE: 220

His Leu Phe Val Asp Gln Gln Trp Leu Ala
1               5                   10

<210> SEQ ID NO 221
<211> LENGTH: 10
<212> TYPE: PRT
<213> ORGANISM: Homo sapiens

<400> SEQUENCE: 221

Ala Leu Trp Val Glu Glu Arg Phe Thr Ala
1               5                   10

<210> SEQ ID NO 222
<211> LENGTH: 10
<212> TYPE: PRT
<213> ORGANISM: Homo sapiens

<400> SEQUENCE: 222

Ile Leu Phe Ser Met Asp Gly Phe Arg Ala
1               5                   10

<210> SEQ ID NO 223
<211> LENGTH: 10
<212> TYPE: PRT
<213> ORGANISM: Homo sapiens

<400> SEQUENCE: 223

Leu Leu Ala Leu Leu Val Ile Met Ser Leu
1               5                   10

<210> SEQ ID NO 224
<211> LENGTH: 10
<212> TYPE: PRT
<213> ORGANISM: Homo sapiens

<400> SEQUENCE: 224

Ser Leu Asn His Leu Leu Lys Val Pro Phe
1               5                   10

<210> SEQ ID NO 225
<211> LENGTH: 10
<212> TYPE: PRT
<213> ORGANISM: Homo sapiens

<400> SEQUENCE: 225

Tyr Met Pro Tyr Asn Gly Ser Val Pro Phe

```
 1               5                  10
```

<210> SEQ ID NO 226
<211> LENGTH: 10
<212> TYPE: PRT
<213> ORGANISM: Homo sapiens

<400> SEQUENCE: 226

```
Gly Met Asp Gln Thr Tyr Cys Asn Lys Met
 1               5                  10
```

<210> SEQ ID NO 227
<211> LENGTH: 10
<212> TYPE: PRT
<213> ORGANISM: Homo sapiens

<400> SEQUENCE: 227

```
Phe Val Asp Gln Gln Trp Leu Ala Val Arg
 1               5                  10
```

<210> SEQ ID NO 228
<211> LENGTH: 10
<212> TYPE: PRT
<213> ORGANISM: Homo sapiens

<400> SEQUENCE: 228

```
Ala Leu Leu Val Ile Met Ser Leu Gly Leu
 1               5                  10
```

<210> SEQ ID NO 229
<211> LENGTH: 10
<212> TYPE: PRT
<213> ORGANISM: Homo sapiens

<400> SEQUENCE: 229

```
Asn Leu His Asn Cys Val Asn Ile Ile Leu
 1               5                  10
```

<210> SEQ ID NO 230
<211> LENGTH: 10
<212> TYPE: PRT
<213> ORGANISM: Homo sapiens

<400> SEQUENCE: 230

```
Asn Val Asp His Cys Leu Leu Tyr His Arg
 1               5                  10
```

<210> SEQ ID NO 231
<211> LENGTH: 10
<212> TYPE: PRT
<213> ORGANISM: Homo sapiens

<400> SEQUENCE: 231

```
Ala Ile Asn Gly Ser Phe Pro Ser Ile Tyr
 1               5                  10
```

<210> SEQ ID NO 232
<211> LENGTH: 10
<212> TYPE: PRT
<213> ORGANISM: Homo sapiens

<400> SEQUENCE: 232

```
Phe Val Val Leu Thr Ser Cys Lys Asn Lys
 1               5                  10
```

```
<210> SEQ ID NO 233
<211> LENGTH: 10
<212> TYPE: PRT
<213> ORGANISM: Homo sapiens

<400> SEQUENCE: 233

Leu Thr Leu Ala Thr Glu Gln Pro Val Lys
 1               5                  10

<210> SEQ ID NO 234
<211> LENGTH: 10
<212> TYPE: PRT
<213> ORGANISM: Homo sapiens

<400> SEQUENCE: 234

Gly Ser Phe Pro Ser Ile Tyr Met Pro Tyr
 1               5                  10

<210> SEQ ID NO 235
<211> LENGTH: 10
<212> TYPE: PRT
<213> ORGANISM: Homo sapiens

<400> SEQUENCE: 235

Ile Met Ser Leu Gly Leu Gly Leu Gly Leu
 1               5                  10

<210> SEQ ID NO 236
<211> LENGTH: 10
<212> TYPE: PRT
<213> ORGANISM: Homo sapiens

<400> SEQUENCE: 236

Thr Val Lys Val Asn Leu Pro Phe Gly Arg
 1               5                  10

<210> SEQ ID NO 237
<211> LENGTH: 10
<212> TYPE: PRT
<213> ORGANISM: Homo sapiens

<400> SEQUENCE: 237

Leu Ile Thr Ser Asn Leu Val Pro Met Tyr
 1               5                  10

<210> SEQ ID NO 238
<211> LENGTH: 10
<212> TYPE: PRT
<213> ORGANISM: Homo sapiens

<400> SEQUENCE: 238

Ser Leu Gly Leu Gly Leu Gly Leu Gly Leu
 1               5                  10

<210> SEQ ID NO 239
<211> LENGTH: 10
<212> TYPE: PRT
<213> ORGANISM: Homo sapiens

<400> SEQUENCE: 239

Lys Pro Glu Ala Leu Trp Val Glu Glu Arg
 1               5                  10

<210> SEQ ID NO 240
```

```
<211> LENGTH: 10
<212> TYPE: PRT
<213> ORGANISM: Homo sapiens

<400> SEQUENCE: 240

Phe Pro Arg Ile Asn Phe Phe Tyr Met Tyr
1               5                   10

<210> SEQ ID NO 241
<211> LENGTH: 10
<212> TYPE: PRT
<213> ORGANISM: Homo sapiens

<400> SEQUENCE: 241

Ala Ile Phe Leu Ala His Gly Pro Ser Phe
1               5                   10

<210> SEQ ID NO 242
<211> LENGTH: 10
<212> TYPE: PRT
<213> ORGANISM: Homo sapiens

<400> SEQUENCE: 242

Thr Leu Lys Lys Tyr Lys Ile Ala Cys Ile
1               5                   10

<210> SEQ ID NO 243
<211> LENGTH: 10
<212> TYPE: PRT
<213> ORGANISM: Homo sapiens

<400> SEQUENCE: 243

Val Leu Gln Lys Asn Val Asp His Cys Leu
1               5                   10

<210> SEQ ID NO 244
<211> LENGTH: 10
<212> TYPE: PRT
<213> ORGANISM: Homo sapiens

<400> SEQUENCE: 244

Ser Met Asp Gly Phe Arg Ala Glu Tyr Leu
1               5                   10

<210> SEQ ID NO 245
<211> LENGTH: 10
<212> TYPE: PRT
<213> ORGANISM: Homo sapiens

<400> SEQUENCE: 245

Gln Met Leu Asn Leu Thr Gln Glu Glu Ile
1               5                   10

<210> SEQ ID NO 246
<211> LENGTH: 10
<212> TYPE: PRT
<213> ORGANISM: Homo sapiens

<400> SEQUENCE: 246

Gly Leu Lys Gln Arg Asn Leu His Asn Cys
1               5                   10

<210> SEQ ID NO 247
<211> LENGTH: 10
<212> TYPE: PRT
```

<213> ORGANISM: Homo sapiens

<400> SEQUENCE: 247

Glu Ile Val Arg Asn Leu Ser Cys Arg Lys
1               5                   10

<210> SEQ ID NO 248
<211> LENGTH: 10
<212> TYPE: PRT
<213> ORGANISM: Homo sapiens

<400> SEQUENCE: 248

Thr Gln Glu Glu Ile Thr Ala Thr Val Lys
1               5                   10

<210> SEQ ID NO 249
<211> LENGTH: 10
<212> TYPE: PRT
<213> ORGANISM: Homo sapiens

<400> SEQUENCE: 249

Lys Ile Ala Cys Ile Val Leu Leu Ala Leu
1               5                   10

<210> SEQ ID NO 250
<211> LENGTH: 10
<212> TYPE: PRT
<213> ORGANISM: Homo sapiens

<400> SEQUENCE: 250

Phe Leu Tyr Pro Pro Ala Ser Asn Arg Thr
1               5                   10

<210> SEQ ID NO 251
<211> LENGTH: 9
<212> TYPE: PRT
<213> ORGANISM: Homo sapiens

<400> SEQUENCE: 251

Arg Val Pro Pro Ser Glu Ser Gln Lys
1               5

<210> SEQ ID NO 252
<211> LENGTH: 9
<212> TYPE: PRT
<213> ORGANISM: Homo sapiens

<400> SEQUENCE: 252

Gly Leu Gly Leu Arg Lys Leu Glu Lys
1               5

<210> SEQ ID NO 253
<211> LENGTH: 9
<212> TYPE: PRT
<213> ORGANISM: Homo sapiens

<400> SEQUENCE: 253

Ile Val Arg Asn Leu Ser Cys Arg Lys
1               5

<210> SEQ ID NO 254
<211> LENGTH: 9
<212> TYPE: PRT
<213> ORGANISM: Homo sapiens

```
<400> SEQUENCE: 254

Asn Val Glu Ser Cys Pro Glu Gly Lys
 1               5

<210> SEQ ID NO 255
<211> LENGTH: 9
<212> TYPE: PRT
<213> ORGANISM: Homo sapiens

<400> SEQUENCE: 255

Asn Met Tyr Asp Val Asn Leu Asn Lys
 1               5

<210> SEQ ID NO 256
<211> LENGTH: 9
<212> TYPE: PRT
<213> ORGANISM: Homo sapiens

<400> SEQUENCE: 256

Val Val Leu Thr Ser Cys Lys Asn Lys
 1               5

<210> SEQ ID NO 257
<211> LENGTH: 9
<212> TYPE: PRT
<213> ORGANISM: Homo sapiens

<400> SEQUENCE: 257

Val Pro Met Tyr Glu Glu Phe Arg Lys
 1               5

<210> SEQ ID NO 258
<211> LENGTH: 9
<212> TYPE: PRT
<213> ORGANISM: Homo sapiens

<400> SEQUENCE: 258

Gly Met Asp Gln Thr Tyr Cys Asn Lys
 1               5

<210> SEQ ID NO 259
<211> LENGTH: 9
<212> TYPE: PRT
<213> ORGANISM: Homo sapiens

<400> SEQUENCE: 259

Arg Glu Tyr Val Ser Gly Phe Gly Lys
 1               5

<210> SEQ ID NO 260
<211> LENGTH: 9
<212> TYPE: PRT
<213> ORGANISM: Homo sapiens

<400> SEQUENCE: 260

Ser Thr Arg Ile Trp Met Cys Asn Lys
 1               5

<210> SEQ ID NO 261
<211> LENGTH: 9
<212> TYPE: PRT
<213> ORGANISM: Homo sapiens

<400> SEQUENCE: 261
```

```
Leu Thr Ala Met Tyr Gln Gly Leu Lys
 1               5
```

<210> SEQ ID NO 262
<211> LENGTH: 9
<212> TYPE: PRT
<213> ORGANISM: Homo sapiens

<400> SEQUENCE: 262

```
Gly Pro Val Ser Ala Arg Val Ile Lys
 1               5
```

<210> SEQ ID NO 263
<211> LENGTH: 9
<212> TYPE: PRT
<213> ORGANISM: Homo sapiens

<400> SEQUENCE: 263

```
Asp Thr Leu Met Pro Asn Ile Asn Lys
 1               5
```

<210> SEQ ID NO 264
<211> LENGTH: 9
<212> TYPE: PRT
<213> ORGANISM: Homo sapiens

<400> SEQUENCE: 264

```
Leu Leu Lys Trp Leu Asp Leu Pro Lys
 1               5
```

<210> SEQ ID NO 265
<211> LENGTH: 9
<212> TYPE: PRT
<213> ORGANISM: Homo sapiens

<400> SEQUENCE: 265

```
Lys Cys Ser Phe Tyr Leu Ala Asp Lys
 1               5
```

<210> SEQ ID NO 266
<211> LENGTH: 9
<212> TYPE: PRT
<213> ORGANISM: Homo sapiens

<400> SEQUENCE: 266

```
Leu Pro Lys Arg Leu His Tyr Ala Lys
 1               5
```

<210> SEQ ID NO 267
<211> LENGTH: 9
<212> TYPE: PRT
<213> ORGANISM: Homo sapiens

<400> SEQUENCE: 267

```
Tyr Phe His Ser Val Leu Leu Ile Lys
 1               5
```

<210> SEQ ID NO 268
<211> LENGTH: 9
<212> TYPE: PRT
<213> ORGANISM: Homo sapiens

<400> SEQUENCE: 268

```
Ser Cys Ser Asp Asp Cys Leu Gln Lys
 1               5
```

<210> SEQ ID NO 269
<211> LENGTH: 9
<212> TYPE: PRT
<213> ORGANISM: Homo sapiens

<400> SEQUENCE: 269

Pro Val Lys Lys Asn Thr Leu Lys Lys
 1               5

<210> SEQ ID NO 270
<211> LENGTH: 9
<212> TYPE: PRT
<213> ORGANISM: Homo sapiens

<400> SEQUENCE: 270

Phe Leu Ala His Gly Pro Ser Phe Lys
 1               5

<210> SEQ ID NO 271
<211> LENGTH: 9
<212> TYPE: PRT
<213> ORGANISM: Homo sapiens

<400> SEQUENCE: 271

Leu Val Pro Met Tyr Glu Glu Phe Arg
 1               5

<210> SEQ ID NO 272
<211> LENGTH: 9
<212> TYPE: PRT
<213> ORGANISM: Homo sapiens

<400> SEQUENCE: 272

Thr Leu Ala Thr Glu Gln Pro Val Lys
 1               5

<210> SEQ ID NO 273
<211> LENGTH: 9
<212> TYPE: PRT
<213> ORGANISM: Homo sapiens

<400> SEQUENCE: 273

Tyr Ala Lys Asn Val Arg Ile Asp Lys
 1               5

<210> SEQ ID NO 274
<211> LENGTH: 9
<212> TYPE: PRT
<213> ORGANISM: Homo sapiens

<400> SEQUENCE: 274

Tyr Met Arg Ala Met Tyr Pro Thr Lys
 1               5

<210> SEQ ID NO 275
<211> LENGTH: 9
<212> TYPE: PRT
<213> ORGANISM: Homo sapiens

<400> SEQUENCE: 275

Tyr Phe Val Val Leu Thr Ser Cys Lys
 1               5

```
<210> SEQ ID NO 276
<211> LENGTH: 9
<212> TYPE: PRT
<213> ORGANISM: Homo sapiens

<400> SEQUENCE: 276

Gln Pro Val Lys Lys Asn Thr Leu Lys
 1               5

<210> SEQ ID NO 277
<211> LENGTH: 9
<212> TYPE: PRT
<213> ORGANISM: Homo sapiens

<400> SEQUENCE: 277

Arg Ile Trp Met Cys Asn Lys Phe Arg
 1               5

<210> SEQ ID NO 278
<211> LENGTH: 9
<212> TYPE: PRT
<213> ORGANISM: Homo sapiens

<400> SEQUENCE: 278

Gly Leu Gly Leu Gly Leu Gly Leu Arg
 1               5

<210> SEQ ID NO 279
<211> LENGTH: 9
<212> TYPE: PRT
<213> ORGANISM: Homo sapiens

<400> SEQUENCE: 279

Arg Leu His Tyr Ala Lys Asn Val Arg
 1               5

<210> SEQ ID NO 280
<211> LENGTH: 9
<212> TYPE: PRT
<213> ORGANISM: Homo sapiens

<400> SEQUENCE: 280

Lys Leu Glu Lys Gln Gly Ser Cys Arg
 1               5

<210> SEQ ID NO 281
<211> LENGTH: 9
<212> TYPE: PRT
<213> ORGANISM: Homo sapiens

<400> SEQUENCE: 281

Leu Ala Thr Glu Gln Pro Val Lys Lys
 1               5

<210> SEQ ID NO 282
<211> LENGTH: 9
<212> TYPE: PRT
<213> ORGANISM: Homo sapiens

<400> SEQUENCE: 282

Pro Val Ser Glu Ile Leu Gln Leu Lys
 1               5

<210> SEQ ID NO 283
<211> LENGTH: 9
```

```
<212> TYPE: PRT
<213> ORGANISM: Homo sapiens

<400> SEQUENCE: 283

Asn Cys Arg Cys Asp Val Ala Cys Lys
 1               5

<210> SEQ ID NO 284
<211> LENGTH: 9
<212> TYPE: PRT
<213> ORGANISM: Homo sapiens

<400> SEQUENCE: 284

Leu Met Pro Asn Ile Asn Lys Leu Lys
 1               5

<210> SEQ ID NO 285
<211> LENGTH: 9
<212> TYPE: PRT
<213> ORGANISM: Homo sapiens

<400> SEQUENCE: 285

Ile Leu Phe Ser Met Asp Gly Phe Arg
 1               5

<210> SEQ ID NO 286
<211> LENGTH: 9
<212> TYPE: PRT
<213> ORGANISM: Homo sapiens

<400> SEQUENCE: 286

Tyr Met Tyr Glu Gly Pro Ala Pro Arg
 1               5

<210> SEQ ID NO 287
<211> LENGTH: 9
<212> TYPE: PRT
<213> ORGANISM: Homo sapiens

<400> SEQUENCE: 287

Phe Leu Tyr Pro Pro Ala Ser Asn Arg
 1               5

<210> SEQ ID NO 288
<211> LENGTH: 9
<212> TYPE: PRT
<213> ORGANISM: Homo sapiens

<400> SEQUENCE: 288

Glu Tyr Met Thr Asp Tyr Phe Pro Arg
 1               5

<210> SEQ ID NO 289
<211> LENGTH: 9
<212> TYPE: PRT
<213> ORGANISM: Homo sapiens

<400> SEQUENCE: 289

Pro Tyr Leu Thr Pro Asp Leu Pro Lys
 1               5

<210> SEQ ID NO 290
<211> LENGTH: 9
<212> TYPE: PRT
<213> ORGANISM: Homo sapiens
```

-continued

```
<400> SEQUENCE: 290

Gln Gln Trp Leu Ala Val Arg Ser Lys
1               5

<210> SEQ ID NO 291
<211> LENGTH: 9
<212> TYPE: PRT
<213> ORGANISM: Homo sapiens

<400> SEQUENCE: 291

Lys Thr Phe Pro Asn His Tyr Thr Ile
1               5

<210> SEQ ID NO 292
<211> LENGTH: 9
<212> TYPE: PRT
<213> ORGANISM: Homo sapiens

<400> SEQUENCE: 292

Leu Leu Ile Lys His Ala Thr Glu Arg
1               5

<210> SEQ ID NO 293
<211> LENGTH: 9
<212> TYPE: PRT
<213> ORGANISM: Homo sapiens

<400> SEQUENCE: 293

Gln Val Val Asp His Ala Phe Gly Met
1               5

<210> SEQ ID NO 294
<211> LENGTH: 9
<212> TYPE: PRT
<213> ORGANISM: Homo sapiens

<400> SEQUENCE: 294

Arg Val Ile Lys Ala Leu Gln Val Val
1               5

<210> SEQ ID NO 295
<211> LENGTH: 9
<212> TYPE: PRT
<213> ORGANISM: Homo sapiens

<400> SEQUENCE: 295

Arg Val Leu Gln Lys Asn Val Asp His
1               5

<210> SEQ ID NO 296
<211> LENGTH: 9
<212> TYPE: PRT
<213> ORGANISM: Homo sapiens

<400> SEQUENCE: 296

Val Leu Pro Phe Ile Ile Pro His Arg
1               5

<210> SEQ ID NO 297
<211> LENGTH: 9
<212> TYPE: PRT
<213> ORGANISM: Homo sapiens

<400> SEQUENCE: 297
```

Tyr Leu Thr Pro Asp Leu Pro Lys Arg
1               5

<210> SEQ ID NO 298
<211> LENGTH: 9
<212> TYPE: PRT
<213> ORGANISM: Homo sapiens

<400> SEQUENCE: 298

Met Leu Met Glu Gly Leu Lys Gln Arg
1               5

<210> SEQ ID NO 299
<211> LENGTH: 9
<212> TYPE: PRT
<213> ORGANISM: Homo sapiens

<400> SEQUENCE: 299

Ser Phe Asn Ser Glu Glu Ile Val Arg
1               5

<210> SEQ ID NO 300
<211> LENGTH: 9
<212> TYPE: PRT
<213> ORGANISM: Homo sapiens

<400> SEQUENCE: 300

Trp Leu Asp Leu Pro Lys Ala Glu Arg
1               5

<210> SEQ ID NO 301
<211> LENGTH: 10
<212> TYPE: PRT
<213> ORGANISM: Homo sapiens

<400> SEQUENCE: 301

Leu Val Pro Met Tyr Glu Glu Phe Arg Lys
1               5                   10

<210> SEQ ID NO 302
<211> LENGTH: 10
<212> TYPE: PRT
<213> ORGANISM: Homo sapiens

<400> SEQUENCE: 302

Lys Pro Tyr Leu Thr Pro Asp Leu Pro Lys
1               5                   10

<210> SEQ ID NO 303
<211> LENGTH: 10
<212> TYPE: PRT
<213> ORGANISM: Homo sapiens

<400> SEQUENCE: 303

Lys Tyr Met Arg Ala Met Tyr Pro Thr Lys
1               5                   10

<210> SEQ ID NO 304
<211> LENGTH: 10
<212> TYPE: PRT
<213> ORGANISM: Homo sapiens

<400> SEQUENCE: 304

Gly Leu Gly Leu Gly Leu Gly Leu Arg Lys

-continued

```
<210> SEQ ID NO 305
<211> LENGTH: 10
<212> TYPE: PRT
<213> ORGANISM: Homo sapiens

<400> SEQUENCE: 305

Phe Val Val Leu Thr Ser Cys Lys Asn Lys
1               5                   10

<210> SEQ ID NO 306
<211> LENGTH: 10
<212> TYPE: PRT
<213> ORGANISM: Homo sapiens

<400> SEQUENCE: 306

Leu Thr Leu Ala Thr Glu Gln Pro Val Lys
1               5                   10

<210> SEQ ID NO 307
<211> LENGTH: 10
<212> TYPE: PRT
<213> ORGANISM: Homo sapiens

<400> SEQUENCE: 307

Thr Leu Leu Lys Trp Leu Asp Leu Pro Lys
1               5                   10

<210> SEQ ID NO 308
<211> LENGTH: 10
<212> TYPE: PRT
<213> ORGANISM: Homo sapiens

<400> SEQUENCE: 308

Lys Leu Glu Lys Gln Gly Ser Cys Arg Lys
1               5                   10

<210> SEQ ID NO 309
<211> LENGTH: 10
<212> TYPE: PRT
<213> ORGANISM: Homo sapiens

<400> SEQUENCE: 309

Lys Leu Lys Thr Cys Gly Ile His Ser Lys
1               5                   10

<210> SEQ ID NO 310
<211> LENGTH: 10
<212> TYPE: PRT
<213> ORGANISM: Homo sapiens

<400> SEQUENCE: 310

Thr Val Lys Val Asn Leu Pro Phe Gly Arg
1               5                   10

<210> SEQ ID NO 311
<211> LENGTH: 10
<212> TYPE: PRT
<213> ORGANISM: Homo sapiens

<400> SEQUENCE: 311

Leu Thr Gly Leu Asp Phe Tyr Gln Asp Lys
1               5                   10
```

```
<210> SEQ ID NO 312
<211> LENGTH: 10
<212> TYPE: PRT
<213> ORGANISM: Homo sapiens

<400> SEQUENCE: 312

His Tyr Phe Val Val Leu Thr Ser Cys Lys
1               5                   10

<210> SEQ ID NO 313
<211> LENGTH: 10
<212> TYPE: PRT
<213> ORGANISM: Homo sapiens

<400> SEQUENCE: 313

Asn Val Asp His Cys Leu Leu Tyr His Arg
1               5                   10

<210> SEQ ID NO 314
<211> LENGTH: 10
<212> TYPE: PRT
<213> ORGANISM: Homo sapiens

<400> SEQUENCE: 314

His Tyr Ala Lys Asn Val Arg Ile Asp Lys
1               5                   10

<210> SEQ ID NO 315
<211> LENGTH: 10
<212> TYPE: PRT
<213> ORGANISM: Homo sapiens

<400> SEQUENCE: 315

Gln Pro Val Lys Lys Asn Thr Leu Lys Lys
1               5                   10

<210> SEQ ID NO 316
<211> LENGTH: 10
<212> TYPE: PRT
<213> ORGANISM: Homo sapiens

<400> SEQUENCE: 316

Thr Gln Glu Glu Ile Thr Ala Thr Val Lys
1               5                   10

<210> SEQ ID NO 317
<211> LENGTH: 10
<212> TYPE: PRT
<213> ORGANISM: Homo sapiens

<400> SEQUENCE: 317

Asp Tyr Phe His Ser Val Leu Leu Ile Lys
1               5                   10

<210> SEQ ID NO 318
<211> LENGTH: 10
<212> TYPE: PRT
<213> ORGANISM: Homo sapiens

<400> SEQUENCE: 318

Phe Val Asp Gln Gln Trp Leu Ala Val Arg
1               5                   10

<210> SEQ ID NO 319
```

```
<211> LENGTH: 10
<212> TYPE: PRT
<213> ORGANISM: Homo sapiens

<400> SEQUENCE: 319

Thr Leu Ala Thr Glu Gln Pro Val Lys Lys
 1               5                  10

<210> SEQ ID NO 320
<211> LENGTH: 10
<212> TYPE: PRT
<213> ORGANISM: Homo sapiens

<400> SEQUENCE: 320

His Phe Asp Ala Pro Asp Glu Ile Thr Lys
 1               5                  10

<210> SEQ ID NO 321
<211> LENGTH: 10
<212> TYPE: PRT
<213> ORGANISM: Homo sapiens

<400> SEQUENCE: 321

Trp Leu Thr Ala Met Tyr Gln Gly Leu Lys
 1               5                  10

<210> SEQ ID NO 322
<211> LENGTH: 10
<212> TYPE: PRT
<213> ORGANISM: Homo sapiens

<400> SEQUENCE: 322

Thr Leu Met Pro Asn Ile Asn Lys Leu Lys
 1               5                  10

<210> SEQ ID NO 323
<211> LENGTH: 10
<212> TYPE: PRT
<213> ORGANISM: Homo sapiens

<400> SEQUENCE: 323

Tyr Val Ser Gly Phe Gly Lys Ala Met Arg
 1               5                  10

<210> SEQ ID NO 324
<211> LENGTH: 10
<212> TYPE: PRT
<213> ORGANISM: Homo sapiens

<400> SEQUENCE: 324

Gln Pro Val Ser Glu Ile Leu Gln Leu Lys
 1               5                  10

<210> SEQ ID NO 325
<211> LENGTH: 10
<212> TYPE: PRT
<213> ORGANISM: Homo sapiens

<400> SEQUENCE: 325

Ile Phe Leu Ala His Gly Pro Ser Phe Lys
 1               5                  10

<210> SEQ ID NO 326
<211> LENGTH: 10
<212> TYPE: PRT
```

-continued

<213> ORGANISM: Homo sapiens

<400> SEQUENCE: 326

Asp Leu Pro Lys Arg Leu His Tyr Ala Lys
1               5                   10

<210> SEQ ID NO 327
<211> LENGTH: 10
<212> TYPE: PRT
<213> ORGANISM: Homo sapiens

<400> SEQUENCE: 327

Ser Cys Ser Asp Asp Cys Leu Gln Lys Lys
1               5                   10

<210> SEQ ID NO 328
<211> LENGTH: 10
<212> TYPE: PRT
<213> ORGANISM: Homo sapiens

<400> SEQUENCE: 328

Ser Cys Arg Lys Pro Asp Gln His Phe Lys
1               5                   10

<210> SEQ ID NO 329
<211> LENGTH: 10
<212> TYPE: PRT
<213> ORGANISM: Homo sapiens

<400> SEQUENCE: 329

Ala Phe Gly Met Leu Met Glu Gly Leu Lys
1               5                   10

<210> SEQ ID NO 330
<211> LENGTH: 10
<212> TYPE: PRT
<213> ORGANISM: Homo sapiens

<400> SEQUENCE: 330

Gly Phe Leu Tyr Pro Pro Ala Ser Asn Arg
1               5                   10

<210> SEQ ID NO 331
<211> LENGTH: 10
<212> TYPE: PRT
<213> ORGANISM: Homo sapiens

<400> SEQUENCE: 331

Asp Val Leu Pro Phe Ile Ile Pro His Arg
1               5                   10

<210> SEQ ID NO 332
<211> LENGTH: 10
<212> TYPE: PRT
<213> ORGANISM: Homo sapiens

<400> SEQUENCE: 332

Gly Met Leu Met Glu Gly Leu Lys Gln Arg
1               5                   10

<210> SEQ ID NO 333
<211> LENGTH: 10
<212> TYPE: PRT
<213> ORGANISM: Homo sapiens -continued

```
<400> SEQUENCE: 333

Glu Ile Val Arg Asn Leu Ser Cys Arg Lys
1               5                   10

<210> SEQ ID NO 334
<211> LENGTH: 10
<212> TYPE: PRT
<213> ORGANISM: Homo sapiens

<400> SEQUENCE: 334

Glu Gln Pro Val Lys Lys Asn Thr Leu Lys
1               5                   10

<210> SEQ ID NO 335
<211> LENGTH: 10
<212> TYPE: PRT
<213> ORGANISM: Homo sapiens

<400> SEQUENCE: 335

Phe Tyr Met Tyr Glu Gly Pro Ala Pro Arg
1               5                   10

<210> SEQ ID NO 336
<211> LENGTH: 10
<212> TYPE: PRT
<213> ORGANISM: Homo sapiens

<400> SEQUENCE: 336

Asn Asn Met Tyr Asp Val Asn Leu Asn Lys
1               5                   10

<210> SEQ ID NO 337
<211> LENGTH: 10
<212> TYPE: PRT
<213> ORGANISM: Homo sapiens

<400> SEQUENCE: 337

Val Tyr Asn Leu Met Cys Asp Leu Leu Arg
1               5                   10

<210> SEQ ID NO 338
<211> LENGTH: 10
<212> TYPE: PRT
<213> ORGANISM: Homo sapiens

<400> SEQUENCE: 338

Val Ile Leu Phe Ser Met Asp Gly Phe Arg
1               5                   10

<210> SEQ ID NO 339
<211> LENGTH: 10
<212> TYPE: PRT
<213> ORGANISM: Homo sapiens

<400> SEQUENCE: 339

Lys Pro Glu Ala Leu Trp Val Glu Glu Arg
1               5                   10

<210> SEQ ID NO 340
<211> LENGTH: 10
<212> TYPE: PRT
<213> ORGANISM: Homo sapiens

<400> SEQUENCE: 340
```

Lys Val Asn Leu Pro Phe Gly Arg Pro Arg
1               5                   10

<210> SEQ ID NO 341
<211> LENGTH: 10
<212> TYPE: PRT
<213> ORGANISM: Homo sapiens

<400> SEQUENCE: 341

Asn Leu Val Pro Met Tyr Glu Glu Phe Arg
1               5                   10

<210> SEQ ID NO 342
<211> LENGTH: 10
<212> TYPE: PRT
<213> ORGANISM: Homo sapiens

<400> SEQUENCE: 342

Phe Glu Glu Arg Ile Ser Thr Leu Leu Lys
1               5                   10

<210> SEQ ID NO 343
<211> LENGTH: 10
<212> TYPE: PRT
<213> ORGANISM: Homo sapiens

<400> SEQUENCE: 343

Val Leu Leu Ile Lys His Ala Thr Glu Arg
1               5                   10

<210> SEQ ID NO 344
<211> LENGTH: 10
<212> TYPE: PRT
<213> ORGANISM: Homo sapiens

<400> SEQUENCE: 344

Leu Ala His Gly Pro Ser Phe Lys Glu Lys
1               5                   10

<210> SEQ ID NO 345
<211> LENGTH: 10
<212> TYPE: PRT
<213> ORGANISM: Homo sapiens

<400> SEQUENCE: 345

Asn Val Val Ser Gly Pro Ile Phe Asp Tyr
1               5                   10

<210> SEQ ID NO 346
<211> LENGTH: 10
<212> TYPE: PRT
<213> ORGANISM: Homo sapiens

<400> SEQUENCE: 346

Thr Cys Gly Ile His Ser Lys Tyr Met Arg
1               5                   10

<210> SEQ ID NO 347
<211> LENGTH: 10
<212> TYPE: PRT
<213> ORGANISM: Homo sapiens

<400> SEQUENCE: 347

Met Glu Tyr Met Thr Asp Tyr Phe Pro Arg
1               5                   10

```
<210> SEQ ID NO 348
<211> LENGTH: 10
<212> TYPE: PRT
<213> ORGANISM: Homo sapiens

<400> SEQUENCE: 348

Leu Gly Leu Gly Leu Arg Lys Leu Glu Lys
1               5                   10

<210> SEQ ID NO 349
<211> LENGTH: 10
<212> TYPE: PRT
<213> ORGANISM: Homo sapiens

<400> SEQUENCE: 349

His Arg Glu Tyr Val Ser Gly Phe Gly Lys
1               5                   10

<210> SEQ ID NO 350
<211> LENGTH: 10
<212> TYPE: PRT
<213> ORGANISM: Homo sapiens

<400> SEQUENCE: 350

Thr Asn Val Glu Ser Cys Pro Glu Gly Lys
1               5                   10

<210> SEQ ID NO 351
<211> LENGTH: 9
<212> TYPE: PRT
<213> ORGANISM: Homo sapiens

<400> SEQUENCE: 351

Lys Tyr Lys Ile Ala Cys Ile Val Leu
1               5

<210> SEQ ID NO 352
<211> LENGTH: 9
<212> TYPE: PRT
<213> ORGANISM: Homo sapiens

<400> SEQUENCE: 352

Glu Tyr Leu Tyr Thr Trp Asp Thr Leu
1               5

<210> SEQ ID NO 353
<211> LENGTH: 9
<212> TYPE: PRT
<213> ORGANISM: Homo sapiens

<400> SEQUENCE: 353

Val Tyr Asn Leu Met Cys Asp Leu Leu
1               5

<210> SEQ ID NO 354
<211> LENGTH: 9
<212> TYPE: PRT
<213> ORGANISM: Homo sapiens

<400> SEQUENCE: 354

Asp Tyr Phe Pro Arg Ile Asn Phe Phe
1               5
```

```
<210> SEQ ID NO 355
<211> LENGTH: 9
<212> TYPE: PRT
<213> ORGANISM: Homo sapiens

<400> SEQUENCE: 355

Leu Tyr Pro Glu Ser His Gly Ile Ile
1               5

<210> SEQ ID NO 356
<211> LENGTH: 9
<212> TYPE: PRT
<213> ORGANISM: Homo sapiens

<400> SEQUENCE: 356

Met Tyr Glu Gly Pro Ala Pro Arg Ile
1               5

<210> SEQ ID NO 357
<211> LENGTH: 9
<212> TYPE: PRT
<213> ORGANISM: Homo sapiens

<400> SEQUENCE: 357

Asp Tyr Phe His Ser Val Leu Leu Ile
1               5

<210> SEQ ID NO 358
<211> LENGTH: 9
<212> TYPE: PRT
<213> ORGANISM: Homo sapiens

<400> SEQUENCE: 358

Gly Tyr Asn Asn Glu Phe Arg Ser Met
1               5

<210> SEQ ID NO 359
<211> LENGTH: 9
<212> TYPE: PRT
<213> ORGANISM: Homo sapiens

<400> SEQUENCE: 359

Lys Phe Arg Cys Gly Glu Thr Arg Leu
1               5

<210> SEQ ID NO 360
<211> LENGTH: 9
<212> TYPE: PRT
<213> ORGANISM: Homo sapiens

<400> SEQUENCE: 360

Thr Tyr Cys Asn Lys Met Glu Tyr Met
1               5

<210> SEQ ID NO 361
<211> LENGTH: 9
<212> TYPE: PRT
<213> ORGANISM: Homo sapiens

<400> SEQUENCE: 361

Cys Phe Asp Ala Ser Phe Arg Gly Leu
1               5

<210> SEQ ID NO 362
<211> LENGTH: 9
```

```
<212> TYPE: PRT
<213> ORGANISM: Homo sapiens

<400> SEQUENCE: 362

Ala Phe Gly Met Leu Met Glu Gly Leu
 1               5

<210> SEQ ID NO 363
<211> LENGTH: 9
<212> TYPE: PRT
<213> ORGANISM: Homo sapiens

<400> SEQUENCE: 363

Lys Val Gln Pro Val Ser Glu Ile Leu
 1               5

<210> SEQ ID NO 364
<211> LENGTH: 9
<212> TYPE: PRT
<213> ORGANISM: Homo sapiens

<400> SEQUENCE: 364

Gly Phe Asp Leu Pro Pro Val Ile Leu
 1               5

<210> SEQ ID NO 365
<211> LENGTH: 9
<212> TYPE: PRT
<213> ORGANISM: Homo sapiens

<400> SEQUENCE: 365

Lys Tyr Met Arg Ala Met Tyr Pro Thr
 1               5

<210> SEQ ID NO 366
<211> LENGTH: 9
<212> TYPE: PRT
<213> ORGANISM: Homo sapiens

<400> SEQUENCE: 366

Ile Phe Leu Ala His Gly Pro Ser Phe
 1               5

<210> SEQ ID NO 367
<211> LENGTH: 9
<212> TYPE: PRT
<213> ORGANISM: Homo sapiens

<400> SEQUENCE: 367

Thr Tyr Leu Pro Thr Phe Glu Thr Thr
 1               5

<210> SEQ ID NO 368
<211> LENGTH: 9
<212> TYPE: PRT
<213> ORGANISM: Homo sapiens

<400> SEQUENCE: 368

Leu Tyr Pro Pro Ala Ser Asn Arg Thr
 1               5

<210> SEQ ID NO 369
<211> LENGTH: 9
<212> TYPE: PRT
<213> ORGANISM: Homo sapiens
```

```
<400> SEQUENCE: 369

Phe Tyr Gln Asp Lys Val Gln Pro Val
 1               5

<210> SEQ ID NO 370
<211> LENGTH: 9
<212> TYPE: PRT
<213> ORGANISM: Homo sapiens

<400> SEQUENCE: 370

Gln Leu Glu Gln Val Asn Gln Met Leu
 1               5

<210> SEQ ID NO 371
<211> LENGTH: 9
<212> TYPE: PRT
<213> ORGANISM: Homo sapiens

<400> SEQUENCE: 371

Asn Ser Glu Glu Ile Val Arg Asn Leu
 1               5

<210> SEQ ID NO 372
<211> LENGTH: 9
<212> TYPE: PRT
<213> ORGANISM: Homo sapiens

<400> SEQUENCE: 372

Glu Phe Arg Lys Met Trp Asp Tyr Phe
 1               5

<210> SEQ ID NO 373
<211> LENGTH: 9
<212> TYPE: PRT
<213> ORGANISM: Homo sapiens

<400> SEQUENCE: 373

Glu Phe Arg Ser Met Glu Ala Ile Phe
 1               5

<210> SEQ ID NO 374
<211> LENGTH: 9
<212> TYPE: PRT
<213> ORGANISM: Homo sapiens

<400> SEQUENCE: 374

Glu Tyr Val Ser Gly Phe Gly Lys Ala
 1               5

<210> SEQ ID NO 375
<211> LENGTH: 9
<212> TYPE: PRT
<213> ORGANISM: Homo sapiens

<400> SEQUENCE: 375

Arg Ile Ser Thr Leu Leu Lys Trp Leu
 1               5

<210> SEQ ID NO 376
<211> LENGTH: 9
<212> TYPE: PRT
<213> ORGANISM: Homo sapiens

<400> SEQUENCE: 376
```

Thr Leu Met Pro Asn Ile Asn Lys Leu
1               5

<210> SEQ ID NO 377
<211> LENGTH: 9
<212> TYPE: PRT
<213> ORGANISM: Homo sapiens

<400> SEQUENCE: 377

Met Tyr Gln Gly Leu Lys Ala Ala Thr
1               5

<210> SEQ ID NO 378
<211> LENGTH: 9
<212> TYPE: PRT
<213> ORGANISM: Homo sapiens

<400> SEQUENCE: 378

Phe Tyr Leu Ala Asp Lys Asn Ile Thr
1               5

<210> SEQ ID NO 379
<211> LENGTH: 9
<212> TYPE: PRT
<213> ORGANISM: Homo sapiens

<400> SEQUENCE: 379

Ile Tyr Met Pro Tyr Asn Gly Ser Val
1               5

<210> SEQ ID NO 380
<211> LENGTH: 9
<212> TYPE: PRT
<213> ORGANISM: Homo sapiens

<400> SEQUENCE: 380

Met Tyr Glu Glu Phe Arg Lys Met Trp
1               5

<210> SEQ ID NO 381
<211> LENGTH: 9
<212> TYPE: PRT
<213> ORGANISM: Homo sapiens

<400> SEQUENCE: 381

Leu Thr Pro Asp Leu Pro Lys Arg Leu
1               5

<210> SEQ ID NO 382
<211> LENGTH: 9
<212> TYPE: PRT
<213> ORGANISM: Homo sapiens

<400> SEQUENCE: 382

Leu Pro Pro Thr Val Pro Asp Cys Leu
1               5

<210> SEQ ID NO 383
<211> LENGTH: 9
<212> TYPE: PRT
<213> ORGANISM: Homo sapiens

<400> SEQUENCE: 383

Leu Ala Leu Leu Val Ile Met Ser Leu

<210> SEQ ID NO 384
<211> LENGTH: 9
<212> TYPE: PRT
<213> ORGANISM: Homo sapiens

<400> SEQUENCE: 384

Met Tyr Pro Thr Lys Thr Phe Pro Asn
 1               5

<210> SEQ ID NO 385
<211> LENGTH: 9
<212> TYPE: PRT
<213> ORGANISM: Homo sapiens

<400> SEQUENCE: 385

Ala Cys Ile Val Leu Leu Ala Leu Leu
 1               5

<210> SEQ ID NO 386
<211> LENGTH: 9
<212> TYPE: PRT
<213> ORGANISM: Homo sapiens

<400> SEQUENCE: 386

Glu Gln Pro Val Lys Lys Asn Thr Leu
 1               5

<210> SEQ ID NO 387
<211> LENGTH: 9
<212> TYPE: PRT
<213> ORGANISM: Homo sapiens

<400> SEQUENCE: 387

Leu Gly Leu Gly Leu Gly Leu Gly Leu
 1               5

<210> SEQ ID NO 388
<211> LENGTH: 9
<212> TYPE: PRT
<213> ORGANISM: Homo sapiens

<400> SEQUENCE: 388

Glu Ile Leu Gln Leu Lys Thr Tyr Leu
 1               5

<210> SEQ ID NO 389
<211> LENGTH: 9
<212> TYPE: PRT
<213> ORGANISM: Homo sapiens

<400> SEQUENCE: 389

Val Ile Met Ser Leu Gly Leu Gly Leu
 1               5

<210> SEQ ID NO 390
<211> LENGTH: 9
<212> TYPE: PRT
<213> ORGANISM: Homo sapiens

<400> SEQUENCE: 390

Met Ser Leu Gly Leu Gly Leu Gly Leu
 1               5

```
<210> SEQ ID NO 391
<211> LENGTH: 9
<212> TYPE: PRT
<213> ORGANISM: Homo sapiens

<400> SEQUENCE: 391

His Tyr Thr Ile Val Thr Gly Leu Tyr
1               5

<210> SEQ ID NO 392
<211> LENGTH: 9
<212> TYPE: PRT
<213> ORGANISM: Homo sapiens

<400> SEQUENCE: 392

His Tyr Phe Val Val Leu Thr Ser Cys
1               5

<210> SEQ ID NO 393
<211> LENGTH: 9
<212> TYPE: PRT
<213> ORGANISM: Homo sapiens

<400> SEQUENCE: 393

Ala Pro Asp Glu Ile Thr Lys His Leu
1               5

<210> SEQ ID NO 394
<211> LENGTH: 9
<212> TYPE: PRT
<213> ORGANISM: Homo sapiens

<400> SEQUENCE: 394

Met Tyr Asp Val Asn Leu Asn Lys Asn
1               5

<210> SEQ ID NO 395
<211> LENGTH: 9
<212> TYPE: PRT
<213> ORGANISM: Homo sapiens

<400> SEQUENCE: 395

Ser Thr Leu Leu Lys Trp Leu Asp Leu
1               5

<210> SEQ ID NO 396
<211> LENGTH: 9
<212> TYPE: PRT
<213> ORGANISM: Homo sapiens

<400> SEQUENCE: 396

Gln Pro Val Ser Glu Ile Leu Gln Leu
1               5

<210> SEQ ID NO 397
<211> LENGTH: 9
<212> TYPE: PRT
<213> ORGANISM: Homo sapiens

<400> SEQUENCE: 397

Val Cys Gln Gly Glu Thr Ser Trp Leu
1               5

<210> SEQ ID NO 398
```

```
<211> LENGTH: 9
<212> TYPE: PRT
<213> ORGANISM: Homo sapiens

<400> SEQUENCE: 398

Glu Gln Val Asn Gln Met Leu Asn Leu
1               5

<210> SEQ ID NO 399
<211> LENGTH: 9
<212> TYPE: PRT
<213> ORGANISM: Homo sapiens

<400> SEQUENCE: 399

Thr Pro Glu Asn Cys Pro Gly Trp Leu
1               5

<210> SEQ ID NO 400
<211> LENGTH: 9
<212> TYPE: PRT
<213> ORGANISM: Homo sapiens

<400> SEQUENCE: 400

Lys Met Glu Tyr Met Thr Asp Tyr Phe
1               5

<210> SEQ ID NO 401
<211> LENGTH: 10
<212> TYPE: PRT
<213> ORGANISM: Homo sapiens

<400> SEQUENCE: 401

Lys Tyr Lys Ile Ala Cys Ile Val Leu Leu
1               5                   10

<210> SEQ ID NO 402
<211> LENGTH: 10
<212> TYPE: PRT
<213> ORGANISM: Homo sapiens

<400> SEQUENCE: 402

Gln Tyr Asp Ala Leu Ile Thr Ser Asn Leu
1               5                   10

<210> SEQ ID NO 403
<211> LENGTH: 10
<212> TYPE: PRT
<213> ORGANISM: Homo sapiens

<400> SEQUENCE: 403

Met Tyr Asp Val Asn Leu Asn Lys Asn Phe
1               5                   10

<210> SEQ ID NO 404
<211> LENGTH: 10
<212> TYPE: PRT
<213> ORGANISM: Homo sapiens

<400> SEQUENCE: 404

Leu Tyr His Arg Glu Tyr Val Ser Gly Phe
1               5                   10

<210> SEQ ID NO 405
<211> LENGTH: 10
<212> TYPE: PRT
```

<213> ORGANISM: Homo sapiens

<400> SEQUENCE: 405

Glu Tyr Met Thr Asp Tyr Phe Pro Arg Ile
1               5                   10

<210> SEQ ID NO 406
<211> LENGTH: 10
<212> TYPE: PRT
<213> ORGANISM: Homo sapiens

<400> SEQUENCE: 406

Thr Tyr Leu Pro Thr Phe Glu Thr Thr Ile
1               5                   10

<210> SEQ ID NO 407
<211> LENGTH: 10
<212> TYPE: PRT
<213> ORGANISM: Homo sapiens

<400> SEQUENCE: 407

Glu Tyr Val Ser Gly Phe Gly Lys Ala Met
1               5                   10

<210> SEQ ID NO 408
<211> LENGTH: 10
<212> TYPE: PRT
<213> ORGANISM: Homo sapiens

<400> SEQUENCE: 408

Glu Tyr Leu Tyr Thr Trp Asp Thr Leu Met
1               5                   10

<210> SEQ ID NO 409
<211> LENGTH: 10
<212> TYPE: PRT
<213> ORGANISM: Homo sapiens

<400> SEQUENCE: 409

His Phe Lys Pro Tyr Leu Thr Pro Asp Leu
1               5                   10

<210> SEQ ID NO 410
<211> LENGTH: 10
<212> TYPE: PRT
<213> ORGANISM: Homo sapiens

<400> SEQUENCE: 410

Glu Phe Arg Ser Met Glu Ala Ile Phe Leu
1               5                   10

<210> SEQ ID NO 411
<211> LENGTH: 10
<212> TYPE: PRT
<213> ORGANISM: Homo sapiens

<400> SEQUENCE: 411

Phe Tyr Gln Asp Lys Val Gln Pro Val Ser
1               5                   10

<210> SEQ ID NO 412
<211> LENGTH: 10
<212> TYPE: PRT
<213> ORGANISM: Homo sapiens

```
<400> SEQUENCE: 412

Thr Gln Leu Glu Gln Val Asn Gln Met Leu
1               5                   10

<210> SEQ ID NO 413
<211> LENGTH: 10
<212> TYPE: PRT
<213> ORGANISM: Homo sapiens

<400> SEQUENCE: 413

Lys Asn Val Arg Ile Asp Lys Val His Leu
1               5                   10

<210> SEQ ID NO 414
<211> LENGTH: 10
<212> TYPE: PRT
<213> ORGANISM: Homo sapiens

<400> SEQUENCE: 414

Lys Cys Phe Asp Ala Ser Phe Arg Gly Leu
1               5                   10

<210> SEQ ID NO 415
<211> LENGTH: 10
<212> TYPE: PRT
<213> ORGANISM: Homo sapiens

<400> SEQUENCE: 415

Lys Ile Ala Cys Ile Val Leu Leu Ala Leu
1               5                   10

<210> SEQ ID NO 416
<211> LENGTH: 10
<212> TYPE: PRT
<213> ORGANISM: Homo sapiens

<400> SEQUENCE: 416

Asp Ala Pro Asp Glu Ile Thr Lys His Leu
1               5                   10

<210> SEQ ID NO 417
<211> LENGTH: 10
<212> TYPE: PRT
<213> ORGANISM: Homo sapiens

<400> SEQUENCE: 417

Gly Phe Asp Leu Pro Pro Val Ile Leu Phe
1               5                   10

<210> SEQ ID NO 418
<211> LENGTH: 10
<212> TYPE: PRT
<213> ORGANISM: Homo sapiens

<400> SEQUENCE: 418

Ile Phe Asp Tyr Asn Tyr Asp Gly His Phe
1               5                   10

<210> SEQ ID NO 419
<211> LENGTH: 10
<212> TYPE: PRT
<213> ORGANISM: Homo sapiens

<400> SEQUENCE: 419
```

-continued

```
Phe Tyr Glu Pro Ser His Ala Glu Glu Val
 1               5                  10

<210> SEQ ID NO 420
<211> LENGTH: 10
<212> TYPE: PRT
<213> ORGANISM: Homo sapiens

<400> SEQUENCE: 420

Arg Thr Ser Asp Ser Gln Tyr Asp Ala Leu
 1               5                  10

<210> SEQ ID NO 421
<211> LENGTH: 10
<212> TYPE: PRT
<213> ORGANISM: Homo sapiens

<400> SEQUENCE: 421

Lys Met Trp Asp Tyr Phe His Ser Val Leu
 1               5                  10

<210> SEQ ID NO 422
<211> LENGTH: 10
<212> TYPE: PRT
<213> ORGANISM: Homo sapiens

<400> SEQUENCE: 422

Leu Tyr Pro Pro Ala Ser Asn Arg Thr Ser
 1               5                  10

<210> SEQ ID NO 423
<211> LENGTH: 10
<212> TYPE: PRT
<213> ORGANISM: Homo sapiens

<400> SEQUENCE: 423

Gln Val Val Asp His Ala Phe Gly Met Leu
 1               5                  10

<210> SEQ ID NO 424
<211> LENGTH: 10
<212> TYPE: PRT
<213> ORGANISM: Homo sapiens

<400> SEQUENCE: 424

Asp Tyr Phe Pro Arg Ile Asn Phe Phe Tyr
 1               5                  10

<210> SEQ ID NO 425
<211> LENGTH: 10
<212> TYPE: PRT
<213> ORGANISM: Homo sapiens

<400> SEQUENCE: 425

Val Leu Gln Lys Asn Val Asp His Cys Leu
 1               5                  10

<210> SEQ ID NO 426
<211> LENGTH: 10
<212> TYPE: PRT
<213> ORGANISM: Homo sapiens

<400> SEQUENCE: 426

Lys Ala Leu Gln Val Val Asp His Ala Phe
 1               5                  10
```

```
<210> SEQ ID NO 427
<211> LENGTH: 10
<212> TYPE: PRT
<213> ORGANISM: Homo sapiens

<400> SEQUENCE: 427

Lys Pro Asp Gln His Phe Lys Pro Tyr Leu
 1               5                  10

<210> SEQ ID NO 428
<211> LENGTH: 10
<212> TYPE: PRT
<213> ORGANISM: Homo sapiens

<400> SEQUENCE: 428

Asp Thr Leu Met Pro Asn Ile Asn Lys Leu
 1               5                  10

<210> SEQ ID NO 429
<211> LENGTH: 10
<212> TYPE: PRT
<213> ORGANISM: Homo sapiens

<400> SEQUENCE: 429

Asp Tyr Asn Tyr Asp Gly His Phe Asp Ala
 1               5                  10

<210> SEQ ID NO 430
<211> LENGTH: 10
<212> TYPE: PRT
<213> ORGANISM: Homo sapiens

<400> SEQUENCE: 430

Met Tyr Gln Gly Leu Lys Ala Ala Thr Tyr
 1               5                  10

<210> SEQ ID NO 431
<211> LENGTH: 10
<212> TYPE: PRT
<213> ORGANISM: Homo sapiens

<400> SEQUENCE: 431

Ser Cys Pro Glu Gly Lys Pro Glu Ala Leu
 1               5                  10

<210> SEQ ID NO 432
<211> LENGTH: 10
<212> TYPE: PRT
<213> ORGANISM: Homo sapiens

<400> SEQUENCE: 432

Cys Gly Glu Thr Arg Leu Glu Ala Ser Leu
 1               5                  10

<210> SEQ ID NO 433
<211> LENGTH: 10
<212> TYPE: PRT
<213> ORGANISM: Homo sapiens

<400> SEQUENCE: 433

Glu Ser Leu Asp Cys Phe Cys Pro His Leu
 1               5                  10
```

```
<210> SEQ ID NO 434
<211> LENGTH: 10
<212> TYPE: PRT
<213> ORGANISM: Homo sapiens

<400> SEQUENCE: 434

Leu Val Ile Met Ser Leu Gly Leu Gly Leu
 1               5                  10

<210> SEQ ID NO 435
<211> LENGTH: 10
<212> TYPE: PRT
<213> ORGANISM: Homo sapiens

<400> SEQUENCE: 435

His Thr Pro Glu Asn Cys Pro Gly Trp Leu
 1               5                  10

<210> SEQ ID NO 436
<211> LENGTH: 10
<212> TYPE: PRT
<213> ORGANISM: Homo sapiens

<400> SEQUENCE: 436

Phe Ser Val Cys Gly Phe Ala Asn Pro Leu
 1               5                  10

<210> SEQ ID NO 437
<211> LENGTH: 10
<212> TYPE: PRT
<213> ORGANISM: Homo sapiens

<400> SEQUENCE: 437

Met Trp Leu Thr Ala Met Tyr Gln Gly Leu
 1               5                  10

<210> SEQ ID NO 438
<211> LENGTH: 10
<212> TYPE: PRT
<213> ORGANISM: Homo sapiens

<400> SEQUENCE: 438

Phe Ala Asn Pro Leu Pro Thr Glu Ser Leu
 1               5                  10

<210> SEQ ID NO 439
<211> LENGTH: 10
<212> TYPE: PRT
<213> ORGANISM: Homo sapiens

<400> SEQUENCE: 439

Phe Asn Ser Glu Glu Ile Val Arg Asn Leu
 1               5                  10

<210> SEQ ID NO 440
<211> LENGTH: 10
<212> TYPE: PRT
<213> ORGANISM: Homo sapiens

<400> SEQUENCE: 440

Leu Gly Leu Gly Leu Gly Leu Arg Lys Leu
 1               5                  10

<210> SEQ ID NO 441
<211> LENGTH: 10
```

-continued

```
<212> TYPE: PRT
<213> ORGANISM: Homo sapiens

<400> SEQUENCE: 441

Val Gln Pro Val Ser Glu Ile Leu Gln Leu
 1               5                  10

<210> SEQ ID NO 442
<211> LENGTH: 10
<212> TYPE: PRT
<213> ORGANISM: Homo sapiens

<400> SEQUENCE: 442

Gln Ser Gln Cys Pro Glu Gly Phe Asp Leu
 1               5                  10

<210> SEQ ID NO 443
<211> LENGTH: 10
<212> TYPE: PRT
<213> ORGANISM: Homo sapiens

<400> SEQUENCE: 443

Ala Leu Leu Val Ile Met Ser Leu Gly Leu
 1               5                  10

<210> SEQ ID NO 444
<211> LENGTH: 10
<212> TYPE: PRT
<213> ORGANISM: Homo sapiens

<400> SEQUENCE: 444

Leu Met Glu Gly Leu Lys Gln Arg Asn Leu
 1               5                  10

<210> SEQ ID NO 445
<211> LENGTH: 10
<212> TYPE: PRT
<213> ORGANISM: Homo sapiens

<400> SEQUENCE: 445

Ala Pro Asn Asn Gly Thr His Gly Ser Leu
 1               5                  10

<210> SEQ ID NO 446
<211> LENGTH: 10
<212> TYPE: PRT
<213> ORGANISM: Homo sapiens

<400> SEQUENCE: 446

Asp Val Asn Leu Asn Lys Asn Phe Ser Leu
 1               5                  10

<210> SEQ ID NO 447
<211> LENGTH: 10
<212> TYPE: PRT
<213> ORGANISM: Homo sapiens

<400> SEQUENCE: 447

Asn Leu Pro Phe Gly Arg Pro Arg Val Leu
 1               5                  10

<210> SEQ ID NO 448
<211> LENGTH: 10
<212> TYPE: PRT
<213> ORGANISM: Homo sapiens
```

-continued

<400> SEQUENCE: 448

Tyr Phe Trp Pro Gly Ser Glu Val Ala Ile
1               5                   10

<210> SEQ ID NO 449
<211> LENGTH: 10
<212> TYPE: PRT
<213> ORGANISM: Homo sapiens

<400> SEQUENCE: 449

Val Pro Gln Leu Gly Asp Thr Ser Pro Leu
1               5                   10

<210> SEQ ID NO 450
<211> LENGTH: 10
<212> TYPE: PRT
<213> ORGANISM: Homo sapiens

<400> SEQUENCE: 450

Tyr Leu Thr Pro Asp Leu Pro Lys Arg Leu
1               5                   10

<210> SEQ ID NO 451
<211> LENGTH: 9
<212> TYPE: PRT
<213> ORGANISM: Homo sapiens

<400> SEQUENCE: 451

Ala Pro Arg Ile Arg Ala His Asn Ile
1               5

<210> SEQ ID NO 452
<211> LENGTH: 9
<212> TYPE: PRT
<213> ORGANISM: Homo sapiens

<400> SEQUENCE: 452

Phe Pro Arg Ile Asn Phe Phe Tyr Met
1               5

<210> SEQ ID NO 453
<211> LENGTH: 9
<212> TYPE: PRT
<213> ORGANISM: Homo sapiens

<400> SEQUENCE: 453

Asn Val Arg Ile Asp Lys Val His Leu
1               5

<210> SEQ ID NO 454
<211> LENGTH: 9
<212> TYPE: PRT
<213> ORGANISM: Homo sapiens

<400> SEQUENCE: 454

Ile Ala Arg Val Arg Asp Val Glu Leu
1               5

<210> SEQ ID NO 455
<211> LENGTH: 9
<212> TYPE: PRT
<213> ORGANISM: Homo sapiens

<400> SEQUENCE: 455

```
Gln Pro Val Ser Glu Ile Leu Gln Leu
 1               5
```

<210> SEQ ID NO 456
<211> LENGTH: 9
<212> TYPE: PRT
<213> ORGANISM: Homo sapiens

<400> SEQUENCE: 456

```
Leu Pro Phe Gly Arg Pro Arg Val Leu
 1               5
```

<210> SEQ ID NO 457
<211> LENGTH: 9
<212> TYPE: PRT
<213> ORGANISM: Homo sapiens

<400> SEQUENCE: 457

```
Ile Pro Thr His Tyr Phe Val Val Leu
 1               5
```

<210> SEQ ID NO 458
<211> LENGTH: 9
<212> TYPE: PRT
<213> ORGANISM: Homo sapiens

<400> SEQUENCE: 458

```
Leu Pro Pro Thr Val Pro Asp Cys Leu
 1               5
```

<210> SEQ ID NO 459
<211> LENGTH: 9
<212> TYPE: PRT
<213> ORGANISM: Homo sapiens

<400> SEQUENCE: 459

```
Ala Pro Asp Glu Ile Thr Lys His Leu
 1               5
```

<210> SEQ ID NO 460
<211> LENGTH: 9
<212> TYPE: PRT
<213> ORGANISM: Homo sapiens

<400> SEQUENCE: 460

```
Arg Pro Arg Val Leu Gln Lys Asn Val
 1               5
```

<210> SEQ ID NO 461
<211> LENGTH: 9
<212> TYPE: PRT
<213> ORGANISM: Homo sapiens

<400> SEQUENCE: 461

```
Cys Pro Glu Gly Lys Pro Glu Ala Leu
 1               5
```

<210> SEQ ID NO 462
<211> LENGTH: 9
<212> TYPE: PRT
<213> ORGANISM: Homo sapiens

<400> SEQUENCE: 462

```
Thr Pro Glu Asn Cys Pro Gly Trp Leu
```

```
                        1               5

<210> SEQ ID NO 463
<211> LENGTH: 9
<212> TYPE: PRT
<213> ORGANISM: Homo sapiens

<400> SEQUENCE: 463

Glu Val Tyr Asn Leu Met Cys Asp Leu
 1               5

<210> SEQ ID NO 464
<211> LENGTH: 9
<212> TYPE: PRT
<213> ORGANISM: Homo sapiens

<400> SEQUENCE: 464

Lys Val Gln Pro Val Ser Glu Ile Leu
 1               5

<210> SEQ ID NO 465
<211> LENGTH: 9
<212> TYPE: PRT
<213> ORGANISM: Homo sapiens

<400> SEQUENCE: 465

Leu Pro Pro Val Ile Leu Phe Ser Met
 1               5

<210> SEQ ID NO 466
<211> LENGTH: 9
<212> TYPE: PRT
<213> ORGANISM: Homo sapiens

<400> SEQUENCE: 466

Ser Val Cys Gly Phe Ala Asn Pro Leu
 1               5

<210> SEQ ID NO 467
<211> LENGTH: 9
<212> TYPE: PRT
<213> ORGANISM: Homo sapiens

<400> SEQUENCE: 467

Ala Asn Pro Leu Pro Thr Glu Ser Leu
 1               5

<210> SEQ ID NO 468
<211> LENGTH: 9
<212> TYPE: PRT
<213> ORGANISM: Homo sapiens

<400> SEQUENCE: 468

Leu Ala Leu Leu Val Ile Met Ser Leu
 1               5

<210> SEQ ID NO 469
<211> LENGTH: 9
<212> TYPE: PRT
<213> ORGANISM: Homo sapiens

<400> SEQUENCE: 469

Ala Cys Ile Val Leu Leu Ala Leu Leu
 1               5
```

```
<210> SEQ ID NO 470
<211> LENGTH: 9
<212> TYPE: PRT
<213> ORGANISM: Homo sapiens

<400> SEQUENCE: 470

Thr Leu Met Pro Asn Ile Asn Lys Leu
 1               5

<210> SEQ ID NO 471
<211> LENGTH: 9
<212> TYPE: PRT
<213> ORGANISM: Homo sapiens

<400> SEQUENCE: 471

Ile Ala Cys Ile Val Leu Leu Ala Leu
 1               5

<210> SEQ ID NO 472
<211> LENGTH: 9
<212> TYPE: PRT
<213> ORGANISM: Homo sapiens

<400> SEQUENCE: 472

Val Ile Met Ser Leu Gly Leu Gly Leu
 1               5

<210> SEQ ID NO 473
<211> LENGTH: 9
<212> TYPE: PRT
<213> ORGANISM: Homo sapiens

<400> SEQUENCE: 473

Met Pro Met Trp Ser Ser Tyr Thr Val
 1               5

<210> SEQ ID NO 474
<211> LENGTH: 9
<212> TYPE: PRT
<213> ORGANISM: Homo sapiens

<400> SEQUENCE: 474

Val Val Asp His Ala Phe Gly Met Leu
 1               5

<210> SEQ ID NO 475
<211> LENGTH: 9
<212> TYPE: PRT
<213> ORGANISM: Homo sapiens

<400> SEQUENCE: 475

Arg Val Arg Asp Val Glu Leu Leu Thr
 1               5

<210> SEQ ID NO 476
<211> LENGTH: 9
<212> TYPE: PRT
<213> ORGANISM: Homo sapiens

<400> SEQUENCE: 476

Tyr Val Ser Gly Phe Gly Lys Ala Met
 1               5

<210> SEQ ID NO 477
```

```
<211> LENGTH: 9
<212> TYPE: PRT
<213> ORGANISM: Homo sapiens

<400> SEQUENCE: 477

Gln Val Val Asp His Ala Phe Gly Met
1               5

<210> SEQ ID NO 478
<211> LENGTH: 9
<212> TYPE: PRT
<213> ORGANISM: Homo sapiens

<400> SEQUENCE: 478

Gly Thr His Gly Ser Leu Asn His Leu
1               5

<210> SEQ ID NO 479
<211> LENGTH: 9
<212> TYPE: PRT
<213> ORGANISM: Homo sapiens

<400> SEQUENCE: 479

His Asn Cys Val Asn Ile Ile Leu Leu
1               5

<210> SEQ ID NO 480
<211> LENGTH: 9
<212> TYPE: PRT
<213> ORGANISM: Homo sapiens

<400> SEQUENCE: 480

Leu Leu Val Ile Met Ser Leu Gly Leu
1               5

<210> SEQ ID NO 481
<211> LENGTH: 9
<212> TYPE: PRT
<213> ORGANISM: Homo sapiens

<400> SEQUENCE: 481

Arg Pro Arg Phe Tyr Thr Met Tyr Phe
1               5

<210> SEQ ID NO 482
<211> LENGTH: 9
<212> TYPE: PRT
<213> ORGANISM: Homo sapiens

<400> SEQUENCE: 482

Asp Asn Asn Met Tyr Asp Val Asn Leu
1               5

<210> SEQ ID NO 483
<211> LENGTH: 9
<212> TYPE: PRT
<213> ORGANISM: Homo sapiens

<400> SEQUENCE: 483

Glu Gln Val Asn Gln Met Leu Asn Leu
1               5

<210> SEQ ID NO 484
<211> LENGTH: 9
<212> TYPE: PRT
```

-continued

<213> ORGANISM: Homo sapiens

<400> SEQUENCE: 484

Met Ser Leu Gly Leu Gly Leu Gly Leu
 1               5

<210> SEQ ID NO 485
<211> LENGTH: 9
<212> TYPE: PRT
<213> ORGANISM: Homo sapiens

<400> SEQUENCE: 485

Leu Thr Pro Asp Leu Pro Lys Arg Leu
 1               5

<210> SEQ ID NO 486
<211> LENGTH: 9
<212> TYPE: PRT
<213> ORGANISM: Homo sapiens

<400> SEQUENCE: 486

Ser Thr Leu Leu Lys Trp Leu Asp Leu
 1               5

<210> SEQ ID NO 487
<211> LENGTH: 9
<212> TYPE: PRT
<213> ORGANISM: Homo sapiens

<400> SEQUENCE: 487

Trp Ser Ser Tyr Thr Val Pro Gln Leu
 1               5

<210> SEQ ID NO 488
<211> LENGTH: 9
<212> TYPE: PRT
<213> ORGANISM: Homo sapiens

<400> SEQUENCE: 488

Glu Ser Gln Lys Cys Ser Phe Tyr Leu
 1               5

<210> SEQ ID NO 489
<211> LENGTH: 9
<212> TYPE: PRT
<213> ORGANISM: Homo sapiens

<400> SEQUENCE: 489

Val Ser Ala Arg Val Ile Lys Ala Leu
 1               5

<210> SEQ ID NO 490
<211> LENGTH: 9
<212> TYPE: PRT
<213> ORGANISM: Homo sapiens

<400> SEQUENCE: 490

Arg Ile Ser Thr Leu Leu Lys Trp Leu
 1               5

<210> SEQ ID NO 491
<211> LENGTH: 9
<212> TYPE: PRT
<213> ORGANISM: Homo sapiens

```
<400> SEQUENCE: 491

Val Pro Ile Pro Thr His Tyr Phe Val
 1               5

<210> SEQ ID NO 492
<211> LENGTH: 9
<212> TYPE: PRT
<213> ORGANISM: Homo sapiens

<400> SEQUENCE: 492

His Leu Phe Val Asp Gln Gln Trp Leu
 1               5

<210> SEQ ID NO 493
<211> LENGTH: 9
<212> TYPE: PRT
<213> ORGANISM: Homo sapiens

<400> SEQUENCE: 493

Lys Phe Arg Cys Gly Glu Thr Arg Leu
 1               5

<210> SEQ ID NO 494
<211> LENGTH: 9
<212> TYPE: PRT
<213> ORGANISM: Homo sapiens

<400> SEQUENCE: 494

Asn Cys Pro Gly Trp Leu Asp Val Leu
 1               5

<210> SEQ ID NO 495
<211> LENGTH: 9
<212> TYPE: PRT
<213> ORGANISM: Homo sapiens

<400> SEQUENCE: 495

Glu Ile Leu Gln Leu Lys Thr Tyr Leu
 1               5

<210> SEQ ID NO 496
<211> LENGTH: 9
<212> TYPE: PRT
<213> ORGANISM: Homo sapiens

<400> SEQUENCE: 496

Trp Leu Thr Ala Met Tyr Gln Gly Leu
 1               5

<210> SEQ ID NO 497
<211> LENGTH: 9
<212> TYPE: PRT
<213> ORGANISM: Homo sapiens

<400> SEQUENCE: 497

Ser Gln Cys Pro Glu Gly Phe Asp Leu
 1               5

<210> SEQ ID NO 498
<211> LENGTH: 9
<212> TYPE: PRT
<213> ORGANISM: Homo sapiens

<400> SEQUENCE: 498
```

Glu Gln Pro Val Lys Lys Asn Thr Leu
1               5

<210> SEQ ID NO 499
<211> LENGTH: 9
<212> TYPE: PRT
<213> ORGANISM: Homo sapiens

<400> SEQUENCE: 499

Gly Leu Gly Leu Gly Leu Arg Lys Leu
1               5

<210> SEQ ID NO 500
<211> LENGTH: 9
<212> TYPE: PRT
<213> ORGANISM: Homo sapiens

<400> SEQUENCE: 500

Leu Gly Leu Gly Leu Gly Leu Gly Leu
1               5

<210> SEQ ID NO 501
<211> LENGTH: 10
<212> TYPE: PRT
<213> ORGANISM: Homo sapiens

<400> SEQUENCE: 501

Ala Pro Asn Asn Gly Thr His Gly Ser Leu
1               5                   10

<210> SEQ ID NO 502
<211> LENGTH: 10
<212> TYPE: PRT
<213> ORGANISM: Homo sapiens

<400> SEQUENCE: 502

Ile Ala Arg Val Arg Asp Val Glu Leu Leu
1               5                   10

<210> SEQ ID NO 503
<211> LENGTH: 10
<212> TYPE: PRT
<213> ORGANISM: Homo sapiens

<400> SEQUENCE: 503

Cys Pro His Leu Gln Asn Ser Thr Gln Leu
1               5                   10

<210> SEQ ID NO 504
<211> LENGTH: 10
<212> TYPE: PRT
<213> ORGANISM: Homo sapiens

<400> SEQUENCE: 504

Val Pro Gln Leu Gly Asp Thr Ser Pro Leu
1               5                   10

<210> SEQ ID NO 505
<211> LENGTH: 10
<212> TYPE: PRT
<213> ORGANISM: Homo sapiens

<400> SEQUENCE: 505

Val Pro Phe Glu Glu Arg Ile Ser Thr Leu
1               5                   10

```
<210> SEQ ID NO 506
<211> LENGTH: 10
<212> TYPE: PRT
<213> ORGANISM: Homo sapiens

<400> SEQUENCE: 506

Val Pro Met Tyr Glu Glu Phe Arg Lys Met
 1               5                  10

<210> SEQ ID NO 507
<211> LENGTH: 10
<212> TYPE: PRT
<213> ORGANISM: Homo sapiens

<400> SEQUENCE: 507

Lys Pro Asp Gln His Phe Lys Pro Tyr Leu
 1               5                  10

<210> SEQ ID NO 508
<211> LENGTH: 10
<212> TYPE: PRT
<213> ORGANISM: Homo sapiens

<400> SEQUENCE: 508

Gln Val Val Asp His Ala Phe Gly Met Leu
 1               5                  10

<210> SEQ ID NO 509
<211> LENGTH: 10
<212> TYPE: PRT
<213> ORGANISM: Homo sapiens

<400> SEQUENCE: 509

Glu Val Tyr Asn Leu Met Cys Asp Leu Leu
 1               5                  10

<210> SEQ ID NO 510
<211> LENGTH: 10
<212> TYPE: PRT
<213> ORGANISM: Homo sapiens

<400> SEQUENCE: 510

Leu Val Ile Met Ser Leu Gly Leu Gly Leu
 1               5                  10

<210> SEQ ID NO 511
<211> LENGTH: 10
<212> TYPE: PRT
<213> ORGANISM: Homo sapiens

<400> SEQUENCE: 511

Asp Val Asn Leu Asn Lys Asn Phe Ser Leu
 1               5                  10

<210> SEQ ID NO 512
<211> LENGTH: 10
<212> TYPE: PRT
<213> ORGANISM: Homo sapiens

<400> SEQUENCE: 512

Asn Pro Ala Trp Trp His Gly Gln Pro Met
 1               5                  10
```

```
<210> SEQ ID NO 513
<211> LENGTH: 10
<212> TYPE: PRT
<213> ORGANISM: Homo sapiens

<400> SEQUENCE: 513

Ser Val Cys Gln Gly Glu Thr Ser Trp Leu
 1               5                  10

<210> SEQ ID NO 514
<211> LENGTH: 10
<212> TYPE: PRT
<213> ORGANISM: Homo sapiens

<400> SEQUENCE: 514

Phe Ala Asn Pro Leu Pro Thr Glu Ser Leu
 1               5                  10

<210> SEQ ID NO 515
<211> LENGTH: 10
<212> TYPE: PRT
<213> ORGANISM: Homo sapiens

<400> SEQUENCE: 515

Ala Val Arg Ser Lys Ser Asn Thr Asn Cys
 1               5                  10

<210> SEQ ID NO 516
<211> LENGTH: 10
<212> TYPE: PRT
<213> ORGANISM: Homo sapiens

<400> SEQUENCE: 516

Ala Leu Leu Val Ile Met Ser Leu Gly Leu
 1               5                  10

<210> SEQ ID NO 517
<211> LENGTH: 10
<212> TYPE: PRT
<213> ORGANISM: Homo sapiens

<400> SEQUENCE: 517

Asp Ala Pro Asp Glu Ile Thr Lys His Leu
 1               5                  10

<210> SEQ ID NO 518
<211> LENGTH: 10
<212> TYPE: PRT
<213> ORGANISM: Homo sapiens

<400> SEQUENCE: 518

His Ala Phe Gly Met Leu Met Glu Gly Leu
 1               5                  10

<210> SEQ ID NO 519
<211> LENGTH: 10
<212> TYPE: PRT
<213> ORGANISM: Homo sapiens

<400> SEQUENCE: 519

Ile Ala Cys Ile Val Leu Leu Ala Leu Leu
 1               5                  10

<210> SEQ ID NO 520
<211> LENGTH: 10
```

```
<212> TYPE: PRT
<213> ORGANISM: Homo sapiens

<400> SEQUENCE: 520

Ala Pro Arg Ile Arg Ala His Asn Ile Pro
1               5                   10

<210> SEQ ID NO 521
<211> LENGTH: 10
<212> TYPE: PRT
<213> ORGANISM: Homo sapiens

<400> SEQUENCE: 521

Ser Ala Arg Val Ile Lys Ala Leu Gln Val
1               5                   10

<210> SEQ ID NO 522
<211> LENGTH: 10
<212> TYPE: PRT
<213> ORGANISM: Homo sapiens

<400> SEQUENCE: 522

Glu Gly Phe Asp Leu Pro Pro Val Ile Leu
1               5                   10

<210> SEQ ID NO 523
<211> LENGTH: 10
<212> TYPE: PRT
<213> ORGANISM: Homo sapiens

<400> SEQUENCE: 523

Ile Val Leu Leu Ala Leu Leu Val Ile Met
1               5                   10

<210> SEQ ID NO 524
<211> LENGTH: 10
<212> TYPE: PRT
<213> ORGANISM: Homo sapiens

<400> SEQUENCE: 524

Glu Phe Arg Ser Met Glu Ala Ile Phe Leu
1               5                   10

<210> SEQ ID NO 525
<211> LENGTH: 10
<212> TYPE: PRT
<213> ORGANISM: Homo sapiens

<400> SEQUENCE: 525

Thr Gln Leu Glu Gln Val Asn Gln Met Leu
1               5                   10

<210> SEQ ID NO 526
<211> LENGTH: 10
<212> TYPE: PRT
<213> ORGANISM: Homo sapiens

<400> SEQUENCE: 526

Lys Asn Val Arg Ile Asp Lys Val His Leu
1               5                   10

<210> SEQ ID NO 527
<211> LENGTH: 10
<212> TYPE: PRT
<213> ORGANISM: Homo sapiens
```

<400> SEQUENCE: 527

```
Ser Leu Cys Ser Cys Ser Asp Asp Cys Leu
1               5                   10
```

<210> SEQ ID NO 528
<211> LENGTH: 10
<212> TYPE: PRT
<213> ORGANISM: Homo sapiens

<400> SEQUENCE: 528

```
Glu Ile Thr Ala Thr Val Lys Val Asn Leu
1               5                   10
```

<210> SEQ ID NO 529
<211> LENGTH: 10
<212> TYPE: PRT
<213> ORGANISM: Homo sapiens

<400> SEQUENCE: 529

```
Lys Cys Phe Asp Ala Ser Phe Arg Gly Leu
1               5                   10
```

<210> SEQ ID NO 530
<211> LENGTH: 10
<212> TYPE: PRT
<213> ORGANISM: Homo sapiens

<400> SEQUENCE: 530

```
Phe Asn Ser Glu Glu Ile Val Arg Asn Leu
1               5                   10
```

<210> SEQ ID NO 531
<211> LENGTH: 10
<212> TYPE: PRT
<213> ORGANISM: Homo sapiens

<400> SEQUENCE: 531

```
Glu Asn Cys Pro Gly Trp Leu Asp Val Leu
1               5                   10
```

<210> SEQ ID NO 532
<211> LENGTH: 10
<212> TYPE: PRT
<213> ORGANISM: Homo sapiens

<400> SEQUENCE: 532

```
Gln Ser Gln Cys Pro Glu Gly Phe Asp Leu
1               5                   10
```

<210> SEQ ID NO 533
<211> LENGTH: 10
<212> TYPE: PRT
<213> ORGANISM: Homo sapiens

<400> SEQUENCE: 533

```
Leu Gln Lys Asn Val Asp His Cys Leu Leu
1               5                   10
```

<210> SEQ ID NO 534
<211> LENGTH: 10
<212> TYPE: PRT
<213> ORGANISM: Homo sapiens

<400> SEQUENCE: 534

```
Val Leu Gln Lys Asn Val Asp His Cys Leu
 1               5                  10

<210> SEQ ID NO 535
<211> LENGTH: 10
<212> TYPE: PRT
<213> ORGANISM: Homo sapiens

<400> SEQUENCE: 535

Arg Thr Ser Asp Ser Gln Tyr Asp Ala Leu
 1               5                  10

<210> SEQ ID NO 536
<211> LENGTH: 10
<212> TYPE: PRT
<213> ORGANISM: Homo sapiens

<400> SEQUENCE: 536

Leu Gly Leu Gly Leu Gly Leu Arg Lys Leu
 1               5                  10

<210> SEQ ID NO 537
<211> LENGTH: 10
<212> TYPE: PRT
<213> ORGANISM: Homo sapiens

<400> SEQUENCE: 537

Phe Ser Val Cys Gly Phe Ala Asn Pro Leu
 1               5                  10

<210> SEQ ID NO 538
<211> LENGTH: 10
<212> TYPE: PRT
<213> ORGANISM: Homo sapiens

<400> SEQUENCE: 538

Ser Leu Gly Leu Gly Leu Gly Leu Gly Leu
 1               5                  10

<210> SEQ ID NO 539
<211> LENGTH: 10
<212> TYPE: PRT
<213> ORGANISM: Homo sapiens

<400> SEQUENCE: 539

Leu Leu Ala Leu Leu Val Ile Met Ser Leu
 1               5                  10

<210> SEQ ID NO 540
<211> LENGTH: 10
<212> TYPE: PRT
<213> ORGANISM: Homo sapiens

<400> SEQUENCE: 540

His Ile Ala Arg Val Arg Asp Val Glu Leu
 1               5                  10

<210> SEQ ID NO 541
<211> LENGTH: 10
<212> TYPE: PRT
<213> ORGANISM: Homo sapiens

<400> SEQUENCE: 541

Lys Ile Ala Cys Ile Val Leu Leu Ala Leu
```

```
              1               5                  10
```

<210> SEQ ID NO 542
<211> LENGTH: 10
<212> TYPE: PRT
<213> ORGANISM: Homo sapiens

<400> SEQUENCE: 542

```
Asn Leu Pro Phe Gly Arg Pro Arg Val Leu
 1               5                  10
```

<210> SEQ ID NO 543
<211> LENGTH: 10
<212> TYPE: PRT
<213> ORGANISM: Homo sapiens

<400> SEQUENCE: 543

```
Ile Ser Thr Leu Leu Lys Trp Leu Asp Leu
 1               5                  10
```

<210> SEQ ID NO 544
<211> LENGTH: 10
<212> TYPE: PRT
<213> ORGANISM: Homo sapiens

<400> SEQUENCE: 544

```
His Thr Pro Glu Asn Cys Pro Gly Trp Leu
 1               5                  10
```

<210> SEQ ID NO 545
<211> LENGTH: 10
<212> TYPE: PRT
<213> ORGANISM: Homo sapiens

<400> SEQUENCE: 545

```
Lys Met Trp Asp Tyr Phe His Ser Val Leu
 1               5                  10
```

<210> SEQ ID NO 546
<211> LENGTH: 10
<212> TYPE: PRT
<213> ORGANISM: Homo sapiens

<400> SEQUENCE: 546

```
Val Pro Ile Pro Thr His Tyr Phe Val Val
 1               5                  10
```

<210> SEQ ID NO 547
<211> LENGTH: 10
<212> TYPE: PRT
<213> ORGANISM: Homo sapiens

<400> SEQUENCE: 547

```
Asn Gly Thr His Gly Ser Leu Asn His Leu
 1               5                  10
```

<210> SEQ ID NO 548
<211> LENGTH: 10
<212> TYPE: PRT
<213> ORGANISM: Homo sapiens

<400> SEQUENCE: 548

```
Phe Pro Arg Ile Asn Phe Phe Tyr Met Tyr
 1               5                  10
```

```
<210> SEQ ID NO 549
<211> LENGTH: 10
<212> TYPE: PRT
<213> ORGANISM: Homo sapiens

<400> SEQUENCE: 549

Ser Cys Pro Glu Gly Lys Pro Glu Ala Leu
 1               5                  10

<210> SEQ ID NO 550
<211> LENGTH: 10
<212> TYPE: PRT
<213> ORGANISM: Homo sapiens

<400> SEQUENCE: 550

Ile Met Ser Leu Gly Leu Gly Leu Gly Leu
 1               5                  10

<210> SEQ ID NO 551
<211> LENGTH: 9
<212> TYPE: PRT
<213> ORGANISM: Homo sapiens

<400> SEQUENCE: 551

Phe Pro Arg Ile Asn Phe Phe Tyr Met
 1               5

<210> SEQ ID NO 552
<211> LENGTH: 9
<212> TYPE: PRT
<213> ORGANISM: Homo sapiens

<400> SEQUENCE: 552

Arg Pro Arg Phe Tyr Thr Met Tyr Phe
 1               5

<210> SEQ ID NO 553
<211> LENGTH: 9
<212> TYPE: PRT
<213> ORGANISM: Homo sapiens

<400> SEQUENCE: 553

Leu Pro Lys Ala Glu Arg Pro Arg Phe
 1               5

<210> SEQ ID NO 554
<211> LENGTH: 9
<212> TYPE: PRT
<213> ORGANISM: Homo sapiens

<400> SEQUENCE: 554

Glu Pro Phe Glu Asn Ile Glu Val Tyr
 1               5

<210> SEQ ID NO 555
<211> LENGTH: 9
<212> TYPE: PRT
<213> ORGANISM: Homo sapiens

<400> SEQUENCE: 555

Leu Pro Thr Glu Ser Leu Asp Cys Phe
 1               5

<210> SEQ ID NO 556
```

```
<211> LENGTH: 9
<212> TYPE: PRT
<213> ORGANISM: Homo sapiens

<400> SEQUENCE: 556

Leu Pro Pro Val Ile Leu Phe Ser Met
 1               5

<210> SEQ ID NO 557
<211> LENGTH: 9
<212> TYPE: PRT
<213> ORGANISM: Homo sapiens

<400> SEQUENCE: 557

Gln Pro Met Trp Leu Thr Ala Met Tyr
 1               5

<210> SEQ ID NO 558
<211> LENGTH: 9
<212> TYPE: PRT
<213> ORGANISM: Homo sapiens

<400> SEQUENCE: 558

Gln Pro Val Ser Glu Ile Leu Gln Leu
 1               5

<210> SEQ ID NO 559
<211> LENGTH: 9
<212> TYPE: PRT
<213> ORGANISM: Homo sapiens

<400> SEQUENCE: 559

His Ser Lys Tyr Met Arg Ala Met Tyr
 1               5

<210> SEQ ID NO 560
<211> LENGTH: 9
<212> TYPE: PRT
<213> ORGANISM: Homo sapiens

<400> SEQUENCE: 560

Lys Pro Asp Gln His Phe Lys Pro Tyr
 1               5

<210> SEQ ID NO 561
<211> LENGTH: 9
<212> TYPE: PRT
<213> ORGANISM: Homo sapiens

<400> SEQUENCE: 561

Ala Pro Arg Ile Arg Ala His Asn Ile
 1               5

<210> SEQ ID NO 562
<211> LENGTH: 9
<212> TYPE: PRT
<213> ORGANISM: Homo sapiens

<400> SEQUENCE: 562

Arg Pro Arg Val Leu Gln Lys Asn Val
 1               5

<210> SEQ ID NO 563
<211> LENGTH: 9
<212> TYPE: PRT
```

<213> ORGANISM: Homo sapiens

<400> SEQUENCE: 563

Leu Pro Pro Thr Val Pro Asp Cys Leu
1               5

<210> SEQ ID NO 564
<211> LENGTH: 9
<212> TYPE: PRT
<213> ORGANISM: Homo sapiens

<400> SEQUENCE: 564

Leu Pro Phe Gly Arg Pro Arg Val Leu
1               5

<210> SEQ ID NO 565
<211> LENGTH: 9
<212> TYPE: PRT
<213> ORGANISM: Homo sapiens

<400> SEQUENCE: 565

Met Pro Tyr Asn Gly Ser Val Pro Phe
1               5

<210> SEQ ID NO 566
<211> LENGTH: 9
<212> TYPE: PRT
<213> ORGANISM: Homo sapiens

<400> SEQUENCE: 566

Ile Pro Thr His Tyr Phe Val Val Leu
1               5

<210> SEQ ID NO 567
<211> LENGTH: 9
<212> TYPE: PRT
<213> ORGANISM: Homo sapiens

<400> SEQUENCE: 567

Val Ser Lys Phe Ser Val Cys Gly Phe
1               5

<210> SEQ ID NO 568
<211> LENGTH: 9
<212> TYPE: PRT
<213> ORGANISM: Homo sapiens

<400> SEQUENCE: 568

Ala Pro Asp Glu Ile Thr Lys His Leu
1               5

<210> SEQ ID NO 569
<211> LENGTH: 9
<212> TYPE: PRT
<213> ORGANISM: Homo sapiens

<400> SEQUENCE: 569

Ile Ala Arg Val Arg Asp Val Glu Leu
1               5

<210> SEQ ID NO 570
<211> LENGTH: 9
<212> TYPE: PRT
<213> ORGANISM: Homo sapiens

```
<400> SEQUENCE: 570

Lys Asn Val Asp His Cys Leu Leu Tyr
1               5

<210> SEQ ID NO 571
<211> LENGTH: 9
<212> TYPE: PRT
<213> ORGANISM: Homo sapiens

<400> SEQUENCE: 571

Phe Gly Lys Ala Met Arg Met Pro Met
1               5

<210> SEQ ID NO 572
<211> LENGTH: 9
<212> TYPE: PRT
<213> ORGANISM: Homo sapiens

<400> SEQUENCE: 572

Thr Pro Glu Asn Cys Pro Gly Trp Leu
1               5

<210> SEQ ID NO 573
<211> LENGTH: 9
<212> TYPE: PRT
<213> ORGANISM: Homo sapiens

<400> SEQUENCE: 573

Arg Ala Met Tyr Pro Thr Lys Thr Phe
1               5

<210> SEQ ID NO 574
<211> LENGTH: 9
<212> TYPE: PRT
<213> ORGANISM: Homo sapiens

<400> SEQUENCE: 574

Cys Pro Glu Gly Lys Pro Glu Ala Leu
1               5

<210> SEQ ID NO 575
<211> LENGTH: 9
<212> TYPE: PRT
<213> ORGANISM: Homo sapiens

<400> SEQUENCE: 575

Val Pro Phe Glu Glu Arg Ile Ser Thr
1               5

<210> SEQ ID NO 576
<211> LENGTH: 9
<212> TYPE: PRT
<213> ORGANISM: Homo sapiens

<400> SEQUENCE: 576

Ser Asn Arg Thr Ser Asp Ser Gln Tyr
1               5

<210> SEQ ID NO 577
<211> LENGTH: 9
<212> TYPE: PRT
<213> ORGANISM: Homo sapiens

<400> SEQUENCE: 577
```

Arg Ala His Asn Ile Pro His Asp Phe
1               5

<210> SEQ ID NO 578
<211> LENGTH: 9
<212> TYPE: PRT
<213> ORGANISM: Homo sapiens

<400> SEQUENCE: 578

Met Ser Leu Gly Leu Gly Leu Gly Leu
1               5

<210> SEQ ID NO 579
<211> LENGTH: 9
<212> TYPE: PRT
<213> ORGANISM: Homo sapiens

<400> SEQUENCE: 579

Glu Ser Gln Lys Cys Ser Phe Tyr Leu
1               5

<210> SEQ ID NO 580
<211> LENGTH: 9
<212> TYPE: PRT
<213> ORGANISM: Homo sapiens

<400> SEQUENCE: 580

Trp Ser Ser Tyr Thr Val Pro Gln Leu
1               5

<210> SEQ ID NO 581
<211> LENGTH: 9
<212> TYPE: PRT
<213> ORGANISM: Homo sapiens

<400> SEQUENCE: 581

Val Ser Ala Arg Val Ile Lys Ala Leu
1               5

<210> SEQ ID NO 582
<211> LENGTH: 9
<212> TYPE: PRT
<213> ORGANISM: Homo sapiens

<400> SEQUENCE: 582

Asn Val Arg Ile Asp Lys Val His Leu
1               5

<210> SEQ ID NO 583
<211> LENGTH: 9
<212> TYPE: PRT
<213> ORGANISM: Homo sapiens

<400> SEQUENCE: 583

Lys Thr Cys Gly Ile His Ser Lys Tyr
1               5

<210> SEQ ID NO 584
<211> LENGTH: 9
<212> TYPE: PRT
<213> ORGANISM: Homo sapiens

<400> SEQUENCE: 584

Thr Gln Leu Glu Gln Val Asn Gln Met
1               5

<210> SEQ ID NO 585
<211> LENGTH: 9
<212> TYPE: PRT
<213> ORGANISM: Homo sapiens

<400> SEQUENCE: 585

Gln Val Val Asp His Ala Phe Gly Met
1               5

<210> SEQ ID NO 586
<211> LENGTH: 9
<212> TYPE: PRT
<213> ORGANISM: Homo sapiens

<400> SEQUENCE: 586

Met Pro Met Trp Ser Ser Tyr Thr Val
1               5

<210> SEQ ID NO 587
<211> LENGTH: 9
<212> TYPE: PRT
<213> ORGANISM: Homo sapiens

<400> SEQUENCE: 587

Glu Asn Ile Glu Val Tyr Asn Leu Met
1               5

<210> SEQ ID NO 588
<211> LENGTH: 9
<212> TYPE: PRT
<213> ORGANISM: Homo sapiens

<400> SEQUENCE: 588

Val Pro Ile Pro Thr His Tyr Phe Val
1               5

<210> SEQ ID NO 589
<211> LENGTH: 9
<212> TYPE: PRT
<213> ORGANISM: Homo sapiens

<400> SEQUENCE: 589

Ile Pro His Asp Phe Phe Ser Phe Asn
1               5

<210> SEQ ID NO 590
<211> LENGTH: 9
<212> TYPE: PRT
<213> ORGANISM: Homo sapiens

<400> SEQUENCE: 590

Lys Asn Ile Thr His Gly Phe Leu Tyr
1               5

<210> SEQ ID NO 591
<211> LENGTH: 9
<212> TYPE: PRT
<213> ORGANISM: Homo sapiens

<400> SEQUENCE: 591

Ile Ala Cys Ile Val Leu Leu Ala Leu
1               5

```
<210> SEQ ID NO 592
<211> LENGTH: 9
<212> TYPE: PRT
<213> ORGANISM: Homo sapiens

<400> SEQUENCE: 592

Leu Gln Lys Asn Val Asp His Cys Leu
 1               5

<210> SEQ ID NO 593
<211> LENGTH: 9
<212> TYPE: PRT
<213> ORGANISM: Homo sapiens

<400> SEQUENCE: 593

Ser Ser Lys Glu Gln Asn Asn Pro Ala
 1               5

<210> SEQ ID NO 594
<211> LENGTH: 9
<212> TYPE: PRT
<213> ORGANISM: Homo sapiens

<400> SEQUENCE: 594

Leu Ala Leu Leu Val Ile Met Ser Leu
 1               5

<210> SEQ ID NO 595
<211> LENGTH: 9
<212> TYPE: PRT
<213> ORGANISM: Homo sapiens

<400> SEQUENCE: 595

Gln Leu Lys Thr Tyr Leu Pro Thr Phe
 1               5

<210> SEQ ID NO 596
<211> LENGTH: 9
<212> TYPE: PRT
<213> ORGANISM: Homo sapiens

<400> SEQUENCE: 596

Ser Cys Arg Lys Pro Asp Gln His Phe
 1               5

<210> SEQ ID NO 597
<211> LENGTH: 9
<212> TYPE: PRT
<213> ORGANISM: Homo sapiens

<400> SEQUENCE: 597

Val Pro Phe Tyr Glu Pro Ser His Ala
 1               5

<210> SEQ ID NO 598
<211> LENGTH: 9
<212> TYPE: PRT
<213> ORGANISM: Homo sapiens

<400> SEQUENCE: 598

Val Pro Pro Ser Glu Ser Gln Lys Cys
 1               5

<210> SEQ ID NO 599
<211> LENGTH: 9
```

```
<212> TYPE: PRT
<213> ORGANISM: Homo sapiens

<400> SEQUENCE: 599

His Gly Ile Ile Asp Asn Asn Met Tyr
 1               5

<210> SEQ ID NO 600
<211> LENGTH: 9
<212> TYPE: PRT
<213> ORGANISM: Homo sapiens

<400> SEQUENCE: 600

Glu Ala Leu Trp Val Glu Glu Arg Phe
 1               5

<210> SEQ ID NO 601
<211> LENGTH: 10
<212> TYPE: PRT
<213> ORGANISM: Homo sapiens

<400> SEQUENCE: 601

Leu Pro Lys Ala Glu Arg Pro Arg Phe Tyr
 1               5                  10

<210> SEQ ID NO 602
<211> LENGTH: 10
<212> TYPE: PRT
<213> ORGANISM: Homo sapiens

<400> SEQUENCE: 602

Phe Pro Arg Ile Asn Phe Phe Tyr Met Tyr
 1               5                  10

<210> SEQ ID NO 603
<211> LENGTH: 10
<212> TYPE: PRT
<213> ORGANISM: Homo sapiens

<400> SEQUENCE: 603

Val Pro Met Tyr Glu Glu Phe Arg Lys Met
 1               5                  10

<210> SEQ ID NO 604
<211> LENGTH: 10
<212> TYPE: PRT
<213> ORGANISM: Homo sapiens

<400> SEQUENCE: 604

Asn Pro Ala Trp Trp His Gly Gln Pro Met
 1               5                  10

<210> SEQ ID NO 605
<211> LENGTH: 10
<212> TYPE: PRT
<213> ORGANISM: Homo sapiens

<400> SEQUENCE: 605

Tyr Pro Thr Lys Thr Phe Pro Asn His Tyr
 1               5                  10

<210> SEQ ID NO 606
<211> LENGTH: 10
<212> TYPE: PRT
<213> ORGANISM: Homo sapiens
```

-continued

```
<400> SEQUENCE: 606

Val Pro Phe Glu Glu Arg Ile Ser Thr Leu
1               5                   10

<210> SEQ ID NO 607
<211> LENGTH: 10
<212> TYPE: PRT
<213> ORGANISM: Homo sapiens

<400> SEQUENCE: 607

Cys Pro Gly Trp Leu Asp Val Leu Pro Phe
1               5                   10

<210> SEQ ID NO 608
<211> LENGTH: 10
<212> TYPE: PRT
<213> ORGANISM: Homo sapiens

<400> SEQUENCE: 608

Val Pro Gln Leu Gly Asp Thr Ser Pro Leu
1               5                   10

<210> SEQ ID NO 609
<211> LENGTH: 10
<212> TYPE: PRT
<213> ORGANISM: Homo sapiens

<400> SEQUENCE: 609

Ala Pro Asn Asn Gly Thr His Gly Ser Leu
1               5                   10

<210> SEQ ID NO 610
<211> LENGTH: 10
<212> TYPE: PRT
<213> ORGANISM: Homo sapiens

<400> SEQUENCE: 610

Cys Pro His Leu Gln Asn Ser Thr Gln Leu
1               5                   10

<210> SEQ ID NO 611
<211> LENGTH: 10
<212> TYPE: PRT
<213> ORGANISM: Homo sapiens

<400> SEQUENCE: 611

Phe Ser Met Asp Gly Phe Arg Ala Glu Tyr
1               5                   10

<210> SEQ ID NO 612
<211> LENGTH: 10
<212> TYPE: PRT
<213> ORGANISM: Homo sapiens

<400> SEQUENCE: 612

Ser Ser Lys Glu Gln Asn Asn Pro Ala Trp
1               5                   10

<210> SEQ ID NO 613
<211> LENGTH: 10
<212> TYPE: PRT
<213> ORGANISM: Homo sapiens

<400> SEQUENCE: 613
```

Ile Ala Arg Val Arg Asp Val Glu Leu Leu
1               5                   10

<210> SEQ ID NO 614
<211> LENGTH: 10
<212> TYPE: PRT
<213> ORGANISM: Homo sapiens

<400> SEQUENCE: 614

Lys Pro Asp Gln His Phe Lys Pro Tyr Leu
1               5                   10

<210> SEQ ID NO 615
<211> LENGTH: 10
<212> TYPE: PRT
<213> ORGANISM: Homo sapiens

<400> SEQUENCE: 615

Thr Pro Asp Leu Pro Lys Arg Leu His Tyr
1               5                   10

<210> SEQ ID NO 616
<211> LENGTH: 10
<212> TYPE: PRT
<213> ORGANISM: Homo sapiens

<400> SEQUENCE: 616

Gly Ser Phe Pro Ser Ile Tyr Met Pro Tyr
1               5                   10

<210> SEQ ID NO 617
<211> LENGTH: 10
<212> TYPE: PRT
<213> ORGANISM: Homo sapiens

<400> SEQUENCE: 617

Ala Ser Asn Arg Thr Ser Asp Ser Gln Tyr
1               5                   10

<210> SEQ ID NO 618
<211> LENGTH: 10
<212> TYPE: PRT
<213> ORGANISM: Homo sapiens

<400> SEQUENCE: 618

Val Ser Gly Phe Gly Lys Ala Met Arg Met
1               5                   10

<210> SEQ ID NO 619
<211> LENGTH: 10
<212> TYPE: PRT
<213> ORGANISM: Homo sapiens

<400> SEQUENCE: 619

Glu Ser Leu Asp Cys Phe Cys Pro His Leu
1               5                   10

<210> SEQ ID NO 620
<211> LENGTH: 10
<212> TYPE: PRT
<213> ORGANISM: Homo sapiens

<400> SEQUENCE: 620

Val Ser Gly Pro Ile Phe Asp Tyr Asn Tyr

```
                1               5                  10
```

<210> SEQ ID NO 621
<211> LENGTH: 10
<212> TYPE: PRT
<213> ORGANISM: Homo sapiens

<400> SEQUENCE: 621

```
Glu Ser His Gly Ile Ile Asp Asn Asn Met
 1               5                  10
```

<210> SEQ ID NO 622
<211> LENGTH: 10
<212> TYPE: PRT
<213> ORGANISM: Homo sapiens

<400> SEQUENCE: 622

```
Gln Ser Gln Cys Pro Glu Gly Phe Asp Leu
 1               5                  10
```

<210> SEQ ID NO 623
<211> LENGTH: 10
<212> TYPE: PRT
<213> ORGANISM: Homo sapiens

<400> SEQUENCE: 623

```
Cys Asn Lys Met Glu Tyr Met Thr Asp Tyr
 1               5                  10
```

<210> SEQ ID NO 624
<211> LENGTH: 10
<212> TYPE: PRT
<213> ORGANISM: Homo sapiens

<400> SEQUENCE: 624

```
Ala Met Arg Met Pro Met Trp Ser Ser Tyr
 1               5                  10
```

<210> SEQ ID NO 625
<211> LENGTH: 10
<212> TYPE: PRT
<213> ORGANISM: Homo sapiens

<400> SEQUENCE: 625

```
Arg Ala His Asn Ile Pro His Asp Phe Phe
 1               5                  10
```

<210> SEQ ID NO 626
<211> LENGTH: 10
<212> TYPE: PRT
<213> ORGANISM: Homo sapiens

<400> SEQUENCE: 626

```
Asp Ala Pro Asp Glu Ile Thr Lys His Leu
 1               5                  10
```

<210> SEQ ID NO 627
<211> LENGTH: 10
<212> TYPE: PRT
<213> ORGANISM: Homo sapiens

<400> SEQUENCE: 627

```
Gly Pro Ser Phe Lys Glu Lys Thr Glu Val
 1               5                  10
```

```
<210> SEQ ID NO 628
<211> LENGTH: 10
<212> TYPE: PRT
<213> ORGANISM: Homo sapiens

<400> SEQUENCE: 628

Leu Pro Lys Arg Leu His Tyr Ala Lys Asn
 1               5                   10

<210> SEQ ID NO 629
<211> LENGTH: 10
<212> TYPE: PRT
<213> ORGANISM: Homo sapiens

<400> SEQUENCE: 629

Lys Ala Leu Gln Val Val Asp His Ala Phe
 1               5                   10

<210> SEQ ID NO 630
<211> LENGTH: 10
<212> TYPE: PRT
<213> ORGANISM: Homo sapiens

<400> SEQUENCE: 630

Leu Gln Lys Lys Asp Cys Cys Ala Asp Tyr
 1               5                   10

<210> SEQ ID NO 631
<211> LENGTH: 10
<212> TYPE: PRT
<213> ORGANISM: Homo sapiens

<400> SEQUENCE: 631

Leu Ser Cys Arg Lys Pro Asp Gln His Phe
 1               5                   10

<210> SEQ ID NO 632
<211> LENGTH: 10
<212> TYPE: PRT
<213> ORGANISM: Homo sapiens

<400> SEQUENCE: 632

Ile Ser Thr Leu Leu Lys Trp Leu Asp Leu
 1               5                   10

<210> SEQ ID NO 633
<211> LENGTH: 10
<212> TYPE: PRT
<213> ORGANISM: Homo sapiens

<400> SEQUENCE: 633

Lys Ser Val Cys Gln Gly Glu Thr Ser Trp
 1               5                   10

<210> SEQ ID NO 634
<211> LENGTH: 10
<212> TYPE: PRT
<213> ORGANISM: Homo sapiens

<400> SEQUENCE: 634

Phe Ser Val Cys Gly Phe Ala Asn Pro Leu
 1               5                   10

<210> SEQ ID NO 635
```

<211> LENGTH: 10
<212> TYPE: PRT
<213> ORGANISM: Homo sapiens

<400> SEQUENCE: 635

Leu Gln Lys Asn Val Asp His Cys Leu Leu
1               5                   10

<210> SEQ ID NO 636
<211> LENGTH: 10
<212> TYPE: PRT
<213> ORGANISM: Homo sapiens

<400> SEQUENCE: 636

Glu Pro Phe Glu Asn Ile Glu Val Tyr Asn
1               5                   10

<210> SEQ ID NO 637
<211> LENGTH: 10
<212> TYPE: PRT
<213> ORGANISM: Homo sapiens

<400> SEQUENCE: 637

Lys Met Trp Asp Tyr Phe His Ser Val Leu
1               5                   10

<210> SEQ ID NO 638
<211> LENGTH: 10
<212> TYPE: PRT
<213> ORGANISM: Homo sapiens

<400> SEQUENCE: 638

Lys Cys Phe Asp Ala Ser Phe Arg Gly Leu
1               5                   10

<210> SEQ ID NO 639
<211> LENGTH: 10
<212> TYPE: PRT
<213> ORGANISM: Homo sapiens

<400> SEQUENCE: 639

Arg Thr Ser Asp Ser Gln Tyr Asp Ala Leu
1               5                   10

<210> SEQ ID NO 640
<211> LENGTH: 10
<212> TYPE: PRT
<213> ORGANISM: Homo sapiens

<400> SEQUENCE: 640

Pro Pro Ser Glu Ser Gln Lys Cys Ser Phe
1               5                   10

<210> SEQ ID NO 641
<211> LENGTH: 10
<212> TYPE: PRT
<213> ORGANISM: Homo sapiens

<400> SEQUENCE: 641

Lys Thr Cys Gly Ile His Ser Lys Tyr Met
1               5                   10

<210> SEQ ID NO 642
<211> LENGTH: 10
<212> TYPE: PRT

<213> ORGANISM: Homo sapiens

<400> SEQUENCE: 642

Thr Cys Val Glu Ser Thr Arg Ile Trp Met
1               5                   10

<210> SEQ ID NO 643
<211> LENGTH: 10
<212> TYPE: PRT
<213> ORGANISM: Homo sapiens

<400> SEQUENCE: 643

Ile Pro His Asp Phe Phe Ser Phe Asn Ser
1               5                   10

<210> SEQ ID NO 644
<211> LENGTH: 10
<212> TYPE: PRT
<213> ORGANISM: Homo sapiens

<400> SEQUENCE: 644

Leu Pro Thr Glu Ser Leu Asp Cys Phe Cys
1               5                   10

<210> SEQ ID NO 645
<211> LENGTH: 10
<212> TYPE: PRT
<213> ORGANISM: Homo sapiens

<400> SEQUENCE: 645

Val Pro Ile Pro Thr His Tyr Phe Val Val
1               5                   10

<210> SEQ ID NO 646
<211> LENGTH: 10
<212> TYPE: PRT
<213> ORGANISM: Homo sapiens

<400> SEQUENCE: 646

Lys Ala Glu Arg Pro Arg Phe Tyr Thr Met
1               5                   10

<210> SEQ ID NO 647
<211> LENGTH: 10
<212> TYPE: PRT
<213> ORGANISM: Homo sapiens

<400> SEQUENCE: 647

Val Ser Glu Ile Leu Gln Leu Lys Thr Tyr
1               5                   10

<210> SEQ ID NO 648
<211> LENGTH: 10
<212> TYPE: PRT
<213> ORGANISM: Homo sapiens

<400> SEQUENCE: 648

Ala Cys Lys Asp Arg Gly Asp Cys Cys Trp
1               5                   10

<210> SEQ ID NO 649
<211> LENGTH: 10
<212> TYPE: PRT
<213> ORGANISM: Homo sapiens

```
<400> SEQUENCE: 649

Lys Asn Val Arg Ile Asp Lys Val His Leu
 1               5                  10

<210> SEQ ID NO 650
<211> LENGTH: 10
<212> TYPE: PRT
<213> ORGANISM: Homo sapiens

<400> SEQUENCE: 650

Ile Ala Cys Ile Val Leu Leu Ala Leu Leu
 1               5                  10

<210> SEQ ID NO 651
<211> LENGTH: 9
<212> TYPE: PRT
<213> ORGANISM: Homo sapiens

<400> SEQUENCE: 651

Asn Met Tyr Asp Val Asn Leu Asn Lys
 1               5

<210> SEQ ID NO 652
<211> LENGTH: 9
<212> TYPE: PRT
<213> ORGANISM: Homo sapiens

<400> SEQUENCE: 652

Gly Leu Gly Leu Arg Lys Leu Glu Lys
 1               5

<210> SEQ ID NO 653
<211> LENGTH: 9
<212> TYPE: PRT
<213> ORGANISM: Homo sapiens

<400> SEQUENCE: 653

Gly Met Asp Gln Thr Tyr Cys Asn Lys
 1               5

<210> SEQ ID NO 654
<211> LENGTH: 9
<212> TYPE: PRT
<213> ORGANISM: Homo sapiens

<400> SEQUENCE: 654

Phe Leu Tyr Pro Pro Ala Ser Asn Arg
 1               5

<210> SEQ ID NO 655
<211> LENGTH: 9
<212> TYPE: PRT
<213> ORGANISM: Homo sapiens

<400> SEQUENCE: 655

Leu Leu Lys Trp Leu Asp Leu Pro Lys
 1               5

<210> SEQ ID NO 656
<211> LENGTH: 9
<212> TYPE: PRT
<213> ORGANISM: Homo sapiens

<400> SEQUENCE: 656
```

```
Tyr Met Tyr Glu Gly Pro Ala Pro Arg
1               5

<210> SEQ ID NO 657
<211> LENGTH: 9
<212> TYPE: PRT
<213> ORGANISM: Homo sapiens

<400> SEQUENCE: 657

Lys Met Trp Asp Tyr Phe His Ser Val
1               5

<210> SEQ ID NO 658
<211> LENGTH: 9
<212> TYPE: PRT
<213> ORGANISM: Homo sapiens

<400> SEQUENCE: 658

Tyr Met Arg Ala Met Tyr Pro Thr Lys
1               5

<210> SEQ ID NO 659
<211> LENGTH: 9
<212> TYPE: PRT
<213> ORGANISM: Homo sapiens

<400> SEQUENCE: 659

Phe Leu Ala His Gly Pro Ser Phe Lys
1               5

<210> SEQ ID NO 660
<211> LENGTH: 9
<212> TYPE: PRT
<213> ORGANISM: Homo sapiens

<400> SEQUENCE: 660

Thr Leu Ala Thr Glu Gln Pro Val Lys
1               5

<210> SEQ ID NO 661
<211> LENGTH: 9
<212> TYPE: PRT
<213> ORGANISM: Homo sapiens

<400> SEQUENCE: 661

Ser Met Asp Gly Phe Arg Ala Glu Tyr
1               5

<210> SEQ ID NO 662
<211> LENGTH: 9
<212> TYPE: PRT
<213> ORGANISM: Homo sapiens

<400> SEQUENCE: 662

Leu Met Pro Asn Ile Asn Lys Leu Lys
1               5

<210> SEQ ID NO 663
<211> LENGTH: 9
<212> TYPE: PRT
<213> ORGANISM: Homo sapiens

<400> SEQUENCE: 663

Gly Leu Tyr Pro Glu Ser His Gly Ile
1               5
```

<210> SEQ ID NO 664
<211> LENGTH: 9
<212> TYPE: PRT
<213> ORGANISM: Homo sapiens

<400> SEQUENCE: 664

Lys Leu Glu Lys Gln Gly Ser Cys Arg
 1               5

<210> SEQ ID NO 665
<211> LENGTH: 9
<212> TYPE: PRT
<213> ORGANISM: Homo sapiens

<400> SEQUENCE: 665

Val Leu Pro Phe Ile Ile Pro His Arg
 1               5

<210> SEQ ID NO 666
<211> LENGTH: 9
<212> TYPE: PRT
<213> ORGANISM: Homo sapiens

<400> SEQUENCE: 666

Gln Leu Lys Thr Tyr Leu Pro Thr Phe
 1               5

<210> SEQ ID NO 667
<211> LENGTH: 9
<212> TYPE: PRT
<213> ORGANISM: Homo sapiens

<400> SEQUENCE: 667

Tyr Leu Thr Pro Asp Leu Pro Lys Arg
 1               5

<210> SEQ ID NO 668
<211> LENGTH: 9
<212> TYPE: PRT
<213> ORGANISM: Homo sapiens

<400> SEQUENCE: 668

Met Leu Met Glu Gly Leu Lys Gln Arg
 1               5

<210> SEQ ID NO 669
<211> LENGTH: 9
<212> TYPE: PRT
<213> ORGANISM: Homo sapiens

<400> SEQUENCE: 669

Lys Met Glu Tyr Met Thr Asp Tyr Phe
 1               5

<210> SEQ ID NO 670
<211> LENGTH: 9
<212> TYPE: PRT
<213> ORGANISM: Homo sapiens

<400> SEQUENCE: 670

Leu Leu Ile Lys His Ala Thr Glu Arg
 1               5

```
<210> SEQ ID NO 671
<211> LENGTH: 9
<212> TYPE: PRT
<213> ORGANISM: Homo sapiens

<400> SEQUENCE: 671

Trp Leu Asp Leu Pro Lys Ala Glu Arg
 1               5

<210> SEQ ID NO 672
<211> LENGTH: 9
<212> TYPE: PRT
<213> ORGANISM: Homo sapiens

<400> SEQUENCE: 672

Ile Leu Phe Ser Met Asp Gly Phe Arg
 1               5

<210> SEQ ID NO 673
<211> LENGTH: 9
<212> TYPE: PRT
<213> ORGANISM: Homo sapiens

<400> SEQUENCE: 673

Gly Leu Gly Leu Gly Leu Gly Leu Arg
 1               5

<210> SEQ ID NO 674
<211> LENGTH: 9
<212> TYPE: PRT
<213> ORGANISM: Homo sapiens

<400> SEQUENCE: 674

Tyr Met Thr Asp Tyr Phe Pro Arg Ile
 1               5

<210> SEQ ID NO 675
<211> LENGTH: 9
<212> TYPE: PRT
<213> ORGANISM: Homo sapiens

<400> SEQUENCE: 675

Ser Thr Arg Ile Trp Met Cys Asn Lys
 1               5

<210> SEQ ID NO 676
<211> LENGTH: 9
<212> TYPE: PRT
<213> ORGANISM: Homo sapiens

<400> SEQUENCE: 676

Asn Leu Val Pro Met Tyr Glu Glu Phe
 1               5

<210> SEQ ID NO 677
<211> LENGTH: 9
<212> TYPE: PRT
<213> ORGANISM: Homo sapiens

<400> SEQUENCE: 677

Val Val Ser Gly Pro Ile Phe Asp Tyr
 1               5

<210> SEQ ID NO 678
<211> LENGTH: 9
```

```
<212> TYPE: PRT
<213> ORGANISM: Homo sapiens

<400> SEQUENCE: 678

Arg Leu His Tyr Ala Lys Asn Val Arg
 1               5

<210> SEQ ID NO 679
<211> LENGTH: 9
<212> TYPE: PRT
<213> ORGANISM: Homo sapiens

<400> SEQUENCE: 679

Tyr Leu Tyr Thr Trp Asp Thr Leu Met
 1               5

<210> SEQ ID NO 680
<211> LENGTH: 9
<212> TYPE: PRT
<213> ORGANISM: Homo sapiens

<400> SEQUENCE: 680

Ala Leu Gln Val Val Asp His Ala Phe
 1               5

<210> SEQ ID NO 681
<211> LENGTH: 9
<212> TYPE: PRT
<213> ORGANISM: Homo sapiens

<400> SEQUENCE: 681

Arg Val Pro Pro Ser Glu Ser Gln Lys
 1               5

<210> SEQ ID NO 682
<211> LENGTH: 9
<212> TYPE: PRT
<213> ORGANISM: Homo sapiens

<400> SEQUENCE: 682

His Leu Phe Val Asp Gln Gln Trp Leu
 1               5

<210> SEQ ID NO 683
<211> LENGTH: 9
<212> TYPE: PRT
<213> ORGANISM: Homo sapiens

<400> SEQUENCE: 683

Asn Leu Met Cys Asp Leu Leu Arg Ile
 1               5

<210> SEQ ID NO 684
<211> LENGTH: 9
<212> TYPE: PRT
<213> ORGANISM: Homo sapiens

<400> SEQUENCE: 684

Lys Cys Ser Phe Tyr Leu Ala Asp Lys
 1               5

<210> SEQ ID NO 685
<211> LENGTH: 9
<212> TYPE: PRT
<213> ORGANISM: Homo sapiens
```

```
<400> SEQUENCE: 685

Glu Leu Leu Thr Gly Leu Asp Phe Tyr
 1               5

<210> SEQ ID NO 686
<211> LENGTH: 9
<212> TYPE: PRT
<213> ORGANISM: Homo sapiens

<400> SEQUENCE: 686

Thr Leu Met Pro Asn Ile Asn Lys Leu
 1               5

<210> SEQ ID NO 687
<211> LENGTH: 9
<212> TYPE: PRT
<213> ORGANISM: Homo sapiens

<400> SEQUENCE: 687

Lys Thr Phe Pro Asn His Tyr Thr Ile
 1               5

<210> SEQ ID NO 688
<211> LENGTH: 9
<212> TYPE: PRT
<213> ORGANISM: Homo sapiens

<400> SEQUENCE: 688

Gln Thr Tyr Cys Asn Lys Met Glu Tyr
 1               5

<210> SEQ ID NO 689
<211> LENGTH: 9
<212> TYPE: PRT
<213> ORGANISM: Homo sapiens

<400> SEQUENCE: 689

Ile Val Arg Asn Leu Ser Cys Arg Lys
 1               5

<210> SEQ ID NO 690
<211> LENGTH: 9
<212> TYPE: PRT
<213> ORGANISM: Homo sapiens

<400> SEQUENCE: 690

Asn Val Glu Ser Cys Pro Glu Gly Lys
 1               5

<210> SEQ ID NO 691
<211> LENGTH: 9
<212> TYPE: PRT
<213> ORGANISM: Homo sapiens

<400> SEQUENCE: 691

Tyr Leu Pro Thr Phe Glu Thr Thr Ile
 1               5

<210> SEQ ID NO 692
<211> LENGTH: 9
<212> TYPE: PRT
<213> ORGANISM: Homo sapiens

<400> SEQUENCE: 692
```

Asn Ile Pro His Asp Phe Phe Ser Phe
1               5

<210> SEQ ID NO 693
<211> LENGTH: 9
<212> TYPE: PRT
<213> ORGANISM: Homo sapiens

<400> SEQUENCE: 693

Ser Met Glu Ala Ile Phe Leu Ala His
1               5

<210> SEQ ID NO 694
<211> LENGTH: 9
<212> TYPE: PRT
<213> ORGANISM: Homo sapiens

<400> SEQUENCE: 694

Gly Leu Lys Ala Ala Thr Tyr Phe Trp
1               5

<210> SEQ ID NO 695
<211> LENGTH: 9
<212> TYPE: PRT
<213> ORGANISM: Homo sapiens

<400> SEQUENCE: 695

Gly Leu Asp Phe Tyr Gln Asp Lys Val
1               5

<210> SEQ ID NO 696
<211> LENGTH: 9
<212> TYPE: PRT
<213> ORGANISM: Homo sapiens

<400> SEQUENCE: 696

Leu Leu Val Ile Met Ser Leu Gly Leu
1               5

<210> SEQ ID NO 697
<211> LENGTH: 9
<212> TYPE: PRT
<213> ORGANISM: Homo sapiens

<400> SEQUENCE: 697

Asn Leu His Asn Cys Val Asn Ile Ile
1               5

<210> SEQ ID NO 698
<211> LENGTH: 9
<212> TYPE: PRT
<213> ORGANISM: Homo sapiens

<400> SEQUENCE: 698

Ser Leu Asp Cys Phe Cys Pro His Leu
1               5

<210> SEQ ID NO 699
<211> LENGTH: 9
<212> TYPE: PRT
<213> ORGANISM: Homo sapiens

<400> SEQUENCE: 699

Trp Leu Asp Val Leu Pro Phe Ile Ile

```
<210> SEQ ID NO 700
<211> LENGTH: 9
<212> TYPE: PRT
<213> ORGANISM: Homo sapiens

<400> SEQUENCE: 700

Val Val Leu Thr Ser Cys Lys Asn Lys
 1               5

<210> SEQ ID NO 701
<211> LENGTH: 4
<212> TYPE: PRT
<213> ORGANISM: Homo sapiens

<400> SEQUENCE: 701

Asn Phe Ser Leu
 1

<210> SEQ ID NO 702
<211> LENGTH: 4
<212> TYPE: PRT
<213> ORGANISM: Homo sapiens

<400> SEQUENCE: 702

Asn Gly Ser Phe
 1

<210> SEQ ID NO 703
<211> LENGTH: 4
<212> TYPE: PRT
<213> ORGANISM: Homo sapiens

<400> SEQUENCE: 703

Asn Gly Ser Val
 1

<210> SEQ ID NO 704
<211> LENGTH: 4
<212> TYPE: PRT
<213> ORGANISM: Homo sapiens

<400> SEQUENCE: 704

Asn Leu Ser Cys
 1

<210> SEQ ID NO 705
<211> LENGTH: 4
<212> TYPE: PRT
<213> ORGANISM: Homo sapiens

<400> SEQUENCE: 705

Asn Gly Thr His
 1

<210> SEQ ID NO 706
<211> LENGTH: 4
<212> TYPE: PRT
<213> ORGANISM: Homo sapiens

<400> SEQUENCE: 706

Asn Ser Thr Gln
 1
```

```
<210> SEQ ID NO 707
<211> LENGTH: 4
<212> TYPE: PRT
<213> ORGANISM: Homo sapiens

<400> SEQUENCE: 707

Asn Leu Thr Gln
 1

<210> SEQ ID NO 708
<211> LENGTH: 4
<212> TYPE: PRT
<213> ORGANISM: Homo sapiens

<400> SEQUENCE: 708

Asn Ile Thr His
 1

<210> SEQ ID NO 709
<211> LENGTH: 4
<212> TYPE: PRT
<213> ORGANISM: Homo sapiens

<400> SEQUENCE: 709

Asn Arg Thr Ser
 1

<210> SEQ ID NO 710
<211> LENGTH: 4
<212> TYPE: PRT
<213> ORGANISM: Homo sapiens

<400> SEQUENCE: 710

Asn Lys Ser His
 1

<210> SEQ ID NO 711
<211> LENGTH: 4
<212> TYPE: PRT
<213> ORGANISM: Homo sapiens

<400> SEQUENCE: 711

Lys Lys Asn Thr
 1

<210> SEQ ID NO 712
<211> LENGTH: 4
<212> TYPE: PRT
<213> ORGANISM: Homo sapiens

<400> SEQUENCE: 712

Thr Cys Val Glu
 1

<210> SEQ ID NO 713
<211> LENGTH: 4
<212> TYPE: PRT
<213> ORGANISM: Homo sapiens

<400> SEQUENCE: 713

Thr Arg Leu Glu
 1

<210> SEQ ID NO 714
```

```
<211> LENGTH: 4
<212> TYPE: PRT
<213> ORGANISM: Homo sapiens

<400> SEQUENCE: 714

Ser Cys Ser Asp
 1

<210> SEQ ID NO 715
<211> LENGTH: 4
<212> TYPE: PRT
<213> ORGANISM: Homo sapiens

<400> SEQUENCE: 715

Ser Trp Leu Glu
 1

<210> SEQ ID NO 716
<211> LENGTH: 4
<212> TYPE: PRT
<213> ORGANISM: Homo sapiens

<400> SEQUENCE: 716

Ser Ser Lys Glu
 1

<210> SEQ ID NO 717
<211> LENGTH: 4
<212> TYPE: PRT
<213> ORGANISM: Homo sapiens

<400> SEQUENCE: 717

Ser Phe Lys Glu
 1

<210> SEQ ID NO 718
<211> LENGTH: 4
<212> TYPE: PRT
<213> ORGANISM: Homo sapiens

<400> SEQUENCE: 718

Thr Glu Val Glu
 1

<210> SEQ ID NO 719
<211> LENGTH: 4
<212> TYPE: PRT
<213> ORGANISM: Homo sapiens

<400> SEQUENCE: 719

Ser His Ala Glu
 1

<210> SEQ ID NO 720
<211> LENGTH: 4
<212> TYPE: PRT
<213> ORGANISM: Homo sapiens

<400> SEQUENCE: 720

Thr Gln Leu Glu
 1

<210> SEQ ID NO 721
<211> LENGTH: 4
<212> TYPE: PRT
```

<213> ORGANISM: Homo sapiens

<400> SEQUENCE: 721

Thr Gln Glu Glu
1

<210> SEQ ID NO 722
<211> LENGTH: 4
<212> TYPE: PRT
<213> ORGANISM: Homo sapiens

<400> SEQUENCE: 722

Thr Val Pro Asp
1

<210> SEQ ID NO 723
<211> LENGTH: 4
<212> TYPE: PRT
<213> ORGANISM: Homo sapiens

<400> SEQUENCE: 723

Ser Gln Tyr Asp
1

<210> SEQ ID NO 724
<211> LENGTH: 4
<212> TYPE: PRT
<213> ORGANISM: Homo sapiens

<400> SEQUENCE: 724

Thr Asn Val Glu
1

<210> SEQ ID NO 725
<211> LENGTH: 4
<212> TYPE: PRT
<213> ORGANISM: Homo sapiens

<400> SEQUENCE: 725

Ser Cys Pro Glu
1

<210> SEQ ID NO 726
<211> LENGTH: 4
<212> TYPE: PRT
<213> ORGANISM: Homo sapiens

<400> SEQUENCE: 726

Thr Gly Leu Asp
1

<210> SEQ ID NO 727
<211> LENGTH: 7
<212> TYPE: PRT
<213> ORGANISM: Homo sapiens

<400> SEQUENCE: 727

Arg Thr Ser Asp Ser Gln Tyr
1               5

<210> SEQ ID NO 728
<211> LENGTH: 6
<212> TYPE: PRT
<213> ORGANISM: Homo sapiens

```
<400> SEQUENCE: 728

Gly Leu Gly Leu Gly Leu
1               5

<210> SEQ ID NO 729
<211> LENGTH: 6
<212> TYPE: PRT
<213> ORGANISM: Homo sapiens

<400> SEQUENCE: 729

Gly Leu Gly Leu Gly Leu
1               5

<210> SEQ ID NO 730
<211> LENGTH: 6
<212> TYPE: PRT
<213> ORGANISM: Homo sapiens

<400> SEQUENCE: 730

Gly Leu Gly Leu Gly Leu
1               5

<210> SEQ ID NO 731
<211> LENGTH: 6
<212> TYPE: PRT
<213> ORGANISM: Homo sapiens

<400> SEQUENCE: 731

Gly Leu Gly Leu Gly Leu
1               5

<210> SEQ ID NO 732
<211> LENGTH: 6
<212> TYPE: PRT
<213> ORGANISM: Homo sapiens

<400> SEQUENCE: 732

Gly Leu Glu Asn Cys Arg
1               5

<210> SEQ ID NO 733
<211> LENGTH: 6
<212> TYPE: PRT
<213> ORGANISM: Homo sapiens

<400> SEQUENCE: 733

Gly Ile Ile Asp Asn Asn
1               5

<210> SEQ ID NO 734
<211> LENGTH: 6
<212> TYPE: PRT
<213> ORGANISM: Homo sapiens

<400> SEQUENCE: 734

Gly Leu Lys Ala Ala Thr
1               5

<210> SEQ ID NO 735
<211> LENGTH: 6
<212> TYPE: PRT
<213> ORGANISM: Homo sapiens

<400> SEQUENCE: 735
```

-continued

Gly Ser Glu Val Ala Ile
1               5

<210> SEQ ID NO 736
<211> LENGTH: 6
<212> TYPE: PRT
<213> ORGANISM: Homo sapiens

<400> SEQUENCE: 736

Gly Ser Phe Pro Ser Ile
1               5

<210> SEQ ID NO 737
<211> LENGTH: 6
<212> TYPE: PRT
<213> ORGANISM: Homo sapiens

<400> SEQUENCE: 737

Gly Gly Pro Val Ser Ala
1               5

<210> SEQ ID NO 738
<211> LENGTH: 6
<212> TYPE: PRT
<213> ORGANISM: Homo sapiens

<400> SEQUENCE: 738

Gly Met Asp Gln Thr Tyr
1               5

<210> SEQ ID NO 739
<211> LENGTH: 3
<212> TYPE: PRT
<213> ORGANISM: Homo sapiens

<400> SEQUENCE: 739

Arg Gly Asp
1

<210> SEQ ID NO 740
<211> LENGTH: 21
<212> TYPE: PRT
<213> ORGANISM: Homo sapiens

<400> SEQUENCE: 740

Cys Arg Cys Asp Val Ala Cys Lys Asp Arg Gly Asp Cys Cys Trp Asp
1               5                   10                  15

Phe Glu Asp Thr Cys
            20

<210> SEQ ID NO 741
<211> LENGTH: 21
<212> TYPE: PRT
<213> ORGANISM: Homo sapiens

<400> SEQUENCE: 741

Cys Ser Cys Ser Asp Asp Cys Leu Gln Lys Lys Asp Cys Cys Ala Asp
1               5                   10                  15

Tyr Lys Ser Val Cys
            20

<210> SEQ ID NO 742
<211> LENGTH: 182
<212> TYPE: DNA

-continued

```
<213> ORGANISM: Homo sapiens
<220> FEATURE:
<221> NAME/KEY: misc_feature
<222> LOCATION: (1)...(182)
<223> OTHER INFORMATION: n = A, T, C or G

<400> SEQUENCE: 742
gatcacacat taggttatng acttcaatat tttcaaatgg ttcaacttca gtcttctctt      60
taaaactggg tccatgtgcc aagaaagata gcctccatgc tcctaaactc attgttataa    120
ccatggttgc ctcctccaca atttgtattt gatttactcc taacagccag ccactgttga    180
tc                                                                   182

<210> SEQ ID NO 743
<211> LENGTH: 875
<212> TYPE: PRT
<213> ORGANISM: Homo sapiens

<400> SEQUENCE: 743
```

Met Glu Ser Thr Leu Thr Leu Ala Thr Glu Gln Pro Val Lys Lys Asn
1               5                   10                  15

Thr Leu Lys Lys Tyr Lys Ile Ala Cys Ile Val Leu Ala Leu Leu
            20                  25                  30

Val Ile Met Ser Leu Gly Leu Gly Leu Gly Leu Gly Leu Arg Lys Leu
        35                  40                  45

Glu Lys Gln Gly Ser Cys Arg Lys Lys Cys Phe Asp Ala Ser Phe Arg
    50                  55                  60

Gly Leu Glu Asn Cys Arg Cys Asp Val Ala Cys Lys Asp Arg Gly Asp
65                  70                  75                  80

Cys Cys Trp Asp Phe Glu Asp Thr Cys Val Glu Ser Thr Arg Ile Trp
                85                  90                  95

Met Cys Asn Lys Phe Arg Cys Gly Glu Thr Arg Leu Glu Ala Ser Leu
            100                 105                 110

Cys Ser Cys Ser Asp Asp Cys Leu Gln Lys Lys Asp Cys Cys Ala Asp
        115                 120                 125

Tyr Lys Ser Val Cys Gln Gly Glu Thr Ser Trp Leu Glu Glu Asn Cys
    130                 135                 140

Asp Thr Ala Gln Gln Ser Gln Cys Pro Glu Gly Phe Asp Leu Pro Pro
145                 150                 155                 160

Val Ile Leu Phe Ser Met Asp Gly Phe Arg Ala Glu Tyr Leu Tyr Thr
                165                 170                 175

Trp Asp Thr Leu Met Pro Asn Ile Asn Lys Leu Lys Thr Cys Gly Ile
            180                 185                 190

His Ser Lys Tyr Met Arg Ala Met Tyr Pro Thr Lys Thr Phe Pro Asn
        195                 200                 205

His Tyr Thr Ile Val Thr Gly Leu Tyr Pro Glu Ser His Gly Ile Ile
    210                 215                 220

Asp Asn Asn Met Tyr Asp Val Asn Leu Asn Lys Asn Phe Ser Leu Ser
225                 230                 235                 240

Ser Lys Glu Gln Asn Asn Pro Ala Trp Trp His Gly Gln Pro Met Trp
                245                 250                 255

Leu Thr Ala Met Tyr Gln Gly Leu Lys Ala Ala Thr Tyr Phe Trp Pro
            260                 265                 270

Gly Ser Glu Val Ala Ile Asn Gly Ser Phe Pro Ser Ile Tyr Met Pro
        275                 280                 285

Tyr Asn Gly Ser Val Pro Phe Glu Glu Arg Ile Ser Thr Leu Leu Lys

-continued

```
            290                 295                 300
Trp Leu Asp Leu Pro Lys Ala Glu Arg Pro Arg Phe Tyr Thr Met Tyr
305                 310                 315                 320

Phe Glu Glu Pro Asp Ser Ser Gly His Ala Gly Gly Pro Val Ser Ala
                325                 330                 335

Arg Val Ile Lys Ala Leu Gln Val Asp His Ala Phe Gly Met Leu
            340                 345                 350

Met Glu Gly Leu Lys Gln Arg Asn Leu His Asn Cys Val Asn Ile Ile
                355                 360                 365

Leu Leu Ala Asp His Gly Met Asp Gln Thr Tyr Cys Asn Lys Met Glu
370                 375                 380

Tyr Met Thr Asp Tyr Phe Pro Arg Ile Asn Phe Phe Tyr Met Tyr Glu
385                 390                 395                 400

Gly Pro Ala Pro Arg Ile Arg Ala His Asn Ile Pro His Asp Phe Phe
                405                 410                 415

Ser Phe Asn Ser Glu Glu Ile Val Arg Asn Leu Ser Cys Arg Lys Pro
                420                 425                 430

Asp Gln His Phe Lys Pro Tyr Leu Thr Pro Asp Leu Pro Lys Arg Leu
            435                 440                 445

His Tyr Ala Lys Asn Val Arg Ile Asp Lys Val His Leu Phe Val Asp
            450                 455                 460

Gln Gln Trp Leu Ala Val Arg Ser Lys Ser Asn Thr Asn Cys Gly Gly
465                 470                 475                 480

Gly Asn His Gly Tyr Asn Asn Glu Phe Arg Ser Met Glu Ala Ile Phe
                485                 490                 495

Leu Ala His Gly Pro Ser Phe Lys Glu Lys Thr Glu Val Glu Pro Phe
            500                 505                 510

Glu Asn Ile Glu Val Tyr Asn Leu Met Cys Asp Leu Leu Arg Ile Gln
            515                 520                 525

Pro Ala Pro Asn Asn Gly Thr His Gly Ser Leu Asn His Leu Leu Lys
            530                 535                 540

Val Pro Phe Tyr Glu Pro Ser His Ala Glu Glu Val Ser Lys Phe Ser
545                 550                 555                 560

Val Cys Gly Phe Ala Asn Pro Leu Pro Thr Glu Ser Leu Asp Cys Phe
                565                 570                 575

Cys Pro His Leu Gln Asn Ser Thr Gln Leu Glu Gln Val Asn Gln Met
            580                 585                 590

Leu Asn Leu Thr Gln Glu Glu Ile Thr Ala Thr Val Lys Val Asn Leu
            595                 600                 605

Pro Phe Gly Arg Pro Arg Val Leu Gln Lys Asn Val Asp His Cys Leu
610                 615                 620

Leu Tyr His Arg Glu Tyr Val Ser Gly Phe Gly Lys Ala Met Arg Met
625                 630                 635                 640

Pro Met Trp Ser Ser Tyr Thr Val Pro Gln Leu Gly Asp Thr Ser Pro
                645                 650                 655

Leu Pro Pro Thr Val Pro Asp Cys Leu Arg Ala Asp Val Arg Val Pro
            660                 665                 670

Pro Ser Glu Ser Gln Lys Cys Ser Phe Tyr Leu Ala Asp Lys Asn Ile
            675                 680                 685

Thr His Gly Phe Leu Tyr Pro Pro Ala Ser Asn Arg Thr Ser Asp Ser
            690                 695                 700

Gln Tyr Asp Ala Leu Ile Thr Ser Asn Leu Val Pro Met Tyr Glu Glu
705                 710                 715                 720
```

```
Phe Arg Lys Met Trp Asp Tyr Phe His Ser Val Leu Ile Lys His
                725                 730                 735

Ala Thr Glu Arg Asn Gly Val Asn Val Val Ser Gly Pro Ile Phe Asp
            740                 745                 750

Tyr Asn Tyr Asp Gly His Phe Asp Ala Pro Asp Glu Ile Thr Lys His
        755                 760                 765

Leu Ala Asn Thr Asp Val Pro Ile Pro Thr His Tyr Phe Val Val Leu
    770                 775                 780

Thr Ser Cys Lys Asn Lys Ser His Thr Pro Glu Asn Cys Pro Gly Trp
785                 790                 795                 800

Leu Asp Val Leu Pro Phe Ile Ile Pro His Arg Pro Thr Asn Val Glu
                805                 810                 815

Ser Cys Pro Glu Gly Lys Pro Glu Ala Leu Trp Val Glu Glu Arg Phe
            820                 825                 830

Thr Ala His Ile Ala Arg Val Arg Asp Val Glu Leu Leu Thr Gly Leu
        835                 840                 845

Asp Phe Tyr Gln Asp Lys Val Gln Pro Val Ser Glu Ile Leu Gln Leu
    850                 855                 860

Lys Thr Tyr Leu Pro Thr Phe Glu Thr Thr Ile
865                 870                 875

<210> SEQ ID NO 744
<211> LENGTH: 3858
<212> TYPE: DNA
<213> ORGANISM: Homo sapiens

<400> SEQUENCE: 744
ctactttatt ctgataaaac aggtctatgc agctaccagg acaatggaat ctacgttgac    60
tttagcaacg gaacaacctg ttaagaagaa cactcttaag aaatataaaa tagcttgcat   120
tgttcttctt gctttgctgg tgatcatgtc acttggatta ggcctggggc ttggactcag   180
gaaactggaa aagcaaggca gctgcaggaa gaagtgcttt gatgcatcat ttagaggact   240
ggagaactgc cggtgtgatg tggcatgtaa agaccgaggt gattgctgct gggattttga   300
agacacctgt gtggaatcaa ctcgaatatg gatgtgcaat aaatttcgtt gtggagagac   360
cagattagag gccagccttt gctcttgttc agatgactgt ttgcagaaga agattgctg    420
tgctgactat aagagtgttt gccaaggaga acctcatgg ctggaagaaa actgtgacac   480
agcccagcag tctcagtgcc agaagggtt tgacctgcca ccagttatct tgttttctat   540
ggatggattt agagctgaat atttatacac atgggatact ttaatgccaa atatcaataa   600
actgaaaaca tgtggaattc attcaaaata catgagagct atgtatccta ccaaaacctt   660
cccaaatcat tacaccattg tcacgggctt gtatccagag tcacatggca tcattgacaa   720
taatatgtat gatgtaaatc tcaacaagaa ttttttcactt tcttcaaagg aacaaaataa   780
tccagcctgg tggcatgggc aaccaatgtg gctgacagca atgtatcaag gtttaaaagc   840
cgctacctac ttttggcccg gatcagaagt ggctataaat ggctcctttc cttccatata   900
catgccttac aacggaagtg tcccatttga agagaggatt tctacactgt taaaatggct   960
ggacctgccc aaagctgaaa gacccaggtt ttataccatg tattttgaag aacctgattc  1020
ctctggacat gcaggtggac cagtcagtgc cagagtaatt aaagccttac aggtagtaga  1080
tcatgctttt gggatgttga tggaaggcct gaagcagcgg aatttgcaca actgtgtcaa  1140
tatcatcctt ctggctgacc atggaatgga ccagacttat gtgtaacaaga tggaatacat  1200
```

```
gactgattat tttcccagaa taaacttctt ctacatgtac gaagggcctg ccccccgcat   1260
ccgagctcat aatatacctc atgactttt  tagtttaat  tctgaggaaa ttgttagaaa   1320
cctcagttgc cgaaaacctg atcagcattt caagccctat ttgactcctg atttgccaaa   1380
gcgactgcac tatgccaaga acgtcagaat cgacaaagtt catctctttg tggatcaaca   1440
gtggctggct gttaggagta aatcaaatac aaattgtgga ggaggcaacc atggttataa   1500
caatgagttt aggagcatgg aggctatctt tctggcacat ggacccagtt ttaaagagaa   1560
gactgaagtt gaaccatttg aaaatattga agtctataac ctaatgtgtg atcttctacg   1620
cattcaacca gcaccaaaca atggaaccca tggtagttta aaccatcttc tgaaggtgcc   1680
tttttatgag ccatcccatg cagaggaggt gtcaaagttt tctgtttgtg ctttgctaa    1740 tccattgccc acagagtctc ttgactgttt ctgccctcac ctacaaaata gtactcagct   1800
ggaacaagtg aatcagatgc taaatctcac caagaagaa  ataacagcaa cagtgaaagt   1860
aaatttgcca tttgggaggc ctagggtact gcagaagaac gtggaccact gtctccttta   1920
ccacagggaa tatgtcagtg gatttggaaa agctatgagg atgcccatgt ggagttcata   1980
cacagtcccc cagttgggag acacatcgcc tctgcctccc actgtcccag actgtctgcg   2040
ggctgatgtc agggttcctc cttctgagag ccaaaaatgt tccttctatt tagcagacaa   2100
gaatatcacc cacggcttcc tctatcctcc tgccagcaat agaacatcag atagccaata   2160
tgatgcttta attactagca atttggtacc tatgtatgaa gaattcagaa aaatgtggga   2220
ctacttccac agtgttcttc ttataaaaca tgccacagaa agaaatggag taaatgtggt   2280
tagtggacca atatttgatt ataattatga tggccatttt gatgctccag atgaaattac   2340
caaacattta gccaacactg atgttcccat cccaacacac tactttgtgg tgctgaccag   2400
ttgtaaaaac aagagccaca caccggaaaa ctgccctggg tggctggatg tcctacccTT   2460
tatcatccct caccgaccta ccaacgtgga gagctgtcct gaaggtaaac cagaagctct   2520
ttgggttgaa gaaagattta cagctcacat tgcccgggtc cgtgatgtag aacttctcac   2580
tgggcttgac ttctatcagg ataaagtgca gcctgtctct gaaattttgc aactaaagac   2640
atatttacca acatttgaaa ccactattta acttaataat gtctacttaa tatataattt   2700
actgtataaa gtaattttgg caaaatataa gtgattttt  ctggagaatt gtaaataaa    2760 gttttctatt tttccttaaa aaaaaaccg  gaattccggg cttgggaggc tgaggcagga   2820
gactcgcttg aacccgggag gcagaggttg cagtgagcca agattgcgcc attgcactcc   2880
agagcctggg tgacagagca agactacatc tcaaaaaata aataaataaa ataaaagtaa   2940
caataaaaat aaaagaaca  gcagagagaa tgagcaagga gaaatgtcac aaactattgc   3000
aaaatactgt tacactgggt tggctctcca agaagatact ggaatctctt cagccatttg   3060
cttttcagaa gtagaaacca gcaaaccacc tctaagcgga gaacatacga ttctttatta   3120
agtagctctg gggaaggaaa gaataaaagt tgatagctcc ctgattggga aaaatgcac    3180 aattaataaa gaatgaagat gaaagaaagc atgcttatgt tgtaacacaa aaaaaattca   3240
caaacgttgg tggaaggaaa acagtataga aaacattact ttaactaaaa gctggaaaaa   3300
ttttcagttg ggatgcgact gacaaaaaga acgggatttc caggcataaa gttggcgtga   3360
gctacagagg gcaccatgtg gctcagtgga agacccttca agattcaaag ttccatttga   3420
cagagcaaag gcacttcgca aggagaaggg tttaaattat gggtccaaaa gccaagtggt   3480
aaagcgagca atttgcagca taactgcttc tcctagacag ggctgagtgg gcaaaatacg   3540
acagtacaca cagtgactat tagccactgc cagaaacagg ctgaacagcc ctgggagaca   3600
```

-continued

```
agggaaggca ggtggtggga gttgttcatg gagagaaagg agagttttag aaccagcaca    3660
tccactggag atgctgggcc accagacccc tcccagtcaa taaagtctgg tgcctcattt    3720
gatctcagcc tcatcatgac cctggagaga ccctgatacc atctgccagt ccccgacagc    3780
ttaggcactc cttgccatca acctgacccc ccgagtggtt ctccaggctc cctgccccac    3840
ccattcaggc cggaattc                                                  3858
```

<210> SEQ ID NO 745
<211> LENGTH: 875
<212> TYPE: PRT
<213> ORGANISM: Homo sapiens

<400> SEQUENCE: 745

```
Met Glu Ser Thr Leu Thr Leu Ala Thr Glu Gln Pro Val Lys Lys Asn
  1               5                  10                  15

Thr Leu Lys Lys Tyr Lys Ile Ala Cys Ile Val Leu Ala Leu Leu
             20                  25                  30

Val Ile Met Ser Leu Gly Leu Gly Leu Gly Leu Arg Lys Leu
         35                  40                  45

Glu Lys Gln Gly Ser Cys Arg Lys Cys Phe Asp Ala Ser Phe Arg
     50                  55                  60

Gly Leu Glu Asn Cys Arg Cys Asp Val Ala Cys Lys Asp Arg Gly Asp
 65                  70                  75                  80

Cys Cys Trp Asp Phe Glu Asp Thr Cys Val Glu Ser Thr Arg Ile Trp
                 85                  90                  95

Met Cys Asn Lys Phe Arg Cys Gly Glu Thr Arg Leu Glu Ala Ser Leu
            100                 105                 110

Cys Ser Cys Ser Asp Asp Cys Leu Gln Arg Lys Asp Cys Cys Ala Asp
        115                 120                 125

Tyr Lys Ser Val Cys Gln Gly Glu Thr Ser Trp Leu Glu Glu Asn Cys
    130                 135                 140

Asp Thr Ala Gln Gln Ser Gln Cys Pro Glu Gly Phe Asp Leu Pro Pro
145                 150                 155                 160

Val Ile Leu Phe Ser Met Asp Gly Phe Arg Ala Glu Tyr Leu Tyr Thr
                165                 170                 175

Trp Asp Thr Leu Met Pro Asn Ile Asn Lys Leu Lys Thr Cys Gly Ile
            180                 185                 190

His Ser Lys Tyr Met Arg Ala Met Tyr Pro Thr Lys Thr Phe Pro Asn
        195                 200                 205

His Tyr Thr Ile Val Thr Gly Leu Tyr Pro Glu Ser His Gly Ile Ile
    210                 215                 220

Asp Asn Asn Met Tyr Asp Val Asn Leu Asn Lys Asn Phe Ser Leu Ser
225                 230                 235                 240

Ser Lys Glu Gln Asn Asn Pro Ala Trp Trp His Gly Gln Pro Met Trp
                245                 250                 255

Leu Thr Ala Met Tyr Gln Gly Leu Lys Ala Ala Thr Tyr Phe Trp Pro
            260                 265                 270

Gly Ser Glu Val Ala Ile Asn Gly Ser Phe Pro Ser Ile Tyr Met Pro
        275                 280                 285

Tyr Asn Gly Ser Val Pro Phe Glu Glu Arg Ile Ser Thr Leu Leu Lys
    290                 295                 300

Trp Leu Asp Leu Pro Lys Ala Glu Arg Pro Arg Phe Tyr Thr Met Tyr
305                 310                 315                 320
```

-continued

```
Phe Glu Glu Pro Asp Ser Ser His Ala Gly Pro Val Ser Ala
            325                 330                 335

Arg Val Ile Lys Ala Leu Gln Val Val Asp His Ala Phe Gly Met Leu
            340                 345                 350

Met Glu Gly Leu Lys Gln Arg Asn Leu His Asn Cys Val Asn Ile Ile
            355                 360                 365

Leu Leu Ala Asp His Gly Met Asp Gln Thr Tyr Cys Asn Lys Met Glu
        370                 375                 380

Tyr Met Thr Asp Tyr Phe Pro Arg Ile Asn Phe Phe Tyr Met Tyr Glu
385                 390                 395                 400

Gly Pro Ala Pro Arg Ile Arg Ala His Asn Ile Pro His Asp Phe Phe
                    405                 410                 415

Ser Phe Asn Ser Glu Glu Ile Val Arg Asn Leu Ser Cys Arg Lys Pro
                420                 425                 430

Asp Gln His Phe Lys Pro Tyr Leu Thr Pro Asp Leu Pro Lys Arg Leu
            435                 440                 445

His Tyr Ala Lys Asn Val Arg Ile Asp Lys Val His Leu Phe Val Asp
        450                 455                 460

Gln Gln Trp Leu Ala Val Arg Ser Lys Ser Asn Thr Asn Cys Gly Gly
465                 470                 475                 480

Gly Asn His Gly Tyr Asn Asn Glu Phe Arg Ser Met Glu Ala Ile Phe
                    485                 490                 495

Leu Ala His Gly Pro Ser Phe Lys Glu Lys Thr Glu Val Glu Pro Phe
                500                 505                 510

Glu Asn Ile Glu Val Tyr Asn Leu Met Cys Asp Leu Leu Arg Ile Gln
            515                 520                 525

Pro Ala Pro Asn Asn Gly Thr His Gly Ser Leu Asn His Leu Leu Lys
        530                 535                 540

Val Pro Phe Tyr Glu Pro Ser His Ala Glu Glu Val Ser Lys Phe Ser
545                 550                 555                 560

Val Cys Gly Phe Ala Asn Pro Leu Pro Thr Glu Ser Leu Asp Cys Phe
                    565                 570                 575

Cys Pro His Leu Gln Asn Ser Thr Gln Leu Glu Gln Val Asn Gln Met
                580                 585                 590

Leu Asn Leu Thr Gln Glu Glu Ile Thr Ala Thr Val Lys Val Asn Leu
            595                 600                 605

Pro Phe Gly Arg Pro Arg Val Leu Gln Lys Asn Val Asp His Cys Leu
        610                 615                 620

Leu Tyr His Arg Glu Tyr Val Ser Gly Phe Gly Lys Ala Met Arg Met
625                 630                 635                 640

Pro Met Trp Ser Ser Tyr Thr Val Pro Gln Leu Gly Asp Thr Ser Pro
                    645                 650                 655

Leu Pro Pro Thr Val Pro Asp Cys Leu Arg Ala Asp Val Arg Val Pro
                660                 665                 670

Pro Ser Glu Ser Gln Lys Cys Ser Phe Tyr Leu Ala Asp Lys Asn Ile
            675                 680                 685

Thr His Gly Phe Leu Tyr Pro Pro Ala Ser Asn Arg Thr Ser Asp Ser
        690                 695                 700

Gln Tyr Asp Ala Leu Ile Thr Ser Asn Leu Val Pro Met Tyr Glu Glu
705                 710                 715                 720

Phe Arg Lys Met Trp Asp Tyr Phe His Ser Val Leu Leu Ile Lys His
                    725                 730                 735

Ala Thr Glu Arg Asn Gly Val Asn Val Val Ser Gly Pro Ile Phe Asp
```

```
            740                 745                 750
Tyr Asn Tyr Asp Gly His Phe Asp Ala Pro Asp Glu Ile Thr Lys His
            755                 760                 765

Leu Ala Asn Thr Asp Val Pro Ile Pro Thr His Tyr Phe Val Val Leu
    770                 775                 780

Thr Ser Cys Lys Asn Lys Ser His Thr Pro Glu Asn Cys Pro Gly Trp
785                 790                 795                 800

Leu Asp Val Leu Pro Phe Ile Ile Pro His Arg Pro Thr Asn Val Glu
                805                 810                 815

Ser Cys Pro Glu Gly Lys Pro Glu Ala Leu Trp Val Glu Glu Arg Phe
            820                 825                 830

Thr Ala His Ile Ala Arg Val Arg Asp Val Glu Leu Leu Thr Gly Leu
        835                 840                 845

Asp Phe Tyr Gln Asp Lys Val Gln Pro Val Ser Glu Ile Leu Gln Leu
    850                 855                 860

Lys Thr Tyr Leu Pro Thr Phe Glu Thr Thr Ile
865                 870                 875
```

<210> SEQ ID NO 746
<211> LENGTH: 3858
<212> TYPE: DNA
<213> ORGANISM: Homo sapiens

<400> SEQUENCE: 746

| | | | |
|---|---|---|---|
| ctactttatt ctgataaaac aggtctatgc agctaccagg acaatggaat ctacgttgac | 60 |
| tttagcaacg gaacaacctg ttaagaagaa cactcttaag aaatataaaa tagcttgcat | 120 |
| tgttcttctt gctttgctgg tgatcatgtc acttggatta ggcctggggc ttggactcag | 180 |
| gaaactggaa aagcaaggca gctgcaggaa gaagtgcttt gatgcatcat ttagaggact | 240 |
| ggagaactgc cggtgtgatg tggcatgtaa agaccgaggt gattgctgct gggattttga | 300 |
| agacacctgt gtggaatcaa ctcgaatatg gatgtgcaat aaatttcgtt gtggagagac | 360 |
| cagattagag gccagccttt gctcttgttc agatgactgt ttgcagagga agattgctg | 420 |
| tgctgactat aagagtgttt gccaaggaga acctcatgg ctggaagaaa actgtgacac | 480 |
| agcccagcag tctcagtgcc agaagggtt tgacctgcca ccagttatct tgttttctat | 540 |
| ggatggattt agagctgaat atttatacac atgggatact ttaatgccaa atatcaataa | 600 |
| actgaaaaca tgtggaattc attcaaaata catgagagct atgtatccta ccaaaacctt | 660 |
| cccaaatcat tacaccattg tcacgggctt gtatccagag tcacatggca tcattgacaa | 720 |
| taatatgtat gatgtaaatc tcaacaagaa ttttttcactt tcttcaaagg aacaaaataa | 780 |
| tccagcctgg tggcatgggc aaccaatgtg gctgacagca atgtatcaag gtttaaaagc | 840 |
| cgctacctac ttttggcccg gatcagaagt ggctataaat ggctcctttc cttccatata | 900 |
| catgccttac aacggaagtg tcccatttga agagaggatt tctacactgt aaaatggct | 960 |
| ggacctgccc aaagctgaaa gacccaggtt ttataccatg tattttgaag aacctgattc | 1020 |
| ctctggacat gcaggtggac cagtcagtgc cagagtaatt aaagccttac aggtagtaga | 1080 |
| tcatgctttt gggatgttga tggaaggcct gaagcagcgg aatttgcaca actgtgtcaa | 1140 |
| tatcatcctc ctggctgacc atggaatgga ccagacttat tgtaacaaga tggaatacat | 1200 |
| gactgattat tttcccagaa taaacttctt ctacatgtac gaagggcctg ccccccgcat | 1260 |
| ccgagctcat aatatacctc atgctttttt agtttttaat tctgaggaaa ttgttagaaa | 1320 |
| cctcagttgc cgaaaacctg atcagcattt caagccctat ttgactcctg atttgccaaa | 1380 |

```
gcgactgcac tatgccaaga acgtcagaat cgacaaagtt catctctttg tggatcaaca    1440
gtggctggct gttaggagta aatcaaatac aaattgtgga ggaggcaacc atggttataa    1500
caatgagttt aggagcatgg aggctatctt tctggcacat ggacccagtt ttaaagagaa    1560
gactgaagtt gaaccatttg aaaatattga agtctataac ctaatgtgtg atcttctacg    1620
cattcaacca gcaccaaaca atggaaccca tggtagttta aaccatcttc tgaaggtgcc    1680
tttttatgag ccatcccatg cagaggaggt gtcaaagttt tctgtttgtg ctttgctaa     1740 tccattgccc acagagtctc ttgactgttt ctgccctcac ctacaaaata gtactcagct    1800
ggaacaagtg aatcagatgc taaatctcac ccaagaagaa ataacagcaa cagtgaaagt    1860
aaatttgcca tttgggaggc ctagggtact gcagaagaac gtggaccact gtctcctta    1920 ccacagggaa tatgtcagtg gatttggaaa agctatgagg atgcccatgt ggagttcata    1980
cacagtcccc cagttgggag acacatcgcc tctgcctccc actgtcccag actgtctgcg    2040
ggctgatgtc agggttcctc cttctgagag ccaaaaatgt tccttctatt tagcagacaa    2100
gaatatcacc cacggcttcc tctatcctcc tgccagcaat agaacatcag atagccaata    2160
tgatgcttta attactagca atttggtacc tatgtatgaa gaattcagaa aaatgtggga    2220
ctacttccac agtgttcttc ttataaaaca tgccacagaa agaaatggag taaatgtggt    2280
tagtggacca atatttgatt ataattatga tggccatttt gatgctccag atgaaattac    2340
caaacattta gccaacactg atgttcccat cccaacacac tactttgtgg tgctgaccag    2400
ttgtaaaaac aagagccaca caccggaaaa ctgccctggg tggctggatg tcctacccct    2460
tatcatccct caccgaccta ccaacgtgga gagctgtcct gaaggtaaac cagaagctct    2520
ttgggttgaa gaaagattta cagctcacat tgcccgggtc cgtgatgtag aacttctcac    2580
tgggcttgac ttctatcagg ataaagtgca gcctgtctct gaaattttgc aactaaagac    2640
atatttacca acatttgaaa ccactatttta acttaataat gtctacttaa tatataattt    2700
actgtataaa gtaattttgg caaaatataa gtgatttttt ctggagaatt gtaaaataaa    2760
gttttctatt tttccttaaa aaaaaaccg gaattccggg cttgggaggc tgaggcagga    2820
gactcgcttg aacccgggag gcagaggttg cagtgagcca agattgcgcc attgcactcc    2880
agagcctggg tgacagagca agactacatc tcaaaaaata aataaataaa ataaagtaa    2940 caataaaaat aaaaagaaca gcagagagaa tgagcaagga gaaatgtcac aaactattgc    3000
aaaatactgt tacactgggt tggctctcca agaagatact ggaatctctt cagccatttg    3060
cttttcagaa gtagaaacca gcaaaccacc tctaagcgga gaacatacga ttctttatta    3120
agtagctctg gggaaggaaa gaataaaagt tgatagctcc ctgattggga aaaaatgcac    3180
aattaataaa gaatgaagat gaaagaaagc atgcttatgt tgtaacacaa aaaaaattca    3240
caaacgttgg tggaaggaaa acagtataga aacattact ttaactaaaa gctgaaaaa     3300 ttttcagttg ggatgcgact gacaaaaaga acgggatttc caggcataaa gttggcgtga    3360
gctacagagg gcaccatgtg gctcagtgga agacccttca agattcaaag ttccatttga    3420
cagagcaaag gcacttcgca aggagaaggg tttaaattat gggtccaaaa gccaagtggt    3480
aaagcgagca atttgcagca taactgcttc tcctagacag ggctgagtgg gcaaaatacg    3540
acagtacaca cagtgactat tagccactgc cagaaacagg ctgaacagcc ctgggagaca    3600
agggaaggca ggtggtggga gttgttcatg gagagaaagg agagttttag aaccagcaca    3660
tccactggag atgctgggcc accagacccc tcccagtcaa taaagtctgg tgcctcattt    3720
```

-continued

```
gatctcagcc tcatcatgac cctggagaga ccctgatacc atctgccagt ccccgacagc   3780
ttaggcactc cttgccatca acctgacccc ccgagtggtt ctccaggctc cctgcccac    3840 ccattcaggc cggaattc                                                 3858
```

<210> SEQ ID NO 747
<211> LENGTH: 875
<212> TYPE: PRT
<213> ORGANISM: Homo sapiens

<400> SEQUENCE: 747

```
Met Glu Ser Thr Leu Thr Leu Ala Thr Glu Gln Pro Val Lys Lys Asn
 1               5                  10                  15

Thr Leu Lys Lys Tyr Lys Ile Ala Cys Ile Val Leu Ala Leu Leu
            20                  25                  30

Val Ile Met Ser Leu Gly Leu Gly Leu Gly Leu Arg Lys Leu
        35                  40                  45

Glu Lys Gln Gly Ser Cys Arg Lys Lys Cys Phe Asp Ala Ser Phe Arg
 50                  55                  60

Gly Leu Glu Asn Cys Arg Cys Asp Val Ala Cys Lys Asp Arg Gly Asp
 65                  70                  75                  80

Cys Cys Trp Asp Phe Glu Asp Thr Cys Val Glu Ser Thr Arg Ile Trp
                85                  90                  95

Met Cys Asn Lys Phe Arg Cys Gly Glu Thr Arg Leu Glu Ala Ser Leu
            100                 105                 110

Cys Ser Cys Ser Asp Asp Cys Leu Gln Lys Lys Asp Cys Cys Ala Asp
        115                 120                 125

Tyr Lys Ser Val Cys Gln Gly Glu Thr Ser Trp Leu Glu Glu Asn Cys
130                 135                 140

Asp Thr Ala Gln Gln Ser Gln Cys Pro Glu Gly Phe Asp Leu Pro Pro
145                 150                 155                 160

Val Ile Leu Phe Ser Met Asp Gly Phe Arg Ala Glu Tyr Leu Tyr Thr
                165                 170                 175

Trp Asp Thr Leu Met Pro Asn Ile Asn Lys Leu Lys Thr Cys Gly Ile
            180                 185                 190

His Ser Lys Tyr Met Arg Ala Met Tyr Pro Thr Lys Thr Phe Pro Asn
        195                 200                 205

His Tyr Thr Ile Val Thr Gly Leu Tyr Pro Glu Ser His Gly Ile Ile
210                 215                 220

Asp Asn Asn Met Tyr Asp Val Asn Leu Asn Lys Asn Phe Ser Leu Ser
225                 230                 235                 240

Ser Lys Glu Gln Asn Asn Pro Ala Trp Trp His Gly Gln Pro Met Trp
                245                 250                 255

Leu Thr Ala Met Tyr Gln Gly Leu Lys Ala Ala Thr Tyr Phe Trp Pro
            260                 265                 270

Gly Ser Glu Val Ala Ile Asn Gly Ser Phe Pro Ser Ile Tyr Met Pro
        275                 280                 285

Tyr Asn Gly Ser Val Pro Phe Glu Glu Arg Ile Ser Thr Leu Leu Lys
290                 295                 300

Trp Leu Asp Leu Pro Lys Ala Glu Arg Pro Arg Phe Tyr Thr Met Tyr
305                 310                 315                 320

Phe Glu Glu Pro Asp Ser Ser Gly His Ala Gly Gly Pro Val Ser Ala
                325                 330                 335

Arg Val Ile Lys Ala Leu Gln Val Val Asp His Ala Phe Gly Met Leu
            340                 345                 350
```

```
Met Glu Gly Leu Lys Gln Arg Asn Leu His Asn Cys Val Asn Ile Ile
            355                 360                 365

Leu Leu Ala Asp His Gly Met Asp Gln Thr Tyr Cys Asn Lys Met Glu
        370                 375                 380

Tyr Met Thr Asp Tyr Phe Pro Arg Ile Asn Phe Phe Tyr Met Tyr Glu
385                 390                 395                 400

Gly Pro Ala Pro Arg Ile Arg Ala His Asn Ile Pro His Asp Phe Phe
                405                 410                 415

Ser Phe Asn Ser Glu Glu Ile Val Arg Asn Leu Ser Cys Arg Lys Pro
            420                 425                 430

Asp Gln His Phe Lys Pro Tyr Leu Thr Pro Asp Leu Pro Lys Arg Leu
        435                 440                 445

His Tyr Ala Lys Asn Val Arg Ile Asp Lys Val His Leu Phe Val Asp
    450                 455                 460

Gln Gln Trp Leu Ala Val Arg Ser Lys Ser Asn Thr Asn Cys Gly Gly
465                 470                 475                 480

Gly Asn His Gly Tyr Asn Asn Glu Phe Arg Ser Met Glu Ala Ile Phe
                485                 490                 495

Leu Ala His Gly Pro Ser Phe Lys Glu Lys Thr Glu Val Glu Pro Phe
            500                 505                 510

Glu Asn Ile Glu Val Tyr Asn Leu Met Cys Asp Leu Leu Arg Ile Gln
        515                 520                 525

Pro Ala Pro Asn Asn Gly Thr His Gly Ser Leu Asn His Leu Leu Lys
    530                 535                 540

Val Pro Phe Tyr Glu Pro Ser His Ala Glu Glu Val Ser Lys Phe Ser
545                 550                 555                 560

Val Cys Gly Phe Ala Asn Pro Leu Pro Thr Glu Ser Leu Asp Cys Phe
                565                 570                 575

Cys Pro His Leu Gln Asn Ser Thr Gln Leu Glu Gln Val Asn Gln Met
            580                 585                 590

Leu Asn Leu Thr Gln Glu Glu Ile Thr Ala Thr Val Lys Val Asn Leu
        595                 600                 605

Pro Phe Gly Arg Pro Arg Val Leu Gln Lys Asn Val Asp His Cys Leu
    610                 615                 620

Leu Tyr His Arg Glu Tyr Val Ser Gly Phe Gly Lys Ala Met Arg Met
625                 630                 635                 640

Pro Met Trp Ser Ser Tyr Thr Val Pro Gln Leu Gly Asp Thr Ser Pro
                645                 650                 655

Leu Pro Pro Thr Val Pro Asp Cys Leu Arg Ala Asp Val Arg Val Pro
            660                 665                 670

Pro Ser Glu Ser Gln Lys Cys Ser Phe Tyr Leu Ala Asp Lys Asn Ile
        675                 680                 685

Thr His Gly Phe Leu Tyr Pro Pro Ala Ser Asn Arg Thr Ser Asp Ser
    690                 695                 700

Gln Tyr Asp Ala Leu Ile Thr Ser Asn Leu Val Pro Met Tyr Glu Glu
705                 710                 715                 720

Phe Arg Lys Met Trp Asp Tyr Phe His Ser Val Leu Leu Ile Lys His
                725                 730                 735

Ala Thr Glu Arg Asn Gly Val Asn Val Ser Gly Pro Ile Phe Asp
            740                 745                 750

Tyr Asn Tyr Asp Gly His Phe Asp Ala Pro Asp Glu Ile Thr Lys His
        755                 760                 765
```

-continued

```
Leu Ala Asn Thr Asp Val Pro Ile Pro Thr His Tyr Phe Val Leu
    770                 775                 780

Thr Ser Cys Lys Asn Lys Ser His Thr Pro Glu Asn Cys Pro Gly Trp
785                 790                 795                 800

Leu Asp Val Leu Pro Phe Ile Ile Pro His Arg Pro Thr Asn Val Glu
                805                 810                 815

Ser Cys Pro Glu Gly Lys Pro Glu Ala Leu Trp Val Glu Arg Phe
                820                 825                 830

Thr Ala His Ile Ala Arg Val Arg Asp Val Glu Leu Leu Thr Gly Leu
                835                 840                 845

Asp Phe Tyr Gln Asp Lys Val Gln Pro Val Ser Glu Ile Leu Gln Leu
    850                 855                 860

Lys Thr Tyr Leu Pro Thr Phe Glu Thr Thr Ile
865                 870                 875

<210> SEQ ID NO 748
<211> LENGTH: 875
<212> TYPE: PRT
<213> ORGANISM: Homo sapiens

<400> SEQUENCE: 748

Met Glu Ser Thr Leu Thr Leu Ala Thr Glu Gln Pro Val Lys Lys Asn
1               5                   10                  15

Thr Leu Lys Lys Tyr Lys Ile Ala Cys Ile Val Leu Ala Leu Leu
                20                  25                  30

Val Ile Met Ser Leu Gly Leu Gly Leu Gly Leu Arg Lys Leu
            35                  40                  45

Glu Lys Gln Gly Ser Cys Arg Lys Lys Cys Phe Asp Ala Ser Phe Arg
    50                  55                  60

Gly Leu Glu Asn Cys Arg Cys Asp Val Ala Cys Lys Asp Arg Gly Asp
65                  70                  75                  80

Cys Cys Trp Asp Phe Glu Asp Thr Cys Val Glu Ser Thr Arg Ile Trp
                85                  90                  95

Met Cys Asn Lys Phe Arg Cys Gly Glu Thr Arg Leu Glu Ala Ser Leu
                100                 105                 110

Cys Ser Cys Ser Asp Asp Cys Leu Gln Arg Lys Asp Cys Cys Ala Asp
            115                 120                 125

Tyr Lys Ser Val Cys Gln Gly Glu Thr Ser Trp Leu Glu Glu Asn Cys
    130                 135                 140

Asp Thr Ala Gln Gln Ser Gln Cys Pro Glu Gly Phe Asp Leu Pro Pro
145                 150                 155                 160

Val Ile Leu Phe Ser Met Asp Gly Phe Arg Ala Glu Tyr Leu Tyr Thr
                165                 170                 175

Trp Asp Thr Leu Met Pro Asn Ile Asn Lys Leu Lys Thr Cys Gly Ile
                180                 185                 190

His Ser Lys Tyr Met Arg Ala Met Tyr Pro Thr Lys Thr Phe Pro Asn
            195                 200                 205

His Tyr Thr Ile Val Thr Gly Leu Tyr Pro Glu Ser His Gly Ile Ile
    210                 215                 220

Asp Asn Asn Met Tyr Asp Val Asn Leu Asn Lys Asn Phe Ser Leu Ser
225                 230                 235                 240

Ser Lys Glu Gln Asn Asn Pro Ala Trp Trp His Gly Gln Pro Met Trp
                245                 250                 255

Leu Thr Ala Met Tyr Gln Gly Leu Lys Ala Ala Thr Tyr Phe Trp Pro
                260                 265                 270
```

```
Gly Ser Glu Val Ala Ile Asn Gly Ser Phe Pro Ser Ile Tyr Met Pro
            275                 280                 285
Tyr Asn Gly Ser Val Pro Phe Glu Glu Arg Ile Ser Thr Leu Leu Lys
            290                 295                 300
Trp Leu Asp Leu Pro Lys Ala Glu Arg Pro Arg Phe Tyr Thr Met Tyr
305                 310                 315                 320
Phe Glu Glu Pro Asp Ser Ser Gly His Ala Gly Gly Pro Val Ser Ala
                325                 330                 335
Arg Val Ile Lys Ala Leu Gln Val Val Asp His Ala Phe Gly Met Leu
            340                 345                 350
Met Glu Gly Leu Lys Gln Arg Asn Leu His Asn Cys Val Asn Ile Ile
            355                 360                 365
Leu Leu Ala Asp His Gly Met Asp Gln Thr Tyr Cys Asn Lys Met Glu
        370                 375                 380
Tyr Met Thr Asp Tyr Phe Pro Arg Ile Asn Phe Phe Tyr Met Tyr Glu
385                 390                 395                 400
Gly Pro Ala Pro Arg Ile Arg Ala His Asn Ile Pro His Asp Phe Phe
                405                 410                 415
Ser Phe Asn Ser Glu Glu Ile Val Arg Asn Leu Ser Cys Arg Lys Pro
            420                 425                 430
Asp Gln His Phe Lys Pro Tyr Leu Thr Pro Asp Leu Pro Lys Arg Leu
        435                 440                 445
His Tyr Ala Lys Asn Val Arg Ile Asp Lys Val His Leu Phe Val Asp
    450                 455                 460
Gln Gln Trp Leu Ala Val Arg Ser Lys Ser Asn Thr Asn Cys Gly Gly
465                 470                 475                 480
Gly Asn His Gly Tyr Asn Asn Glu Phe Arg Ser Met Glu Ala Ile Phe
                485                 490                 495
Leu Ala His Gly Pro Ser Phe Lys Glu Lys Thr Glu Val Glu Pro Phe
            500                 505                 510
Glu Asn Ile Glu Val Tyr Asn Leu Met Cys Asp Leu Leu Arg Ile Gln
            515                 520                 525
Pro Ala Pro Asn Asn Gly Thr His Gly Ser Leu Asn His Leu Leu Lys
        530                 535                 540
Val Pro Phe Tyr Glu Pro Ser His Ala Glu Val Ser Lys Phe Ser
545                 550                 555                 560
Val Cys Gly Phe Ala Asn Pro Leu Pro Thr Glu Ser Leu Asp Cys Phe
                565                 570                 575
Cys Pro His Leu Gln Asn Ser Thr Gln Leu Glu Gln Val Asn Gln Met
            580                 585                 590
Leu Asn Leu Thr Gln Glu Glu Ile Thr Ala Thr Val Lys Val Asn Leu
        595                 600                 605
Pro Phe Gly Arg Pro Arg Val Leu Gln Lys Asn Val Asp His Cys Leu
    610                 615                 620
Leu Tyr His Arg Glu Tyr Val Ser Gly Phe Gly Lys Ala Met Arg Met
625                 630                 635                 640
Pro Met Trp Ser Ser Tyr Thr Val Pro Gln Leu Gly Asp Thr Ser Pro
                645                 650                 655
Leu Pro Pro Thr Val Pro Asp Cys Leu Arg Ala Asp Val Arg Val Pro
            660                 665                 670
Pro Ser Glu Ser Gln Lys Cys Ser Phe Tyr Leu Ala Asp Lys Asn Ile
        675                 680                 685
```

-continued

```
Thr His Gly Phe Leu Tyr Pro Pro Ala Ser Asn Arg Thr Ser Asp Ser
    690                 695                 700

Gln Tyr Asp Ala Leu Ile Thr Ser Asn Leu Val Pro Met Tyr Glu Glu
705                 710                 715                 720

Phe Arg Lys Met Trp Asp Tyr Phe His Ser Val Leu Ile Lys His
                725                 730                 735

Ala Thr Glu Arg Asn Gly Val Asn Val Val Ser Gly Pro Ile Phe Asp
            740                 745                 750

Tyr Asn Tyr Asp Gly His Phe Asp Ala Pro Asp Glu Ile Thr Lys His
        755                 760                 765

Leu Ala Asn Thr Asp Val Pro Ile Pro Thr His Tyr Phe Val Val Leu
    770                 775                 780

Thr Ser Cys Lys Asn Lys Ser His Thr Pro Glu Asn Cys Pro Gly Trp
785                 790                 795                 800

Leu Asp Val Leu Pro Phe Ile Ile Pro His Arg Pro Thr Asn Val Glu
                805                 810                 815

Ser Cys Pro Glu Gly Lys Pro Glu Ala Leu Trp Val Glu Glu Arg Phe
            820                 825                 830

Thr Ala His Ile Ala Arg Val Arg Asp Val Glu Leu Leu Thr Gly Leu
        835                 840                 845

Asp Phe Tyr Gln Asp Lys Val Gln Pro Val Ser Glu Ile Leu Gln Leu
    850                 855                 860

Lys Thr Tyr Leu Pro Thr Phe Glu Thr Thr Ile
865                 870                 875
```

<210> SEQ ID NO 749
<211> LENGTH: 384
<212> TYPE: PRT
<213> ORGANISM: Homo sapiens

<400> SEQUENCE: 749

```
Met Glu Ala Ile Phe Leu Ala His Gly Pro Ser Phe Lys Glu Lys Thr
1               5                   10                  15

Glu Val Glu Pro Phe Glu Asn Ile Glu Val Tyr Asn Leu Met Cys Asp
            20                  25                  30

Leu Leu Arg Ile Gln Pro Ala Pro Asn Asn Gly Thr His Gly Ser Leu
        35                  40                  45

Asn His Leu Leu Lys Val Pro Phe Tyr Glu Pro Ser His Ala Glu Glu
    50                  55                  60

Val Ser Lys Phe Ser Val Cys Gly Phe Ala Asn Pro Leu Pro Thr Glu
65                  70                  75                  80

Ser Leu Asp Cys Phe Cys Pro His Leu Gln Asn Ser Thr Gln Leu Glu
                85                  90                  95

Gln Val Asn Gln Met Leu Asn Leu Thr Gln Glu Glu Ile Thr Ala Thr
            100                 105                 110

Val Lys Val Asn Leu Pro Phe Gly Arg Pro Arg Val Leu Gln Lys Asn
        115                 120                 125

Val Asp His Cys Leu Leu Tyr His Arg Glu Tyr Val Ser Gly Phe Gly
    130                 135                 140

Lys Ala Met Arg Met Pro Met Trp Ser Ser Tyr Thr Val Pro Gln Leu
145                 150                 155                 160

Gly Asp Thr Ser Pro Leu Pro Thr Val Pro Asp Cys Leu Arg Ala
                165                 170                 175

Asp Val Arg Val Pro Pro Ser Glu Ser Gln Lys Cys Ser Phe Tyr Leu
            180                 185                 190
```

-continued

```
Ala Asp Lys Asn Ile Thr His Gly Phe Leu Tyr Pro Pro Ala Ser Asn
        195                 200                 205

Arg Thr Ser Asp Ser Gln Tyr Asp Ala Leu Ile Thr Ser Asn Leu Val
    210                 215                 220

Pro Met Tyr Glu Glu Phe Arg Lys Met Trp Asp Tyr Phe His Ser Val
225                 230                 235                 240

Leu Leu Ile Lys His Ala Thr Glu Arg Asn Gly Val Asn Val Val Ser
                245                 250                 255

Gly Pro Ile Phe Asp Tyr Asn Tyr Asp Gly His Phe Asp Ala Pro Asp
            260                 265                 270

Glu Ile Thr Lys His Leu Ala Asn Thr Asp Val Pro Ile Pro Thr His
        275                 280                 285

Tyr Phe Val Val Leu Thr Ser Cys Lys Asn Lys Ser His Thr Pro Glu
    290                 295                 300

Asn Cys Pro Gly Trp Leu Asp Val Leu Pro Phe Ile Pro His Arg
305                 310                 315                 320

Pro Thr Asn Val Glu Ser Cys Pro Glu Gly Lys Pro Glu Ala Leu Trp
                325                 330                 335

Val Glu Glu Arg Phe Thr Ala His Ile Ala Arg Val Arg Asp Val Glu
            340                 345                 350

Leu Leu Thr Gly Leu Asp Phe Tyr Gln Asp Lys Val Gln Pro Val Ser
        355                 360                 365

Glu Ile Leu Gln Leu Lys Thr Tyr Leu Pro Thr Phe Glu Thr Thr Ile
    370                 375                 380

<210> SEQ ID NO 750
<211> LENGTH: 384
<212> TYPE: PRT
<213> ORGANISM: Homo sapiens

<400> SEQUENCE: 750

Met Glu Ala Ile Phe Leu Ala His Gly Pro Ser Phe Lys Glu Lys Thr
1               5                   10                  15

Glu Val Glu Pro Phe Glu Asn Ile Glu Val Tyr Asn Leu Met Cys Asp
            20                  25                  30

Leu Leu Arg Ile Gln Pro Ala Pro Asn Asn Gly Thr His Gly Ser Leu
        35                  40                  45

Asn His Leu Leu Lys Val Pro Phe Tyr Glu Pro Ser His Ala Glu Glu
    50                  55                  60

Val Ser Lys Phe Ser Val Cys Gly Phe Ala Asn Pro Leu Pro Thr Glu
65                  70                  75                  80

Ser Leu Asp Cys Phe Cys Pro His Leu Gln Asn Ser Thr Gln Leu Glu
                85                  90                  95

Gln Val Asn Gln Met Leu Asn Leu Thr Gln Glu Glu Ile Thr Ala Thr
            100                 105                 110

Val Lys Val Asn Leu Pro Phe Gly Arg Pro Arg Val Leu Gln Lys Asn
        115                 120                 125

Val Asp His Cys Leu Leu Tyr His Arg Glu Tyr Val Ser Gly Phe Gly
    130                 135                 140

Lys Ala Met Arg Met Pro Met Trp Ser Ser Tyr Thr Val Pro Gln Leu
145                 150                 155                 160

Gly Asp Thr Ser Pro Leu Pro Pro Thr Val Pro Asp Cys Leu Arg Ala
                165                 170                 175

Asp Val Arg Val Pro Pro Ser Glu Ser Gln Lys Cys Ser Phe Tyr Leu
```

-continued

```
                180                 185                 190
Ala Asp Lys Asn Ile Thr His Gly Phe Leu Tyr Pro Ala Ser Asn
            195                 200                 205
Arg Thr Ser Asp Ser Gln Tyr Asp Ala Leu Ile Thr Ser Asn Leu Val
        210                 215                 220
Pro Met Tyr Glu Glu Phe Arg Lys Met Trp Asp Tyr Phe His Ser Val
225                 230                 235                 240
Leu Leu Ile Lys His Ala Thr Glu Arg Asn Gly Val Asn Val Val Ser
                245                 250                 255
Gly Pro Ile Phe Asp Tyr Asn Tyr Asp Gly His Phe Asp Ala Pro Asp
            260                 265                 270
Glu Ile Thr Lys His Leu Ala Asn Thr Asp Val Pro Ile Pro Thr His
        275                 280                 285
Tyr Phe Val Val Leu Thr Ser Cys Lys Asn Lys Ser His Thr Pro Glu
        290                 295                 300
Asn Cys Pro Gly Trp Leu Asp Val Leu Pro Phe Ile Ile Pro His Arg
305                 310                 315                 320
Pro Thr Asn Val Glu Ser Cys Pro Gly Lys Pro Glu Ala Leu Trp
                325                 330                 335
Val Glu Glu Arg Phe Thr Ala His Ile Ala Arg Val Arg Asp Val Glu
            340                 345                 350
Leu Leu Thr Gly Leu Asp Phe Tyr Gln Asp Lys Val Gln Pro Val Ser
        355                 360                 365
Glu Ile Leu Gln Leu Lys Thr Tyr Leu Pro Thr Phe Glu Thr Pro Ile
        370                 375                 380

<210> SEQ ID NO 751
<211> LENGTH: 875
<212> TYPE: PRT
<213> ORGANISM: Homo sapiens

<400> SEQUENCE: 751

Met Glu Ser Thr Leu Thr Leu Ala Thr Glu Gln Pro Val Lys Lys Asn
1               5                   10                  15
Thr Leu Lys Lys Tyr Lys Ile Ala Cys Ile Val Leu Ala Leu Leu
            20                  25                  30
Val Ile Met Ser Leu Gly Leu Gly Leu Gly Leu Arg Lys Leu
        35                  40                  45
Glu Lys Gln Gly Ser Cys Arg Lys Lys Cys Phe Asp Ala Ser Phe Arg
50                  55                  60
Gly Leu Glu Asn Cys Arg Cys Asp Val Ala Cys Lys Asp Arg Gly Asp
65                  70                  75                  80
Cys Cys Trp Asp Phe Glu Asp Thr Cys Val Glu Ser Thr Arg Ile Trp
                85                  90                  95
Met Cys Asn Lys Phe Arg Cys Gly Glu Thr Arg Leu Glu Ala Ser Leu
            100                 105                 110
Cys Ser Cys Ser Asp Asp Cys Leu Gln Lys Lys Asp Cys Cys Ala Asp
        115                 120                 125
Tyr Lys Ser Val Cys Gln Gly Glu Thr Ser Trp Leu Glu Glu Asn Cys
    130                 135                 140
Asp Thr Ala Gln Gln Ser Gln Cys Pro Glu Gly Phe Asp Leu Pro Pro
145                 150                 155                 160
Val Ile Leu Phe Ser Met Asp Gly Phe Arg Ala Glu Tyr Leu Tyr Thr
                165                 170                 175
```

-continued

```
Trp Asp Thr Leu Met Pro Asn Ile Asn Lys Leu Lys Thr Cys Gly Ile
            180                 185                 190
His Ser Lys Tyr Met Arg Ala Met Tyr Pro Thr Lys Thr Phe Pro Asn
        195                 200                 205
His Tyr Thr Ile Val Thr Gly Leu Tyr Pro Glu Ser His Gly Ile Ile
    210                 215                 220
Asp Asn Asn Met Tyr Asp Val Asn Leu Asn Lys Asn Phe Ser Leu Ser
225                 230                 235                 240
Ser Lys Glu Gln Asn Asn Pro Ala Trp Trp His Gly Gln Pro Met Trp
                245                 250                 255
Leu Thr Ala Met Tyr Gln Gly Leu Lys Ala Ala Thr Tyr Phe Trp Pro
            260                 265                 270
Gly Ser Glu Val Ala Ile Asn Gly Ser Phe Pro Ser Ile Tyr Met Pro
        275                 280                 285
Tyr Asn Gly Ser Val Pro Phe Glu Glu Arg Ile Ser Thr Leu Leu Lys
    290                 295                 300
Trp Leu Asp Leu Pro Lys Ala Glu Arg Pro Arg Phe Tyr Thr Met Tyr
305                 310                 315                 320
Phe Glu Glu Pro Asp Ser Ser Gly His Ala Gly Gly Pro Val Ser Ala
                325                 330                 335
Arg Val Ile Lys Ala Leu Gln Val Val Asp His Ala Phe Gly Met Leu
            340                 345                 350
Met Glu Gly Leu Lys Gln Arg Asn Leu His Asn Cys Val Asn Ile Ile
        355                 360                 365
Leu Leu Ala Asp His Gly Met Asp Gln Thr Tyr Cys Asn Lys Met Glu
    370                 375                 380
Tyr Met Thr Asp Tyr Phe Pro Arg Ile Asn Phe Phe Tyr Met Tyr Glu
385                 390                 395                 400
Gly Pro Ala Pro Arg Ile Arg Ala His Asn Ile Pro His Asp Phe Phe
                405                 410                 415
Ser Phe Asn Ser Glu Glu Ile Val Arg Asn Leu Ser Cys Arg Lys Pro
            420                 425                 430
Asp Gln His Phe Lys Pro Tyr Leu Thr Pro Asp Leu Pro Lys Arg Leu
        435                 440                 445
His Tyr Ala Lys Asn Val Arg Ile Asp Lys Val His Leu Phe Val Asp
    450                 455                 460
Gln Gln Trp Leu Ala Val Arg Ser Lys Ser Asn Thr Asn Cys Gly Gly
465                 470                 475                 480
Gly Asn His Gly Tyr Asn Asn Glu Phe Arg Ser Met Glu Ala Ile Phe
                485                 490                 495
Leu Ala His Gly Pro Ser Phe Lys Glu Lys Thr Glu Val Glu Pro Phe
            500                 505                 510
Glu Asn Ile Glu Val Tyr Asn Leu Met Cys Asp Leu Leu Arg Ile Gln
        515                 520                 525
Pro Ala Pro Asn Asn Gly Thr His Gly Ser Leu Asn His Leu Leu Lys
    530                 535                 540
Val Pro Phe Tyr Glu Pro Ser His Ala Glu Val Ser Lys Phe Ser
545                 550                 555                 560
Val Cys Gly Phe Ala Asn Pro Leu Pro Thr Glu Ser Leu Asp Cys Phe
                565                 570                 575
Cys Pro His Leu Gln Asn Ser Thr Gln Leu Glu Gln Val Asn Gln Met
            580                 585                 590
Leu Asn Leu Thr Gln Glu Glu Ile Thr Ala Thr Val Lys Val Asn Leu
```

```
                    595                 600                 605
Pro Phe Gly Arg Pro Arg Val Leu Gln Lys Asn Val Asp His Cys Leu
    610                 615                 620
Leu Tyr His Arg Glu Tyr Val Ser Gly Phe Gly Lys Ala Met Arg Met
625                 630                 635                 640
Pro Met Trp Ser Ser Tyr Thr Val Pro Gln Leu Gly Asp Thr Ser Pro
                645                 650                 655
Leu Pro Pro Thr Val Pro Asp Cys Leu Arg Ala Asp Val Arg Val Pro
                660                 665                 670
Pro Ser Glu Ser Gln Lys Cys Ser Phe Tyr Leu Ala Asp Lys Asn Ile
            675                 680                 685
Thr His Gly Phe Leu Tyr Pro Pro Ala Ser Asn Arg Thr Ser Asp Ser
        690                 695                 700
Gln Tyr Asp Ala Leu Ile Thr Ser Asn Leu Val Pro Met Tyr Glu Glu
705                 710                 715                 720
Phe Arg Lys Met Trp Asp Tyr Phe His Ser Val Leu Ile Lys His
                725                 730                 735
Ala Thr Glu Arg Asn Gly Val Asn Val Val Ser Gly Pro Ile Phe Asp
            740                 745                 750
Tyr Asn Tyr Asp Gly His Phe Asp Ala Pro Asp Glu Ile Thr Lys His
            755                 760                 765
Leu Ala Asn Thr Asp Val Pro Ile Pro Thr His Tyr Phe Val Val Leu
        770                 775                 780
Thr Ser Cys Lys Asn Lys Ser His Thr Pro Glu Asn Cys Pro Gly Trp
785                 790                 795                 800
Leu Asp Val Leu Pro Phe Ile Ile Pro His Arg Pro Thr Asn Val Glu
                805                 810                 815
Ser Cys Pro Glu Gly Lys Pro Glu Ala Leu Trp Val Glu Glu Arg Phe
            820                 825                 830
Thr Ala His Ile Ala Arg Val Arg Asp Val Glu Leu Leu Thr Gly Leu
        835                 840                 845
Asp Phe Tyr Gln Asp Lys Val Gln Pro Val Ser Glu Ile Leu Gln Leu
    850                 855                 860
Lys Thr Tyr Leu Pro Thr Phe Glu Thr Thr Ile
865                 870                 875

<210> SEQ ID NO 752
<211> LENGTH: 14
<212> TYPE: DNA
<213> ORGANISM: Homo sapiens

<400> SEQUENCE: 752
ttttgatcaa gctt                                                    14

<210> SEQ ID NO 753
<211> LENGTH: 42
<212> TYPE: DNA
<213> ORGANISM: Homo sapiens

<400> SEQUENCE: 753
ctaatacgac tcactatagg gctcgagcgg ccgcccgggc ag                      42

<210> SEQ ID NO 754
<211> LENGTH: 12
<212> TYPE: DNA
<213> ORGANISM: Homo sapiens
```

-continued

<400> SEQUENCE: 754 gatcctgcccgg                                                        12

<210> SEQ ID NO 755
<211> LENGTH: 40
<212> TYPE: DNA
<213> ORGANISM: Homo sapiens

<400> SEQUENCE: 755
gtaatacgac tcactatagg gcagcgtggt cgcggccgag                          40

<210> SEQ ID NO 756
<211> LENGTH: 10
<212> TYPE: DNA
<213> ORGANISM: Homo sapiens

<400> SEQUENCE: 756
gatcctcggc                                                          10

<210> SEQ ID NO 757
<211> LENGTH: 22
<212> TYPE: DNA
<213> ORGANISM: Homo sapiens

<400> SEQUENCE: 757
ctaatacgac tcactatagg gc                                            22

<210> SEQ ID NO 758
<211> LENGTH: 22
<212> TYPE: DNA
<213> ORGANISM: Homo sapiens

<400> SEQUENCE: 758
tcgagcggcc gcccgggcag ga                                            22

<210> SEQ ID NO 759
<211> LENGTH: 20
<212> TYPE: DNA
<213> ORGANISM: Homo sapiens

<400> SEQUENCE: 759
agcgtggtcg cggccgagga                                               20

<210> SEQ ID NO 760
<211> LENGTH: 14
<212> TYPE: PRT
<213> ORGANISM: Homo sapiens

<400> SEQUENCE: 760

Gln Tyr Ile Lys Ala Asn Ser Lys Phe Ile Gly Ile Thr Glu
 1               5                   10

<210> SEQ ID NO 761
<211> LENGTH: 21
<212> TYPE: PRT
<213> ORGANISM: Homo sapiens

<400> SEQUENCE: 761

Asp Ile Glu Lys Lys Ile Ala Lys Met Glu Lys Ala Ser Ser Val Phe
 1               5                   10                  15

Asn Val Val Asn Ser
             20

```
<210> SEQ ID NO 762
<211> LENGTH: 16
<212> TYPE: PRT
<213> ORGANISM: Homo sapiens

<400> SEQUENCE: 762

Gly Ala Val Asp Ser Ile Leu Gly Gly Val Ala Thr Tyr Gly Ala Ala
1               5                   10                  15

<210> SEQ ID NO 763
<211> LENGTH: 11
<212> TYPE: PRT
<213> ORGANISM: Homo sapiens
<220> FEATURE:
<221> NAME/KEY: VARIANT
<222> LOCATION: (1)...(11)
<223> OTHER INFORMATION: Xaa = cyclohexylalanine, phenylalanine, or
      tyrosine

<400> SEQUENCE: 763

Lys Xaa Val Ala Ala Trp Thr Leu Lys Ala Ala
1               5                   10

<210> SEQ ID NO 764
<211> LENGTH: 24
<212> TYPE: DNA
<213> ORGANISM: Homo sapiens

<400> SEQUENCE: 764
gattacaagg atgacgacga taag                                          24

<210> SEQ ID NO 765
<211> LENGTH: 871
<212> TYPE: PRT
<213> ORGANISM: Homo sapiens

<400> SEQUENCE: 765

Met Glu Ser Thr Leu Thr Leu Ala Thr Glu Gln Pro Val Lys Lys Asn
1               5                   10                  15

Thr Leu Lys Lys Tyr Lys Ile Ala Cys Ile Val Leu Leu Ala Leu Leu
                20                  25                  30

Val Ile Met Ser Leu Gly Leu Gly Leu Gly Leu Gly Leu Arg Lys Leu
            35                  40                  45

Glu Lys Gln Gly Ser Cys Arg Lys Lys Cys Phe Asp Ala Ser Phe Arg
    50                  55                  60

Gly Leu Glu Asn Cys Arg Cys Asp Val Ala Cys Lys Asp Arg Gly Asp
65                  70                  75                  80

Cys Cys Trp Asp Phe Glu Asp Thr Cys Val Glu Ser Thr Arg Ile Trp
                85                  90                  95

Met Cys Asn Lys Phe Arg Cys Gly Glu Thr Arg Leu Glu Ala Ser Leu
                100                 105                 110

Cys Ser Cys Ser Asp Asp Cys Leu Gln Lys Lys Asp Cys Cys Ala Asp
            115                 120                 125

Tyr Lys Ser Val Cys Gln Gly Glu Thr Ser Trp Leu Glu Glu Asn Cys
    130                 135                 140

Asp Thr Ala Gln Gln Ser Gln Cys Pro Glu Gly Phe Asp Leu Pro Pro
145                 150                 155                 160

Val Ile Leu Phe Ser Met Asp Gly Phe Arg Ala Glu Tyr Leu Tyr Thr
                165                 170                 175

Trp Asp Thr Leu Met Pro Asn Ile Asn Lys Leu Lys Thr Cys Gly Ile
```

-continued

```
                180                 185                 190
His Ser Lys Tyr Met Arg Ala Met Tyr Pro Thr Lys Thr Phe Pro Asn
        195                 200                 205
His Tyr Thr Ile Val Thr Gly Leu Tyr Pro Glu Ser His Gly Ile Asp
    210                 215                 220
Asn Asn Met Tyr Asp Val Leu Asn Lys Asn Phe Ser Leu Ser Ser Lys
225                 230                 235                 240
Glu Gln Asn Pro Ala Trp Trp His Gly Gln Pro Met Trp Leu Thr Ala
                245                 250                 255
Met Tyr Gln Gly Leu Lys Ala Ala Thr Tyr Phe Trp Pro Gly Ser Glu
        260                 265                 270
Val Ala Ile Asn Gly Ser Phe Pro Ser Ile Tyr Met Pro Tyr Asn Gly
    275                 280                 285
Ser Val Pro Phe Glu Glu Arg Ile Ser Thr Leu Leu Lys Trp Leu Asp
290                 295                 300
Leu Pro Lys Ala Glu Arg Pro Arg Phe Tyr Thr Met Tyr Phe Glu Glu
305                 310                 315                 320
Pro Asp Ser Ser Gly His Ala Gly Pro Val Ser Ala Arg Val Ile
                325                 330                 335
Lys Ala Leu Gln Val Val Asp His Ala Phe Gly Met Leu Met Glu Gly
        340                 345                 350
Leu Lys Gln Arg Asn Ile Leu His Asn Arg Val Asn Ile Ile Leu Leu
        355                 360                 365
Ala Asp His Gly Met Asp Gln Thr Tyr Cys Asn Lys Met Glu Tyr Met
    370                 375                 380
Thr Asp Tyr Phe Pro Arg Ile Asn Phe Phe Tyr Met Tyr Glu Gly Pro
385                 390                 395                 400
Ala Pro Arg Ile Arg Ala His Asn Ile Pro His Asp Phe Phe Ser Phe
                405                 410                 415
Asn Ser Glu Glu Ile Val Arg Asn Leu Ser Cys Arg Lys Pro Asp Gln
                420                 425                 430
His Phe Lys Pro Tyr Leu Thr Pro Asp Leu Pro Lys Arg Leu His Tyr
        435                 440                 445
Ala Lys Asn Val Arg Ile Asp Lys Val His Leu Phe Val Asp Gln Gln
    450                 455                 460
Trp Leu Ala Val Arg Ser Lys Ser Asn Thr Asn Cys Gly Gly Gly Asn
465                 470                 475                 480
His Gly Tyr Asn Asn Glu Phe Arg Ser Met Glu Ala Ile Phe Leu Ala
                485                 490                 495
His Gly Pro Ser Phe Lys Glu Lys Thr Glu Val Glu Pro Phe Glu Asn
                500                 505                 510
Ile Glu Val Tyr Asn Leu Met Cys Asp Leu Leu Arg Ile Gln Pro Ala
        515                 520                 525
Pro Asn Asn Gly Thr His Gly Ser Leu Asn His Leu Leu Lys Val Pro
        530                 535                 540
Phe Tyr Glu Pro Ser His Ala Glu Glu Val Ser Lys Phe Ser Val Cys
545                 550                 555                 560
Gly Phe Ala Asn Pro Leu Pro Thr Glu Ser Leu Asp Cys Phe Cys Pro
                565                 570                 575
His Leu Gln Asn Ser Thr Gln Leu Glu Gln Val Asn Gln Met Leu Asn
                580                 585                 590
Leu Thr Gln Glu Glu Ile Thr Ala Thr Val Lys Val Asn Leu Pro Phe
                595                 600                 605
```

-continued

```
Gly Arg Pro Arg Val Leu Gln Lys Asn Val Asp His Cys Leu Leu Tyr
    610             615             620

His Arg Glu Tyr Val Ser Gly Phe Gly Lys Ala Met Arg Met Pro Met
625             630             635             640

Trp Ser Ser Tyr Thr Val Pro Gln Leu Gly Asp Thr Ser Pro Leu Pro
            645             650             655

Pro Thr Val Pro Asp Cys Leu Arg Ala Asp Val Arg Val Pro Pro Ser
            660             665             670

Glu Ser Gln Lys Cys Ser Phe Tyr Leu Ala Asp Lys Asn Ile Thr His
        675             680             685

Gly Phe Leu Tyr Pro Pro Ala Ser Asn Arg Thr Ser Asp Ser Gln Tyr
    690             695             700

Asp Ala Leu Ile Thr Ser Asn Leu Val Pro Met Tyr Glu Glu Phe Arg
705             710             715             720

Lys Met Trp Asp Tyr Phe His Ser Val Leu Leu Ile Lys His Ala Thr
            725             730             735

Glu Arg Asn Gly Val Asn Val Val Ser Gly Pro Phe Asp Tyr Asn Tyr
            740             745             750

Asp Gly His Phe Asp Ala Pro Asp Glu Ile Thr Lys His Leu Ala Asn
        755             760             765

Thr Asp Val Pro Ile Pro Thr His Tyr Phe Val Val Leu Thr Ser Cys
    770             775             780

Lys Asn Ser His Thr Pro Glu Asn Cys Pro Gly Trp Leu Asp Val Leu
785             790             795             800

Pro Phe Ile Ile Pro His Arg Pro Thr Asn Val Glu Ser Cys Pro Glu
            805             810             815

Gly Lys Pro Glu Ala Leu Trp Val Glu Glu Arg Phe Thr Ala His Ile
            820             825             830

Ala Arg Val Arg Asp Val Glu Leu Leu Thr Gly Leu Asp Phe Tyr Gln
        835             840             845

Asp Lys Val Gln Pro Val Ser Glu Ile Leu Gln Leu Lys Thr Tyr Leu
    850             855             860

Pro Thr Phe Glu Thr Thr Ile
865             870
```